(12) United States Patent
Mason et al.

(10) Patent No.: US 12,257,302 B2
(45) Date of Patent: Mar. 25, 2025

(54) UNIVERSAL VACCINE PLATFORM

(71) Applicants: Hugh Mason, Phoenix, AZ (US);
Andrew Diamos, Tempe, AZ (US);
Mary Pardhe, Phoenix, AZ (US);
Brandon Favre, Los Gatos, CA (US)

(72) Inventors: Hugh Mason, Phoenix, AZ (US);
Andrew Diamos, Tempe, AZ (US);
Mary Pardhe, Phoenix, AZ (US);
Brandon Favre, Los Gatos, CA (US)

(73) Assignee: Arizona Board of Regents on Behalf of Arizona State University, Scottsdale, AZ (US)

(*) Notice: Subject to any disclaimer, the term of this patent is extended or adjusted under 35 U.S.C. 154(b) by 0 days.

(21) Appl. No.: 18/504,962

(22) Filed: Nov. 8, 2023

(65) Prior Publication Data

US 2024/0216502 A1 Jul. 4, 2024

Related U.S. Application Data

(63) Continuation of application No. 17/367,296, filed on Jul. 2, 2021, now Pat. No. 11,865,174, which is a continuation of application No. 16/404,698, filed on May 6, 2019, now Pat. No. 11,058,766.

(60) Provisional application No. 62/821,599, filed on Mar. 21, 2019, provisional application No. 62/667,414, filed on May 4, 2018.

(51) Int. Cl.
| A61K 39/12 | (2006.01) |
| A61K 39/00 | (2006.01) |
| A61K 39/145 | (2006.01) |
| A61K 39/29 | (2006.01) |
| A61P 31/20 | (2006.01) |
| C12N 7/00 | (2006.01) |

(52) U.S. Cl.
CPC ............ *A61K 39/292* (2013.01); *A61K 39/12* (2013.01); *A61K 39/145* (2013.01); *A61P 31/20* (2018.01); *C12N 7/00* (2013.01); *A61K 2039/505* (2013.01); *A61K 2039/5258* (2013.01); *A61K 2039/575* (2013.01); *A61K 2039/6056* (2013.01); *A61K 2039/70* (2013.01); *C12N 2710/20023* (2013.01); *C12N 2710/20034* (2013.01); *C12N 2710/20071* (2013.01); *C12N 2730/10123* (2013.01); *C12N 2730/10134* (2013.01); *C12N 2730/10171* (2013.01); *C12N 2760/16123* (2013.01); *C12N 2760/16134* (2013.01); *C12N 2760/16171* (2013.01); *C12N 2770/24134* (2013.01); *C12N 2770/24171* (2013.01)

(58) Field of Classification Search
CPC ............ A61K 39/12; A61K 2039/6075; A61K 39/385; A61K 2039/64; A61P 31/20
See application file for complete search history.

(56) References Cited

U.S. PATENT DOCUMENTS

| 7,883,843 B2 | 2/2011 | Milich |
| 8,513,397 B2 | 8/2013 | Mason |
| 9,506,079 B2 | 11/2016 | Mason |
| 10,080,799 B2 | 9/2018 | Mason |
| 10,125,373 B2 | 11/2018 | Mason |
| 2014/0127749 A1 | 5/2014 | Mason |
| 2019/0194680 A1 | 6/2019 | Mason |
| 2020/0222521 A1 | 7/2020 | Roland |
| 2020/0407741 A1 | 12/2020 | Mason |
| 2021/0115456 A1 | 4/2021 | Mason |

FOREIGN PATENT DOCUMENTS

| WO | 2010025285 | 3/2010 |
| WO | 2011100508 | 8/2011 |
| WO | 2012145759 | 10/2012 |
| WO | 2014116721 | 7/2014 |
| WO | 2019010135 | 1/2019 |
| WO | 2019169409 | 9/2019 |
| WO | 2020223516 | 11/2020 |

OTHER PUBLICATIONS

Dreyfus, C. et al., "Highly Conserved Protective Epitopes on Influenza B Viruses", Science, Sep. 2012, vol. 337, No. 6100, pp. 1343-1348 <DOI:10.1126/science.1222908>.

Durbin, A. et al., "An update on Zika vaccine developments", Expert Review of Vaccines, Jul. 2017 (available online Jun. 2017), vol. 16, No. 8, pp. 781-787 <DOI:10.1080/14760584.2017.1345309>.

Ebrahimi, S. et al., "In contrast to conventional inactivated influenza vaccines, 4xM2e.HSP70c fusion protein fully protected mice against lethal dose of H1, H3 and H9 influenza a isolates circulating in Iran", Virology, Aug. 2012 (available online May 2012), vol. 430, No. 1, pp. 63-72 <DOI:10.1016/j.virol.2012.04.015>.

Eichelberger, M. et al., "Neuraminidase as an influenza vaccine antigen: a low hanging fruit, ready for picking to improve vaccine effectiveness", Current Opinion in Immunology, Aug. 2018 (available online Apr. 2018), vol. 53, pp. 38-44 <DOI:10.1016/j.coi.2018.03.025>.

Eisenberg, R., "The specificity and polyvalency of binding of a monoclonal rheumatoid factor", Immunochemistry, Apr. 1976 (available online Mar. 2003), vol. 13, No. 4, pp. 355-359 <DOI:10.1016/0019-2791(76)90347-5>.

Eisfeld, A. et al., "At the centre: influenza A virus ribonucleoproteins", Nature Reviews Microbiology, Jan. 2015 (available online Nov. 2014), vol. 13, No. 1, pp. 28-41 <DOI:10.1038/nrmicro3367>.

El Bakkouri, K. et al., "Universal Vaccine Based on Ectodomain of Matrix Protein 2 of Influenza A: Fc Receptors and Alveolar Macrophages Mediate Protection", The Journal of Immunology, Jan. 2011, vol. 186, No. 2, pp. 1022-1031 <DOI:10.4049/jimmunol.0902147>.

(Continued)

*Primary Examiner* — Barry A Chestnut
(74) *Attorney, Agent, or Firm* — Booth Udall Fuller, PLC; Rodney J. Fuller

(57) ABSTRACT

The disclosure relates to vaccination compositions, for example, against human papillomavirus, Zika virus, and flu virus. The disclosure also relates to vectors for producing the virus-like particles and immune complex platforms of the vaccination compositions.

17 Claims, 24 Drawing Sheets

Specification includes a Sequence Listing.

(56) References Cited

OTHER PUBLICATIONS

Eliasson, D. et al., "M2e-tetramer-specific memory CD4 T cells are broadly protective against influenza infection", Mucosal Immunology, Jan. 2018 (available online Mar. 2017), vol. 11, No. 1, pp. 273-289 <DOI:10.1038/mi.2017.14>.

Ellebedy, A. et al., "Induction of broadly cross-reactive antibody responses to the influenza HA stem region rollowing H5N1 vaccination in humans", Proceedings of the National Academy of Sciences of the United States of America, Sep. 2014 (available online Aug. 2014), vol. 111, No. 36, pp. 13133-13138 <DOI:10.1073/pnas.1414070111>.

Embers, M. et al., "Protective Immunity to Rabbit Oral and Cutaneous Papillomaviruses by Immunization with Short Peptides of L2, the Minor Capsid Protein", Journal of Virology, Oct. 2002, vol. 76, No. 19, pp. 9798-9805 <DOI:10.1128/JVI.76.19.9798-9805.2002>.

Fan, J. et al., "Preclinical study of influenza virus A M2 peptide conjugate vaccines in mice, ferrets, and rhesus monkeys", Vaccine, Aug. 2004 (available online Mar. 2004), vol. 22, No. 23-24, pp. 2993-3003 <DOI:10.1016/j.vaccine.2004.02.021>.

Favre, B., "The Development of a Plant-Expressed M2e-Based Universal Influenza Vaccine", undergraduate thesis defense, Apr. 2018, 50 slides.

Fiers, W. et al., "A "universal" human influenza A vaccine", Virus Research, Jul. 2004 (available online Apr. 2004), vol. 103, No. 1-2, pp. 173-176 <DOI:10.1016/j.virusres.2004.02.030>.

Fiers, W. et al., "M2e-based universal influenza A vaccine", Vaccine, Oct. 2009, vol. 27, No. 45, pp. 6280-6283 <DOI:10.1016/j.vaccine.2009.07.007>.

Fischer, R. et al., "Molecular farming of pharmaceutical proteins", Transgenic Research, Aug. 2000, vol. 9, No. 4-5, pp. 279-299 <DOI:10.1023/A:1008975123362>.

Flannery, B. et al., "Early Estimates of Seasonal Influenza Vaccine Effectiveness—United States, Jan. 2015", Morbidity and Mortality Weekly Report, Jan. 2015, vol. 64, No. 1, pp. 10-15.

Flannery, B. et al., "Interim Estimates of 2013-14 Seasonal Influenza Vaccine Effectiveness—United States, Feb. 2014", Morbidity and Mortality Weekly Report, Feb. 2014, vol. 63, No. 7, pp. 137-142.

Flannery, B. et al., "Interim Estimates of 2016-17 Seasonal Influenza Vaccine Effectiveness—United States, Feb. 2017", Morbidity and Mortality Weekly Report, Feb. 2017, vol. 66, No. 6, pp. 167-171 <DOI:10.15585/mmwr.mm6606a3>.

Flannery, B. et al., "Interim Estimates of 2017-18 Seasonal Influenza Vaccine Effectiveness—United States, Feb. 2018", Morbidty and Mortality Weekly Report, Feb. 2018, vol. 67, No. 6, pp. 180-185 <DOI:10.15585/mmwr.mm6706a2>.

Fridman, W., "Fc receptors and immunoglobulin binding factors", The FASEB Journal, Sep. 1991, vol. 5, No. 12, pp. 2684-2690 <DOI: 10.1096/fasebj.5.12.1916092>.

Fu, T. et al., "Comparative immunogenicity evaluations of influenza A virus M2 peptide as recombinant virus like particle or conjugate vaccines in mice and monkeys", Vaccine, Feb. 2009 (available online Jan. 2009), vol. 27. No. 9, pp. 1440-1447 <DOI:10.1016/j.vaccine.2008.12.034>.

Gallie, D., "The 5'-leader of tobacco mosaic virus promotes translation through enhanced recruitment of Eif4f", Nucleic Acids Research, Aug. 2002, vol. 30, No. 15, pp. 3401-3411 <DOI:10.1093/nar/gkf457>.

Gambhira, R. et al., "A Protective and Broadly Cross-Neutralizing Epitope of Human Papillomavirus L2", Journal of Virology, Dec. 2007, vol. 81, No. 24, pp. 13927-13931 <DOI:10.1128/JVI.00936-07>.

Gambhira, R. et al., "Protection of Rabbits against Challenge with Rabbit Papillomaviruses by Immunization with the N Terminus of Human Papillomavirus Type 16 Minor Capsid Antigen L2", Journal of Virology, Nov. 2007, vol. 81, No. 21, p. 11585-11592 <DOI:10.1128/JVI.01577-07>.

Gaukroger, J. et al., "Vaccination of cattle with bovine papillomavirus type 4 L2 elicits the production of virus- neutralizing antibodies", Journal of General Virology, Jan. 1996 (available online Jul. 1996), vol. 77, pp. 1577-1583 <DOI:10.1099/0022-1317-77-7-1577>.

Gerhard, W. et al., "Role of the B-cell response in recovery of mice from primary influenza virus infection", Immunological Reviews, Oct. 1997 (available online Apr. 2006), vol. 159, No. 1, pp. 95-103 <DOI:10.1111/i.1600-065X.1997.tb01009.x>.

Grgacic, E. et al., "Virus-like particles: Passport to immune recognition", Methods, Sep. 2006, vol. 40, No. 1, pp. 60-65 <DOI:10.1016/j.ymeth.2006.07.018>.

Guerrero, R. et al., "Recombinant Norwalk Virus-Like Particles Administered Intranasally to Mice Induce Systemic and Mucosal (Fecal and Vaginal) Immune Responses", Journal of Virology, Oct. 2001, vol. 75, No. 20, pp. 9713-9722 <DOI:10.1128/JVI.75.20.9713-9722.2001>.

Halweg, C. et al., "The Rb7 Matrix Attachment Region Increases the Likelihood and Magnitude of Transgene Expression in Tobacco Cells: A Flow Cytometric Study", The Plant Cell, Feb. 2005, vol. 17, No. 2, pp. 418-429 <DOI:10.1105/tpc.104.028100>.

Hause, B. et al., "Characterization of a Novel Influenza Virus in Cattle and Swine: Proposal for a New Genus in the Orthomyxoviridae Family", mBio, Mar./Apr. 2014, vol. 5, No. 2, article e00031, 10 pages <DOI:10.1128/mBio.00031-14>.

Hay, A. et al., "The evolution of human influenza viruses", Philosophical Transactions of the Royal Society B, Dec. 2001, vol. 356, No. 1416, pp. 1861-1870 <DOI:10.1098/rstb.2001.0999>.

Hefferon, K., "DNA Virus Vectors for Vaccine Production in Plants: Spotlight on Geminiviruses", Vaccines, Aug. 2014, vol. 2, No. 3, pp. 642-653 <DOI:10.3390/vaccines2030642>.

Heinz, F. et al., "Field effectiveness of vaccination against tick-borne encephalitis", Vaccine, Oct. 2007 (available online Aug. 2007), vol. 25, No. 43, pp. 7559-7567 <DOI:10.1016/j.vaccine.2007.08.024>.

Herr, R. et al., "Evaluation of Two Homologous Proline-Rich Proteins of Coccidioides posadasii as Candidate Vaccines against Coccidioidomycosis", Infection and Immunity, Dec. 2007, vol. 75, No. 12, pp. 5777-5787 <DOI:10.1128/IAI.00807-07>.

Hiatt, A. et al., "Glycan variants of a respiratory syncytial virus antibody with enhanced effector function and in vivo efficacy", Proceedings of the National Academy of Sciences of the United States of America, Apr. 2014, vol. 111, No. 16, pp. 5992-5997 <DOI:10.1073/pnas.1402458111>.

Hiatt, A. et al., "Plant-Derived Monoclonal Antibodies for Prevention and Treatment of Infectious Disease", Microbiology Spectrum, Jan. 2014, vol. 2, No. 1, 10 pages <DOI:10.1128/microbiolspec.AID-0004-2012>.

Hioe, C. et al., "The use of immune complex vaccines to enhance antibody responses against neutralizing epitopes on HIV-1 envelope gp120", Vaccine, Dec. 2009 (available online Oct. 2009), vol. 28, No. 2, pp. 352-360 <DOI:10.1016/j.vaccine.2009.10.040>.

Huang, Z. et al., "A DNA replicon system for rapid high-level production of virus-like particles in plants", Biotechnology and Bioengineering, Jul. 2009 (available online Feb. 2009), vol. 103, No. 4, pp. 706-714 <DOI:10.1002/bit.22299>.

Huang, Z. et al., "Conformational analysis of hepatitis B surface antigen fusions in an Agrobacterium-mediated transient expression system", Plant Biotechnology Journal, May 2004 (available online Mar. 2004), vol. 2, No. 3, pp. 241-249 <DOI:10.1111/j.1467-7652.2004.00068.x>.

Huang, Z. et al., "High-level rapid production of full-size monoclonal antibodies in plants by a single-vector DNA replicon system", Biotechnology and Bioengineering, May 2010 (available online Dec. 2009), vol. 106, No. 1, pp. 9-17 <DOI:10.1002/bit.22652>.

Huang, Z. et al., "Rapid, high-level production of hepatitis B core antigen in plant leaf and its immunogenicity in mice", Vaccine, Mar. 2006 (available online Dec. 2005), vol. 24, No. 14, pp. 2506-2513 <DOI:10.1016/j.vaccine.2005.12.024>.

Huber, V. et al., "Distinct Contributions of Vaccine-Induced Immunoglobulin G1 (IgG1) and IgG2a Antibodies to Protective Immunity

(56) References Cited

OTHER PUBLICATIONS against Influenza", Clinical and Vaccine Immunology, Sep. 2006, vol. 13, No. 9, pp. 981-990 <DOI:10.1128/CVI.00156-06>.
Ina, Y. et al., "Statistical analysis of nucleotide sequences of the hemagglutinin gene of human influenza A viruses", Proceedings of the National Academy of Sciences of the United States of America, Aug. 1994, vol. 91, No. 18, pp. 8388-8392 <DOI:10.1073/pnas.91.18.8388>.
Ingle, N. et al., "Inter-Clade Protection Offered by Mw-Adjuvanted Recombinant HA, NP Proteins, and M2e Peptide Combination Vaccine in Mice Correlates with Cellular Immune Response", Frontiers in Immunology, Jan. 2017, vol. 7, article 674, 13 pages <DOI:10.3389/fimmu.2016.00674>.
Inglis, S. et al., "Polypeptides specified by the influenza virus genome: I. Evidence for eight distinct gene products specified by fowl plague virus", Virology, Oct. 1976 (available Jun. 2004), vol. 74, No. 2, pp. 489-503 <DOI:10.1016/0042-6822(76)90355-X>.
Iuliano, A. et al., "Estimates of global seasonal influenza-associated respiratory mortality: a modelling study", The Lancet, Mar. 2018 (available online Dec. 2017), vol. 391, No. 10127, pp. 1285-1300 <DOI:10.1016/S0140-6736(17)33293-2>.
Jackson, L. et al., "Interim adjusted estimates of seasonal influenza vaccine effectiveness—United States, Feb. 2013", Morbidity and Mortality Weekly Report, Feb. 2013, vol. 62, No. 7, pp. 119-123.
Jackson, M. et al., "Burden of medically attended influenza infection and cases averted by vaccination—United States, 2013/14 through 2015/16 influenza seasons", Vaccine, Jan. 2018 (available online Dec. 2017), vol. 36, No. 4, pp. 467-472 <DOI:10.1016/j.vaccine.2017.12.014>.
Jackson, M. et al., "Influenza Vaccine Effectiveness in the United States during the 2015-2016 Season", The New England Journal of Medicine, Aug. 2017, vol. 377, No. 6, pp. 534-543 <DOI:10.1056/NEJMoa1700153>.
Jefferis, R., "Glycosylation as a strategy to improve antibody-based therapeutics", Nature Reviews Drug Discovery, Mar. 2009, vol. 8, pp. 226-234 <DOI:10.1038/nrd2804>.
Jegerlehner, A. et al., "A molecular assembly system that renders antigens of choice highly repetitive for induction of protective B cell responses", Vaccine, Aug. 2002 (available online Jun. 2002), vol. 20, No. 25-26, pp. 3104-3112 <DOI:10.1016/S0264-410X(02)00266-9>.
Jegerlehner, A. et al., "Influenza A Vaccine Based on the Extracellular Domain of M2: Weak Protection Mediated via Antibody-Dependent NK Cell Activity", Journal of Immunology, May 2004 (available online Apr. 2004), vol. 172, No. 9, pp. 5598-5605 <DOI:10.4049/jimmuno1.172.9.5598 >.
Kanda, Y. et al., "Comparison of biological activity among nonfucosylated therapeutic IgG1 antibodies with three different N-linked Fc oligosaccharides: the high-mannose, hybrid, and complex types", Glycobiology, Jan. 2007 (available online Sep. 2006), vol. 17, No. 1, pp. 104-118 <DOI:10.1093/glycob/cwl057>.
Kawana, K. et al., "Common Neutralization Epitope in Minor Capsid Protein L2 of Human Papillomavirus Types 16 and 6", Journal of Virology, Jul. 1999, vol. 73, No. 7, pp. 6188-6190.
Kim, K-H. et al., "Virus-Like Particles Are a Superior Platform for Presenting M2e Epitopes to Prime Humoral and Cellular Immunity against Influenza Virus", Vaccines, Sep. 2018, vol. 6, No. 4, article 66, 18 pages <DOI:10.3390/vaccines6040066>.
Kim, M-Y. et al., "Novel vaccination approach for dengue infection based on recombinant immune complex universal platform", Vaccine, Apr. 2015 (available Feb. 2015), vol. 33, No. 15, pp. 1830-1838 <DOI:10.1016/j.vaccine.2015.02.036>.
Kim, M-Y. et al., "Plant-expressed Fc-fusion protein tetravalent dengue vaccine with inherent adjuvant properties", Plant Biotechnology Journal, Jul. 2018 (available online Dec. 2017), vol. 16, No. 7, pp. 1283-1294 <DOI:10.1111/pbi.12869>.
Kim, M. et al., "Multiple heterologous M2 extracellular domains presented on virus-like particles confer broader and stronger M2 immunity than live influenza A virus infection", Antiviral Research, Sep. 2013 (available online Jun. 2013), vol. 99, No. 3, pp. 328-335 <DOI:10.1016/j.antiviral.2013.06.010>.
Kines, R. et al., "The initial steps leading to papillomavirus infection occur on the basement membrane prior to cell surface binding", Proceedings of the National Academy of Sciences of the United States of America, Dec. 2009, vol. 106, No. 48, pp. 20458-20463 <DOI:10.1073/pnas.0908502106>.
Kirkland, T. et al., "Evaluation of the Proline-Rich Antigen of Coccidioides immitis as a Vaccine Candidate in Mice", Infection and Immunity, Aug. 1998, vol. 66, No. 8, pp. 3519-3522.
Kirnbauer, R. et al., "Papillomavirus L1 major capsid protein self-assembles into virus-like particles that are highly immunogenic", Proceedings of the National Academy of Sciences of the United States of America, Dec. 1992, vol. 89, No. 24, pp. 12180-12184 <DOI:10.1073/pnas.89.24.12180>.
Kolpe, A. et al., "Passively transferred M2e-specific monoclonal antibody reduces influenza A virus transmission in mice", Antiviral Research, Oct. 2018 (available online Sep. 2018), vol. 158, pp. 244-254 <DOI:10.1016/j.antiviral.2018.08.017>.
Kondo, K. et al., "Modification of human papillomavirus-like particle vaccine by insertion of the cross-reactive L2-epitopes", Journal of Medical Virology, May 2008 (available online Mar. 2008), vol. 80, No. 5, pp. 841-846 <DOI:10.1002/jmv.21124>.
Kondo, K. et al., "Neutralization of HPV16, 18, 31, and 58 pseudovirions with antisera induced by immunizing rabbits with synthetic peptides representing segments of the HPV16 minor capsid protein L2 surface region", Virology, Feb. 2007 (available online Sep. 2006), vol. 358, No. 2, pp. 266-272 <DOI:10.1016/j.virol.2006.08.037>.
Kosik, I. et al., "Neuraminidase inhibition contributes to influenza A virus neutralization by anti-hemagglutinin stem antibodies", Journal of Experimental Medicine, Jan. 2019, vol. 216, No. 2, pp. 304-316 <DOI:10.1084/iem.20181624>.
Koutsky, L. et al., "A Controlled Trial of a Human Papillomavirus Type 16 Vaccine", The New England Journal of Medicine, Nov. 2002, vol. 347, No. 21, pp. 1645-1651 <DOI:10.1056/NEJMoa020586>.
Krammer, F. et al., "Universal Influenza Virus Vaccines That Target the Conserved Hemagglutinin Stalk and Conserved Sites in the Head Domain", The Journal of Infectious Diseases, Apr. 2019, vol. 219, No. 1, pp. S62-S67 <DOI:10.1093/infdis/jiy711>.
Krieger, G. et al., "Binding characteristics of three complement dependent assays for the detection of immune complexes in human serum", Journal of Clinical & Laboratory Immunology, Nov. 1985, vol. 18, No. 3, pp. 129-134.
Krishnavajhala, H. et al., "An influenza A virus vaccine based on an M2e-modified alphavirus", Archives of Virology, Feb. 2018 (available online Oct. 2017), vol. 163, No. 2, pp. 483-488 <DOI:10.1007/s00705-017-3578-8>.
Lamb, R. et al', "Influenza virus M2 protein is an integral membrane protein expressed on the infected-cell surface", Cell, Mar. 1985 (available online Apr. 2004), vol. 40, No. 3, pp. 627-633 <DOI:10.1016/0092-8674(85)90211-9>.
Lamb, R., "The Influenza Virus RNA Segments and Their Encoded Proteins", Genetics of Influenza Viruses (Springer, Vienna), 1983, pp. 21-69.
Lazarowitz, S. et al., "Geminiviruses: Genome structure and gene function", Critical Reviews in Plant Sciences, 1992 (available online Dec. 2008), vol. 11, No. 4, pp. 327-349 <DOI:10.1080/07352689209382350>.
Lee, S-Y. et al., "Nucleoprotein vaccine induces cross-protective cytotoxic T lymphocytes against both lineages of influenza B virus", Clinical and Experimental Vaccine Research, Jan. 2019, vol. 8, No. 1, pp. 54-63 <DOI:10.7774/cevr.2019.8.1.54>.
Liu, W. et al., "Sequence comparison between the extracellular domain of M2 protein human and avian influenza A virus provides new information for bivalent influenza vaccine design", Microbes and Infection, Feb. 2005 (available online Dec. 2004), vol. 7, No. 2, pp. 171-177 <DOI:10.1016/j.micinf.2004.10.006>.
Lowy, D. et al., "Prophylactic human papillomavirus vaccines", The Journal of Clinical Investigation, May 2006, vol. 116, No. 5, pp. 1167-1173 <DOI:10.1172/JCI28607>.

(56) References Cited

OTHER PUBLICATIONS

Lund, J. et al., "Oligosaccharide-protein interactions in IgG can modulate recognition by Fc gamma receptors", FASEB Journal, Jan. 1995, vol. 9, No. 1, pp. 115-119 <DOI:10.1096/fasebj9.1.7821750>.

MacArthur, M. et al., "Influence of proline residues on protein conformation", Journal of Molecular Biology, Mar. 1991 (available online Oct. 2004), vol. 218, No. 2, pp. 397-412 <DOI:10.1016/0022-2836(91)90721-H>.

Mardanova, E. et al., "High immunogenicity of plant-produced candidate influenza vaccine based on the M2e peptide fused to flagellin", Bioengineered, 2015 (available online Feb. 2016), vol. 7, No. 1, pp. 28-32 <DOI:10.1080/21655979.2015.1126017>.

Mardanova, E. et al., "Plant-produced Recombinant Influenza A Vaccines Based on the M2e Peptide", Current Pharmaceutical Design, 2018, vol. 24, No. 12, pp. 1317-1324 <DOI:10.2174/1381612824666180309125344>.

Mardanova, E. et al., "Rapid high-yield expression of a candidate influenza vaccine based on the ectodomain of M2 protein linked to flagellin in plants using viral vectors", BMC Biotechnology, May 2015, vol. 15, article 42 <DOI:10.1186/s12896-015-0164-6>.

Mariani, L. et al., "HPV vaccine: an overview of immune response, clinical protection, and new approaches for the future", Journal of Translational Medicine, Oct. 2010, vol. 8, No. 105, 8 pages <DOI:10.1186/1479-5876-8-105>.

Marillonnet, S. et al., "In planta engineering of viral RNA replicons: Efficient assembly by recombination of DNA modules delivered by Agrobacterium", Proceedings of the National Academy of Sciences of the United States of America, May 2004, vol. 101, No. 18, pp. 6852-6857 <DOI:10.1073/pnas.0400149101>.

Markine-Goriaynoff, D. et al., "Increased Efficacy of the Immunoglobulin G2a Subclass in Antibody-Mediated Protection against Lactate Dehydrogenase-Elevating Virus-Induced Polioencephalomyelitis Revealed with Switch Mutants", Journal of Virology, Jan. 2002, vol. 76, No. 1, pp. 432-435 <DOI:10.1128/JVI.76.1.432-435.2002>.

Marusic, C. et al., "N-glycan engineering of a plant-produced anti-CD20-hIL-2 immunocytokine significantly enhances its effector functions", Biotechnology and Bioengineering, Mar. 2018 (available online Nov. 2017), vol. 115, No. 3, pp. 565-576 <DOI:10.1002/bit.26503>.

Mason, H., "Recombinant immune complexes as versatile and potent vaccines", Human Vaccines & Immunotherapeutics, Mar. 2016 (available online Jan. 2016), vol. 12, No. 4, pp. 988-989 <DOI:10.1080/21645515.2015.1116655>.

Matic, S. et al., "Efficient production of chimeric Human papillomavirus 16 L1 protein bearing the M2e influenza epitope in Nicotiana benthamiana plants", BMC Biotechnology, Nov. 2011, vol. 11, article 106 <DOI:10.1186/1472-6750-11-106>.

Matsuzaki, Y. et al., "Clinical Features of Influenza C Virus Infection in Children", The Journal of Infectious Diseases, May 2006, vol. 193, No. 9, pp. 1229-1235 <DOI:10.1086/502973>.

Maverakis, E. et al., "Glycans in the immune system and The Altered Glycan Theory of Autoimmunity: A critical review", Journal of Autoimmunity, Feb. 2015 (available online Jan. 2015), vol. 57, pp. 1-13 <DOI:10.1016/j.iaut.2014.12.002>.

McGeoch, D. et al., "Influenza virus genome consists of eight distinct RNA species", Proceedings of the National Academy of Sciences of the United States of America, Sep. 1976, vol. 73, No. 9, pp. 3045-3049 <DOI:10.1073/pnas.73.9.3045>.

Mechtchriakova, I. et al., "The use of viral vectors to produce hepatitis B virus core particles in plants", Journal of Virological Methods, Jan. 2006 (available online Aug. 2005), vol. 131, No. 1, pp. 10-15 <DOI:10.1016/j.iviromet.2005.06.020>.

Milich, D. et al., "Preferential Recognition of Hepatitis B Nucleocapsid Antigens by Th1 or Th2 Cells Is Epitope and Major Histocompatibility Complex Dependent", Journal of Virology, May 1995, vol. 69, No. 5, pp. 2776-2785.

Milich, D. et al., "The nucleocapsid of hepatitis B virus is both a T-cell-independent and a T-cell-dependent antigen", Science, Dec. 1986, vol. 234, No. 4782, pp. 1398-1401 <DOI:10.1126/science.3491425>.

Mitnaul, L. et al., "Balanced Hemagglutinin and Neuraminidase Activities Are Critical for Efficient Replication of Influenza A Virus", Journal of Virology, Jul. 2000, vol. 74, No. 13, pp. 6015-6020 <DOI:10.1128/JVI.74.13.6015-6020.2000>.

Moñoz, N. et al., "Against which human papillomavirus types shall we vaccinate and screen? the international perspective", International Journal of Cancer, Aug. 2004 (available online Apr. 2004), vol. 111, No. 2, pp. 278-285 <DOI:10.1002/ijc.20244>.

Moscicki, A-B., "Hpv Vaccines: Today and in the Future", Journal of Adolescent Health, Oct. 2008 (available online Sep. 2008), vol. 43, No. 4, pp. S26-S40 <DOI:10.1016/j.jadohealth.2008.07.010>.

Mosmann, T. et al., "TH1 and TH2 Cells: Different Patterns of Lymphokine Secretion Lead to Different Functional Properties", Annual Review of Immunology, Apr. 1989, vol. 7, No. 1, pp. 145-173 <DOI:10.1146/annurev.iy.07.040189.001045>.

Mosnier, A. et al., "Influenza B burden during seasonal influenza epidemics in France", Medecine et Maladies Infectieuses, Feb. 2017 (available online Jan. 2017), vol. 47, No. 1, pp. 11-17 <DOI:10.1016/j.medmal.2016.11.006>.

Most, J. et al., "Consecutive Infections With Influenza A and B Virus in Children During the 2014-2015 Seasonal Influenza Epidemic", The Journal of Infectious Diseases, Oct. 2016 (available online Apr. 2016), vol. 214, No. 8, pp. 1139-1141 <DOI:10.1093/infdis/jiw104>.

Murray, K. et al., "The Core Antigen of Hepatitis B Virus as a Carrier for Immunogenic Peptides", Biological Chemistry, Mar. 1999 (available online Jun. 2005), vol. 380, No. 3, pp. 277-283 <DOI:10.1515/BC.1999.038>.

Nair, H. et al., "Global burden of respiratory infections due to seasonal influenza in young children: a systematic review and meta-analysis", The Lancet, Dec. 2011 (available online Nov. 2011), vol. 378, No. 9807, pp. 1917-1930 <DOI:10.1016/S0140-6736(11)61051-9>.

Nandi, S. et al., "Techno-economic analysis of a transient plant-based platform for monoclonal antibody production", mAbs, Sep. 2016 (available online Aug. 2016), vol. 8, No. 8, pp. 1456-1466 <DOI:10.1080/19420862.2016.1227901>.

Nardelli-Haefliger, D. et al., "Specific Antibody Levels at the Cervix During the Menstrual Cycle of Women Vaccinated With Human Papillomavirus 16 Virus-Like Particles", Journal of the National Cancer Institute, Aug. 2003, vol. 95, No. 15, pp. 1128-1137 <DOI:10.1093/jnci/djg018>.

National Institute of Allergy and Infectious Diseases (NIAID)., "VRC 705: A Zika Virus DNA Vaccine in Healthy Adults and Adolescents (DNA)" [online], U.S. National Library of Medicine: ClinicalTrials.gov, Apr. 2017 [retrieved Jul. 23, 2019 from archive.org, as it appeared on Aug. 17, 2017], retrieved from the internet: <URL:https://web.archive.org/web/20170817202056/https://clinicaltrials.gov/ct2/show/NCT03110770>.

Neirynck, S. et al., "A universal influenza A vaccine based on the extracellular domain of the M2 protein", Nature Medicine, Oct. 1999, vol. 5, No. 10, pp. 1157-1163 <DOI:10.1038/13484>.

Nemchinov, L. et al., "Transient expression of the ectodomain of matrix protein 2 (M2e) of avian influenza A virus in plants", Protein Expression and Purification, Dec. 2007 (available online Jun. 2007), vol. 56, No. 2, pp. 153-159 <DOI:10.1016/j.pep.2007.05.015>.

Neuberger, M. et al., "Activation of mouse complement by monoclonal mouse antibodies", European Journal of Immunology, 1981, vol. 11, No. 12, pp. 1012-1016 <DOI:10.1002/eji.1830111212>.

Niwa, R. et al., "IgG subclass-independent improvement of antibody-dependent cellular cytotoxicity by fucose removal from Asn297-linked oligosaccharides", Journal of Immunological Methods, Nov. 2005 (available online Sep. 2005), vol. 306, No. 1-2, pp. 151-160 <DOI:10.1016/j.jim.2005.08.009>.

Nobusawa, E. et al., "Comparison of the Mutation Rates of Human Influenza A and B Viruses", Journal of Virology, Apr. 2006, vol. 80, No. 7, pp. 3675-3678 <DOI:10.1128/JVI.80.7.3675-3678.2006>.

Office Action (Non-Final Rejection) dated May 8, 2023 for U.S. Appl. No. 17/367,296 (pp. 1-6).

(56) References Cited

OTHER PUBLICATIONS

Office Action (Notice of Allowance and Fees Due (PTOL-85)) dated Aug. 16, 2023 for U.S. Appl. No. 17/367,296 (pp. 1-5).
Oliveira, E. et al., "The flavivirus capsid protein: Structure, function and perspectives towards drug design", Virus Research, Jan. 2017 (available online Oct. 2016), vol. 227, pp. 115-123 <DOI:10.1016/j.virusres.2016.10.005>.
Osterholm, M. et al., "Efficacy and effectiveness of influenza vaccines: a systematic review and meta-analysis", Lancet Infectious Diseases, Jan. 2012 (available online Oct. 2011), vol. 12, No. 1, pp. 36-44 <DOI:10.1016/S1473-3099(11)70295-X>.
Ozawa, S. et al., "Modeling the Economic Burden of Adult Vaccine-Preventable Diseases in the United States", Health Affairs, Nov. 2016, vol. 35, No. 11, pp. 2124-2132 <DOI:10.1377/hlthaff.2016.0462>.
Palmer, K. et al., "Protection of rabbits against cutaneous papillomavirus infection using recombinant tobacco mosaic virus containing L2 capsid epitopes", Vaccine, Jun. 2006 (available online May 2006), vol. 24, No. 26, pp. 5516-5525 <DOI:10.1016/j.vaccine.2006.04.058>.
Paprotka, T. et al., "Form follows function in geminiviral minichromosome architecture", Virus Research, Jan. 2015 (available online Nov. 2014), vol. 196, pp. 44-55 <DOI:10.1016/j.virusres.2014.11.004>.
Pastrana, D. et al., "Cross-neutralization of cutaneous and mucosal Papillomavirus types with anti-sera to the amino terminus of L2", Virology, Jul. 2005 (available online May 2005), vol. 337, No. 2, pp. 365-372 <DOI:10.1016/j.virol.2005.04.011>.
Paules, C. et al., "Chasing Seasonal Influenza-The Need for a Universal Influenza Vaccine", The New England Journal of Medicine, Jan. 2018, vol. 378, No. 1, pp. 7-9 <DOI:10.1056/NEJMp1714916>.
Pejoski, D. et al., "A lipopeptide based on the M2 and HA proteins of influenza A viruses induces protective antibody", Immunology and Cell Biology, Feb. 2010, vol. 88, No. 5, pp. 601-611 <DOI:10.1038/icb.2010.15>.
Pena-Cortes, H. et al., "Signals involved in wound-induced proteinase inhibitor II gene expression in tomato and potato plants", Proceedings of the National Academy of Sciences of the United States of America, May 1995, vol. 92, vol. 10, pp. 4106-4113 <DOI:10.1073/pnas.92.10.4106>.
Pepponi, I. et al., "Plant-derived recombinant immune complexes as self-adjuvanting TB immunogens for mucosal boosting of BCG", Plant Biotechnology Journal, Sep. 2014 (available online Mar. 2014), vol. 12, No. 7, pp. 840-850 <DOI:10.1111/pbi.12185>.
Petukhova, N. et al., "Immunogenicity and protective efficacy of candidate universal influenza A nanovaccines produced in plants by Tobacco mosaic virus-based vectors", Current Pharmaceutical Design, Feb. 2013 (preprint), vol. 19, 14 pages.
Peyret, H. et al., "A protocol for the gentle purification of virus-like particles produced in plants", Journal of Virological Methods, Dec. 2015 (available online Sep. 2015), vol. 225, pp. 59-63 <DOI:10.1016/j.iviromet.2015.09.005>.
Peyret, H. et al., "Tandem Fusion of Hepatitis B Core Antigen Allows Assembly of Virus-Like Particles in Bacteria and Plants with Enhanced Capacity to Accommodate Foreign Proteins", PLoS One, Apr. 2015, vol. 10, No. 4, article e0120751, 20 pages <DOI:10.1371/journal.pone.0120751>.
Phoolcharoen, W. et al., "A nonreplicating subunit vaccine protects mice against lethal Ebola virus challenge", Proceedings of the National Academy of Sciences of the United States of America, Dec. 2011, vol. 108, No. 51, pp. 20695-20700 <DOI:10.1073/pnas.1117715108>.
Phoolcharoen, W. et al., "Expression of an immunogenic Ebola immune complex in Nicotiana benthamiana", Plant Biotechnology Journal, Sep. 2011 (available online Feb. 2011), vol. 9, No. 7, pp. 807-816 <DOI:10.1111/j.467-7652.2011.00593.x>.
Pumpens, P. et al., "HBV Core Particles as a Carrier for B Cell/T Cell Epitopes", Intervirology, 2001, vol. 44, No. 2-3, pp. 98-114 <DOI:10.1159/000050037>.
Pushko, P. et al., "Virus-like particles displaying H5, H7, H9 hemagglutinins and N1 neuraminidase elicit protective immunity to heterologous avian influenza viruses in chickens", Virology, Jan. 2017 (available online Dec. 2016), vol. 501, pp. 176-182 <DOI:10.1016/j.virol.2016.12.001>.
Putri, W. et al., "Economic burden of seasonal influenza in the United States", Vaccine, Jun. 2018 (available online May 2018), vol. 36, No. 27, pp. 3960-3966 <DOI:10.1016/j.vaccine.2018.05.057>.
Rabaan, A. et al., "Overview of Zika infection, epidemiology, transmission and control measures", Journal of Infection and Public Health, Mar.-Apr. 2017 (available online Jun. 2016), vol. 10, No. 2, pp. 141-149 <DOI:10.1016/j.jiph.2016.05.007>.
Radaev, S. et al., "Recognition of immunoglobulins by Fcγ receptors", Molecular Immunology, May 2002 (available online Mar. 2002), vol. 38, No. 14, pp. 1073-1083 <DOI:10.1016/S0161-5890(02)00036-6>.
Ramirez, A. et al., "A virus-like particle vaccine candidate for influenza A virus based on multiple conserved antigens presented on hepatitis B tandem core particles", Vaccine, Feb. 2018 (available online Jan. 2018), vol. 36, No. 6, pp. 873-880 <DOI:10.1016/j.vaccine.2017.12.053>.
Reed, C. et al., "Estimating Influenza Disease Burden from Population-Based Surveillance Data in the United States", Plos One, Mar. 2015, vol. 10, No. 3, article e0118369 <10.1371/journal.pone.0118369>.
Regnault, A. et al., "FCV Receptor-mediated Induction of Dendritic Cell Maturation and Major Histocompatibility Complex Class I-restricted Antigen Presentation after Immune Complex Internalization", Journal of Experimental Medicine, vol. 189, No. 2, pp. 371-380. 1999.
Roden, R. et al., "Minor Capsid Protein of Human Genital Papillomaviruses Contains Subdominant, Cross-Neutralizing Epitopes", Virology, May 2000 (available online May 2002), vol. 270, No. 2, pp. 254-257 <DOI:10.1006/viro.2000.0272>.
Rohovie, M. et al., "Virus-like particles: Next-generation nanoparticles for targeted therapeutic delivery", Bioengineering & Translational Medicine, Mar. 2017 (available online Dec. 2016), vol. 2, No. 1, pp. 43-57 <DOI:10.1002/btm2.10049>.
Rolfes, M. et al., "Annual estimates of the burden of seasonal influenza in the United States: A tool for strengthening influenza surveillance and preparedness", Influenza and other respiratory viruses, Feb. 2018 (available online Jan. 2018), vol. 12, No. 1, pp. 132-137 <DOI:10.1111/irv.12486>.
Rosenthal et al., "An intronless form of the tobacco extensin gene terminator strongly enhances transient gene expression in plant leaves", Plant Mol Biol, (Feb. 10, 2018), vol. 96, pp. 429-443.
Rybicki, E., "Plant-made vaccines for humans and animals", Plant Biotechnology Journal, Jun. 2010 (available online May 2010), vol. 8, No. 5, pp. 620-637 <DOI:10.1111/j.1467-7652.2010.00507.x>.
Santi, L. et al., "An efficient plant viral expression system generating orally immunogenic Norwalk virus-like particles", Vaccine, Mar. 2008 (available online Feb. 2008), vol. 26, No. 15, pp. 1846-1854 <DOI:10.1016/j.vaccine.2008.01.053>.
Schellenbacher, C. et al., "Developments in L2-based human papillomavirus (HPV) vaccines", Virus Research, Mar. 2017 (available online Nov. 2016), vol. 231, pp. 166-175 <DOI:10.1016/j.virusres.2016.11.020>.
Schmidt, N. et al., "Influenza virus a M2 protein generates negative Gaussian membrane curvature necessary for budding and scission", Journal of the American Chemical Society, Sep. 2013, vol. 135, No. 37, pp. 13710-13719 <DOI:10.1021/ja400146z>.
Schnell, J. et al., "Structure and mechanism of the M2 proton channel of influenza A virus", Nature, Jan. 2008, vol. 451, No. 7178, pp. 591-595 <DOI:10.1038/nature06531>.
Schodel, F. et al., "The Position of Heterologous Epitopes Inserted in Hepatitis B Virus Core Particles Determines Their Immunogenicity", Journal of Virology, Jan. 1992, vol. 66, No. 1, pp. 106-114.
Scorza, F. et al., "Universal influenza vaccines: Shifting to better vaccines", Vaccine, Jun. 2016 (available online Mar. 2016), vol. 34, No. 26, pp. 2926-2933 <DOI:10.1016/j.vaccine.2016.03.085>.
Sharma, D. et al., "Interleukin-4 Mediates Down Regulation of Antiviral Cytokine Expression and Cytotoxic T-Lymphocyte Responses

(56) References Cited

OTHER PUBLICATIONS and Exacerbates Vaccinia Virus Infection In Vivo", Journal of Virology, Oct. 1996, vol. 70, No. 10, pp. 7103-7107.
Shields, R. et al., "Lack of Fucose on Human IgG1 N-Linked Oligosaccharide Improves Binding to Human FcγRIII and Antibody-dependent Cellular Toxicity", The Journal of Biological Chemistry, Jul. 2002 (available online May 2002), vol. 277, No. 30, p. 26733-26740 <DOI:10.1074/jbc.M202069200>.
Simón, D. et al., "Host influence in the genomic composition of flaviviruses: A multivariate approach", Biochemical and Biophysical Research Communications, Oct. 2017 (available online Jun. 2017), vol. 492, No. 4, pp. 572-578 <DOI:10.1016/j.bbrc.2017.06.088>.
Skehel, J. et al., "Receptor Binding and Membrane Fusion in Virus Entry: The Influenza Hemagglutinin", Annual Review of Biochemistry, Jul. 2000, vol. 69, No. 1, pp. 531-569 <DOI:10.1146/annurev.biochem.69.1.531>.
Skowronski, D. et al., "Early season co-circulation of influenza A(H3N2) and B(Yamagata): interim estimates of 2017/18 vaccine effectiveness, Canada, Jan. 2018", Eurosurveillance, Feb. 2018, vol. 23, No. 5, 7 pp. <DOI:10.2807/1560-7917.ES.2018.23.5.18-00035>.
Smith, D. et al., "Detection of influenza C virus but not influenza D virus in Scottish respiratory samples", Journal of Clinical Virology, Jan. 2016 (available online Nov. 2015), vol. 74, pp. 50-53 <DOI:10.1016/j.jcv.2015.11.036>.
Aguilar, J. et al., "Development of a nasal vaccine for chronic hepatitis B infection that uses the ability of hepatitis B core antigen to stimulate a strong Th1 response against hepatitis B surface antigen", Immunology & Cell Biology, Oct. 2004, vol. 82, No. 5, pp. 539-546 <DOI:10.1111/j.0818-9641.2004.01278.x>.
Alam, A. et al., "Technoeconomic Modeling of Plant-Based Griththsin Manufacturing", Frontiers in Bioengineering and Biotechnology, Jul. 2018, vol. 6, No. 102, 13 pages <DOI:10.3389/fbioe.2018.00102>.
Ali, S. et al., "Mitigation of Influenza B Epidemic with School Closures, Hong Kong, 2018", Emerging Infectious Diseases, Nov. 2018, vol. 24, No. 11, pp. 2071-2073 <DOI:10.3201/eid2411.180612>.
Alphs, H. et al., "Protection against heterologous human papillomavirus challenge by a synthetic lipopeptide vaccine containing a broadly cross-neutralizing epitope of L2", Proceedings of the National Academy of Sciences of the United States of America, Apr. 2008, vol. 105, No. 15, pp. 5850-5855 <DOI:10.1073/pnas.0800868105>.
Atsmon, J. et al., "Safety and Immunogenicity of Multimeric-001—a Novel Universal Influenza Vaccine", Journal of Clinical Immunology, Jun. 2012 (available online Feb. 2012), vol. 32, No. 3, pp. 595-603 <DOI:10.1007/s10875-011-9632-5>.
Avalos, A. et al., "Early BCR events and antigen capture, processing, and loading on MHC class II on B cells", Frontiers in Immunology, Mar. 2014, vol. 5, No. 92, 5 pages <DOI:10.3389/fimmu.2014.00092>.
Bajtay, Z. et al., "Expression and role of Fc- and complement-receptors on human dendritic cells", Immunology Letters, Apr. 2006 (available online Dec. 2005), vol. 104, No. 1-2, pp. 46-52 <DOI:10.1016/j.imlet.2005.11.023>.
Barzon, L. et al., "Current views on Zika virus vaccine development", Expert Opinion on Biological Therapy, Jun. 2017, vol. 17, No. 10, pp. 1185-1192 <DOI:10.1080/14712598.2017.1346081>.
Belmusto-Worn, V. et al., "Randomized, double-blind, phase III, pivotal field trial of the comparative immunogenicity, safety, and tolerability of two yellow fever 17D vaccines (Arilvax and YF-VAX) in healthy infants and children in Peru", American Journal of Tropical Medicine and Hygiene, 2005, vol. 72, No. 2, pp. 189-197.
Bianchi, E. et al., "Universal Influenza B Vaccine Based on the Maturational Cleavage Site of the Hemagglutinin Precursor", Journal of Virology, Jun. 2005, vol. 79, No. 12, pp. 7380-7388 <DOI:10.1128/JVI.79.12.7380-7388.2005>.
Black, R. et al., "Antibody response to the M2 protein of influenza A virus expressed in insect cells", Journal of General Virology, Jan. 1993, vol. 74, No. 1, pp. 143-146 <DOI:10.1099/0022-1317-74-1-143>.
Blokhina, E. et al., "A molecular assembly system for presentation of antigens on the surface of HBc virus-like particles", Virology, Jan. 2013 (available online Oct. 2012), vol. 435, No. 2, pp. 293-300 <DOI:10.1016/j.virol.2012.09.014>.
Boigard, H. et al., "Zika virus-like particle (VLP) based vaccine", PLoS Neglected Tropical Diseases, May 2017, vol. 11, No. 5, article e0005608, 20 pages <DOI:10.1371/journal.pntd.0005608>.
Breese, J. et al., "Estimated influenza illnesses and hospitalizations averted by influenza vaccination-United States, 2012-13 influenza season", Morbidity and Mortality Weekly Report, Dec. 2013, vol. 62, No. 49, pp. 997-1000.
Breitburd, F. et al., "Immunization with Viruslike Particles from Cottontail Rabbit Papillomavirus (CRPV) Can Protect against Experimental CRPV Infection", Journal of Virology, Jun. 1995, vol. 69, No. 6, pp. 3959-3963.
Bresee, J. et al., "Progress and Remaining Gaps in Estimating the Global Disease Burden of Influenza", Emerging Infectious Diseases, Jul. 2018, vol. 24, No. 7, pp. 1173-1177 <DOI:10.3201/eid2407.171270>.
Brown, A. et al., "Foreign epitopes in immunodominant regions of hepatitis B core particles are highly immunogenic and conformationally restricted", Vaccine, Aug. 1991 (available online Dec. 2002), vol. 9, No. 8, pp. 595-601 <DOI:10.1016/0264-410X(91)90248-5>.
Brown, D. et al., "The Impact of Quadrivalent Human Papillomavirus (HPV; Types 6, 11, 16, and 18) L1 Virus-Like Particle Vaccine on Infection and Disease Due to Oncogenic Nonvaccine HPV Types in Generally HPV-Naive Women Aged 16-26 Years", The Journal of Infectious Diseases, Apr. 2009, vol. 199, No. 7, pp. 926-935 <DOI:10.1086/597307>.
Buck, C. et al., "Arrangement of L2 within the Papillomavirus Capsid", Journal of Virology, Jun. 2008 (available online Mar. 2008), vol. 82, No. 11, pp. 5190-5197 <DOI:10.1128/JVI.02726-07>.
Buck, C. et al., "Generation of HPV Pseudovirions Using Transfection and Their Use in Neutralization Assays", Human Papillomaviruses, 2005, vol. 119, pp. 445-462 <DOI:10.1385/1-59259-982-6:445>.
Buck, C. et al., "Production of Papillomavirus-Based Gene Transfer Vectors", Current Protocols in Cell Biology, Dec. 2007, vol. 37, No. 1, pp. 26.1.1-26.1.19 <DOI:10.1002/0471143030.cb2601s37>.
Burns, A. et al., "Evaluating the Economic Consequences of Avian Influenza", The World Bank: Documents and Reports, Jun. 2006, vol. 1, No. 47417, 6 pages.
Caini, S. et al., "Characteristics of seasonal influenza A and B in Latin America: Influenza surveillance data from ten countries", PLoS One, Mar. 2017, vol. 12, No. 3, article e0174592, 12 pages <DOI:10.1371/journal.pone.0174592>.
Castilho, A. et al., "Glyco-engineering in plants to produce human-like N-glycan structures", Biotechnology Journal, Sep. 2012 (available online Aug. 2012), vol. 7, No. 9, pp. 1088-1098 <DOI:10.1002/biot.201200032>.
Centers for Disease Control and Prevention (CDC)., "Summary of the 2017-2018 Influenza Season" [online], Influenze (Flu), 2017 [retrieved Jul. 23, 2019 from archive.org, as it appeared on Nov. 2, 2018], retrieved from the internet: <URL:https://web.archive.org/web/20181102004826/https://www.cdc.gov/flu/about/season/flu-season-2017-2018.htm>.
Cerovska, N. et al., “ Transient expression of Human papillomavirus type 16 L2 epitope fused to N- and C-terminus of coat protein of Potato virus X in plants, Journal of Biosciences, Mar. 2012 (available online Jan. 2012), vol. 37, No. 1, pp. 125-133 <DOI:10.1007/s12038-011-9177-z>.
Chackerian, B., "Virus-like particles: flexible platforms for vaccine development", Expert Review of Vaccines, 2007 (available online Jan. 2014), vol. 6, No. 3, pp. 381-390 <DOI:10.1586/14760584.6.3.381>.
Chargelegue, D. et al., "Highly Immunogenic and Protective Recombinant Vaccine Candidate Expressed in Transgenic Plants", Infec-

(56) References Cited

OTHER PUBLICATIONS tion and Immunity, Sep. 2005, vol. 73, No. 9, pp. 5915-5922 <DOI:10.1128/IAI.73.9.5915-5922.2005>.
Chen, Q. et al., "Geminiviral vectors based on bean yellow dwarf virus for production of vaccine antigens and monoclonal antibodies in plants", Human Vaccines, Mar. 2011, vol. 7, No. 3, pp. 331-338 <DOI:10.4161/hv.7.3.14262>.
Clarkson, S. et al., "Blockade of clearance of immune complexes by an anti-F(cγ) receptor monoclonal antibody", Journal of Experimental Medicine, Aug. 1986, vol. 164, No. 2, pp. 474-489 <DOI:10.1084/jem.164.2.474>.
Cohen, J., "High Hopes and Dilemmas for a Cervical Cancer Vaccine", Science, Apr. 2005, vol. 308, No. 5722, pp. 618-621 <DOI:10.1126/science.308.5722.618>.
Cooper, A. et al., "Cytokine Induction by the Hepatitis B Virus Capsid in Macrophages Is Facilitated by Membrane Heparan Sulfate and Involves TLR2", The Journal of Immunology, Sep. 2005, vol. 175, No. 5, pp. 3165-3176 <DOI:10.4049/jimmunol.175.5.3165>.
Cornacoff, J. et al., "Primate erythrocyte-immune complex-clearing mechanism", Journal of Clinical Investigation, Feb. 1983, vol. 7, No. 2, pp. 236-247 <DOI:10.1172/JCI110764>.
Coutelier, J. et al., "Virally induced modulation of murine IgG antibody subclasses", Journal of Experimental Medicine, Dec. 1988, vol. 168, No. 6, pp. 2373-2378 <DOI:10.1084/jem.168.6.2373>.
Crow, J., "HPV: The global burden", Nature, Aug. 2012, vol. 488, pp. S2-S3 <DOI:10.1038/488S2a>.
Dai, L. et al., "Structures of the Zika Virus Envelope Protein and Its Complex with a Flavivirus Broadly Protective Antibody", Cell Host & Microbe, May 2016, vol. 19, No. 5, pp. 696-704 <DOI:10.1016/j.chom.2016.04.013>.
Davies, J. et al., "Geminivirus genes and vectors", Trends in Genetics, 1989 (available online Jan. 2003), vol. 5, pp. 77-81 <DOI:10.1016/0168-9525(89)90030-9>.
Davies, K. et al., "Splenic uptake of immune complexes in man is complement-dependent", Journal of Immunology, Oct. 1993, vol. 151, No. 7, pp. 3866-3873.
De Filette, M. et al., "An Influenza A Vaccine Based on Tetrameric Ectodomain of Matrix Protein 2", Journal of Biological Chemistry, Apr. 2008, vol. 283, No. 17, pp. 11383-11387 <DOI:10.1074/jbc.M800650200>.
De Jong, J. et al., "Murine Fc receptors for IgG are redundant in facilitating presentation of immune complex derived antigen to CD8+ T cells in vivo", Molecular Immunology, May 2006 (available online Feb. 2006), vol. 43, No. 13, pp. 2045-2050 <DOI:10.1016/j.molimm.2006.01.002>.
Deng, L. et al., "M2e-Based Universal Influenza A Vaccines", Vaccines, Mar. 2015 (available online Feb. 2015), vol. 3, No. 1, pp. 105-136 <DOI:10.3390/vaccines3010105>.
Diamos et al., "5' and 3' Untranslated Regions Strongly Enhance Performance of Geminiviral Replicons in Nicotiana benthamiana Leaves", Front Plant Sci, (Feb. 24, 2016), vol. 7, No. 200, pp. 1-15.
Diamos et al., "Chimeric 3' flanking regions strongly enhance gene expression in plants", Plant Biotechnol J, (May 21, 2018), vol. 16, pp. 1971-1982.
Diamos, A. et al., "Codelivery of improved immune complex and virus-like particle vaccines containing Zika virus envelope domain III synergistically enhances immunogenicity", Vaccine, Apr. 2020 (available online Mar. 2020), vol. 38, No. 18, pp. 3455-3463 <DOI:10.1016/j.vaccine.2020.02.089>.
Diamos, A. et al., "High Level Production of Monoclonal Antibodies Using an Optimized Plant System", Frontiers in Bioengineering and Biotechnology, Jan. 2020, vol. 7, article 472 <DOI:10.3389/fbioe.2019.00472>.
Diamos, A. et al., "High-level expression and enrichment of norovirus virus-like particles in plants using modified geminiviral vectors", Protein Expression and Purification, Nov. 2018 (Jun. 2018), vol. 151, pp. 86-92 >DOI:10.1016/j.pep.2018.06.011>.

Diamos, A. et al., "Modifying the Replication of Geminiviral Vectors Reduces Cell Death and Enhances Expression of Biopharmaceutical Proteins in Nicotiana benthamiana Leaves", Frontiers in Plant Science, Jan. 2019, vol. 9, article 1974, 13 pages <DOI:10.3389/fpls.2018.01974>.
Diamos, A. et al., "Vaccine synergy with virus-like particle and immune complex platforms for delivery of human papillomavirus L2 antigen", Vaccine, Jan. 2019 (available online Nov. 2018), vol. 37, No. 1, pp. 137-144 <DOI:10.1016/j.vaccine.2018.11.021>.
Division of STD Prevention., "Prevention of Genital HPV Infection and Sequelae: Report of an External Consultants' Meeting", Department of Health and Human Services, Atlanta: Centers of Disease Control and Prevention, Dec. 1999, 41 pages.
Doorbar, J. et al., "Human papillomavirus molecular biology and disease association", Reviews in Medical Virology, Mar. 2015, vol. 25, No. S1, pp. 2-23 <D01:10.1002/rmv.1822>.
Spreitzer, R. et al., "Rubisco: Structure, Regulatory Interactions, and Possibilities for a Better Enzyme", Annual Review of Plant Biology, Jun. 2002, vol. 53, pp. 449-475 <DOI:10.1146/annurev.arplant.53.100301.135233>.
Stahl, S. et al., "Immunogenicity of peptide fusions to hepatitis B virus core antigen", Proceedings of the National Academy of Sciences of the United States of America, Aug. 1989, vol. 86, No. 16, pp. 6283-6287 <DOI:10.1073/pnas.86.16.6283>.
Stanley, J., "Geminiviruses: plant viral vectors", Current Opinion in Genetics & Development, Feb. 1993 (available online Aug. 2005), vol. 3, No. 1, pp. 91-96 <DOI:10.1016/S0959-437X(05)80347-8>.
Stanley, M. et al., "Immunobiology of Human Papillomavirus Infection and Vaccination—Implications for Second Generation Vaccines", Vaccine, Aug. 2008 (available online Sep. 2008), vol. 26, Supplement 10, pp. K62-K67 <DOI:10.1016/j.vaccine.2008.05.066>.
Stemmer, W. et al., "Single-step assembly of a gene and entire plasmid from large numbers of oligodeoxyribonucleotides", Gene, Oct. 1995 (available online Dec. 1999), vol. 164, No. 1, pp. 49-53 <DOI:10.1016/0378-1119(95)00511-4>.
Stepanova, L. et al., "Flagellin-fused protein targeting M2e and HA2 induces potent humoral and T-cell responses and protects mice against various influenza viruses a subtypes", Journal of Biomedical Science, Apr. 2018, vol. 25, No. 33, 15 pages <DOI:10.1186/s12929-018-0433-5>.
Stettler, K. et al., "Specificity, cross-reactivity, and function of antibodies elicited by Zika virus infection", Science, Aug. 2016, vol. 353, No. 6301, pp. 823-826 <DOI:10.1126/science.aaf8505>.
Strasser, R. et al., "Controlled glycosylation of plant-produced recombinant proteins", Current Opinion in Biotechnology, Dec. 2014 (available online Jul. 2014), vol. 30, pp. 95-100 <DOI:10.1016/j.copbio.2014.06.008>.
Strasser, R. et al., "Generation of glyco-engineered Nicotiana benthamiana for the production of monoclonal antibodies with a homogeneous human-like N-glycan structure", Plant Biotechnology Journal, May 2008 (available online Mar. 2008), vol. 6, No. 4, pp. 392-402 <DOI:10.1111/j.1467-7652.2008.00330.x>.
Streatfield, S. et al., "Plant-based vaccines: unique advantages", Vaccine, Mar. 2001, vol. 19, No. 17-19, pp. 2742-2748 <DOI:10.1016/S0264-410X(00)00512-0>.
Su, S. et al., "Novel Influenza D virus: Epidemiology, pathology, evolution and biological characteristics", Virulence, Aug. 2017, vol. 8, No. 8, pp. 1580-1591 <DOI:10.1080/21505594.2017.1365216>.
Suarez, D., "Influenza A virus", Animal Influenza, Nov. 2016, 2nd edition, 29 pages <DOI:10.1002/9781118924341.ch1>.
Sullivan, S. et al., "Low interim influenza vaccine effectiveness, Australia, May 1 to Sep. 24, 2017", Eurosurveillance, Oct. 2017, vol. 22, No. 43, 7 pages <DOI:10/807/1560-7917.ES.2017.22.43.17-00707>.
Takai, T. et al., "FcR γ chain deletion results in pleiotrophic effector cell defects", Cell, Feb. 1994 (available online Apr. 2004), vol. 76, No. 3, pp. 519-529 <DOI:10.1016/0092-8674(94)90115-5>.
Taylor, A. et al., "Fc receptors in antibody-dependent enhancement of viral infections", Immunological Reviews, Nov. 2015 (available online Oct. 2015), vol. 268, No. 1, pp. 340-364 <DOI:10.1111/imr.12367>.

(56) References Cited

OTHER PUBLICATIONS

Thielens, N. et al., "C1q: A fresh look upon an old molecule", Molecular Immunology, Sep. 2017 (Jun. 2017), vol. 89, pp. 73-83 <DOI:10.1016/j.molimm.2017.05.025>.

Thompson, W. et al., "Influenza-Associated Hospitalizations in the United States", JAMA, Sep. 2004, vol. 292, No. 11, pp. 1333-1340 <DOI:10.1001/jama.292.11.1333>.

Tiwari, S. et al., "Plants as bioreactors for the production of vaccine antigens", Biotechnology Advances, Jul.-Aug. 2009 (available online Apr. 2009), vol. 27, No. 4, pp. 449-467 <DOI:10.1016/j.biotechadv.2009.03.006>.

Turley, C. et al., "Safety and immunogenicity of a recombinant M2e-flagellin influenza vaccine (STF2.4xM2e) in healthy adults", Vaccine, Jul. 2011 (available online May 2011), vol. 29, No. 32, pp. 5145-5152 <DOI:10.1016/j.vaccine.2011.05.041>.

Tusé, D., Tu, T., and McDonald, K. A. (2014). "Manufacturing Economics of Plant-Made Biologics: Case Studies in Therapeutic and Industrial Enzymes." Biomed Res. Int. 2014, 1-16. doi: 10.1155/2014/256135.

Van Den Hoecke, S. et al., "Hierarchical and Redundant Roles of Activating FcRs in Protection against Influenza Disease by M2e-Specific IgG1 and IgG2a Antibodies", Journal of Virology, Apr. 2017, vol. 91, No. 7, article e02500, 13 pages <DOI:10.1128/JVI.02500-16>.

Vesikari, T. et al., "A Randomized, Double-Blind, Phase III Study of the Immunogenicity and Safety of a 9-Valent Human Papillomavirus L1 Virus-Like Particle Vaccine (V503) Versus Gardasil® in 9-15-Year-Old Girls", The Pediatric Infectious Disease Journal, Sep. 2015, vol. 34, No. 9, pp. 992-998 <DOi:10.1097/INF.0000000000000773>.

Vignesh, P. et al., "Complement in autoimmune diseases", Clinica Chimica Acta, Feb. 2017 (available online Dec. 2016), vol. 465, pp. 123-130 <DOI:10.1016/j.cca.2016.12.017>.

Villa, L. et al., "Prophylactic quadrivalent human papillomavirus (types 6, 11, 16, and 18) L1 virus-like particle vaccine in young women: a randomised double-blind placebo-controlled multicentre phase II efficacy trial", The Lancet: Oncology, May 2005 (available online Apr. 2005), vol. 6, No. 5, pp. 271-278 <DOI:10.1016/S1470-2045(05)70101-7>.

Wang, J. et al., "L2, the minor capsid protein of papillomavirus", Virology, Oct. 2013 (available online May 2013), vol. 445, No. 1-2, pp. 175-186 <DOI:10.1016/j.virol.2013.04.017>.

Wang, J. et al., "Roles of Fc Domain and Exudation in L2 Antibody-Mediated Protection against Human Papillomavirus", Journal of Virology, Aug. 2018 (available online May 2018), vol. 92, No. 15, 17 pages <DOI:10.1128/JV1.00572-18.JVI.00572-18>.

Webster, G. et al., "A polymeric immunoglobulin-antigen fusion protein strategy for enhancing vaccine immunogenicity", Plant Biotechnology Journal, Dec. 2018 (available online Apr. 2018), vol. 16, No. 12, pp. 1983-1996 <DOI:10.1111/pbi.12932>.

Webster, R. et al., "Molecular mechanisms of variation in influenza viruses", Nature, Mar. 1982, vol. 296, pp. 115-121 <DOI:10.1038/296115a0>.

Wen, Y-M, et al., "Immunoregulatory functions of immune complexes in vaccine and therapy", EMBO Molecular Medicine, Oct. 2016 (available online Aug. 2016), vol. 8, No. 10, pp. 1120-1133 <DOI:10.15252/emmm.201606593>.

Wheeler, C. et al., "The Impact of Quadrivalent Human Papillomavirus (HPV; Types 6, 11, 16, and 18) L1 Virus-Like Particle Vaccine on Infection and Disease Due to Oncogenic Nonvaccine HPV Types in Sexually Active Women Aged 16-26 Years", The Journal of Infectious Diseases, Apr. 2009, vol. 199, No. 7, pp. 936-944 <DOI:10.1086/597309>.

Whitacre, D. et al., "Use of hepadnavirus core proteins as vaccine platforms", Expert Review of Vaccines, Jan. 2009 (available online Jan. 2014), vol. 8, No. 11, pp. 1565-1573 <DOI:10.1586/erv.09.121>.

Wilder-Smith, A. et al., "Zika vaccines and therapeutics: landscape analysis and challenges ahead", BMC Medicine, Jun. 2018, vol. 16, No. 84, 15 pages <DOI:10.1186/s12916-018-1067-x>.

Wilson, J. et al., "Epitopes Involved in Antibody-Mediated Protection from Ebola Virus", Science, Mar. 2000, vol. 287, No. 5458, pp. 1664-1666 <DOI:10.1126/science.287.5458.1664>.

World Health Organization., "Influenza (Seasonal) Fact Sheet" [online], WHO, 2018 [retrieved on Jul. 26, 2019 from archive.org, as it appeared on Mar. 24, 2019], retrieved from the internet: <URL:https://web.archive.org/web/20190324130325/https://www.who.int/en/news-room/fact-sheets/detail/influenza-(seasonal)>.

Yang, M. et al., "Immunization of Zika virus envelope protein domain III induces specific and neutralizing immune responses against Zika virus", Vaccine, Jul. 2017 (available online Jun. 2017), vol. 35, No. 33, pp. 4287-4294 <DOI:10.1016/j.vaccine.2017.04.052>.

Yang, M. et al., "Plant-produced Zika virus envelope protein elicits neutralizing immune responses that correlate with protective immunity against Zika virus in mice", Plant Biotechnology Journal, Feb. 2018 (available online Jul. 2017), vol. 16, No. 2, pp. 572-580 <DOI:10.1111/pbi.12796>.

Yang, M. et al., "Virus-like particles that display Zika virus envelope protein domain III induce potent neutralizing immune responses in mice", Scientific Reports, Aug. 2017, vol. 7, No. 7679, 12 pages <DOI:10.1038/s41598-017-08247-9>.

Yang, R. et al., "Cell Surface-Binding Motifs of L2 That Facilitate Papillomavirus Infection", Journal of Virology, Mar. 2003, vol. 77, No. 6, pp. 3531-3541 <DOI:10.1128/JVI.77.6.3531-3541.2003>.

Zebedee, S. et al., "Influenza A Virus M2 Protein: Monoclonal Antibody Restriction of Virus Growth and Detection of M2 in Virions", Journal of Virology, Aug. 1988, vol. 62, No. 8, pp. 2762-2772.

Zeitlin, L. et al., "Enhanced potency of a fucose-free monoclonal antibody being developed as an Ebola virus immunoprotectant", Proceedings of the National Academy of Sciences of the United States of America, Dec. 2011, vol. 108, No. 51, pp. 20690-20694 <DOI:10.1073/pnas.1108360108>.

Zhai, L. et al., "A novel candidate HPV vaccine: MS2 phage VLP displaying a tandem Hpv L2 peptide offers similar protection in mice to Gardasil-9", Antiviral Research, Nov. 2017 (available online Sep. 2017), vol. 147, pp. 116-123 <DOI:10.1016/j.antiviral.2017.09.012>.

Zhang, J. et al., "Recombinant baculovirus vaccine containing multiple M2e and adjuvant LTB induces T cell dependent, cross-clade protection against H5N1 influenza virus in mice", Vaccine, Jan. 2016 (available online Dec. 2015), vol. 34, No. 5, pp. 622-629 <DOI:10.1016/j.vaccine.2015.12.039>.

Zhang, X. et al., "Structures and Functions of the Envelope Glycoprotein in Flavivirus Infections", Viruses, Nov. 2017, vol. 9, No. 11, 14 pages <DOI:10.3390/v9110338>.

Zhao H. et al., "Structural Basis of Zika Virus-Specific Antibody Protection", Cell, Aug. 2016 (available online Jul. 2016), vol. 166, No. 4, pp. 1016-1027 <DOI:10.1016/j.cell.2016.07.020>.

Zhou, C. et al., "Immunization with high epitope density of M2e derived from 2009 pandemic H1N1 elicits protective immunity in mice", Vaccine, May 2012 (available online Mar. 2012), vol. 30, No. 23, pp. 3463-3469 <DOI:10.1016/j.vaccine.2012.03.021>.

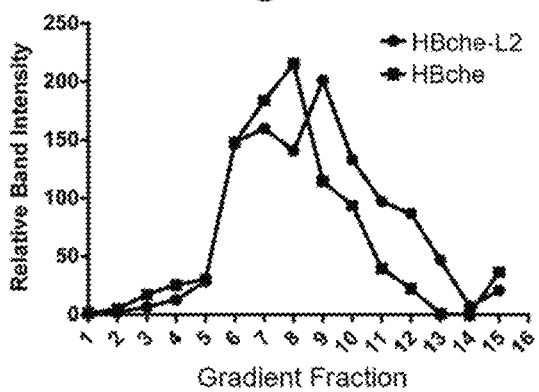
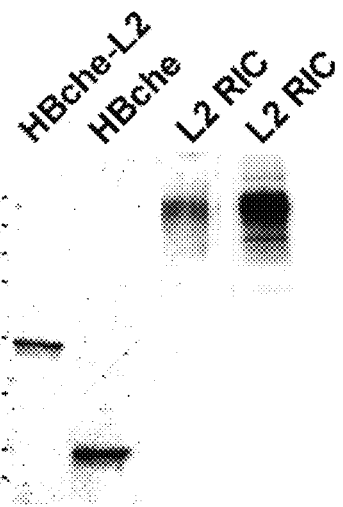
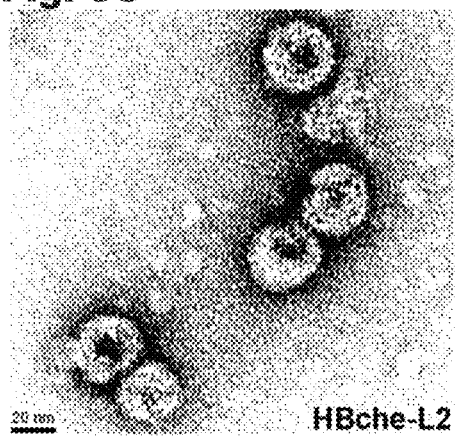
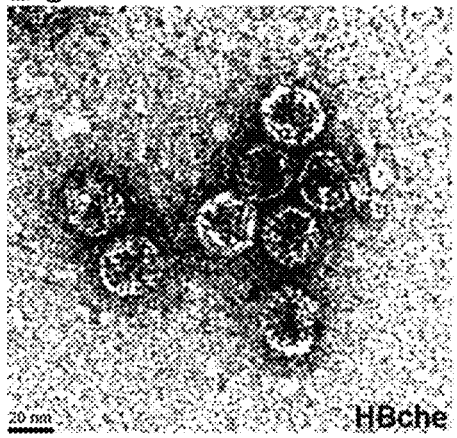
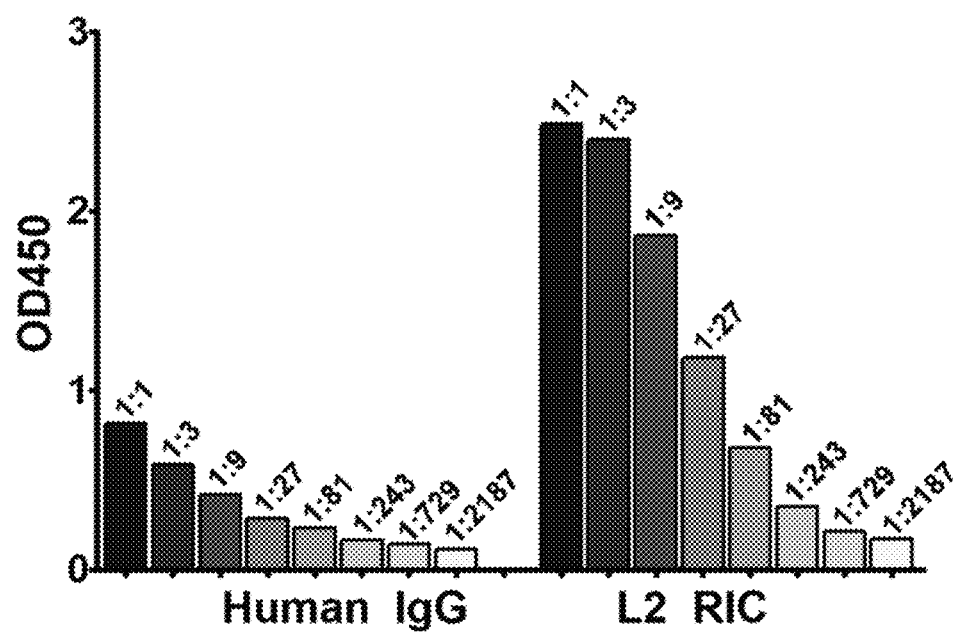

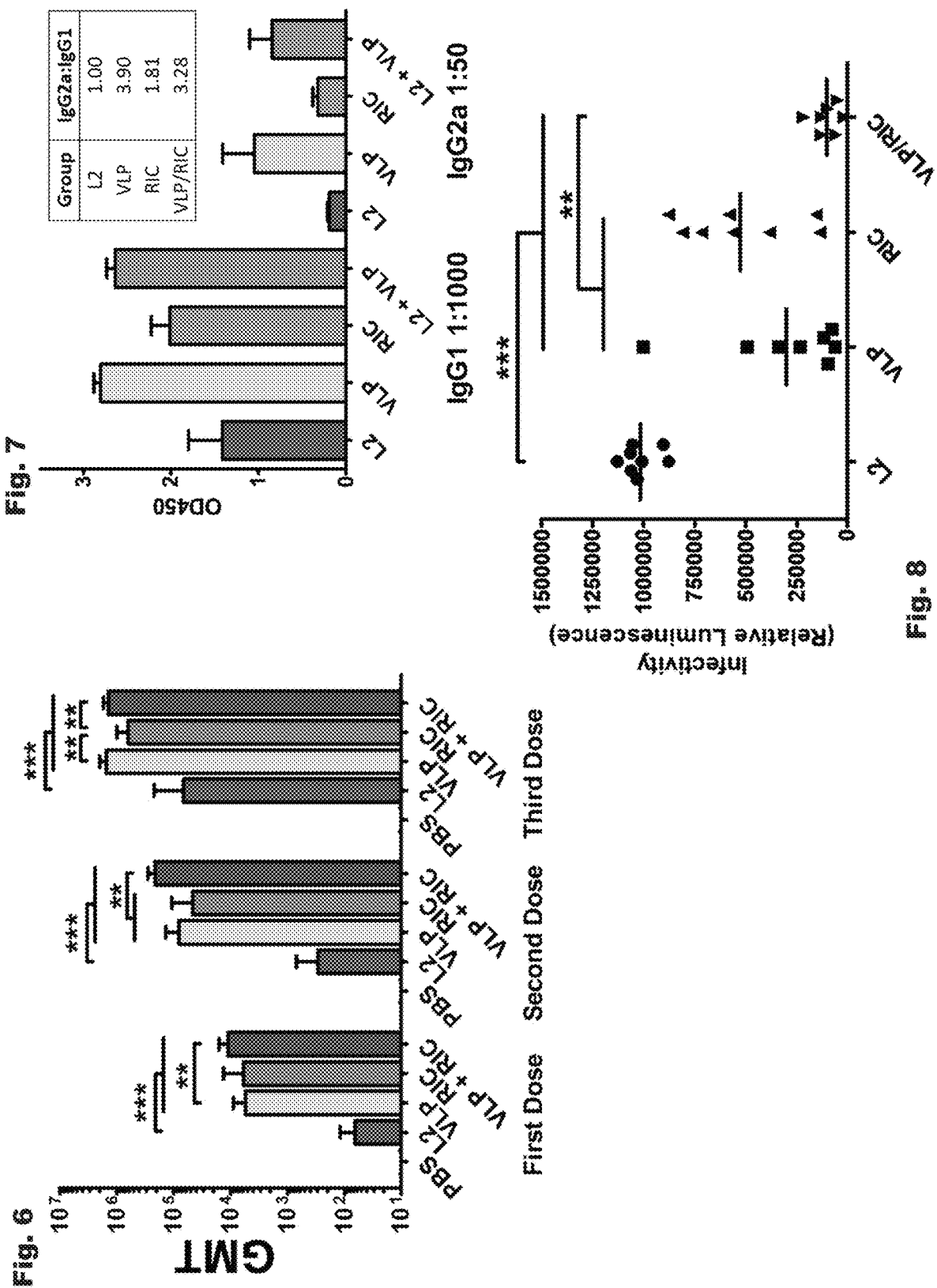

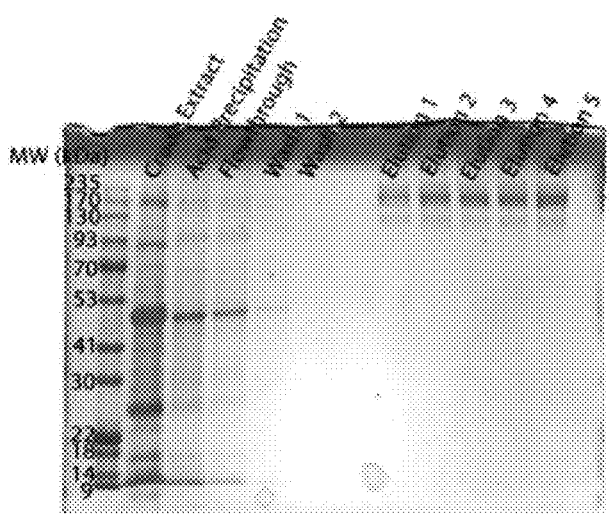 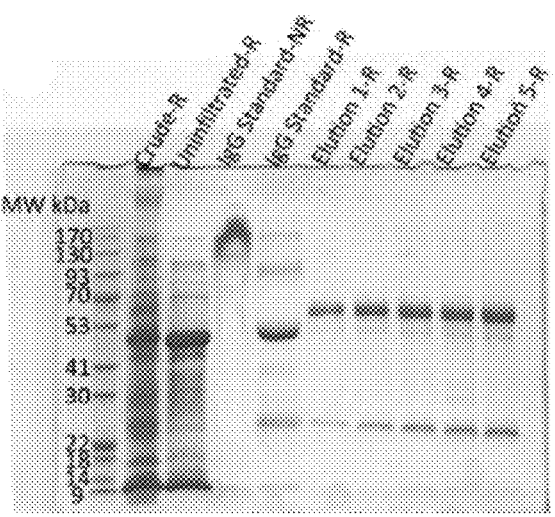
Fig. 11A　　　　　　　　　Fig. 11B
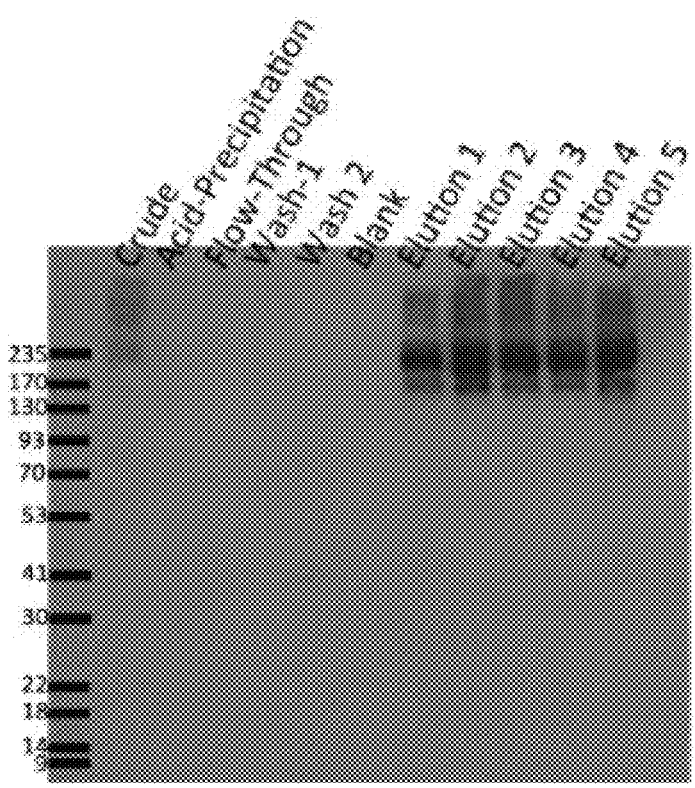 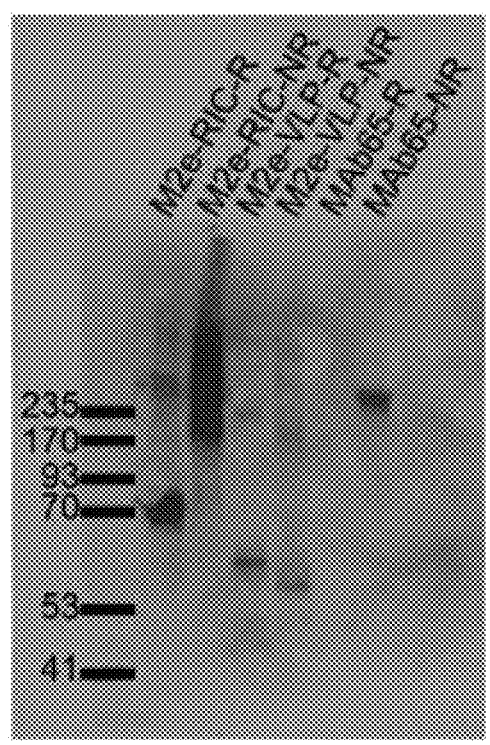
Fig. 12A　　　　　　　　　Fig. 12B

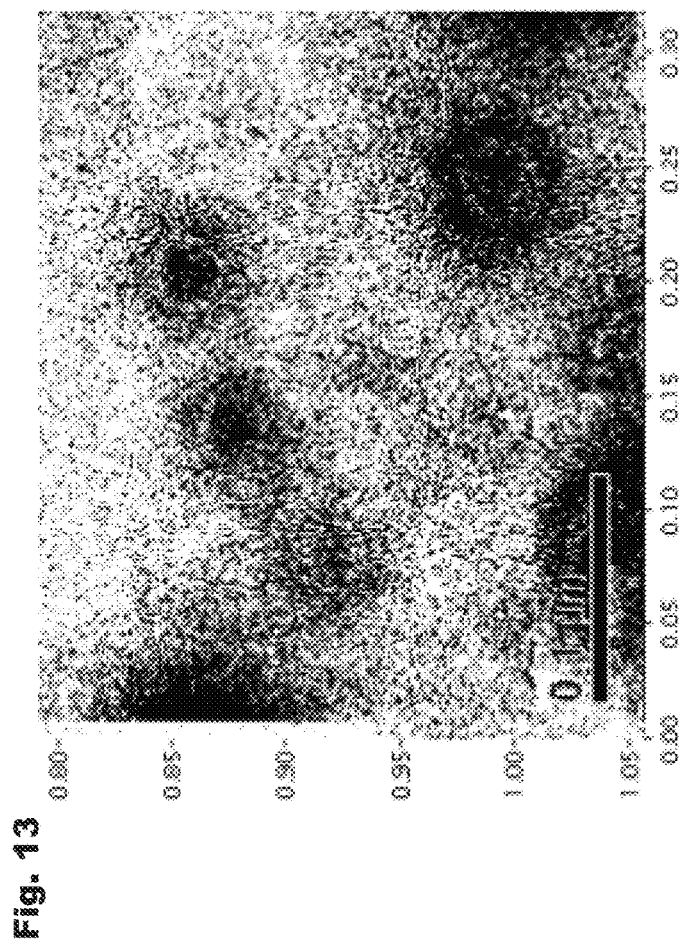
Fig. 13
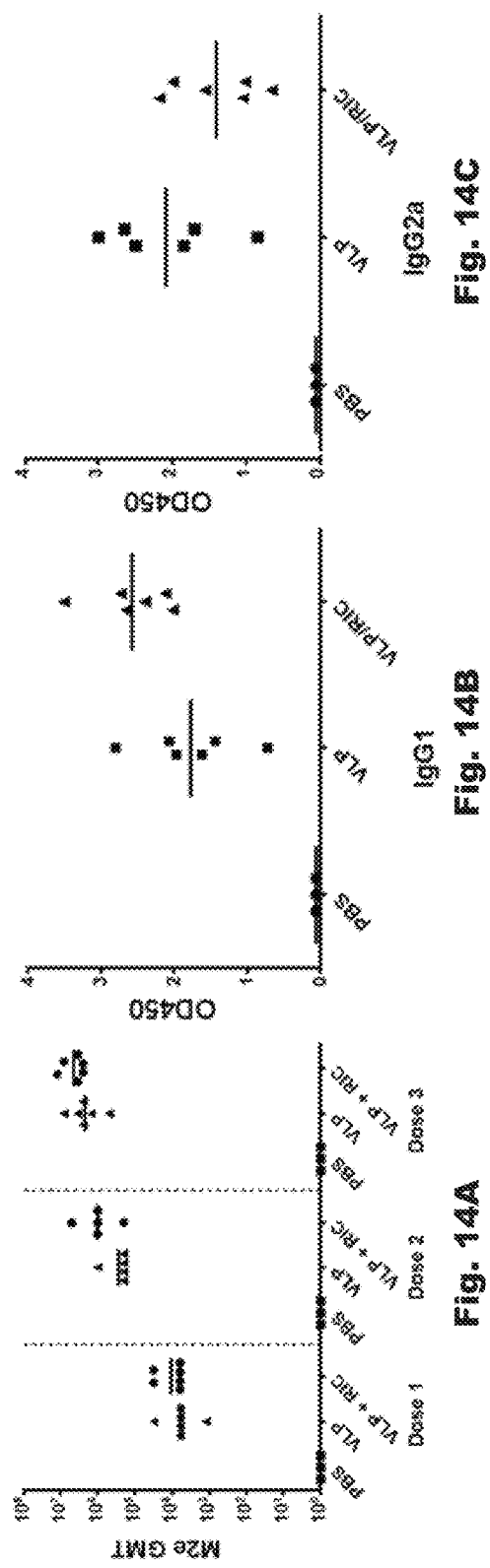
Fig. 14A
Fig. 14B
Fig. 14C

Purified ZE3 C-RIC

Fig. 21A     Fig. 21B

Purified ZE3 N-RIC

Fig. 21C     Fig. 21D

HBche-ZE3 VLP

Fig. 22A     Fig. 22B

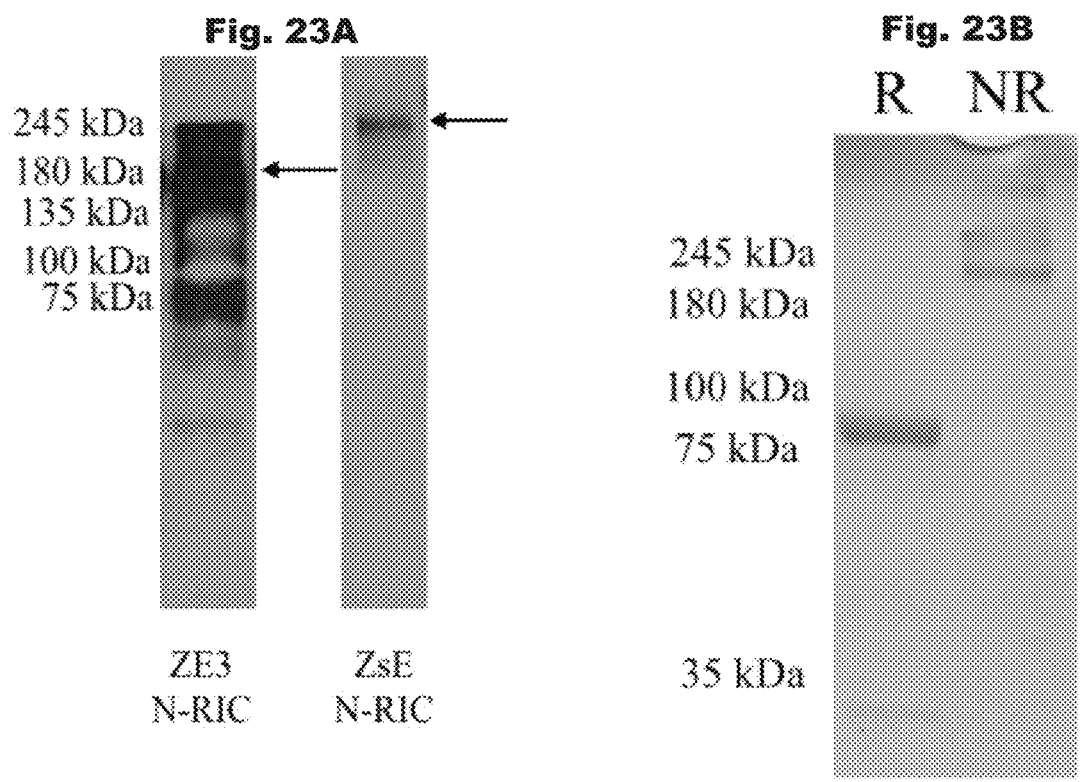
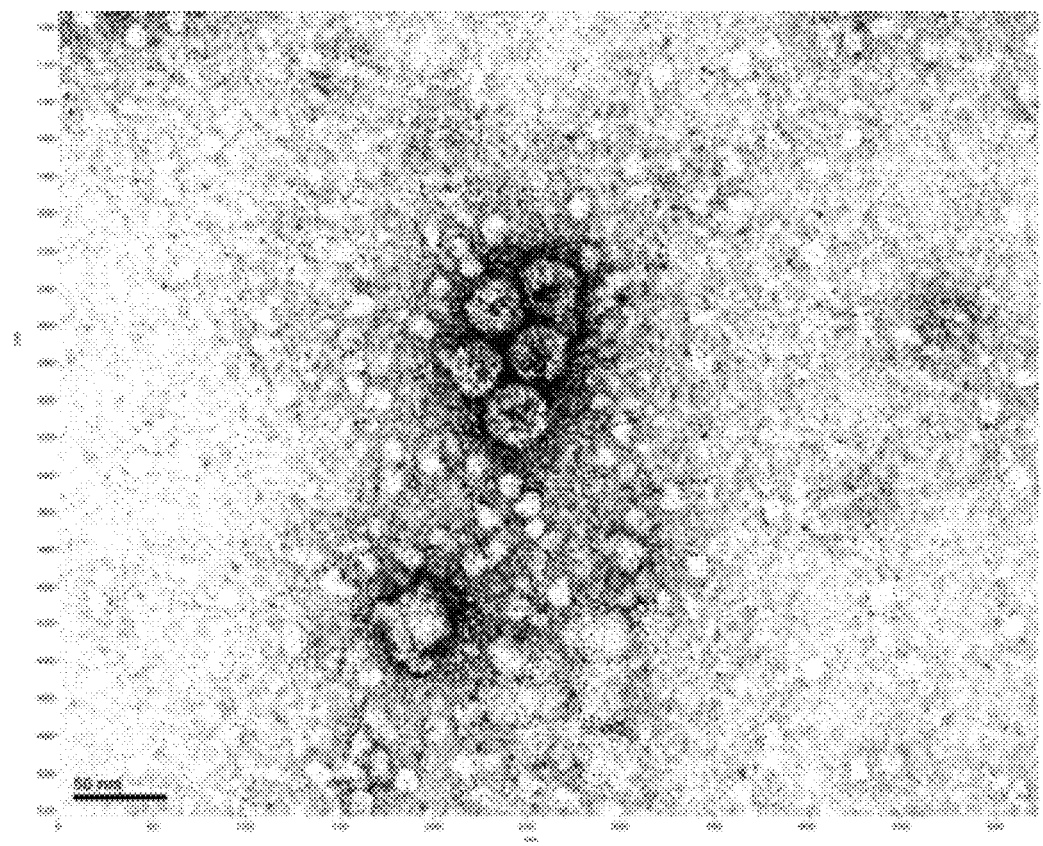
Fig. 24

```
SEQUENCE LISTING

Sequence total quantity: 45
SEQ ID NO: 1            moltype = DNA  length = 30
FEATURE                 Location/Qualifiers
misc_feature            1..30
                        note = primer
source                  1..30
                        mol_type = other DNA
                        organism = synthetic construct
SEQUENCE: 1
cgtctagagt ccgcaaccca actttacaag                                  30

SEQ ID NO: 2            moltype = DNA  length = 23
FEATURE                 Location/Qualifiers
misc_feature            1..23
                        note = primer
source                  1..23
                        mol_type = other DNA
                        organism = synthetic construct
SEQUENCE: 2
ggactagttg gggcaccagc atc                                         23

SEQ ID NO: 3            moltype = DNA  length = 28
FEATURE                 Location/Qualifiers
misc_feature            1..28
                        note = primer
source                  1..28
                        mol_type = other DNA
                        organism = synthetic construct
SEQUENCE: 3
caggatccgc aacccaactt tacaagac                                    28

SEQ ID NO: 4            moltype = AA  length = 109
FEATURE                 Location/Qualifiers
source                  1..109
                        mol_type = protein
                        note = Type 16
                        organism = Human papillomavirus
SEQUENCE: 4
SATQLYKTCK QAGTCPPDII PKVEGKTIAD QILQYGSMGV FFGGLGIGTG SGTGGRTGYI  60
PLGTRPPTAT DTLAPVRPPL TVDPVGPSDP SIVSLVEETS FIDAGAPTS             109

SEQ ID NO: 5            moltype = AA  length = 20
FEATURE                 Location/Qualifiers
source                  1..20
                        mol_type = protein
                        note = Type 16
                        organism = Human papillomavirus
SEQUENCE: 5
QLYKTCKQAG TCPPDIIPKV                                             20

SEQ ID NO: 6            moltype = AA  length = 20
FEATURE                 Location/Qualifiers
source                  1..20
                        mol_type = protein
                        note = Type 16
                        organism = Human papillomavirus
```

```
SEQUENCE: 6
LQYGSMGVFF GGLGIGTGSG                                               20

SEQ ID NO: 7            moltype = AA  length = 21
FEATURE                 Location/Qualifiers
source                  1..21
                        mol_type = protein
                        note = Type 16
                        organism = Human papillomavirus
SEQUENCE: 7
FGGLGIGTGS GTGGRTGYIP L                                             21

SEQ ID NO: 8            moltype = AA  length = 20
FEATURE                 Location/Qualifiers
source                  1..20
                        mol_type = protein
                        note = Type 16
                        organism = Human papillomavirus
SEQUENCE: 8
DPVGPSDPSI VSLVEETSFI                                               20

SEQ ID NO: 9            moltype = AA  length = 23
FEATURE                 Location/Qualifiers
source                  1..23
                        mol_type = protein
                        note = Type A
                        organism = Influenza virus
SEQUENCE: 9
SLLTEVETPI RNEWGCRCND SSD                                           23

SEQ ID NO: 10           moltype = AA  length = 51
FEATURE                 Location/Qualifiers
source                  1..51
                        mol_type = protein
                        note = Type A
                        organism = Influenza virus
SEQUENCE: 10
SLLTEVETPI RNEWGCRCND SSDGGSGGSL LTEVETPIRN EWGCRCNDSS D             51

SEQ ID NO: 11           moltype = DNA  length = 210
FEATURE                 Location/Qualifiers
misc_feature            1..210
                        note = primer
source                  1..210
                        mol_type = other DNA
                        organism = synthetic construct
SEQUENCE: 11
gtaaaacgac ggccagtgga tcctctttgc ttaccgaggt tgagacccct attagaaacg    60
agtggggttg cagatgtaac gattcttccg acggaggttc tggaggttcc cttttgactg   120
aagtggagac tccaatcagg aacgaatggg gatgcagatg caacgactcc tctgacggag   180
gtggaactag tcatggtcat agctgtttcc                                   210

SEQ ID NO: 12           moltype = DNA  length = 27
FEATURE                 Location/Qualifiers
misc_feature            1..27
                        note = primer
source                  1..27
                        mol_type = other DNA
                        organism = synthetic construct
SEQUENCE: 12
tagccatggg atcctctttg cttaccg                                       27

SEQ ID NO: 13           moltype = DNA  length = 27
FEATURE                 Location/Qualifiers
misc_feature            1..27
                        note = primer
source                  1..27
                        mol_type = other DNA
                        organism = synthetic construct
SEQUENCE: 13
tcgctcgaga ctagttccac ctccgtc                                       27

SEQ ID NO: 14           moltype = DNA  length = 18
FEATURE                 Location/Qualifiers
misc_feature            1..18
                        note = primer
source                  1..18
                        mol_type = other DNA
                        organism = synthetic construct
```

```
SEQUENCE: 14
tgaggctctt cacaatca                                                      18

SEQ ID NO: 15            moltype = DNA   length = 26
FEATURE                  Location/Qualifiers
misc_feature             1..26
                         note = primer
source                   1..26
                         mol_type = other DNA
                         organism = synthetic construct
SEQUENCE: 15
cttcttcttc ttctttctc attgtc                                              26

SEQ ID NO: 16            moltype = DNA   length = 22
FEATURE                  Location/Qualifiers
misc_feature             1..22
                         note = primer
source                   1..22
                         mol_type = other DNA
                         organism = synthetic construct
SEQUENCE: 16
caatttgctt tgcattcttg ac                                                 22

SEQ ID NO: 17            moltype = DNA   length = 17
FEATURE                  Location/Qualifiers
misc_feature             1..17
                         note = primer
source                   1..17
                         mol_type = other DNA
                         organism = synthetic construct
SEQUENCE: 17
gtaaaacgac ggccagt                                                       17

SEQ ID NO: 18            moltype = DNA   length = 19
FEATURE                  Location/Qualifiers
misc_feature             1..19
                         note = primer
source                   1..19
                         mol_type = other DNA
                         organism = synthetic construct
SEQUENCE: 18
ggaaacagct atgaccatg                                                     19

SEQ ID NO: 19            moltype = DNA   length = 14158
FEATURE                  Location/Qualifiers
misc_feature             1..14158
                         note = pBYR2eK2M-HBcheM2e
source                   1..14158
                         mol_type = other DNA
                         organism = synthetic construct
SEQUENCE: 19
cgatcggtcg attcatagaa gattagattt tcatagtat tttttttaaag taaaccttta          60
actacggtta ggacactttt aagttaaatt taatttgaac ccttaaatta attttttaaa        120
tagataaata tcaatcatcc tgatatgctt ttgaaaaaat gaatgagaaa gatgattcaa        180
ttaaggccac attttaatca tgactaaaaa aatatacagt ataatttcat atatatttgc        240
tttaaaaaaa aattgacaat ccattcgttt ctagcaataa atttcttcaa ccacaaatat        300
attaaagata actacggcat agaaacaaaa atctatgaag aatttttgta tacttcatat        360
gaaattaaaa aaaacttcat tgaacatcaa aataataata ataatcataa actcctcaat        420
atttatattc ctagcttctt gaattaaatt gtttacatat tcaacgatgt aaaaaattat        480
ttctctatct attttcctta tatcatgcat ggtttcacat atatcaaagg ataaaagcaa        540
tctatgtaaa ttatctcact ttattaagtt ttctatctga attattgaga acgtagattt        600
cttttttgcac tatccccccaa taattagcaa acacacccta gactagattt gttttgctaa     660
cccaattgat attaattata tatgattaat atttatatgt atatggaatt ggttaataaa        720
atgcatctgg ttcatcaaag aattataaag acacgtgaca ttcatttagg ataagaaata        780
tggatgatct ctttctctta ttcagataat tagtaattac acataacaca caactttgat        840
gcccacatta tagtgattag catgtcacta tgtgtgcatc cttttatttc atacattaat        900
taacttggcc aatccagaag atggacaagt ctagggtcac attgcagggt actctagctt        960
actcgcctcc ttttttcgaag gtttgagtac cttcagggca tcctcttgat acattacttt      1020
ccacttcgat tggggcaagc tgtagcagtt cttgcttaga ccgaattgcc atctcacaga      1080
gatgctgaag agttcgcgac cctcagaaa cggtgatact aactcctcga accgaatac         1140
tataggtaca tccgatctgg tcgaaaccga aaaatcgaga tgctgcatag ttaaccgaat      1200
ctcccgtcca agatccaagg actctgtgca gtgaagcttc cgtcctgtcg tatctgagat      1260
atctcttaaa tacaactttc ccgaaacccc agctttcctt gaaaccaagg ggattatctt      1320
gattccgaatt cgtctcatcg ttatgtagcc gccactcagt ccaactcgga ctttcgtcag      1380
gaagtttgaa gggagaagtt gtacctcctg atcctccatc caacgttca ctgttagcaa        1440
gttccctagc gtcgtttcct tgtatagctc gttccatgga ttgtaaatag taattgtaat      1500
gttgtttgtt gtttgttgtt gttggtaatt gttgtaaaaa tacgctctcc aaatgaaatg      1560
aacttcctta tatagaggaa gggtcttgcg aaggatagtg ggattgtgcg tcatccctta      1620
cgtcagtgga gatatcacat caatccactt gctttgaaga cgtggttgga acgtcttctt      1680
```

```
tttccacgat gctcctcgtg ggtggggtc catctttggg accactgtcg gcagaggcat  1740
cttcaacgat ggccttttcct ttatcgcaat gatggcattt gtaggagcca ccttcctttt  1800
ccactatctt cacaataaag tgacagatag ctgggcaatg gaatccgagg aggtttccgg  1860
atattaccct ttgttgaaaa gtctcaattg ccctttggtc ttctgagact gtatctttga  1920
tattttggga gtagacaagt gtgtcgtgct ccaccatgtt ctggcaattc cggttcgctt  1980
gctgtccata aaaccgccca gtctagctat cgccatgtaa gcccactgca agctacctgc  2040
tttctctttg cgcttgcgtt ttcccttgtc cagatagccc agtagctgac attcatccgg  2100
ggtcagcacc gtttctgcgg actggctttc tacgtgttcc gcttcctta gcagcccttg  2160
cgccctgagt gcttgcggca gcgtgaagct ggcgcgccgc tctagcagaa ggcatgttgt  2220
tgtgactccg aggggttgcc tcaaactcta tcttataacc ggcgtgggagg catggaggca  2280
agggcatttt ggtaatttaa gtagttagtg gaaaatgacg tcatttactt aaagacgaag  2340
tcttgcgaca agggggggccc acgccgaatt taaatattac cggcgtgcc ccaccttatc  2400
gcgagtgctt tagcacgagc ggtccagatt taaagtagaa aagttcccgc ccactagggt  2460
taaaggtgtt cacactataa aagcatatac gatgtggtac ttatttgatgg agcgtatatt  2520
gtatcaggta tttccgtcgg atacgaatta ttcgtacgac cctcctgcag gtcaacatgg  2580
tggagcacga cacacttgtc tactccaaaa atatcaaaga tacagtctca gaagaccaaa  2640
gggcaattga gacttttcaa caaagggtaa tatccggaaa cctcctcgga ttccattgcc  2700
cagctatctg tcactttatt gtgaagatag tggaaaagga aggtggctcc tacaaatgcc  2760
atcattgcga taaaggaaag gccatcgttg aagatgcctc tgccgacagt ggtcccaaag  2820
atggaccccc acccacgagg agcatcgtgg aaaaagaaga cgttccaacc acgtcttcaa  2880
agcaagtgga ttgatgtgat aacatggtgg agcacgacac acttgtctac tccaaaaata  2940
tcaaagatac agtctcagaa gaccaaaggg caattgactt ttcaacaa agtgaatat  3000
ccggaaacct cctcggattc cattgccag ctatctgtca ctttattgtg aagatagtgt  3060
aaaaggaagg tggctcctac aaatgccatc attgcgataa aggaaggcc atcgttgaag  3120
atgcctctgc cgacagtggt cccaaagatg acccccacc cacgaggagc atcgtggaaa  3180
aagaagacgt tccaaccacg tcttcaaagc aagtggattg atgtgatatc tccactgacg  3240
taagggatga cgcacaatcc cactatcctt cgcaagaccc ttcctctata taaggaagtt  3300
catttcattt ggagaggacc tcgagaaaca aacaaaatca acaatatag aaaataacgc  3360
atttccaatt ctttgaaatt tctgcaacac catggacatt gacccttaca aagaatttgg  3420
agctactgtg gagcttctca gctttttgcc ttctgacttc ttttccttctg tcagggatct  3480
ccttgacact gcctcagctc tttataggga agccttggag tctcctgagc attgctcacc  3540
tcaccatact gcactcaggc aagccattct ctgctgggga gaattgatga ctcttgctac  3600
ctgggtgggt aacaatctag aggatccagc atccagagat cttgttgtta actatgttaa  3660
tactaatgtg ggtttgaaga tcaggcaact cttggttctt catatatctt gccttacttt  3720
tggaagagag actgtacttg aatatttggt ctcttttgga gtgtggatta gaactcctcc  3780
agcctataga ccaccaaatg cccctatctt gtcgactctt ccagaaacta ctgttgttgg  3840
aggttctggt ggatcaggag gttccggtgg ttctggaggt tccggaatgg acattgaccc  3900
ttacaaagaa tttggagcta ctgtggagct tctcagcttt ttgccttctg acttctttcc  3960
ttctgtcagg gatctccttg acactgcctc agctctttat agggaagcct tggagtctcc  4020
tgagcattgc tcacctccacc atactgcact caggcaagcc attctctgct ggggagaatt  4080
gatgactctt gctacctggg tgggtaacaa tctagagggt accggtggag gcggttcagg  4140
cggaggtgga tcctctttgc ttaccgaggt tgagacccct attagaaacg agtgggggttg  4200
cagatgtaac gattcttccg acggaggttc tggaggttcc cttttgactg aagtgggagac  4260
tccaatcagg aacgaatggg gatgcagatg caacgactcc tctgacggag gtggaactag  4320
tggaggttct ggaggatctg gttctagtgg aggttctggt ggagatccag catccagaga  4380
tcttgttgtt aactatgtta atactaatgt gggtttgaag atcaggcaac tcttgtggtt  4440
tcatatatct tgccttactt ttggaagaga gactgtactt gaatatttgg tctcttttgg  4500
agtgtggatt agaactcctc cagcctatag accaccaaat gcccctatct tgtcgactct  4560
tccagaaact actgttgttc gaagaaggga caggggcaga tccctagac gtagaactcc  4620
cagccctaga agaaggagat ccccatctcc taggcgtaga taagagctcg aagtgacatc  4680
acaaagttga aggtaataaa gccaaattaa ttaagacatt ttcataatga tgtcaagaat  4740
gcaaagcaaa ttgcataact gcctttatgc aaaacattaa tataatataa attataaaga  4800
actgcgctct ctgcttctta ttttcttagc ttcatttatt agtcactagc tgttcagaat  4860
tttcagtatc ttttgatatt actaagaacc taatcacaca atgtatattc ttatgcagga  4920
aaagcagaat gctgagctaa aagaaaggct ttttccatttt tcgagagaca atgagaaaag  4980
aagaagaaga agaagaagaa gaagaagaag aaaaagagtaa ataataaagc cccacaggag  5040
gcgaagttct tgtagctcca tgttatctaa gttattgata ttgtttgccc tatatttat  5100
ttctgtcatt gtgtatgttt tgttcagttt cgatctcctt gcaaaatgca gagattatga  5160
gatgaataaa ctaagttata ttattacg tgttaatatt ctcctcctct ctctagctag  5220
cctttttgttt tctctttttc ttatttgatt ttctttaaat caatccattt taggagaggg  5280
ccagggagtg atccagcaaa acatgaagat tagaagaaac ttcccttctt tttttcctga  5340
aaacaattta acgtcgagat ttatctcttt ttgtaatgga atcatttcta cagttatgac  5400
gaattctcga ttaaaaatcc caattatatt tggtctaatt tagtttggta ttgagtaaaa  5460
caaattcgaa ccaaaccaaa atataaatat ataagttttta tataatgcc tttaagactt  5520
tttatagaat tttctttaaa aaatatctag aaatatttgc gactcttctg gcatgtaata  5580
tttcgttaaa tatgaagtgc tccatttttta ttaactttaa ataattggtt gtacgatcac  5640
tttcttatca agtgttacta aaatgcgtca atctctttgt tcttccatat tcatatgtca  5700
aaatctatca aaattcttat atatcttttt cgaatttgaa gtgaaatttc gataatttaa  5760
aattaaatag aacatatcat tatttaggta tcatattgat ttttatactt aattactaaa  5820
tttggttaac tttgaaagtg tacatcaacg aaaaattagt caaacgacta aaataaaataa  5880
atatcatgtg ttattaagaa aattctccta taagaatatt ttaatagatc atatgttgt  5940
aaaaaaaatt aattttact aacacatata tttacttatc aaaatttga caagtaga  6000
ttaaaataat attcatctaa caaaaaaaaa accagaaaat gctgaaaacc cggcaaaacc  6060
gaaccaatcc aaaccgatat agttggtttg gtttgatttt gatataaacc gaaccaactc  6120
ggtccatttg caccctaatt cataatagct ttaatattc aagatattat taagttaacg  6180
ttgtcaatat cctggaaatt ttgcaaatg aatcaagcct atatggctgt aatatgaatt  6240
taaagcagc tcgatgtggt ggtaatatgt aattacttg attctaaaaa aatatcccaa  6300
gtattaataa tttctgctag gaagaaggtt agctacgatt tacagcaaag ccagaataca  6360
aagaaccata aagtgattga agctcgaaat atacgaagga acaaatatttt ttaaaaaaat  6420
```

-continued

```
acgcaatgac ttggaacaaa agaaagtgat atattttttg ttcttaaaca agcatcccct   6480
ctaaagaatg gcagttttcc tttgcatgta actattatgc tcccttcgtt acaaaaattt   6540
tggactacta ttgggaactt cttctgaaaa tagtggtacc gagtgtactt caagtcagtt   6600
ggaaatcaat aaaatgatta ttttatgaat atatttcatt gtgcaagtag atagaaatta   6660
catatgttac ataacacacg aaataaacaa aaaaacacaa tccaaaacaa acaccccaaa   6720
caaaataaca ctatatatat cctcgtatga ggagaggcac gttcagtgac tcgacgattc   6780
ccgagcaaaa aaagtctccc cgtcacacat atagtgggtg acgcaattat cttcaaagta   6840
atccttctgt tgacttgtca ttgataacat ccagtcttcg tcaggattgc aaagaattat   6900
agaagggatc ccaccttta ttttcttctt ttttccatat ttagggttga cagtgaaatc   6960
agactggcaa cctattaatt gcttccacaa tgggacgaac ttgaagggga tgtcgtcgat   7020
gatattatag gtggcgtgtt catcgtagtt ggtgaagtcg atggtcccgt tccagtagtt   7080
gtgtcgcccg agacttctag cccaggtggt ctttccggta cgagttggtc cgcagatgta   7140
gaggctgggg tgtctgaccc cagtccttcc ctcatcctgg ttagatcggc catccatcta   7200
aggtcagatt gtgcttgatc gtaggagaca ggatgtatga aagtgtaggc atcgatgctt   7260
acatgatata ggtgcgtctc tctccagttg tgcagatctt cgtggcagcg gagatctgat   7320
tctgtgaagg gcgacacgta ctgctcaggt tgtggaggaa ataatttgtt ggctgaatat   7380
tccagccatt gaagctttgt tgcccattca tgagggaact cttctttgat catgtcaaga   7440
tactcctcct tagacgttgc agtctggata atagttcgac atcgtgcgtc agatttgcga   7500
ggagacacct tatgatctcg gaaatctcct ctggttttaa tatctccgtc ctttgatatg   7560
taatcaagga cttgtttaga gttctagct ggctggatat tagggtgatt tccttcaaaa   7620
tcgaaaaaag aaggatccct aatacaaggt tttttatcaa gctggataag agcatgatag   7680
tgggtagtgc catcttgatg aagctcagaa gcaacaccaa ggaagaaaat aagaaaaggt   7740
gtgagtttct cccagagaaa ctgaataaaa tcatctcttt gagatgagca cttggggtag   7800
gtaaggaaaa catatttaga ttggagtctg aagttcttgc tagcagaagg catgttgttg   7860
tgactccgag gggttgcctc aaactctatc ttataaccgg cgtggaggca tggaggcaag   7920
ggcattttgg taatttaagt agttagtgga aaatgacgtc atttacttaa agacgaagtc   7980
ttgcgacaag ggggcccac gccgaatttt aatattaccg gcgtggcccc accttatcgc   8040
gagtgcttta gcacgagcgg tccagattta aagtagaaaa gttcccgccc actaggtta   8100
aaggtgttca cactataaaa gcatacgga tgtgatggta tttgatggag cgtatattgt   8160
atcaggtatt tccgtcggat acgaattatt cgtacggccg gaccggtccc ctaggccggc   8220
caattcgaga tcgccgcgg ctgagtggcc ccttcaatcg ttgcggttct gtcagttcca   8280
aacgtaaaac ggcttgtccc gcgtcatcgg cggggggtcat aacgtgactc ccttaattct   8340
ccgctcatga tcagattgtc gtttcccgcc ttcagtttaa actatcagtg tttgacagga   8400
tatattggcg ggtaaaccta agagaaaaga gcgtttatta gaataatcgg atattaaaa   8460
gggcgtgaaa aggtttatcc gttcgtccat ttgtatgtgc atgccaacca cagggttccc   8520
cagatctggc gccggccagc gagacgagca agattggccg ccgcccgaaa cgatccgaca   8580
gcgcgcccag cacaggtgcg caggcaaatt gcaccaacgc atacagcgcc agcagaatgc   8640
catagtgggc ggtgacgtcg ttcgagtgaa ccagatcgcg caggaggccc ggcagcaccg   8700
gcataatcag gccgatgccg acagcgtcga gcgcgacagt gctcagaatt acgatcaggg   8760
gtatgttggg tttcacgtct ggcctccgga gactgtcata cgcgtaaaaa ggccgcgttg   8820
ctggcgtttt tccataggct ccgccccct gacgagcatc acaaaaatcg acgctcaagt   8880
cagaggtggc gaaacccgac aggactataa agataccagg cgtttccccc tggaagctcc   8940
ctcgtgcgct ctcctgttcc gaccctgccg cttaccggat acctgtccgc ctttctccct   9000
tcggaagcg tggcgctttc tcatagctca cgctgtaggt atctcagttc ggtgtaggtc   9060
gttcgctcca agctgggctg tgtgcacgaa ccccccgttc agcccgaccg ctgcgcctta   9120
tccggtaact atcgtcttga gtccaacccg gtaagcacg acttatcgcc actggcagca   9180
gccactggta acaggattag cagagcgagg tatgtaggcg gtgctacaga gttcttgaag   9240
tggtggccta actacggcta cactagaagg acagtatttg gtatctgcgc tctgctgaag   9300
ccagttacct tcggaaaaag agttggtagc tcttgatccg gcaaacaaac caccgctggt   9360
agcggtggtt ttttgtttg caagcagcag attacgcgca gaaaaaaagg atctcaagaa   9420
gatcctttga tcttttctac ggggtctgac gctcagtgga acgaaaactc acgttaaggg   9480
attttggtca tgagattatc aaaaaggatc ttcacctaga tccttttaaa ttaaaaatga   9540
agttttaaat caatctaaag tatatatgag taaacttggt ctgacagttgc catgttttac   9600
ggcagtgaga gcagagatag cgctgatgtc cggcggtgct tttgccgtta cgcaccaccc   9660
cgtcagtagc tgaacaggag ggacactgta tagacacaga agccactgga cacctcaaa   9720
aacaccatca tacactaaat cagtaagttg gcagcatcac ccataattgt ggtttcaaaa   9780
tcggctccgt cgatactatg ttatacgcca actttgaaaa caactttgaa aaagctgttt   9840
tctggtattt aaggttttag aatgcaagga acagtgaatt ggagttcgtc ttgttataat   9900
tagcttcttg gggtatcttt aaatactgta gaaaagagga aggaaataat aattggctaa   9960
aatgagaata tcaccggaat tgaaaaaact gatcgaaaaa taccgctgcg taaaagatac  10020
ggaaggaatg tctcctgcta aggtatataa gctggtggga gaaatgaaa acctatattt  10080
aaaaatgacg gacagccggt ataaagggac cacctatgat gtggaacggg aaaaggacat  10140
gatgctatgg ctggaaggaa agctgcctgt tccaaaggtc ctgcactttg aacggcatga  10200
tggctggaca aatctgctca tgagtgaggc cgatgcgtc ctttgctcgg aagagtatga  10260
agatgaacaa agccctgaaa agattatcga gctgtatgcg gagtgcatca ggctctttca  10320
ctccatcgac atatcggatt gtccctacga gaatagctta gacagccgct tagccgaatt  10380
ggattactta ctgaataacg atctggccga tgtggattgc gaaaactggg aagaagacac  10440
tccatttaaa gatccgcgcg agctgtatga ttttttaaag acggaaaagc ccgaagagga  10500
acttgtcttt tcccacgcg acctgggaga cagcaacatc tttgtgaaag atggcaaagt  10560
aagtggcttt attgatcttg ggagaagcgg cagggcggac aagtggtatg acattgcctt  10620
ctgcgtccgg tcgatcaggg aggatatcgg ggaagaacag tatgtcgagc tattttttga  10680
cttactgggg atcaagcctg attgggagaa aataaaatat tatattttac tggatgaatt  10740
gttttagtac ctagatgtgg cgcaacgatg ccggcgacaa gcaggagcgc accgacttct  10800
tccgcatcaa gtgttttggc tctcaggccg aggcccacga caagtatttg ggcaagggt  10860
cgctggtatt cgtgcagggc aagattcgga ataccaagta cgagaaggac ggccagacgg  10920
tctacgggac cgacttcatt gccgataagg tggattatct ggacaccaag gcaccaggcg  10980
ggtcaaatca ggaataaggg cacattgccc ggcgtgagt cggggcaatc ccgcaaggag  11040
ggtgaatgaa tcggacgttt gaccggaagg catacaggca agaactgatc gacgcgggt  11100
tttccgccga ggatgccgaa accatcgcaa gccgcaccgt catgcgtgcg cccgcgaaa  11160
```

```
ccttccagtc cgtcggctcg atggtccagc aagctacggc caagatcgag cgcgacagcg   11220
tgcaactggc tccccctgcc ctgcccgcgc catcggccgc cgtggagcgt tcgcgtcgtc   11280
tcgaacagga ggcggcaggt ttggcgaagt cgatgaccat cgacacgcga ggaactatga   11340
cgaccaagaa gcgaaaaacc gccggcgagg acctggcaaa acaggtcagc gaggccaagc   11400
aggccgcgtt gctgaaacac acgaagcagc agatcaagga aatgcagctt tccttgttcg   11460
atattgcgcc gtggccggac acgatgcgag cgatgccaaa cgacacggcc cgctctgccc   11520
tgttcaccac gcgcaacaag aaaatcccgc gcgaggcgct gcaaaacaag gtcatttccc   11580
acgtcaacaa ggacgtgaag atcacctaca ccggcgtcga gctgcgggcc gacgatgacg   11640
aactggtgtg gcagcaggtg ttggagtacg cgaagcgcac ccctatcggc gagccgatca   11700
ccttcacgtt ctacgagctt tgccaggacc tgggctggtc gatcaatgac cggtattaca   11760
cgaaggccga ggaatgcctg tcgcgcctac aggcgacggc gatgggcttc acgtccgacc   11820
gcgttgggca cctggaatcg gtgtcgctgc tgcaccgctt ccgcgtcctg accgtggca    11880
agaaaacgtc ccgttgccag gtcctgatcg acgaggaaat cgtcgtgctg tttgctggcg   11940
accactacac gaaattcata tgggagaagt accgcaagct gtcgccgacg gcccgacgga   12000
tgttcgacta tttcagctcg caccgggagc cgtacccgct caagctggaa accttccgcc   12060
tcatgtgcgg atcggattcc acccgcgtga agaagtggcg cgagcaggtc ggcgaagcct   12120
gcgaagagtt gcgaggcagc ggcctggtgg aacacgcctg ggtcaatgat gacctggtgc   12180
attgcaaacg ctagggcctt gtggggtcag tccggctgga ggttcagca gccagcgctt    12240
tactggcatt tcaggaacaa gcgggcactg ctcgacgcac ttgcttcgct cagtatcgct   12300
cgggacgcac ggcgcgctct acgaactgcc gataaacaga ggattaaaat tgacaattca   12360
atggcaagga ctgccagcgc tgccattttt ggggtgaggc cgttcgcggc cgaggggcgc   12420
agcccctggg gggatgggag gcccgcgtta gcgggccggg agggttcgag aaggggggc    12480
accccccttc ggcgtgcgcg gtcacgcgca cagggcgcga ccctggttaa aaacaaggtt   12540
tataaatatt ggtttaaaag caggttaaaa gacaggttag cggtggccga aaaacgggcg   12600
gaaacccttg caaatgctgg attttctgcc tgtggacagc ccctcaaatg tcaataggtg   12660
cgcccctcat ctgtcagcac tctgccccctc aagtgtcaag gatcgcgccc ctcatctgtc   12720
agtagtcgcg cccctcaagt gtcaataccg caggcacttt atccccaggc ttgtccacat   12780
catctgtggg aaactcgcgt aaaatcaggc gttttcgccg atttgcgagg ctggccagct   12840
ccacgtcgcg ggccgaaatc gagcctgccc ctcatctgtc aacgccgcgc cgggtgagtc   12900
ggcccctcaa gtgtcaacgt ccgcccctca tctgtcaggt agggccaagt tttccgcgag   12960
gtatccacaa cgccggccgg cgcggtgtct cgcacacggc ttcgacgcg tttctggcgc    13020
gtttgcaggg ccatagacgg ccgccagccc agcggcgagg gcaaccagcc cggtgagcgt   13080
cgcaaaggcc ctcggtcttg ccttgctcgt cgagatctgg ggtcgatcag ccggggatgc   13140
atcaggccga cagtcggaac ttcggttccc cgacctgca cattcggtga gcaatggata    13200
ggggagttga tatcgtcaac gttcacttct aagaaaatag cgccactcag cttcctcagc   13260
ggctttatcc agcgatttcc tattatgtcg gcatagttct caagatcgac agcctgtcac   13320
ggttaagcga gaaatgaata agaaggctga taattcggat ctctgcgagg gagatgatat   13380
ttgatcacag gcagcaacgc tctgtcatcg ttacaatcaa catgctaccc tccgcgagat   13440
catccgtgtt tcaaacccgg cagcttagtt gccgttcttc cgaatagcat cggtaacatg   13500
agcaaagtct gccgccttac aacggctctc ccgctgacgc cgtcccggac tgatgggctg   13560
cctgtatcga gtggtgattt tgtgccgagc tgccggtcgg ggagctgttg gctggctggt   13620
ggcaggatat attgtggtgt aaacaaattg acgcttagca aacttaataa cacattgcgg   13680
acgttttaa tgtactgggg tggtttttct tttcaccagt gagacgggca acagctgatt   13740
gcccttcacc gcctgccct gagagagttg cagcaagcgg tccacgctgg tttgccccag    13800
caggcgaaaa tcctgtttga tggtggttcc gaaatcggca aaatccctta taatcaaaa    13860
gaatagcccg agatagggtt gagtgttgtt ccagtttgga acaagagtcc actattaaag   13920
aacgtggact ccaacgtcaa agggcgaaaa accgtctatc agggcgatgg cccactacgt   13980
gaaccatcac ccaaatcaag ttttttgggg tcgaggtgcc gtaaagcact aaatcggaac   14040
cctaaaggga gcccccgatt tagagcttga cggggaaagc cggcgaacgt ggcgagaaag   14100
gaagggaaga agcgaaagg agcgggcgcc attcaggctg cgcaactgtt gggaaggg     14158
```

SEQ ID NO: 20            moltype = DNA   length = 18342
FEATURE                  Location/Qualifiers
misc_feature             1..18342
                         note = pBYR11eMa-h6D8M2e
source                   1..18342
                         mol_type = other DNA
                         organism = synthetic construct
SEQUENCE: 20
```
cgatcggtcg attcatagaa gattagattt ttcatagtat ttttttaaag taaaccttta     60
actacggtta ggcacttttt aagttaaatt taatttgaac ccttaaatta attttttaaa    120
tagataaata tcaatcatcc tgatatgctt ttgaaaaaat gaatgagaaa gatgattcaa    180
ttaaggccac attttaatca tgactaaaat aatatacagt ataatttcat atatatttgc    240
tttaaaaaaa aattgacaat ccattcgttt ctagcaataa atttcttcaa ccacaaatat    300
attaaagata actacggcat agaaacaaaa atctatgaag aattttttgta tacttccatt    360
gaaattaaaa aaaacttcat tgaacatcaa aataataata ataatcataa actcctcaat    420
atttatattc ctagcttctt gaattaaatt gtttacatat tcaacgatgt aaaaaattat    480
ttctctatct atttttcctta tatcatgcat ggtttcacat atcaaaagg ataaaagcaa    540
tctatgtaaa ttatctcact ttattaagtt ttctatctga attattgaga acgtagattt    600
cttttttgcac tatcccccaa taattagcaa aacacaccta gactagattt gttttgctaa    660
cccaattgat attaattata tatgattaat atttatgt atatgaatt ggttaataaa      720
atgcatctgt tcatcaaag aattataaag acacgtgaca ttcatttagg ataagaaata    780
tggatgatct ctttctctta ttcagataat tagtaattac acataacaca caactttgat    840
gccccacatta tagtgattag catgtcacta tgttgtgcate cttttattc atacattaat    900
taacttggcc aatccagaag atggacaagt ctagggtcac attgcagggt actctagctt    960
actcgccttc ttttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
```

```
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtggggggtc catctttggg accactgtcg gcagaggcat   1740
cttcaacgat ggccttttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg cccttttggtc ttctgagact gtatctttga   1920
tattttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttcctttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggctgggagg catgaggca   2280
agggcatttt ggtaatttaa gtagttagtg gaaaatgacg tcatttactt aaagacgaag   2340
tcttgcgaca aggggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgatgg acgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccgaaaa cctcctcgga ttccattgcc   2700
cagctatctg tcacttttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gaccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
catttcattt ggagaggacc tcgagaaaca aacaaaatca acaaatatag aaaataacgc   3360
atttccaatt ctttgaaatt tctgcaacat ctagaacaat gggatggtct tgcatcatac   3420
tctttcttgt tgcaactgct acaggtgtcc actctgatgt tcagcttctc gagtctggag   3480
gtggtcttgt gcaacctgga ggttccttga gactctcctg tgcagcttca gggtttgact   3540
tcagtaggta ctggatgagt tgggttcgtc aagctcctgg gaaaggacta gaatggattg   3600
gagagatcaa tccagattca agtaccatca actatactcc atctctgaag gatcgcttca   3660
ccatttccag agacaatgcc aagaacacgt tgtatcttca gatgaacagc ttgaggactg   3720
aagacacagc cttgtactac tgcacaagac agggctatgg ctacaactac tgggtcaag   3780
gcaccactgt cacagtgtct tcagctagca ccaaaggtcc atcggtcttt ccactggcac   3840
cttcttccaa gagtacttct ggaggcacag ctgcactggg ttgtcttgtc aaggactact   3900
ttccagaacc tgttacggtt tcgtggaact caggtgtctc taccagtgga gtgcacacct   3960
ttccagctgt tcttcagtcc tcaggattgt attctcttag cagtgttgtg actgttccat   4020
cctcaagctt gggcactcag acctacatct gcaatgtgaa tcacaaaccc agcaacacca   4080
aggttgacaa gaaagttgag cccagtcttg tgacaagac tcatacgtgt ccaccgtgcc   4140
cagcacctga acttcttgga ggaccgtcag tcttcttgtt tcctccaaag cctaaggata   4200
ccttgatgat ctccaggact cctgaagtca catgtgtagt tgtggatgtg agccatgaag   4260
atcctgaggt gaagttcaac tggtatgtgg atggtgtgga agtgcacaat gccaagacaa   4320
agccgagaga ggaacagtac aacagcacgt acagggttgt ctcagttctc actgttctcc   4380
atcaagattg gttgaatggc aaagagtaca agtgcaaggt ctccaacaaa gcctcccag   4440
ccccattgga gaagaccatt tccaaagcga aagggcaacc ccgtgaacca caagtgtaca   4500
cacttcctcc atctcgcgat gaactgacca gaaccaggt cagcttgact tgcctggtga   4560
aaggcttcta tccctctgac atagctgtag agtgggagag caatgggcaa ccggagaaca   4620
actacaagc tacacctccc gttctcgatt ctgacggctc cttcttcctc tacagcaagc   4680
tcacagtgga caagagcagg tggcaacaag ggaatgtctt ctcatgctcc gtgatgcatg   4740
aggctcttca caatcactac acacagaaga gtctctcctt gtctccgggt aaaggaggtg   4800
gcggatcagg tggagcggt tcaggcggag gtggatcctc tttgcttacc gaggttgaga   4860
ccctattag aaacgagtgg ggttgcagat gtaacgattc ttccgacgga ggttctggag   4920
gttccctttt gactgaagtg gagactccaa tcaggaacga atgggggatgc agatgcaacg   4980
actcctctga cggaggtgga actagtcata acactcctgt ttacaagctg gacatatctg   5040
aggcaactca ataagagctc gaagtgacat cacaaagttg aaggtaataa agccaaatta   5100
attaagacat tttcataatg atgtcaagaa tgcaaagcaa attgcataac tgcctttatg   5160
caaaacatta atataatata aattataaag aactgcgctc tctgcttctt atttctttag   5220
cttcatttat tagtcactag ctgttcagaa tttttcagtat cttttgatat tactaagaac   5280
ctaatcacac aatgtatatt cttatgcagg aaaagcagaa tgctagcta aagaaaaggc   5340
ttttttccatt ttcgagagac aatgagaaaa aagaagaag aagaagaaga agaagaagaa   5400
gaaaagagta aataataaag ccccacagga ggcgaagttc ttgtagctcc atgttatcta   5460
agttattgat attgtttgcc ctatattta tttctgtcat tgtgtatgtt ttgttcagtt   5520
tcgatctcct tgcaaaatgc agagattatg agatgaataa actaagttat attattatac   5580
tgtgtaaatat tctcctcctc tctctagcta gcctttttgt ttctttttt cttatttgat   5640
tttcttttaaa tcaatccatt ttaggagagg gccagggagt gatccagcaa aacatgaaga   5700
ttagaagaaa cttccctctt tttttttcctg aaaacaattt aacgtcgaga tttatctctt   5760
tttgtaatgg aatcatttct acagttatga cgaattctcg attaaaaatc ccaattatat   5820
ttggtctaat ttagtttggt attgagtaaa acaaattcga accaaaccaa aatataaata   5880
tatagttttt atatatatgc ctttaagact ttttatagaa ttttctttaa aaaatatcta   5940
```

```
gaaatatttg cgactcttct ggcatgtaat atttcgttaa atatgaagtg ctccattttt    6000
attaacttta aataattggt tgtacgatca ctttcttatc aagtgttact aaaatgcgtc    6060
aatctctttg ttcttccata ttcatatgtc aaaatctatc aaaattctta tatatctttt    6120
tcgaatttga agtgaaattt cgataattta aaattaaata gaacatatca ttatttaggt    6180
atcatattga ttttatact taattactaa atttggttga ctttgaaagt gtacatcaac    6240
gaaaaattag tcaaacgact aaaataaata aatatcatgt gttattaaga aaattctcct    6300
ataagaatat tttaatagat catatgtttg taaaaaaat taattttac taacacatat    6360
atttacttat caaaaatttg acaaagtaag attaaaataa tattcatcta acaaaaaaaa    6420
aaccagaaaa tgctgaaaac ccggcaaaac cgaaccaatc caaaccgata tagttggttt    6480
ggtttgattt tgatataaac cgaaccaact cggtccattt gcaccctaa tcataatagc    6540
tttaatatt caagatatta ttaagttaac gttgtcaata tcctggaaat tttgcaaaat    6600
gaatcaagcc tatatggctg taatatgaat ttaaaagcag ctcgatgtgg tggtaatatg    6660
taatttactt gattctaaaa aaatatccca agtattaata atttctgcta ggaagaaggt    6720
tagctacgat ttacagcaaa gccagaatac aagaaccat aaagtgattg aagctcgaaa    6780
tatacgaagg aacaaatatt tttaaaaaaa tacgcaatga cttggaacaa aagaaagtga    6840
tatattttt gttcttaaac aagcatcccc tctaaagaat ggcagttttc ctttgcatgt    6900
aactatatg ctcccttcgt tacaaaaatt ttggactact attgggaact tcttctgaaa    6960
atagtggtac cgagtgtact tcaagtcagt tggaaatcaa taaaatgatt attttatgaa    7020
tatatttcat tgtgcaagta gatagaaatt acatatgtta cataacacac gaaataaaca    7080
aaaaaacaca atccaaaaca aacaccccaa acaaataaac actatatata tcctcgtatg    7140
aggagaggca cgttcagtga ctcgacgatt cccgagcaaa aaaagtctcc ccgtcacaca    7200
tatagtgggt gacgcaatta tcttcaaagt aatccttctg ttgactttgtc attgataaca    7260
tccagtcttc gtcaggattc caagaattaa tagaagggat cggtcaacat ggtggagcac    7320
gacacacttg tctactccaa aaatatcaaa gatacagtct cagaagacca aagggcaatt    7380
gagacttttc aacaaagggt aatatccgga aacctcctcg gattccattg cccagctatc    7440
tgtcacttta ttgtgaagat agtggaaaag gaaggtgctg cctacaaatg ccatcattgc    7500
gataaaggaa aggccatcgt tgaagatgcc tctgccgaca gtggtcccaa agatggaccc    7560
ccacccacga ggagcatcgt ggaaaagaa gacgttccaa ccacgtcttc aaagcaagtg    7620
gattgatgtg ataacatggt ggagcacgac acacttgtct actccaaaaa tatcaaagat    7680
acagtctcag aagaccaaag ggcaattgag acttttcaac aaagggtaat atccggaaac    7740
ctcctcggat tccattgccc agctatctgt cactttattg tgaagatagt ggaaaaggaa    7800
ggtggctcct acaaatgcca tcattgcgat aaaggaaagg ccatcgttga agatgcctct    7860
gccgacagtg gtcccaaaga tggaccccca cccacgagga gcatcgtgga aaagaagac    7920
gttccaacca cgtcttcaaa gcaagtggat tgatgtgata tctccactga cgtcaaggat    7980
gacgcacaat cccactatcc ttcgcaagac ccttcctcta tataaggaag ttcatttcat    8040
ttggagagga cctcgagtat ttttacaaca attaccaaca acaacaaaca acaaacaaca    8100
ttacaattac tatttacaat ctagaacaat gggatggtct tgcatcattc tcttcttggt    8160
agccacagct acaggtgtcc actccgatgt tttgatgact caaagccctc tctccacttcc    8220
tgtgactctt ggacagcccg catccatatc ttgcagatct agtcagagta ttgttcatag    8280
taacggcaac acctacttgg aatggtatct gcagaaacca ggccagtctc caaagcttct    8340
gatctacaag gcttccaatc gtttctctgg tgtcccagac aggtttagtg gcagtggatc    8400
agggactgac ttcacattga agatcagcag agttgaggct gaagatgcgg gagtgtacta    8460
ttgtcttcaa ggttcacatg ttccgtcaac gtttggaggt gggaccaaag tggagatcaa    8520
gactgttgcg gcgccatctg tcttcatctt tcctccatct gatgaacaac tcaagtctgg    8580
aactgcttct gttgtgtgcc ttctgaacaa cttctatcct agagaagcca agtacagtg    8640
gaaggttgac aatgctcttc aatcaggtaa ctcccaggag agtgtcacag agcaagattc    8700
caaggattcc acctacagcc tctcaagtac cttgacgttg agcaaggcag actatgagaa    8760
acacaaagtg tacgcatgcg aagtcactca tcagggcctg tcatcacccg tgacaaagag    8820
cttcaacagg ggagagtgtt aggtaccgag ctcgaagtga catcacaaag ttgaaggtaa    8880
taaagccaaa ttaattaaga cattttcata atgatgtcaa gaatgcaaag caaattgcat    8940
aactgccttt atgcaaaaca ttaatataat ataaattata aagaactgcg ctctctgctt    9000
cttattttct tagcttcatt tattagtcac tagctgttca gaattttcag tatctttga    9060
tattactaag aacctaatca cacaatgtat attcttatgc aggaaaagca gaatgctgag    9120
ctaaaagaaa ggcttttttcc atttcgaga gacaatgaga aaagaagaag aagaagaaga    9180
agaagaagaa gaagaaagaa gtaaataata aagcccaca ggaggcgaag ttcttgtagc    9240
tccatgttat ctaagttatt gatattgttt gccctatatt ttattctgt cattgtgtat    9300
gttttgttca gtttcgatct ccttgcaaaa tgcagagatt atgagatgaa taaactaagt    9360
tatattatta tacgtgttaa tattctcctc ctctctctag ctagccttt gttttctctt    9420
tttcttattt gatttttcttt aaatcaatcc attttaggag agggccaggg agtgatccag    9480
caaaacatga agattagaag aaacttccct cttttttttc ctgaaaacaa tttaacgtcg    9540
agatttatct cttttttgtaa tggaatcatt tctacagtta tgacgaattc tcgattaaaa    9600
atcccaatta tatttggtct aatttagttt ggtattgagt aaaacaaatt cgaaccaaac    9660
caaaatataa atatatagtt tttatatata tgcctttaag acttttttata gaattttctt    9720
taaaaaatat ctagaaatat ttgcgactct tctggcactct taatatgaa    9780
gtgctccatt tttattaact ttaaataatt ggttgtacga tcactttctt atcaagtgtt    9840
actaaaatgc gtcaatctct ttgttcttcc atattcatat gtcaaaatct atcaaaattc    9900
ttatatatct ttttcgaatt tgaagtgaaa tttcgataat ttaaaattaa atagaacata    9960
tcattattta ggttaattcat tgatttttat acttaattac taaatttggt taactttaa    10020
agtgtacatc aacgaaaaat tagtcaaacg actaaaataa ataaatatca tgtgttatta    10080
agaaaattct cctataagaa tattttaata gatcatatgt ttgtaaaaaa aattaatttt    10140
tactaacaca tatattact tatcaaaaat ttgacaaagt aagattaaaa taatattcat    10200
ctaacaaaaa aaaaaccaga aatgctgaaa acccggcaa aaccgaacca atccaaaccg    10260
atatagtggg tttggtttga tttgatata aaccgaacca actcggtcca tttgcacccc    10320
taatcataat agctttaata gttcaagata ttattaagt cacgttgtca atatcctga    10380
aatttttgcaa aatgaatcaa gcctatatgg ctgtaatatg aatttaaaag cagctcgatg    10440
tggtggtaat atgtaattta cttgattcta aaaaaatatc ccaagtatta ataatttctg    10500
ctaggaagaa ggttagctac gatttacagc aaagccagaa tacaaagaac cataaagtga    10560
ttgaagctcg aaatatacga aggaacaaat attttttaaaa aaatacgcaa tgacttggaa    10620
caaaagaaag tgatatattt tttgttctta aacaagcatc ccctctaaag aatggcagtt    10680
```

```
ttcctttgca tgtaactatt atgctccctt cgttacaaaa attttggact actattggga   10740
acttcttctg aaaatagtgg taccgagtgt acttcaagtc agttggaaat caataaaatg   10800
attattttat gaatatattt cattgtgcaa gtagatagaa attacatatg ttacataaca   10860
cacgaaataa acaaaaaaac acaatccaaa acaaacaccc caaacaaaat aacactatat   10920
atatcctcgt atgaggagag gcacgttcag tgactcgacg attcccgagc aaaaaaagtc   10980
tccccgtcac acatatagtg ggtgacgaca ttatcttcaa agtaatcctt ctgttgactt   11040
gtcattgata acatccagtc ttcgtcagga ttgcaaagaa ttatagaagg gatcccacct   11100
tttattttct tcttttttcc atatttaggg ttgacagtga aatcagactg caacctatt    11160
aattgcttcc acaatgggac gaacttgaag gggatgtcgt cgatgatatt ataggtggcg   11220
tgttcatcgt agttggtgaa gtcgatggtc ccgttccagt agttgtgtcg cccgagactt   11280
ctagcccagg tggtctttcc ggtacgagtt ggtccgcaga tgtagaggct ggggtgtctg   11340
accccagtcc ttccctcatc ctggttagat cggccatcca ctcaaggtca gattgtgctt   11400
gatcgtagga gacaggatgt atgaaagtgt aggcatcgat gcttacatga tataggtgcg   11460
tctctctcca gttgtgcaga tcttcgtggc agcggagatc tgattctgtg aagggcgaca   11520
cgtactgctc aggttgtgga ggaaataatt tgttggctga atattccagc cattgaagct   11580
ttgttgccca ttcatgaggg aactcttctt tgatcatgtc aagatactcc tccttagacg   11640
ttgcagtctg gataatagtt cgccatcgtg cgtcagattt gcgaggagac accttatgat   11700
ctcggaaatc tcctctggtt ttaatatctc cgtccttttga tatgtaatca aggacttgtt   11760
tagagtttct agctggctgg atattagggt gatttccttc aaaatcgaaa aaagaaggat   11820
ccctaataca aggttttttta tcaagctgga taagagcatg atagtgggta gtgccatctt   11880
gatgaagctc agaagcaaca ccaaggaaga aaataagaaa aggtgtgagt ttctcccaga   11940
gaaactggaa taaatcatct ctttgagatg agcacttggg gtaggtaagg aaaacatatt   12000
tagattggag tctgaagttc ttgctagcag aaggcatgtt gttgtgactc cgaggggttg   12060
cctcaaactc tatcttataa ccggcgtgga ggcatggagg caagggcatt ttggtaattt   12120
aagtagttag tggaaaatga cgtcatttac ttaaagacga agtcttgcga caaggggggc   12180
ccacgccgaa ttttaatatt accggcgtgg ccccaccttta tcgcgagtgc tttagcacga   12240
gcggtccgaa tttaaagtag aaaagttccc gcccactagg gttaaaggtg ttcacactat   12300
aaaagcatat acgatgtgat ggtatttgat ggagcgtata ttgtatcagg tatttccgtc   12360
ggatacgaat tattcgtacg gccggaccgg tcccctaggc cggccaattc gagatcggcc   12420
gcggctgagt ggctccttca atcgttgcgg ttctgtcagt tccaaacgta aaacggcttg   12480
tcccgcgtca tcggcggggg tcataacgtg actcccttaa ttctccgctc atgatcagat   12540
tgtcgtttcc cgccttcagt ttaaactatc agtgtttgac aggatatatt ggcgggtaaa   12600
cctaagagaa aagagcgttt attagaataa tcggatattt aaaagggcgt gaaaaggttt   12660
atccgttcgt ccatttgtat gtgcatgcca accacgggt tcccccagatc tggcgccggc   12720
cagcgagacg agcaagattg gccgccgccc gaaacgatcc gacagcgcgc ccagcacagg   12780
tgcgcaggca aattgcacca acgcatacag cgccagcaga atgccatagt gggcggtgac   12840
gtcgttcgat tgaaccagat cgcgcaggag gcccggcagc accggcataa tcaggccgat   12900
gccgacagcg tcgagcgcga cagtgctcag aattacgatc aggggtatgt tgggttttcac  12960
gtctggcctc cggagactgt catacgcgta aaaaggccgc gttgctggcg ttttttccata  13020
ggctccgccc ccctgacgag catcacaaaa atcgacgctc aagtcagagg tggcgaaacc   13080
cgacaggact ataaagatac caggcgtttc cccctggaag ctccctcgtg cgctctcctg   13140
ttccgaccct gccgcttacc ggatacctgt ccgcctttct cccttcggga agcgtggcgc   13200
tttctcatag ctcacgctgt aggtatctca gttcggtgta ggtcgttcgc tccaagctgg   13260
gctgtgtgca cgaaccccc gttcagcccg accgctgcgc cttatccggt aactatcgtc   13320
ttgagtccaa cccggtaaga cacgacttat cgccactggc agcagccact ggtaacagga   13380
ttagcagagc gaggtatgta ggcggtgcta cagagttctt gaagtggtgg cctaactacg   13440
gctacactag aaggacagta tttggtatct gcgctctgct gaagccagtt accttcggaa   13500
aaagagttgg tagctcttga tccggcaaac aaaccaccgc tggtagcggt ggtttttttg   13560
tttgcaagca gcagattacg cgcagaaaaa aaggatctca agaagatcct ttgatctttt   13620
ctacgggtc tgacgctcag tggaacgaaa actcacgtta agggattttg gtcatgagat   13680
tatcaaaaag gatcttcacc tagatccttt taaattaaaa atgaagtttt aaatcaatct   13740
aaagtatata tgagtaaact tggtctgcag ttgccatgtt ttacggcagt gagagcagag   13800
atagcgctga tgtccggcgg tgcttttgcc gttacgcacc accccgtcag tagctgaaca   13860
ggagggacag ctgatagaca cagaagccac tggagcacct caaaaacacc atcatacact   13920
aaatcagtaa gttggcagca tcacccataa ttgtggtttc aaaatcggct ccgtcgatac   13980
tatgttatac gccaactttg aaaacaactt tgaaaagct gttttctggt atttaaggtt   14040
ttagaatgca aggaacagtg aattggagtt cgtcttgtta taattagctt cttgggtat    14100
cttttaaatac tgtagaaaag aggaaggaaa taataaatgg ctaaaatgag aatatcaccg   14160
gaattgaaaa aactgatcga aaaataccgc tgcgtaaaag atacggaagg aatgtctcct   14220
gctaaggtat ataagctggt gggagaaaat gaaaacctat atttaaaaat gacggacagc   14280
cggtataaag ggaccaccta tgatgtggaa cgggaaaagg acatgatgct atggctggaa   14340
ggaaagctgc ctgttccaaa ggtcctgcac tttgaacggc atgatggctg gagcaatctg   14400
ctcatgagtg aggccgatgg cgtcctttgc tcggaagagt atgaagatga acaaagccct   14460
gaaaagatta tcgagctgta tgcggagtgc atcaggctct ttcactccat cgacatatcg   14520
gattgtccct atacgaatag cttagacagc cgcttagccg aattggatta cttactgaat   14580
aacgatctgg ccgatgtgga ttgcgaaaac tgggaagaag acactccatt taaagatccg   14640
cgcgagctgt atgatttttt aaagacgaa aagcccgaag gaacttgt ctttttccac     14700
ggcgacctgg gagacagcaa catctttgtg aaagatgaag aagtaagtgg ctttattgat   14760
cttgggagaa gcggcagggc ggacaagtgg tatgacattg ccttctgcgt ccggtcgatc   14820
agggaggata tcgggaaga acagtatgtc gagctatttt ttgacttact ggggatcaag   14880
cctgattggg agaaaataaa atattatt ttactggatg aattgtttta gtacctagat    14940
gtggcgcaac gatgccggcg acaagcagga gcgcaccgac ttcttccgca tcaagtgttt   15000
tggctctcag gccgaggccc acggcaagta tttgggcaag ggtcgctgg tattcgtgca   15060
gggcaagatt cggaatacca gtacgagga ggacgtctac gaccgactt                15120
cattgccgat aagtggatt atctggacac caaggcacca gcgggtcaa atcaggaata   15180
agggcacatt gccccggcgt gagtcgggc aatcccgcaa ggagggtgaa tgaatcggac    15240
gtttgaccgg aagcatacaa ggcaagaact gatcgacgcg ggttttccg ccgaggatgc    15300
cgaaaccatc gcaagccgca ccgtcatgcg tgcgcccgc gaaaccttcc agtccgtcgg    15360
ctcgatggtc cagcaagcta cggccaagat cgagcgcgac agcgtgcaac tggctccccc   15420
```

```
tgccctgccc gcgccatcgg ccgccgtgga gcgttcgcgt cgtctcgaac aggaggcggc    15480
aggtttggcg aagtcgatga ccatcgacac gcgaggaact atgacgacca agaagcgaaa    15540
aaccgccggc gaggacctgg caaaacaggt cagcgaggcc aagcaggccg cgttgctgaa    15600
acacacgaag cagcagatca aggaaatgca gctttccttg ttcgatattg cgccgtggcc    15660
ggacacgatg cgagcgatgc caaacgacac ggcccgctct gccctgttca ccacgcgcaa    15720
caagaaaatc ccgcgcgagg cgctgcaaaa caaggtcatt ttccacgtca caaggacgtt    15780
gaagatcacc tacaccggcg tcgagctgcg ggccgacgat gacgaactgg tgtggcagca    15840
ggtgttggag tacgcgaagc gcaccccctat cggcgagccg atcaccttca cgttctacga    15900
gctttgccag gacctgggct ggtcgatcaa tggccggtat tacacgaagg ccgaggaatg    15960
cctgtcgcgc ctacaggcga cggcgatggg cttcacgtcc gaccgcgttg ggcacctgga    16020
atcggtgtcg ctgctgcacc gcttccgcgt cctggaccgt ggcaagaaaa cgtcccgttg    16080
ccaggtcctg atcgacgagg aaatcgtcgt gctgtttgct ggcgaccact acacgaaatt    16140
catatgggag aagtaccgca agctgtcgcc gacggcccga cggatgttcg actatttcag    16200
ctcgcaccgg gagccgtacc cgctcaagct ggaaaccttc cgcctcatgt gcggatcgga    16260
ttccacccgc gtgaagaagt ggcgcgagca ggtcggcgaa gcctgcgaag agttgcgagg    16320
cagcggcctg gtggaaacacg cctgggtcaa tgatgacctg gtgcattgca aacgctaggg    16380
ccttgtgggg tcagttccgg ctgggggttc agcagcagc gctttactgg catttcagga    16440
acaagcggga actgctcgac gcacttgctt cgctcagtat cgctcgggac gcacggcgcg    16500
ctctacgaac tgccgataaa cagaggatta aaattgacaa ttcaatggca aggactgcca    16560
gcgctgccat ttttggggtg aggccgttcg cggccgaggg gcgcagcccc tgggggggatg    16620
ggaggcccgc gttagcgggc cgggaggggt cgagaaggg gggcacccccc cttcggcgtg    16680
cgcggtcacg cgcacagggc gcagccctgg ttaaaaacaa ggtttataaa tattggttta    16740
aaagcaggtt aaaagacagg ttagcggtgg ccgaaaaacg ggcggaaacc cttgcaaatg    16800
ctggattttc tgcctgtgga cagccccctca aatgtcaata ggtgcgcccc tcatctgtca    16860
gcactctgcc cctcaagtgt caaggatcgc gcccctcatc tgtcagtagt cgcgcccctc    16920
aagtgtcaat accgcagggc acttatcccc aggcttgtcc acatcatctg tgggaaactc    16980
gcgtaaaatc aggcgttttc gccgatttgc gaggctggcc agctccacgt cgccggccga    17040
aatcgagcct gcccctcatc tgtcaacgcc gcgccgggtg agtcggcccc tcaagtgtca    17100
acgtccgccc ctcatctgtc agtgagggcc aagttttccg cgaggtatcc acaacgccgg    17160
cggccgcggt gtctcgcaca cggcttcgac ggcgtttctg gcgcgtttgc agggccatag    17220
acggccgcca gcccagcggc gagggcaacc agcccggtga gcgtcgcaaa ggcgctcggt    17280
cttgccttgc tcgtcgagat ctgggggtcga tcagccgggg atgcatcagg ccgacagtcg    17340
gaacttcggg tccccgacct gtaccattcg gtgagcaatg gataggggag ttgatatcgt    17400
caacgttcac ttctaaagaa atagcgccac tcagcttcct cagcggcttt atccagcgat    17460
ttcctattat gtcggcatag ttcctcaagat cgacagcctg tcacggttaa gcgagaaatg    17520
aataagaagg ctgataattc ggatctctgc gagggagatg atatttgatc acaggcagca    17580
acgctctgtc atcgttacaa tcaacatgct accctccgcg agatcatccg tgtttcaaac    17640
ccggcagctt agttgccgtt cttccgaata gcatcggtaa catgagcaaa gtctgccgcc    17700
ttacaacggc tctcccgctg acgccgtccc ggactgatgg gctgcctgta tcgagtggtg    17760
attttgtgcc gagctgccgg tcggggagct gttggctggc tggtggcagg atatattgtg    17820
gtgtaaacaa attgacgctt agacaactta ataacatt gcggacgttt ttaatgtact    17880
ggggtggttt ttcttttcac cagtgagacg ggcaacagct gattgccctt caccgcctgg    17940
ccctgagaga gttgcagcaa gcggtccacg ctggtttgcc ccagcaggcg aaaatcctgt    18000
ttgatggtgg ttccgaaatc ggcaaaatcc cttataaatc aaaagaatag cccgagatag    18060
ggttgagtgt tgttccagtt tggaacaaga gtccactatt aaagaacgtg gactccaacg    18120
tcaaaggcgc aaaaaccgtc tatcagggcg atggcccact acgtgaacca tcacccaaat    18180
caagttttt ggggtcgagg tgcctaaag cactaaatcg gaaccctaaa gggagccccc    18240
gatttagagc ttgacgggga aagccggcga acgtggcgag aaaggaaggg aagaaagcga    18300
aaggagcggg cgccattcag gctgcgcaac tgttgggaag gg                      18342

SEQ ID NO: 21           moltype = DNA   length = 18
FEATURE                 Location/Qualifiers
misc_feature            1..18
                        note = primer
source                  1..18
                        mol_type = other DNA
                        organism = synthetic construct
SEQUENCE: 21
aatcccacta tccttcgc                                                  18

SEQ ID NO: 22           moltype = DNA   length = 27
FEATURE                 Location/Qualifiers
misc_feature            1..27
                        note = primer
source                  1..27
                        mol_type = other DNA
                        organism = synthetic construct
SEQUENCE: 22
gcggtctcca ccagaagcaa gagaagc                                        27

SEQ ID NO: 23           moltype = DNA   length = 34
FEATURE                 Location/Qualifiers
misc_feature            1..34
                        note = primer
source                  1..34
                        mol_type = other DNA
                        organism = synthetic construct
SEQUENCE: 23
gtcggatccg atgttcagct tcttgagtct ggag                                34
```

| SEQ ID NO: 24 | moltype = DNA   length = 32 |
| --- | --- |
| FEATURE | Location/Qualifiers |
| misc_feature | 1..32 |
|  | note = primer |
| source | 1..32 |
|  | mol_type = other DNA |
|  | organism = synthetic construct |

SEQUENCE: 24
gcgagctctt atctacgcct aggagatggg ga                                         32

| SEQ ID NO: 25 | moltype = DNA   length = 32 |
| --- | --- |
| FEATURE | Location/Qualifiers |
| misc_feature | 1..32 |
|  | note = primer |
| source | 1..32 |
|  | mol_type = other DNA |
|  | organism = synthetic construct |

SEQUENCE: 25
gcggtctcgt ggtatggaca ttgacccttta ca                                        32

| SEQ ID NO: 26 | moltype = DNA   length = 23 |
| --- | --- |
| FEATURE | Location/Qualifiers |
| misc_feature | 1..23 |
|  | note = primer |
| source | 1..23 |
|  | mol_type = other DNA |
|  | organism = synthetic construct |

SEQUENCE: 26
aagcttgttg ttgtgactcc gag                                                   23

| SEQ ID NO: 27 | moltype = DNA   length = 42 |
| --- | --- |
| FEATURE | Location/Qualifiers |
| misc_feature | 1..42 |
|  | note = primer |
| source | 1..42 |
|  | mol_type = other DNA |
|  | organism = synthetic construct |

SEQUENCE: 27
ctagtggtgg atcaggaggt tctggtggtt ctggaggttc ag                              42

| SEQ ID NO: 28 | moltype = DNA   length = 42 |
| --- | --- |
| FEATURE | Location/Qualifiers |
| misc_feature | 1..42 |
|  | note = primer |
| source | 1..42 |
|  | mol_type = other DNA |
|  | organism = synthetic construct |

SEQUENCE: 28
gatcctgaac ctccagaacc accagaacct cctgatccac ca                              42

| SEQ ID NO: 29 | moltype = DNA   length = 27 |
| --- | --- |
| FEATURE | Location/Qualifiers |
| misc_feature | 1..27 |
|  | note = primer |
| source | 1..27 |
|  | mol_type = other DNA |
|  | organism = synthetic construct |

SEQUENCE: 29
gcgggatcca agggcgtgtc atactcc                                               27

| SEQ ID NO: 30 | moltype = DNA   length = 30 |
| --- | --- |
| FEATURE | Location/Qualifiers |
| misc_feature | 1..30 |
|  | note = primer |
| source | 1..30 |
|  | mol_type = other DNA |
|  | organism = synthetic construct |

SEQUENCE: 30
ggggtctcgt ggtaagggcg tgtcatactc                                            30

| SEQ ID NO: 31 | moltype = DNA   length = 24 |
| --- | --- |
| FEATURE | Location/Qualifiers |
| misc_feature | 1..24 |
|  | note = primer |
| source | 1..24 |
|  | mol_type = other DNA |
|  | organism = synthetic construct |

SEQUENCE: 31

```
ccgactagtg ctaccactcc tgtg                                            24

SEQ ID NO: 32          moltype = DNA   length = 30
FEATURE                Location/Qualifiers
misc_feature           1..30
                       note = primer
source                 1..30
                       mol_type = other DNA
                       organism = synthetic construct
SEQUENCE: 32
gagggatccg aggcttcaat ttcagacatg                                      30

SEQ ID NO: 33          moltype = DNA   length = 27
FEATURE                Location/Qualifiers
misc_feature           1..27
                       note = primer
source                 1..27
                       mol_type = other DNA
                       organism = synthetic construct
SEQUENCE: 33
gggactagtg gagcaagcga atttagc                                         27

SEQ ID NO: 34          moltype = DNA   length = 14339
FEATURE                Location/Qualifiers
misc_feature           1..14339
                       note = pBYe3R2K2Mc-BAHBcheZE3
source                 1..14339
                       mol_type = other DNA
                       organism = synthetic construct
SEQUENCE: 34
cgatcggtcg attcatagaa gattagattt tcatagtat tttttaaag taaacctta       60
actacggtta ggacactttt aagttaaatt taatttgaac ccttaaatta attttaaaa    120
tagataaata tcaatcatcc tgatatgctt ttgaaaaaat gaatgagaaa gatgattcaa   180
ttaaggccac attttaatca tgactaaaat aatatacagt ataattcat atatatttgc    240
tttaaaaaaa aattgacaat ccattcgttt ctagcaataa atttcttcaa ccacaaatat   300
attaaagata actacggcat agaaacaaaa atctatgaag aattttttgta tacttcatat  360
gaaattaaaa aaaacttcat tgaacatcaa aataataata ataatcataa actcctcaat   420
atttatattc ctagcttctt gaattaaatt gtttacatat tcaacgatgt aaaaaaattat 480
ttctctatct atttccctta tatcatgcat ggtttccat atatcaaagg ataaagcaa    540
tctatgtaaa ttatctcact ttattaagtt ttctatctga attattgaga acgtagattt   600
cttttttgcac tatcccccaa taattagcaa aacacaccta gactagattt gttttgctaa  660
cccaattgat attaattata tatgattaat atttatatgt atatggaatt ggttaataaa  720
atgcatctgg ttcatcaaag aattataaag acacgtgaca ttcatttagg ataagaaata  780
tggatgatct ctttctctta ttcagataat tagtaattac acataacaca aactttgat   840
gcccacatta tagtgattag catgtcacta tgtgtgcatc ctttatttc atacattaat   900
taacttggcc aatccagaag atggacaagt ctagggtcac attgcagggt actctagctt  960
actcgcctttc ttttcgaag gtttgagtac cttcagggca tcctcttgat acattcttt  1020
ccacttcgat tggggcaagc tgtagcagtt cttgcttaga ccgaattgcc atctcacaga 1080
gatgctgaag agttcgcgac cctccagaaa cggtgatact aactcctcga aaccgaatac 1140
tataggtaca tccgatctgg tcgaaaccga aaaatcgaga tgctgcatag ttaaccgaat 1200
ctcccgtcca agatccaagg actctgtgca gtgaagcttc cgtcctgtcg tatctgagat 1260
atctcttaaa tacaactttc ccgaaaaccc agctttcctt gaaaccaagg ggattatctt 1320
gattcgaatt cgtctcatcg ttatgtagcc gccactcagt ccaactcgga cttttcgtcag 1380
gaagtttgaa gggagaagtt gtacctcctg atcctccatc caacgttca ctgttagctt  1440
gttccctagc gtcgttttcct tgtatagctc gttccatgga ttgtaaatag taattgtaat 1500
gttgtttgtt gtttgttgtt gttggtaatt gttgtaaaaa tacgctctcc aaatgaaatg 1560
aacttcctta tatagaggaa gggtcttgcg aaggatagtg ggattgtgcg tcatccctta 1620
cgtcagtgga gatatcacat caatccactt gctttgaaga cgtggttgga acgtcttctt 1680
tttccacgat gctcctcgtg ggtggggtc catctttggg accactgtcg gcagaggcat 1740
cttcaacgat ggccttcc ttatcgcaat gatgcattt gtaggagcca ccttcctttt   1800
ccactatctt cacaataaag tgacagatag ctgggcaatg gaatccgagg aggtttccgg 1860
atattaccct ttgttgaaaa gtctcaattg ccctttggtc ttctgagact gtatctttga 1920
tattttgga gtagacaagt gtgtcgtgct ccaccatgtt ctggcaattc cggttcgctt   1980
gctgtccata aaaccgccca gtctagctat cgccatgtaa cccactgca agctacttgc  2040
tttctctttg cgcttgcgtt tccccttgtc cagatagccc agtagctgac attcatccgg 2100
ggtcagcacc gtttctgcgg actggctttt tacgtgttcc gcttccttta gcagcccttg 2160
cgccctgagt gcttgcggca gcgtgaagct ggcgcgccgc tctagcagaa ggcatgttgt 2220
tgtgactccg aggggttgcc tcaaactcta tcttataacc ggcgtggagg catggaggca 2280
agggcatttt ggtaatttaa gtagtagtg gaaaatgacg tcatttactt aaagacgaag 2340
tcttgcgaca agggggggccc acgccgaatt ttaatattac cggcgtggcc ccacttatc   2400
gcgagtgctt tagcacgagc ggtccagatt taagtagaa aagttccgc ccactagggt  2460
taaaggtgtt cacactataa aagcatatac gatgtgatgg tatttgatgg agcgtatatt 2520
gtatcaggta tttccgtcgg atacgaatta ttcgtacgac cctcctgcag gtcaacatgg 2580
tgagcacga cacacttgtc tactccaaaa atatcaaaga tcagtctca gaagaccaaa    2640
gggcaattga gacttttcaa caaagggtaa tatccggaaa cctcctcgga ttccattgcc 2700
cagctatctg tcacttttatt gtgaagatag tggaaaagga aggtggctcc tacaaatgcc 2760
atcattgcga taaaggaaag gccatcgttg aagatgcctc tgccgacagt ggtcccaaag 2820
atggaccccc acccacgagg agcatcgtgg aaaaagaaga cgttccaacc acgtcttcaa 2880
agcaagtgga ttgatgtgat aacatggtgg agcacgacac acttgtctac tccaaaaata 2940
```

```
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg acccccacc cacgaggagc atcgtggaaa    3180
aagaagacgt tccaaccacg tcttcaaagc aagtggattg atgtgatatc tccactgacg   3240
taaggagtga cgcacaatcc cactatcctt cgcaagaccc ttcctctata taaggaagtt   3300
catttcattt ggagaggacc tcgagaaaca aacaaaatca acaaatatag aaaataacgc   3360
atttccaatt ctttgaaatt tctgcaacat ctagaacaat ggctaacaag cacctctcat   3420
tgtctctctt ccttgtgctc cttggtcttt ctgcttctct tgcttctggt atggacattg   3480
acccttacaa agaatttgga gctactgtgg agcttctcag ctttttgcct tctgacttct   3540
ttccttctgt cagggatctc cttgacactg cctcagctct ttatagggaa gccttggagt   3600
ctcctgagca ttgctcacct caccatactg cactcaggca agccattctc tgctggggag   3660
aattgatgac tcttgctacc tgggtgggta acaatctaga ggatccagca tccagagatc   3720
ttgttgttaa ctatgttaat actaatgtgg gtttgaagat caggcaactc ttgtggtttc   3780
atatatcttg ccttacttt ggaagagaga ctgtacttga atatttggtc tcttttggag    3840
tgtggattag aactcctcca gcctatagac caccaaatgc ccctatcttg tcgactcttc   3900
cagaaactac tgttgttgga ggttctggtg atcaggagg ttccggtggt tctggaggtt    3960
ccggaatgga cattgaccct tacaaagaat ttggagctac tgtggagctc ctcagcttt    4020
tgccttctga cttcttttcct tctgtcaggg atctccttga cactgcctca gctctttata   4080
gggaagcctt ggagtctcct gagcattgct cacctcacca tactgcactc aggcaagcca   4140
ttctctgctg ggagaattg atgactcttg ctacctgggt gggtaacaat ctagagggta    4200
ccggtgggag cggttcaggc ggaggtgat ccaagggcgt gtcatactcc ttgtgtaccg    4260
ctgccttcac attcaccaag atcccggctg aaacactgca cggaaccgtt accgtggagg   4320
tccaatacgc cggtacagat ggaccttgca aggttccagc tcagatggcg gtggacatgc   4380
aaaactctta cccagttgga aggttgatta ccgctaaccc cgttatcact gaaagcactg   4440
agaactctaa gatgatgttg gaacttgatc caccattcgg tgactcttac attgtcattg   4500
gtgtgggaga agaagatc acccaccact ggcacaggag tggtagcact agtgtgaggtt    4560
ctggaggatc tggttctagt ggaggttctg gtggagatcc agcatccaga gatcttgttg   4620
ttaactatgt taatactaat gtgggtttga agatcaggca actcttgtgg tttcatatat   4680
cttgccttac ttttggaaga gagactgtac ttgaatattt ggtctctttt ggagtgtgaa   4740
ttagaactcc tccagcctat agaccaccaa atgcccctat cttgtcgact cttccagaaa   4800
ctactgttgt tcgaagaagg gacaggggca gatcccctag acgtagaact cccagccta    4860
gaagaaggag atccccatct cctaggcgta gataagagc cgaagtgaca tcacaaagtt    4920
gaaggtaata aagccaaatt aattaagaca ttttcataat gatgtcaaga atgcaaagca   4980
aattgcataa ctgcctttat gcaaaacatt aatataatat aaattataaa gaactgcgct   5040
ctctgcttct tatttttctta gcttcattta ttagtcacta gctgttcaga attttcagta   5100
tcttttgata ttactaagaa cctaatcaca caatgtatat tctatgcag gaaaagcaga    5160
atgctgagct aaaagaaagg cttttttccat tttcgagaga caatgagaaa agagaagaa   5220
gaagaagaag aagaagaaga agaaaagagt aaataataaa gccccacagg aggcgaagtt   5280
cttgtagctc catgttatct aagttattga tattgtttgc cctatatttt atttctgtca   5340
ttgtgtatgt tttgttcagt ttcgatctcc ttgcaaaatg cagagattat gagatgaata   5400
aactaagtta tattattata cgtgttaata ttctcctcct ctctctagct agccttttgt   5460
ttctcttttt tcttatttga ttttctttaa atcaatccat tttaggagag ggccagggag   5520
tgatccagca aaacatgaag attagaagaa acttccctct tttttttcct gaaaacaatt   5580
taacgtcgag atttatctct tttttgtaatg gaatcatttc tacagttatg acgaattgtc   5640
cgcaaaaatc accagtctct ctctacaaat ctatctctc ctatttttct ccagaataat    5700
gtgtgagtag ttcccagata agggaattag ggttcttata gggtttcgt catgtggtga    5760
gcatataaga aaccccttagt atgtatttgt atttgtaaaa tacttctatc aataaaattt   5820
ctaattccta aaaccaaaat ccagtgaccc taaaaccaaa atccagtgac gaattctcga   5880
ttaaaaatcc caattatatt tggtctaatt tagtttggta ttgagtaaaa caattcgaa    5940
ccaaaccaaa atataaatat atagttttta tatatatgcc tttaagactt tttatagaat   6000
tttctttaaa aaatatctag gtacatcaac gaaaaattag tcaaacgact aaaataaata   6060
aatatcatgt gttattaaga aaattctcct ataagaatat tttaatagat catatgtttg   6120
taaaaaaaat taatttttac taacacatat atttacttat caaaaatttg acaaagtaag   6180
attaaaataa tattcatcta acaaaaaaaa aaccagaaaa tgctgaaaac ccggcaaaac   6240
cgaaccaatc caaaccgata tagttggttt ggtttgattt tgatataaac cgaaccaact   6300
cggtccattt gcacccctaa tcataatagc tttaatattt caagatatta ttaagttaac   6360
gttgtcaata tcctggaaat tttgcaaaat gaatcaagcc tatatggctg taatatgaat   6420
ttaaaagcag ctcgatgtgg tggtaatatg taatttactt gattctaaaa aaatatccca   6480
agtattaata atttctgcta ggaagaaggt tagctacgat ttacagcaaa gccagaatac   6540
aaagaaccat aaagtgattg aagctcgaaa tatacgaagg aacaaatatt tttaaaaaaa   6600
tacgcaatga cttggaacaa aagaaagtga tatatttttt gttcttaaac aagcatcccc   6660
tctaaagaat ggcagttttc ctttgcatgt aactattatg ctcccttcgt tacaaaaatt   6720
ttggactact attgggaact tcttctgaaa atagtcgtat gctgctcagt tcaagtcagt   6780
tggaaatcaa taaaatgatt attttatgaa tatatttcat tgtgcaagta gatgaaaatt   6840
acatatgtta cataacacac gaaataaaca aaaaaacaca atccaaaaca aacaccccaa   6900
acaaaataac actatatata tcctcgtatg aggagaggca cgttcagtga ctcgacgatt   6960
cccgagcaaa aaaagtctcc ccgtcacaca tatagtgggt gacgcaatta tcttcaaagt   7020
aatccttctg ttgacttgtc attgataaca tccagtcttc gtcaggattg caagaattaa   7080
tagaagggat cccacctttt attttcttct tttttccata tttagggttg acagtgaaat   7140
cagactggca acctattaat tgcttccaca atgggacgaa cttgaagggg atgtcgtcga   7200
tgatattata ggtggcgtgt tcatcgtagt tggtgaagtc gatggtcccg ttccagtagt   7260
tgtgtcgccc gagacttcta gcccaggtgg tctttccggt acgagttggt ccgcagatgt   7320
agaggctggg gtgtctgacc ccagtcctt cctcatcctg gttagatcgg catccactc    7380
aaggtcagat tgtgcttgat cgtaggagac aggatgtatg aaagtgtagg catcgatgct   7440
tacatgatat aggtgcgtct ctctccagtt gtgcagatct tcgtggcagc ggagatctga   7500
ttctgtgaag ggcgacacgt actgctcagg ttgtggagga ataaatttgt tggctgaata   7560
ttccagccat tgaagctttg ttgcccattc atgagggaac tcttctttga tcatgtcaag   7620
atactcctcc ttagacgttg cagtctggat aatagttcgc catcgtgcgt cagatttgcg   7680
```

```
aggagacacc ttatgatctc ggaaatctcc tctggttttta atatctccgt cctttgatat   7740
gtaatcaagg acttgtttag agtttctagc tggctggata ttagggtgat ttccttcaaa   7800
atcgaaaaaa gaaggatccc taatacaagg tttttttatca agctggataa gagcatgata   7860
gtgggtagtg ccatcttgat gaagctcaga agcaacacca aggaagaaaa taagaaaagg   7920
tgtgagtttc tcccagagaa actggaataa atcatctctt tgagatgagc acttggggta   7980
ggtaaggaaa acatatttag attggagtct gaagttcttg ctagcagaag gcatgtggtt   8040
gtgactccga ggggttgcct caaactctat cttataaccg gcgtggaggc atggaggcaa   8100
gggcattttg gtaatttaag tagttagtgg aaaatgacgt catttactta aagacgaagt   8160
cttgcgacaa gggggggccca cgccgaatttt taatattacc ggcgtggcc caccttatcg   8220
cgagtgcttt agcacgagcg gtccagattt aaagtagaaa agttcccgcc cactagggtt   8280
aaaggtgttc acactataaa agcatatacg atgtgatggt atttgatgga gcgtatattg   8340
tatcaggtat ttccgtcgga tacgaattat tcgtacggcc ggaccggtcc cctaggccgg   8400
ccaattcgag atcggccgcg gctgagtggc tccttcaatc gttgcggttc tgtcagttcc   8460
aaacgtaaaa cggcttgtcc cgcgtcatcg gcgggggtca taacgtgact ccccttaattc   8520
tccgctcatg atcagattgt cgtttcccgc cttcagttta aactatcagt gtttgacagg   8580
atatattggc gggtaaacct aagagaaaag agcgttatt tgaataatcg gatatttaaa   8640
agggcgtgaa aaggtttatc cgttcgtcca ttttgtatgtg catgccaacc acagggttcc   8700
ccagatctgg cgccggccag cgagacgagc aagattggcg gccgcccgaa acgatccgat   8760
agcgcgccca gcacaggtgc gcaggcaaat tgcaccaacg catacagcgc agcagaatg   8820
ccatagtggg cggtgacgtc gttcgagtga accagatcgc gcaggaggcc cggcagcacc   8880
ggcataatca ggccgatgcc gacagcgtcg agcgcgacag tgctcagaat tacgatcagg   8940
ggtatgttgg gtttcacgtc tggcctccgg agactgcat acgcgtaaaa aggccgcgtt   9000
gctggcgttt ttccataggc tccgcccccc tgacgagcat cacaaaaatc gacgctcaag   9060
tcagaggtgg cgaaacccga caggactata aagataccag gcgtttcccc ctggaagctc   9120
cctcgtgcgc tctcctgttc cgaccctgcc gcttaccgga tacctgtccg cctttctccc   9180
ttcgggaagc gtggcgcttt ctcatagctc acgctgtagg tatctcagtt cggtgtaggt   9240
cgttcgctcc aagctgggct gtgtgcacga accccccgtt cagcccgacc gctgcgcctt   9300
atccggtaac tatcgtcttg agtccaaccc ggtaagacac gacttatcgc cactggcagc   9360
agccactggt aacaggatta gcagagcgag gtatgtaggc ggtgctacag agttcttgaa   9420
gtggtggcct aactacggct acactagaag gacagtattt ggtatctgcg ctctgctgaa   9480
gccagttacc ttcggaaaaa gagttggtag ctcttgatcc ggcaaacaaa ccaccgctgt   9540
tagcggtggt ttttttgttt gcaagcagca gattacgcgc agaaaaaaag gatctcaaga   9600
agatcctttg atcttttcta cggggtctga cgctcagtgg aacgaaaact cacgttaagg   9660
gattttggtc atgagattat caaaaaggat cttcacctag atccttttaa attaaaaatg   9720
aagttttaaa tcaatctaaa gtatatatga gtaaacttgg tctgcagttg ccatgttta   9780
cggcagtgag agcagagata gcgctgatgt ccggcggtgc ttttgccgtt acgcaccacc   9840
ccgtcagtag ctgaacagga gggacagctg atagacacag aagccactgg agcacctcaa   9900
aaacaccatc atacactaaa tcagtaagtt ggcagcatca cccataattg tggttttcaaa   9960
atcggctccg tcgatactat gttatacgcc aactttgaaa acaactttga aaaagctgtt  10020
ttctggtatt taaggtttta gaatgcaagg aacagtgaat tggagttcgt cttgttataa  10080
ttagcttctt ggggtatctt taaatactgt agaaagagg aaggaaataa taatgcta  10140
aaatgagaat atcaccggaa ttgaaaaaac tgatcgaaaa ataccgctgc gtaaagata  10200
cggaaggaat gtctcctgct aaggtatata agctggtggg aggaaaatgaa aacctatatt  10260
taaaaatgac ggacagccgg tataagggaa ccacctatga tgtggaacgg gaaaaggaca  10320
tgatgctatg gctggaagga aagctgcctg ttccaaaggt cctgcacttt gaacggcatg  10380
atggctggag caatctgctc atgagtgagg ccgatgcgt cctttgctcg gaagagtatg  10440
aagatgaaca aagcccctgaa aagattatcg agctgtatgc ggagaagtcat aggctctttc  10500
actccatcga catatcggat tgtccctata cgaatagctt agacagccgc ttagccgaat  10560
tggattactt actgaataac gatctggccg atgtggattg cgaaaactgg gaagaagaca  10620
ctccatttaa agatccgcgc gagctgtatg attttttaaa gacggaaaag cccgaagagg  10680
aacttgtctt ttcccacggc gacctgggaa acagcaacat ctttgtgaaa gatggcaaag  10740
taagtggctt tattgatctt gggagaagcg gcagggcgga caagtggtat gacattgcct  10800
tctgcgtccg gtcgatcagg gaggatatcg gggaagaaca gtatgtcgag ctatttttg  10860
acttactggg gatcaagcct gattgggaga aaataaaata ttatatttta ctggatgaat  10920
tgttttagta cctagatgtg gcgcaacgat gccggcgaca agcaggagcg caccgacttc  10980
ttccgcatca agtgttttgg ctctcaggcc gaggcccacg gcaagtattt gggcaagggg  11040
tcgctggtat tcgtgcaggg caagattcgg aataccaagt acgagaagga cggccagacg  11100
gtctacggga ccgacttcat tgccgataag gtggattatc tggacaccaa ggcaccaggc  11160
gggtcaaatc aggaataagg gcacattgcc ccggcgtgag tcggggcaat cccgcaaggga  11220
gggtgaatga atcggacgtt tgaccggaag gcatacaggc aggaactgat cgacgcggga  11280
ttttccgccg aggatgccga aaccatcgca agccgcaccg tcatgcgtgc gccccgcgaa  11340
accttccagt ccgtcggctc gatggtccag caagctacgg ccaagatcga gcgcgacagc  11400
gtgcaactgg ctcccctgc cctgcccgcg ccatcggccg ccgtggagcg ttcgcgtcgt  11460
ctcgaacagg aggcggcagg tttggcaagg tcgatgacga tcgacacgcg aggaactatg  11520
acgaccaaga agcgaaaaac cgccggcgag gacctggcaa aacaggtcag cgaggccaag  11580
caggccgcgt tgctgaaaca cacgaagcag cagatcaagg aaatgcagct ttccttgttc  11640
gatattgcgc cgtggccgga cacgatgcga gcgatgccaa cgacacggc ccgctctgcc  11700
ctgttcacca cgcgcaacaa gaaaatcccg cgcgaggcgc tgcaaacaa ggtcattttc  11760
cacgtcaaca aggacgtgaa gatcacctac accggcgtg agctgcgggc cgacgatgac  11820
gaactggtgt ggcagcaggt gttggagtac gcgaagcgca ccctatcgg cgagccgatc  11880
accttcacgt tctacgagct ttgccaggac ctggcctggt cgatcaatgg ccggtattac  11940
acgaaggcca aggaatgcct gtcgcgccta caggcgacgg cgatgggctt cacgtccgac  12000
cgcgttgggc acctggaatc ggtgtcgctg ctgcaccgct tccgcgtcct ggaccgtggc  12060
aagaaaacgt ccgttgcca ggtcctgatc gacgaggaaa tcgtcgtgct gtttgctgac  12120
gaccactaca cgaaattcat atgggagaag taccgcaagc tgtcgccgac ggcccgacgg  12180
atgttcgact atttcagctc gcaccgggag ccgtacccgc tcaagctgga aaccttccgc  12240
ctcatgtgcg gatcggattc cacccgcgtg aagaagtggc gcgagcaggt cggcgaagcc  12300
tgcgaagagt tgcgaggcag cggcctggtg gaacacgcct gggtcaatga tgacctggtg  12360
cattgcaaac gctagggcct tgtggggtca gttccggctc ggggttcagc agccagcgct  12420
```

```
ttactggcat ttcaggaaca agcgggcact gctcgacgca cttgcttcgc tcagtatcgc 12480
tcgggacgca cggcgcgctc tacgaactgc cgataaacag aggattaaaa ttgacaattc 12540
aatggcaagg actgccagcg ctgccatttt tggggtgagg ccgttcgcgg ccgaggggcg 12600
cagccctgg ggggatggga ggcccgcgtt agcgggccgg gagggttcga gaaggggggg 12660
caccccctt cggcgtgcgc ggtcacgcgc acagggcgca gccctggtta aaaacaaggt 12720
ttataaatat tggtttaaaa gcaggttaaa agacaggtta gcggtggccg aaaaacgggc 12780
ggaaaccctt gcaaatgctg gattttctgc ctgtggacag cccctcaaat gtcaataggt 12840
gcgcccctca tctgtcagca ctctgcccct caagtgtcaa ggatcgcgcc cctcatctgt 12900
cagtagtcgc gcccctcaag tgtcaatacc gcagggcact tatccccagg cttgtccaca 12960
tcatctgtgg gaaactcgcg taaaatcagg cgttttcgcc gatttgcgag gctggccagc 13020
tccacgtcgc cggccgaaat cgagcctgcc cctcatctgt caacgccgcg ccgggtgagt 13080
cggcccctca agtgtcaacg tccgccctc atctgtcagt gagggccaag ttttccgcga 13140
ggtatccaca acgccggcgg ccgcggtgtc tcgcacacgc cttcgacggc gtttctggcg 13200
cgtttgcagg gccatagacg gccgccagcc cagcggcgag gcaaccagc ccggtgagcg 13260
tcgcaaaggc gctcggtctt gccttgctcg tcgagatctg gggtcgatca gccggggatg 13320
catcaggccg acagtcggaa cttcgggtcc ccgacctgta ccattcggtg agcaatggat 13380
aggggagttg atatcgtcaa cgttcacttc taaagaaata gcgccactca gcttcctcag 13440
cggctttatc cagcgatttc ctattatgtc ggcatagttc tcaagatcga cagcctgtca 13500
cggttaagcg agaaatgaat aagaaggctg ataattcgga tctctgcgag ggagatgata 13560
tttgatcaca ggcagcaacg ctcgtcatc gttacaatca acatgctacc ctccgcgaga 13620
tcatccgtgt tcaaacccg gcagcttagt tgccgttctt ccgaatagca tcggtaacat 13680
gagcaaagtc tgccgcctta caacggctct cccgctgacg ctgtcccgga ctgatgggct 13740
gcctgtatcg agtggtgatt ttgtgccgag ctgccggtcg gggagctgtt ggctggctgg 13800
tggcaggata tattgtggtg taaacaaatt gacgcttaga caacttaata acacattgcg 13860
gacgttttta atgtactggg gtggttttc ttttcaccag tgagacgggc aacagctgat 13920
tgcccttcac cgcctggccc tgagagagtt gcagcaagcg gcacacgctg gtttgcccca 13980
gcaggcgaaa atcctgtttg atggtggttc cgaaatcggc aaaatcccctt ataaatcaaa 14040
agaatagccc gagatagggt tgagtgttgt tccagtttgg aacaagagtc cactattaaa 14100
gaacgtggac tccaacgtca aagggcgaaa accgtctat cagggcgatg gcccactacg 14160
tgaaccatca cccaaatcaa gttttttggg gtcgaggtgc cgtaaagcac taaatcggaa 14220
ccctaaaggg agcccccgat ttagagcttg acggggaaag ccggcgaacg tggcgagaaa 14280
ggaagggaag aaagcgaaag gagcgggcgc cattcaggct gcgcaactgt tgggaaggg 14339

SEQ ID NO: 35           moltype = DNA   length = 14162
FEATURE                 Location/Qualifiers
misc_feature            1..14162
                        note = pBYe3R2K2Mc-BAHBcheZE62-122
source                  1..14162
                        mol_type = other DNA
                        organism = synthetic construct SEQUENCE: 35
cgatcggtcg attcatagaa gattagattt ttcatagtat ttttttaaag taaaccttta 60
actacggtta ggacacttt aagttaaatt taatttgaac ccttaaatta attttaaaa 120
tagataaata tcaatcatcc tgatatgctt ttgaaaaaat gaatgagaaa gatgattcaa 180
ttaaggccac atttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag atttttgta tacttcatat 360
gaaattaaaa aaaacttcat tgaacatcaa aataataata ataatcataa actcctcaat 420
attatattc ctagcttctt gaattaaatt gtttacatat tcaacgatgt aaaaaaattat 480
ttctctatct attttccttta tatcatgcat ggtttcacat atatcaaagg ataaaagcaa 540
tctatgtaaa ttatctcact ttattaagtt ttctatctga attattgaga acgtagattt 600
cttttttgcac tatccccccaa taattagcaa aacacaccta gactagattt gttttgctaa 660
cccaattgat attaattata tatgattaat atttatatgt atatgaatt ggttaataaa 720
atgcatctgg ttcatcaaag aattataaag acacgtgaca ttcattagg ataagaaata 780
tggatgatct cttcctctta ttcagataat tagtaattac acataacaca caactttgat 840
gcccacatta tagtgattag catgtcacta tgtgtgcatc ctttatttc atacattaat 900
taacttggcc aatccagaag atggacaagt ctagggtcac attgcaggg actctagctt 960
actcgccttc tttttcgaag gtttgagtac cttcagggca tcctcttgat acattacttt 1020
ccacttcgat tggggcaagc tgtagcagtt cttgcttaga ccgaattgcc atctcacaga 1080
gatgctgaag agttcgcgac cctccagaaa cggtgatact aactcctcga accgaatac 1140
tataggtaca tccgatctgg tcgaaaccga aaaatcgaga tgctgcatag ttaaccgaat 1200
ctcccgtcca agatccaagg actctgtgca gtgaagcttc cgtcctgtcg tatctgagat 1260
atctcttaaa tacaactttc ccgaaacccc agctttcctt gaaaccaagg ggattatctt 1320
gattcgaatt cgtctcatcg ttatgtagcc gccactcagt ccactcgga ctttcgttag 1380
gaagtttgaa gggagaagtt gtacctcctg atcctccatc ccaacgttca ctgttagctt 1440
gttccctagc gtcgtttcct tgtatagctc gttccatgga ttgtaaatag taattgtaat 1500
gttgtttgtt gtttgttgtt gttggtaatt gttgtaaaaa tacgctctcc aaatgaaatg 1560
aacttcctta tatagaggaa gggtcttgcg aaggatagtg ggattgtgcg tcatcccctta 1620
cgtcagtgga gatatcacat caatccactt gctttgaaga cgtggttgga acgtcttctt 1680
tttccacgat gctcctcgtg ggtgggggtc catctttggg accactgtcg gcagaggcat 1740
cttcaacgat ggccttttcct ttatcgcaat gatggcattt gtaggagcca ccttcctttt 1800
ccactatctt cacaataaag tgacagatag ctgggcaatg gaatccgagg aggtttccgg 1860
atattccct tgttgaaaaa gtctcaattg cccctttggtc ttctgagact gtatctttga 1920
tattttgga gtagacaagt gtgtcgtgct ccaccatgtt ctggcaattc cggttcgctt 1980
gctgtccata aaaccgccca gtctagctat cgccatgtaa gcccactgca agctacctgc 2040
tttctctttg cgcttgcgtt ttcccttgtc cagatagccc agtagctgac attcatccgg 2100
ggtcagcacc gtttctgcgg actggcttc tacgtgttcc gcttcctttta gcagccctg 2160
cgccctgagt gcttgcggca gcgtgaagct ggcgcgccgc tctagcagaa ggcatgtgt 2220
tgtgactccg agggggttgcc tcaaactcta tcttataacc ggcgtggagg catggaggca 2280
```

```
agggcatttt ggtaatttaa gtagttagtg gaaaatgacg tcatttactt aaagacgaag   2340
tcttgcgaca aggggggccc acgccgaatt ttaatattac cggcgtggcc ccacttatc    2400
gcgagtgctt tagcacgagc ggtccagatt taaagtagaa aagttccgc ccactagggt    2460
taaaggtgtt cacactataa aagcatatac gatgtgatgg tatttgatgg agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgctc tgccgacagt ggtcccaaag    2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgccag ctatctgtca ctttattgtg aagatagtgg     3060
aaaaggaagg tggctcctac aaatgccatc attgcgataa aggaaaggcc atcgttgaag   3120
atgcctctgc cgacagtggt cccaaagatg gaccccacc cacgaggagc atcgtggaaa    3180
aagaagacgt tccaaccacg tcttcaaagc aagtggattg atgtgatatc tccactgacg   3240
taagggatga cgcacaatcc cactatcctt cgcaagaccc ttcctctata taggaagtt    3300
catttcattt ggagaggacc tcgagaaaca aacaaaatca acaaatatag aaaataacgc   3360
atttccaatt ctttgaaatt tctgcaacat ctagaacaat ggctaacaag cacctctcat   3420
tgtctctctt ccttgtgctc cttggtcttt ctgcttctct tgcttctggt atggacattg   3480
acccttacaa agaatttgga gctactgtgg agcttctcag cttttttgcct tctgacttct   3540
ttccttctgt cagggatctc cttgacactg cctcagctct ttatagggaa gcctttgaag   3600
ctcctgagca ttgctcacct caccatactg cactcaggca agccattctc tgctggggag   3660
aattgatgac tcttgctacc tgggtgggta acaatctaga ggatccagca tccagagatc   3720
ttgttgttaa ctatgttaat actaatgtgg gtttgaagat caggcaactc ttgtggtttc   3780
atatatcttg ccttacttt ggaagagaga ctgtacttga atttggtc tcttttggag      3840
tgtggattag aactcctcca gcctatagac caccaaatgc cctatccttg tcgactcttc   3900
cagaaactac tgttgttgga ggtctggtg gatcaggagg ttccggtggt tctgaggtt     3960
ccggaatgga cattgaccct acaaagaatt tggagctac tgtggagctt ctcagctttt    4020
tgccttctga cttcttcct tctgtcaggg atctccttga cactgcctca gctctttata   4080
gggaagcctt ggagtctcct gagcattgct cacctcacca tactgcactc aggcaagcca   4140
ttctctgctg gggagaattg atgactcttg ctacctgggt gggtaacaat cttgagggag   4200
gttcaggtgg atccgaggct tcaatttcag acatggctag tgacagccgt tgcccaacac   4260
aaggtgaagc ctaccttgac aagcaatcag cactcaatca tgtgtgcaag agaacattgg   4320
tggacagagg ttgggggaaac ggatgtggac tttccggtaa gggaagcctc gtgacatgcg   4380
ctaaattcgc ttgctccact agtggaggtt ctggtggaga tccagcatcc agagatcttg   4440
ttgttaacta tgttaatact aatgtgggtt tgaagatcag gcaactcttg tggtttcata   4500
tatcttgcct tacttttgga agagagactg tacttgaata tttggtctct tttggagtgt   4560
ggattagaac tcctccagcc tatagaccac caaatgcccc tatcttgtcg actcttccag   4620
aaactactgt tgttcgaaga agggacaggg gcagatcccc tagacgtaga actcccagcc   4680
ctagaagaag gagatcccca tcctctaggc gtagataaga gctcgaagtg acatcacaaa   4740
gttgaaggta ataaagccaa attaattaag acattttcat aatgatgtca agaatgcaaa   4800
gcaaattgca taactgcctt tatgcaaaac attaatataa tataaattat aaagaactgc   4860
gctctctgct tcttatttc ttagcttcat ttattagtca ctagctgttc agaattttca    4920
gtatctttg atattactaa gaacctaatc acacaatgta tattcttatg caggaaaagc    4980
agaatgctga gctaaaagaa aggcttttc catttcgag acaatgag aaaagaagaa        5040
gaagaagaag aagaagaaga agaagaaaag agtaaataat aaagccccac agaggcgaa    5100
gttcttgtag ctccatgtta tctaagttat tgatattgtt tgccctatat tttatttctg   5160
tcattgtgta tgttttgttc agtttcgatc tccttgcaaa atgcagagat tatgagatga   5220
ataaactaag ttatattatt atacgtgtta atattctcct cctctctcta gctagccttt   5280
tgttttctct tttctttatt tgatttttctt taaatcaatc catttagga gagggccagg    5340
gagtgatcca gcaaaacatg aagattagaa gaaacttccc tcttttttt cctgaaaaca    5400
atttaacgtc gagatttatc tcttttgta atggaatcat ttctacagtt atgacgaatt     5460
gtccgcaaaa atcaccagtc tctctctaca aatctatctc tctctatttt tctccagaat   5520
aatgtgtgag tagttcccag ataagggaat tagggttctt atagggtttc gctcatgtgt   5580
tgagcatata agaaacccctt agtatgtatt tgtatttgta aaatacttct atcaataaaa   5640
tttctaattc ctaaaaccaa aatccagtga ccctaaaacc aaaatccagt gacgaattct   5700
cgattaaaaaa tcccaattat atttggtcta atttagtttg gtattgagta aaacaaattc   5760
gaaccaaacc aaaatataaa tatatagttt ttatatatat gcctttaaga cttttttag    5820
aattttcttt aaaaaatatc taggtacatc aacgaaaaat tagtcaaacg actaaaataa   5880
ataaatatca tgtgttatta agaaaattct cctataagaa tattttaata gatcatatgt   5940
ttgtaaaaaa aattaatttt tactaacaca tatatttact tatcaaaaat ttgacaaagt   6000
aagattaaaa taatattcat ctaacaaaaa aaaaaccaga aaatgctgaa aacccggcaa   6060
aaccgaacca atccaaaccg atatagttgg tttggttga ttttgatata aaccgaacca    6120
actcggtcca tttgcacccc taatcataat agctttaata tttcaagata ttattaagtt   6180
aacgttgtca atatcctgga aattttgcaa aatgaatcaa gcctatatgg ctgtaatatg   6240
aatttaaaag cagctcgatg tggtggtaat atgtaattta cttgattcta aaaaaatatc   6300
ccaagtatta ataatttctg ctaggaagaa ggttagctac gatttacagc aaagccagaa   6360
tacaagaaac cataaagtga ttgaagctcg aaatatacga aggaacaaat attttaaaa    6420
aaatacgcaa tgacttggaa caaaagaaag tgatatattt tttgttctta aacaagcatc   6480
ccctctaaag aatggcagtt ttcctttgca tgtaactatt atgctccctt cgttacaaaa   6540
attttggact actattggga acttcttctg aaaaagtgg taccgagtgt acttcaagtc    6600
agttggaaat caataaaatg attatttat gaatatattt cattgtgcaa gtagataaa     6660
attacatatg ttacataaca cacgaaataa acaaaaaaac acaatccaaa acaaacaccc   6720
caaacaaaat aacactatat atatcctcgt atgaggagag gcacgttcag tgactcgacg   6780
attcccgagc aaaaaaagtc tccccgtcac acatatagtg ggtgacgcaa ttatcttcaa   6840
agtaatcctc ctgttgactt gtcattgata acatccagtc ttcgtcagga ttgcaaagaa   6900
ttatagaagg gatcccacct tttatttct tcttttttcc atatttaggg ttgacagtga    6960
aatcagactg gcaacctatt aattgcttcc acaatgggac gaacttgaag gggatgtcgt   7020
```

```
cgatgatatt ataggtggcg tgttcatcgt agttggtgaa gtcgatggtc ccgttccagt   7080
agttgtgtcg cccgagactt ctagcccagg tggtctttcc ggtacgagtt ggtccgcaga   7140
tgtagaggct ggggtgtctg accccagtcc ttccctcatc ctggttagat cggccatcca   7200
ctcaaggtca gattgtgctt gatcgtagga gacaggatgt atgaaagtgt aggcatcgat   7260
gcttacatga tataggtgcg tctctctcca gttgtgcaga tcttcgtggc agcggagatc   7320
tgattctgtg aagggcgaca cgtactgctc aggttgtgga ggaaataatt tgttggctga   7380
atattccagc cattgaagct ttgttgccca ttcatgaggg aactcttctt tgatcatgtc   7440
aagatactcc tccttagacg ttgcagtctg gataatagtt cgccatcgtg cgtcagattt   7500
gcgaggagac acctlatgat ctcggaaatc tcctctggtt ttaatatctc cgtcctttga   7560
tatgtaatca aggacttgtt tagagtttct agctggctga atattagggt gatttccttc   7620
aaaatcgaaa aaagaaggat ccctaataca aggtttttta tcaagctgga taagagcatg   7680
atagtgggta gtgccatctt gatgaagctc agaagcaaca ccaaggaaga aaataagaaa   7740
aggtgtgagt ttctcccaga gaaactggaa taaatcatct ctttgagatg agcacttggg   7800
gtaggtaagg aaaacatatt tagattggag tctgaagttc ttgctagcag aaggcatgtg   7860
gttgtgactc cgaggggttg cctcaaactc tatcttataa ccggcgtgga ggcatggagg   7920
caagggcatt ttggtaattt aagtagttag tggaaaatga cgtcatttac ttaaagacga   7980
agtcttgcga caagggggc ccacgccaaa ttttaatatt accggcgtgg ccccacctta   8040
tcgcgagtgc tttagcacga gcggtccaga tttaaagtag aaaagttccc gcccactagg   8100
gttaaaggtg ttcacactat aaaagcatat acgatgtgat ggtatttgat ggagcgtata   8160
ttgtatcagg tatttccgtc ggatacgaat tattcgtacg gccggaccgg tcccctaggc   8220
cggccaattc gagatcggcc gcggctgagt ggctccttca atcgttgcgg ttctgtcagt   8280
tccaaacgta aaacggcttg tcccgcgtca tcggcgaggg tcataacgtg actcccttaa   8340
ttctccgctc atgatcagat tgtcgtttcc cgccttcagt ttaaactatc agtgtttgac   8400
aggatatatt ggcgggtaaa cctaagagaa aagagcgttt attagaataa tcggatattt   8460
aaaagggcgt gaaaaggttt atccgttcgt ccatttgtat gtgcatgcca accacagggt   8520
tccccagatc tggcgccggc cagcgagacg agcaagattg gccgccgccc gaaacgatcc   8580
gacagcgcgc ccagcacagg tgcgcaggca aattgcacca acgcatacag cgccagcaga   8640
atgccatagt gggcggtgac gtcgttcgag tgaaccagat cgcgcaggag gcccggcagc   8700
accggcataa tcaggccgat gccgacacgc tcgagcgcga cagtgctcag aattacgatc   8760
agggtatgt tgggtttcac gtctggcctc cggagactgt catacgcgta aaaaggccgc   8820
gttgctggcg ttttttccata ggctccgccc cctgacgag catcacaaaa atcgacgctc   8880
aagtcagagg tggcgaaacc cgacaggact ataagatac caggcgtttc ccctggaag   8940
ctccctcgtg cgctctcctg ttccgaccct gccgcttacc ggatacctgt ccgcctttct   9000
cccttcggga agcgtggcgc tttctcatag ctcacgctgt aggtatctca gttcggtgta   9060
ggtcgttcgc tccaagctgg gctgtgtgca cgaaccccc gttcagcccg accgctgcgc   9120
cttatccggt aactatcgtc ttgagtccaa cccggtaaga cacgacttat cgccactggc   9180
agcagccact ggtaacagga ttagcagagc gaggtatgta ggcggtgcta cagagttctt   9240
gaagtggtgg cctaactacg gctacactag aaggacagta tttggtatct gcgctctgct   9300
gaagccagtt accttcggaa aaagagttgg tagctcttga tccggcaaac aaaccaccgc   9360
tggtagcggt ggtttttttg tttgcaagca gcagattacg cgcagaaaaa aaggatctca   9420
agaagatcct ttgatctttt ctacggggtc tgacgctcag tggaacgaaa actcacgtta   9480
agggattttg gtcatgagat tatcaaaaag gatcttcacc tagatccttt taaattaaaa   9540
atgaagttt aaatcaatct aaagtatata tgagtaaact tggtctgaca gttaccatgt   9600
ttacggcagt gagagcagag atagcgctga tgtccggcgg tgcttttgcc gttacgcacc   9660
accccgtcag tagctgaaca ggagggacag ctgatagaca cagaagccac tggagcacct   9720
caaaaacacc atcatacact aaatcagtaa gttggcagca tcacccataa ttgtggtttc   9780
aaaatcgcct ccgtcgatac tatgttatac gccaactttg aaaacaactt tgaaaaagct   9840
gttttctggt atttaaggtt ttagaatgca aggaacagtg aattggagtt cgtcttgtta   9900
taattagctt cttggggtat cttaaatac tgtagaaaag aggaaggaaa taataaatgg   9960
ctaaaatgag aatatcaccg gaattgaaaa aactgatcga aaaataccgc tgcgtaaaag  10020
atacggaagg aatgtctcct gctaaggtat ataagctggt gggagaaaat gaaaacctat  10080
atttaaaaat gacggacagc cggtataaag ggaccaccta tgatgtggaa cgggaaaagg  10140
acatgatgct atggctggaa ggaaagctgc ctgttccaaa ggtcctgcac tttgaacggc  10200
atgatggctg gagcaatctg ctcatgagtg aggccgatgg cgtcctttgc tcggaagagt  10260
atgaagatga acaaagccct gaaaagatta tcgagctgta tgcggagtgc atcaggctct  10320
ttcactccat cgacatatcg gattgtccct atacgaatag cttagacagc cgcttagccg  10380
aattggatta cttactgaat aacgatctgg ccgatgtgga ttgcgaaaac tgggaagaag  10440
acactccatt taaagatccg cgcgagctgt atgatttttt aaagacggaa agcccgaag  10500
aggaacttgt cttttcccac ggcgactgg gagacagcaa catcttttgt aaagatggca  10560
aagtaagtgg ctttattgat cttgggagaa gcggcagggc ggacaagtgg tatgacattg  10620
ccttctgcgt ccggtcgatc agggaggata tcggggaaga acagtatgtc gagctatttt  10680
ttgacttact ggggatcaag cctgattggg agaaaataaa atattatat ttactggatg  10740
aattgtttta gtacctagat gtggcgcaac gatgccggcg acaagcagga gcgcaccgac  10800
ttcttccgca tcaagtgttt tggctctcag gccgaggccc acggcaagta tttgggcaag  10860
gggtcgctgg tattcgtgca gggcaagatt cggaatacca agtacgagaa ggacggccag  10920
acggtctacg gaccgacttc cattgccgat aaggtggatt atctgacac caaggcacca  10980
ggcgggtcaa atcaggaata agggcacatt gccccgcgt gagtcgggc aatcccgcaa  11040
ggagggtgaa tgaatcggac gtttgaccgg aaggcataca ggcaagaact gatcgacgcg  11100
gggttttccg ccgaggatgc cgaaaccatc gcaagccgca acgcaagatca tgcgccccgc  11160
gaaaccttcc agtccgtcgg ctcgatggtc cagcaagcta cggccaagat cgagcgcgac  11220
agcgtcgaac tggctccccc tgccctgccc gcgccatcgg ccgccgtgga gcgttcgcgt  11280
cgtctcgaac aggaggcggc aggtttggcg aagtcgatga ccatcgacac gcgaggaact  11340
atgacgacca agaagcgaaa aaccgccggc gaggacctgc aaaacaggt cagcgaggcc  11400
aagcaggcc cgttgctgaa acacaggaga cagatga aggaaatgca gctttcttg  11460
ttcgatattg cgccgtggcc ggacacgatg cgagcgatgc caaacgacac ggcccgctct  11520
gccctgttca ccacgcgcaa caagaaaatc ccgcgcgagg cgctgcaaaa caaggtcatt  11580
ttccacgtca caaggacgt gaagatcacc tacaccggcg tcgagctgcg ggccgacgat  11640
gacgaactgg tgtggcagca ggtgttggag tacgcgaagc gcaccccat cggcgagccg  11700
atcaccttca cgttctacga ctttgccag gacctgggct ggtcgatcaa tggccggtat  11760
```

```
tacacgaagg ccgaggaatg cctgtcgcgc ctacaggcga cggcgatggg cttcacgtcc    11820
gaccgcgttg ggcacctgga atcggtgtcg ctgctgcacc gcttccgcgt cctggaccgt    11880
ggcaagaaaa cgtcccgttg ccaggtcctg atcgacgagg aaatcgtcgt gctgtttgct    11940
ggcgaccact acacgaaatt catatgggag aagtaccgca agctgtcgcc gacggcccga    12000
cggatgttcg actatttcag ctcgcaccgg gagccgtacc cgctcaagct ggaaaccttc    12060
cgcctcatgt gcggatcgga ttccaccgcg gtgaagaagt ggcgcgagca ggtcggcgaa    12120
gcctgcgaag agttgcgagg cagcggcctg tggaacacg cctgggtcaa tgatgacctg    12180
gtgcattgca aacgctaggg ccttgtgggg tcagttccgg ctgggggttc agcagccagc    12240
gctttactgg catttcagga acaagcgggc actgctcgac gcacttgctt cgctcagtat    12300
cgctcgggac gcacggccgcg ctctacgaac tgccgataaa cagaggatta aaattgacaa    12360
ttcaatggca aggactgcca gcgctgccat ttttggggtg aggccgttcg cggccgaggg    12420
gcgcagcccc tggggggatg ggaggcccgc gttagcgggc cggagggtt cgagaagggg    12480
gggcacccc cttcggcgtg cgcggtcacg cgcacagggc gcagccctgg ttaaaaacaa    12540
ggtttataaa tattggttta aaagcaggtt aaaagacagg ttagcggtgg ccgaaaaacg    12600
ggcggaaacc cttgcaaatg ctggattttc tgcctgtgga cagcccctca aatgtcaata    12660
ggtgcgcccc tcatctgtca gcactctgcc cctcaagtgt caaggatcgc gcccctcatc    12720
tgtcagtagt cgcgcccctc aagtgtcaat accgcagggc acttatcccc aggcttgtcc    12780
acatcatctg tgggaaactc gcgtaaaatc aggcgttttc gccgatttgc gaggctggcc    12840
agctccacgt cgccggccga aatcgagcct gcccctcatc tgtcaacgcc gcgccgggtg    12900
agtcggcccc tcaagtgtca acgtccgccc ctcatctgtc agtgagggcc aagttttccg    12960
cgaggtatcc acaacgccgg cggccgcggt gtctcgcaca cggcttcgac ggcgtttctg    13020
gcgcgtttgc agggcatag acggccgcca gccagcggc gagggcaacc agccggtga    13080
gcgtcgcaaa ggcgctcggt cttgccttgc tcgtcgagat ctgggtcga tcagccgggg    13140
atgcatcagg ccgacagtcg gaacttcggg tccccgacct gtaccattcg gtgagcaatg    13200
gatagggag ttgatatcgt caacgttcac ttctaaagaa atagcgccac tcagcttcct    13260
cagcgccttt atccagcgat ttcctattat gtcggcatag ttctcaagat cgacagccg    13320
tcacggttaa gcgagaaatg aataagaagg ctgataattc ggatctctgc gagggagatg    13380
atatttgatc acaggcagca acgctctgtc atcgttacaa tcaacatgct accctccgcg    13440
agatcatccg tgtttcaaac ccggcagctt agttgccgtt cttccgaata gcatcggtaa    13500
catgagcaaa gtctgcgcc ttacaacggc tctcccgctg acgccgtccc ggactgatgg    13560
gctgcctgta tcgagtggtg attttgtgcc gagctgccgg tcggggagct gttggctggc    13620
tggtggcagg atatattgtg gtgtaaacaa attgacgctt agacaactta ataacacatt    13680
gcggacgttt ttaatgtact ggggtggttt ttcttttcac cagtgagacg ggcaacagct    13740
gattgccctt caccgcctgg ccctgagaga gttgcagcaa gcggtccacg ctggtttgcc    13800
ccagcaggcg aaaatcctgt ttgatggtgg ttccgaaatc ggcaaaatcc cttataaatc    13860
aaaagaatag cccgagatag ggttgagtgt tgttccagtt tggaacaaga gtccactatt    13920
aaagaacgtg gactccaacg tcaaagggcg aaaaaccgtc tatcagggcg atggcccact    13980
acgtgaacca tcacccaaat caagtttttt ggggtcgagg tgccgtaaag cactaaatcg    14040
gaaccctaaa gggagccccc gatttagagc ttgacgggga aagccggcga acgtggcgag    14100
aaaggaaggg aagaaagcga aaggagcggg cgccattcag gctgcgcaac tgttgggaag    14160
gg                                                                  14162

SEQ ID NO: 36         moltype = DNA  length = 17977
FEATURE               Location/Qualifiers
misc_feature          1..17977
                      note = pBYR11eM-h6D8-ZEFL62
source                1..17977
                      mol_type = other DNA
                      organism = synthetic construct
SEQUENCE: 36
cgatcggtcg attcatagaa gattagattt ttcatagtat ttttttaaag taaacctta     60
actacggtta ggacactttt aagttaaatt taatttgaac ccttaaatta attttaaaa    120
tagataaata tcaatcatcc tgatatgctt ttgaaaaaat gaatgagaaa gatgattcaa    180
ttaaggccac attttaatca tgactaaaat aatatacagt ataatttcat atatatttgc    240
tttaaaaaaa aattgacaat ccattcgttt ctagcaataa atttcttcaa ccacaaaatt    300
attaaagata actacggcat agaaacaaaa atctatgaag aattttttgta tacttcatat    360
gaaattaaaa aaaacttcat tgaacatcaa aataataata ataatcataa actcctcaat    420
atttatattc ctagcttctt gaattaaatt gtttacatat tcaacgatgt aaaaaattat    480
ttctctatct atttttcctta tatcatgcat ggtttcacat atcatcaaagg ataaaagcaa    540
tctatgtaaa ttatctcact ttattaagtt ttctatctga attattgaga acgtagattt    600
cttttttgcac tatcccccaa taattagcaa aacacaccta gactagttt gttttgctaa    660
cccaattgat attaattata tatgattaat atttatatgt atatgaatt ggttaataaa    720
atgcatctgg ttcatcaaag aatttataaag acacgtgaca ttcatttagg ataagaaata    780
tggatgatct cttttctctta ttcagataat tagtaattac acataacaca caacttgat    840
gcccacatta tagtgattag catgtcacta tgtgtgcatc cttttatttc atacattaat    900
taacttggcc aatccagaag atggacaagt ctagggtcac attgcagggt actctagctt    960
actcgccttc tttttcgaag gtttgagtac cttcaggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctgca aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtggggtc catctttggg accactgtcg gcagaggcat   1740
```

```
cttcaacgat ggcctttcct ttatcgcaat gatggcattt gtaggagcca ccttccttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttcctta gcagcccttg    2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca aggggggccc acgccgaatt taatattac cggcgtggcc ccacttatc    2400
gcgagtgctt tagcacgagc ggtccagatt taaagtagaa aagttccgc ccactagggt    2460
taaaggtgtt cacactataa aagcatatac gatgtgatgg tatttgatgg agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gactttcaa caaagggtaa tatccggaaa cctcctcgga ttccattgcc     2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gaccccacc cacgaggagc atcgtggaaa    3180
aagaagacgt tccaaccacg tcttcaaagc aagtggattg atgtgatatc tccactgacg   3240
taagggatga cgcacaatcc cactatcctt cgcaagactc ttcctctata taaggaagtt   3300
catttcattt ggagaggacc tcgagaaaca aacaaaatca acaatatag aaaataacgc     3360
atttccaatt ctttgaaatt tctgcaacat ctagaacaat gggatggtct tgcatcatac   3420
tctttcttgt tgcaactgct acaggtgtcc actctgatgt tcagcttctc gagtctggag   3480
gtgtcttgt gcaacctgga ggttccttga gactctcctg tgcagcttca gggtttgact    3540
tcagtaggta ctggatgagt tgggttcgtc aagctcctgg gaaaggacta gaatggattg   3600
gagagatcaa tccagattca agtaccatca actatactcc atctctgaag gatcgcttca   3660
ccatttccag agacaatgcc aagaacacgt tgtatcttca gatgaacagc ttgaggactg   3720
aagacacagc cttgtactac tgcacaagac agggctatgg ctacaactac tggggtccaa   3780
gcaccactgt cacagtgtct tcagctagca ccaaagtcc atcggtcttt ccactggcac   3840
cttcttccaa gagtacttct ggaggcacag ctgcactggg ttgtcttgtc aaggactact   3900
ttccagaacc tgttacggtt tcgtggaact caggtgctct gaccagtgga gtgcacacct   3960
ttccagctgt tcttcagtcc tcaggattgt attctcttag cagtgttgtg actgttccat   4020
cctcagcctt gggcactcag acctacatct gcaatgtgaa tcacaaaccc agcaacacca   4080
aggttgacaa gaaagttgag cccaagtctt gtgacaagaa tcatacgtgt ccaccgtgcc   4140
cagcacctga acttcttgga ggaccgtcag tcttcttgtt tcctccaaag cctaaggata   4200
ccttgatgat ctccaggact cctgaagtca catgtgtagt tgtggatgtg agccatgaag   4260
atcctgaggt gaagttcaac tggtatgtgg atggtgtaa gccaagacaa gccgagaca    4320
agccgagaga ggaacagtac aacagcacgt acagggttgt ctcagttctc actgttctcc   4380
atcaagattg gttgaatggc aaagagtaca gtgcaaggt ctccaacaaa gccctcccag    4440
cccccattga gaagaccatt tccaaagcga agggcaaacc ccgtgaacca caagtgtaca   4500
cacttcctcc atctcgcgat gaactgacca gaaaccaggt cagcttgact tgcctggtga   4560
aaggcttcta tccctctgac atagctgtag agtgggagag caatgggcaa ccggagaaca   4620
actacaagac tacacctccc gttctcgatt ctgacggctc cttcttcctc tacagcaagc   4680
tcacagtgga caagagcagg tggcaacaag gaatgtcttc tcatgctcc gtgatgcatg    4740
aggctcttca caatcactac acacagaaga tctctccttt gtctccgggt aaaggaggtg   4800
gcggatcagg tggaggcggt tcaggcggag gtggatccaa gggcgtgtca tactccttgt   4860
gtaccgctgc cttcacattc accaagatcc cggctgaaac actccacgga accgttaccg   4920
tggaggtcca atacgccggt acagatggac cttgcaaggt tccagctcag atggcggtgg   4980
acatgcaaac tcttacccca gttggaaggt tgattaccgc taaccccgtt atcactgaaa   5040
gcactgagaa ctcaagatg atgttggaac ttgatccacc attcggtgac tcttacattg    5100
tcattggtgt gggagagaag aagatcaccc accactggca caggagtggt agcactagtc   5160
ataacactcc tgtttacaag ctggacatat ctgaggcaac tcaataagag ctcaaagcag   5220
aatgctgagc taaaagaaag gcttttttcca ttttcgagag acaatgagaa aagaagaaga   5280
agaagaagaa gaagaagaa aagaaaagag taaataataa agccccacag gaggcgaagt    5340
tcttgtagct ccatgttatc taagttattg atattgtttg ccctatattt tatttctgtc   5400
attgtgtatg ttttgttcag tttcgagaat tctcgattaa aaatcccaat tatatttggt   5460
ctaatttagt ttggtattga gtaaaacaaa ttcgaaccaa accaaaatat aaatatatag   5520
ttttatata tatgccttta agactttta tagaattttc tttaaaaaat atctagaaat     5580
atttgcgact cttctggcat gtaatatttc gttaaatatg aagtgctcca tttttattaa   5640
ctttaaataa ttggttgtac gatcactttc ttatcaagtg ttactaaaat gcgtcaatct   5700
ctttgttctt ccatattcat atgtcaaaat ctatcaaaat tcttatatat cttttcgaa    5760
tttgaagtga aatttcgata atttaaaatt aaatagaaca tatcattatt taggtatcat   5820
attgatttt atacttaatt actaaatttg gttaacttg aaagtgtaca tcaacgaaaa    5880
attagtcaaa cgactaaaat aaataaatat catgtgttat taagaaaatt ctcctataag   5940
aatatttta tagatcatat gtttgtaaaa aaaattaatt tttactaaca catatattta   6000
cttatcaaaa atttgacaaa gtaagattaa ataatattc atctaacaaa aaaaaaacca    6060
gaaaatgctg aaaaccccggc aaaaccgaac caatccaaac cgatatagtt ggtttggttt   6120
gattttgata taaaccgaac caactcggtc catttgcacc ctaatcata atagctttaa    6180
tatttcaaga tattattaag ttaacgttgt caatatcctg gaattttgc aaaatgaatc     6240
aagcctatat ggctgtaata tgaatttaaa agcagctcga tgtggtggta atatgtaatt   6300
tacttgattc taaaaaaata tcccaagtat taataatttc tgctaggaag aaggttagct   6360
acgatttaca gcaaagccag aatacaaaga accataaagt gattgaagct cgaaatatac   6420
gaaggaacaa atatttttaa aaaatacgc aatgacttgg aacaaaagaa agtgatatat     6480
```

```
tttttgttct taaacaagca tcccctctaa agaatggcag ttttcctttg catgtaacta 6540
ttatgctccc ttcgttacaa aaattttgga ctactattgg gaacttcttc tgaaaatagt 6600
ggtaccgagt gtacttcaag tcagttggaa atcaataaaa tgattatttt atgaatatat 6660
ttcattgtgc aagtagatag aaattacata tgttacataa cacacgaaat aaacaaaaaa 6720
acacaatcca aaacaaacac cccaaacaaa ataacactat atatatcctc gtatgaggag 6780
aggcacgttc agtgactcga cgattcccga gcaaaaaaag tctccccgtc acacatatag 6840
tgggtgacgc aattatcttc aaagtaatcc ttctgttgac ttgtcattga taacatccag 6900
tcttcgtcag gattccaaag aattatagaa gggatcggtc aacatggtgg agcacgacac 6960
acttgtctac tccaaaaata tcaaagatac agtctcagaa gaccaaaggg caattgagac 7020
ttttcaacaa agggtaatat ccggaaacct cctcggattc cattgcccag ctatctgtca 7080
ctttattgtg aagatagtgg aaaaggaagg tggctcctac aaatgccatc attgcgataa 7140
aggaaaggcc atcgttgaag atgcctctgc cgacagtggt cccaaagatg acccccacc 7200
cacgaggagc atcgtggaaa aagaagacgt tccaaccacg tcttcaaagc aagtggattg 7260
atgtgataac atggtggagc acgacacact tgtctactcc aaaaatatca aagatacagt 7320
ctcagaagac caaagggcaa ttgagacttt tcaacaaagg gtaatatccg gaaacctcct 7380
cggattccat tgcccagcta tctgtcactt tattgtgaag atagtggaaa aggaaggtgg 7440
ctcctacaaa tgccatcatt gcgataaagg aaaggccatc gttgaagatg cctctgccga 7500
cagtgtccc aaagatggac cccacccac gaggagcatc gtggaaaaag aagacgttcc 7560
aaccacgtct tcaaagcaag tggattgatg tgatatctcc actgacgtaa gggatgacgc 7620
acaatcccac tatccttcgc aagacccttc ctctatataa ggaagttcat ttcatttgga 7680
gaggacctcg agtattttta caacaattac caacaacaac aaacaacaaa caacattaca 7740
attactattt acaatctaga acaatgggat ggtcttgcat cattctcttc ttggtagcca 7800
cagctacagg tgtccactcc gatgttttga tgactcaaag ccctctctca cttcctgtga 7860
ctcttggaca gcccgcatcc atatcttgca gatctagtca gagtattgtt catagtaacg 7920
gcaacaccta cttggaatgg tatctgcaga aaccaggcca gtctccaaag cttctgatct 7980
acaaggcttc caatcgtttc tctggtgtcc cagacaggtt tagtggcagt ggatcaggga 8040
ctgacttcac attgaagatc agcagagttg aggctgaaga tgcgggagtg tactattgtc 8100
ttcaaggttc acatgttccg tcaacgtttg gaggtgggac caaagtggag atcaagactg 8160
ttgcggcgc atctgtcttc atcttcctc catctgatga acaactcaag tctgaactg 8220
cttctgttgt gtgccttctg aacaacttct atcctagaga agccaaagta cagtggaagg 8280
ttgacaatgc tcttcaatca ggtaactccc aggagagtgt cacagagcaa gattccaagg 8340
attccaccta cagcctctca agtaccttga cgttgagcaa ggcagactat gagaaacaca 8400
aagtgtacgc atgcgaagtc actcatcagg gcctgtcatc acccgtgaca aagagcttca 8460
acaggggaga gtgttaggta ccgagctcga agtgacatca caaagttgaa ggtaataaag 8520
ccaaattaat taagacattt tcataatgat gtcaagaatg caaagcaaat tgcataactg 8580
cctttatgca aaacattaat ataatataaa ttataaagaa ctgcgctctc tgcttcttat 8640
tttcttagct tcatttatta gtcactagct gttcagaatt ttcagtatct tttgatatta 8700
ctaagaacct aatcacacaa tgtatattct tatgcaggaa aagcagaatg ctgagctaaa 8760
agaaaggctt tttccatttt cgagagacaa tgagaaaaga agaagaagaa gaagaagaag 8820
aagaagaaga aaagagtaaa taataaagcc ccacaggagg cgaagttctt gtagctccat 8880
gttatctaag ttattgatat tgtttgccct atatttatt tctgtcattg tgtatgtttt 8940
gttcagtttc gatctccttg caaatgcag agattatgag atgaataaac taagttatat 9000
tattatacgt gttaatattc tcctcctctc tctagctagc cttttgtttt ctcttttttct 9060
tatttgattt tcttaaatc aatccatttt aggagagggc cagggagtga tccagcaaaa 9120
catgaagatt agaagaaact tccctctttt ttttcctgaa aacaatttaa cgtcgagatt 9180
tatctctttt tgtaatggaa tcatttctac agttatgacg aattctcgat taaaatccc 9240
aattatattt ggtctaattt agtttggtat tgagtaaaac aaattcgaac caaaccaaaa 9300
tataaatata tagttttat atatatgcct ttaagacttt ttatagaatt ttctttaaaa 9360
aatatctaga aatatttgcg actcttctgg catgtaatat ttcgttaaat atgaagtgct 9420
ccattttat taacttaaa taattggttg tacgatcact ttcttatcaa gtgttactaa 9480
aatgcgtcaa tctcttttgtt cttccatatt catatgtcaa aatctatcaa aattcttata 9540
tatctttttc gaatttgaag tgaaatttcg ataatttaaa attaaataga acatatcatt 9600
atttaggtat catattgatt tttatactta attactaaat ttggttaact ttgaaagtgt 9660
acatcaacga aaaattagtc aaacgactaa aataaataaa tatcatgtgt tattaagaaa 9720
attctcctat aagaatattt taatagatca tatgttttgta aaaaaaatta attttacta 9780
acacatatat ttacttatca aaaatttgac aaagtaagat taaaataata ttcatctaac 9840
aaaaaaaaaa ccagaaaatg ctgaaaaccc ggcaaaaccg aaccaatcca aaccgatata 9900
gttggtttgg tttgattttg atataaaccg aaccaactcg gtccatttgc acccctaatc 9960
ataatagctt taatatttca agatattatt aagttaacgt tgtcaatatc ctggaaattt 10020
tgcaaaatga atcaagccta tatggctgta atatgaattt aaaagcagct cgatgtggtg 10080
gtaatatgta atttacttga ttctaaaaaa atatcccaag tattaataat ttctgctagg 10140
aagaaggtta gctacgattt acagcaaagc cagaatacaa agaaccataa agtgattgaa 10200
gctcgaaata tacgaaggaa caaatatttt taaaaaaata cgcaatgact tggaacaaaa 10260
gaaagtgata tattttttgt tcttaaacaa gcatccctca taagaatgg cagttttcct 10320
ttgcatgtaa ctattatgct cccttcgtta caaaaatttt ggactactat tgggaacttc 10380
ttctgaaaat agtggtaccg agtgtacttc aagtcagttg gaaatcaata aaatgattat 10440
tttatgaata tatttcattg tgcaagtaga tagaaaattac atatgttaca taacacacga 10500
aataacaaaa ccaaaacaaa caccccaaac aaaataacac tatatatatc 10560
ctcgtatgag gagggcacg ttcagtgact cgacgattcc cgagcaaaaa aagtctcccc 10620
gtcacacata tagtgggtga cgcaattatc ttcaaagtaa tccttctgtt gacttgtcat 10680
tgataacatc cagtctcgt caggattgca agaattata gaagggatcc cacctttat 10740
ttcttcttt tttccatatt tagggttgac agtgaaatca gactggcaac ctattaattg 10800
cttccacaat gggacgaact tgaaggggat gtcgtcgatg atattatagg tggcgtgttc 10860
atcgtagtg gtgaagtcga tggtcccgtt ccagtagttg tgtcgcccga gactctagc 10920
ccaggtggtc tttccggtac gagttggtcc gcagatgtag aggctgggt gtctgaccc 10980
agtccttccc tcatcctggt tagatcggcc atccactcaa ggtcagattg tgcttgatcg 11040
taggagacag gatgtatgaa agtgtaggca tcgatgctta catgatatag gtgcgtctct 11100
ctccagttgt gcagatcttc gtggcagcgg agatctgatt ctgtgaaggg cgacacgtac 11160
tgctcaggtt gtggaggaaa taatttgttg gctgaatatt ccagccattg aagctttgtt 11220
```

```
gcccattcat gagggaactc ttctttgatc atgtcaagat actcctcctt agacgttgca   11280
gtctggataa tagttcgcca tcgtgcgtca gatttgcgag gagacacctt atgatctcgg   11340
aaatctcctc tggttttaat atctccgtcc tttgatatgt aatcaaggac ttgtttagag   11400
tttctagctg gctggatatt agggtgattt ccttcaaaat cgaaaaaaga aggatccta    11460
atacaaggtt ttttatcaag ctggataaga gcatgatagt gggtagtgcc atcttgatga   11520
agctcagaag caacaccaag gaagaaaata agaaaaggtg tgagtttctc ccagagaaac   11580
tggaataaat catctctttg agatgagcac ttggggtagg taaggaaaac atatttagat   11640
tggagtctga agttcttgct agcagaaggc atgttgttgt gactccgagg ggttgcctca   11700
aactctatct tataaccggc gtggaggcat ggaggcaagg gcattttggt aatttaagta   11760
gttagtggaa aatgacgtca tttacttaaa gacgaagtct tgcgacaagg ggggcccacg   11820
ccgaattta atattaccgg cgtggcccca ccttatcgcg agtgctttag cacgagcggt    11880
ccagatttaa agtagaaaag ttcccgccca ctagggttaa aggtgttcac actataaaag   11940
catatacgat gtgatggtat ttgatggagc gtatattgta tcaggtattt ccgtcggata   12000
cgaattattc gtacggccgg accggtcccc taggccgaac aattcgagat cggccgcggc   12060
tgagtggctc cttcaatcgt tgcggttctg tcagttccaa acgtaaaacg gcttgtcccg   12120
cgtcatcggc gggggtcata acgtgactcc cttaattctc cgctcatgat cagattgtcg   12180
tttcccgcct tcagtttaaa ctatcagtgt ttgacaggat atattggcgg gtaaacctaa   12240
gagaaagag cgtttattag aataatcgga tatttaaaag ggcgtgaaaa ggtttatccg    12300
ttcgtccatt tgtatgtgca tgccaaccac agggttcccc agatctggcg ccggccagcg   12360
agacgagcaa gattggccgc cgcccgaaac gatccgacag cgcgcccagc acaggtgcgc   12420
aggcaaattg caccaacgca tacagcgcca gcagaatgcc atagtgggcg gtgacgtcgt   12480
tcgagtgaac cagatcgcgc aggaggcccg gcagcaccgg cataatcagg ccgatgccga   12540
cagcgtcgag cgcgacagtg ctcagaatta cgatcagggg tatgttgggt ttcacgtctg   12600
gcctccggaa actgtcatac gcgtaaaaag gccgcgttgc tggcgttttt ccataggctc   12660
cgccccctg acgagcatca caaaaatcga cgctcaagtc agaggtggcg aaacccgaca    12720
ggactataaa gataccaggc gtttccccct ggaagctccc tcgtgcgctc tcctgttccg   12780
accctgccgc ttaccggata cctgtccgcc tttctccctt cgggaagcgt ggcgctttct   12840
catagctcac gctgtaggta tctcagttcg gtgtaggtcg ttcgctccaa gctgggctgt   12900
gtgcacgaac cccccgttca gcccgaccgc tgcgccttat ccggtaacta tcgtcttgag   12960
tccaacccgg taagacacga cttatcgcca ctggcagcag ccactggtaa caggattagc   13020
agagcgaggt atgtaggcgg tgctacagag ttcttgaagt ggtggcctaa ctacggctac   13080
actagaagga cagtatttgg tatctgcgct ctgctgaagc cagttacctt cggaaaaaga   13140
gttggtagct cttgatccgg caaacaaacc accgctggta gcggtggttt ttttgtttgc   13200
aagcagcaga ttacgcgcag aaaaaaagga tctcaagaag atcctttgat cttttctacg   13260
gggtctgacg ctcagtggaa cgaaaactca cgttaaggga ttttggtcat gagattatca   13320
aaaaggatc tcacctagat ccttttaaat taaaaatgaa gttttaaatc aatctaaagt    13380
atatatgagt aaacttggtc tgcagttgcc atgttttacg gcagtgagag cagagatagc   13440
gctgatgtcc ggcggtgctt ttgccgttac gcaccacccc gtcagtagct gaacaggagg   13500
gacagctgat agacacagaa gccactggag cacctcaaaa acaccatcat acactaaatc   13560
agtaagttgg cagcatcacc cataattgtg gtttcaaaat cggctccgtc gatactatgt   13620
tatacgccaa ctttgaaaac aactttgaaa aagctgtttt ctggtattta aggttttaga   13680
atgcaaggaa cagtgaattg gagttcgtct tgttataatt agcttcttgg ggtatcttta   13740
aatactgtag aaaagaggaa ggaaataata aatggctaaa atgagaatat caccggaatt   13800
gaaaaaactg atcgaaaaat accgctgcgt aaaagatacg gaaggaatgt ctcctgctaa   13860
ggtatataag ctggtgggag aaaatgaaaa cctatattta aaaatgacgg acagccggta   13920
taaagggacc acctatgatg tggaacggga aaaggacatg atgctatggc tggaaggaaa   13980
gctgcctgtt ccaaaggtcc tgcactttga acggcatgat ggctggagca atctgctcat   14040
gagtgaggcc gatggcgtcc tttgctcgga agagtatgaa gatgaacaaa gccctgaaaa   14100
gattatcgag ctgtatgcgg agtgcatcag gctctttcac tccatcgaca tatcggattg   14160
tccctatacg aatagcttag acagccgctt agccgaattg gattacttac tgaataacga   14220
tctgccgat gtggattgcg aaaactggga agaagcacct ccatttaaag atccgcgcga    14280
gctgtatgat ttttaaaga cggaaaagcc cgaagaggaa cttgtctttt cccacgcgca    14340
cctgggagac agcaacatct ttgtgaaaga tggcaaagta agtggcttta ttgatcttgg   14400
gagaagcggc agggcggaca agtggtatga cattgccttc tgcgtccggt cgatcaggga   14460
ggatatcggg gaagaacagt atgtcgagct attttttgac ttactgggga tcaagcctga   14520
ttggagaaa ataaaatatt atattttact ggatgaattg ttttagtacc tagatgtggc    14580
gcaacgatgc cggcgacaag caggagcgca ccgacttctt ccgcatcaag tgttttggct   14640
ctcaggccga ggcccacggc aagtatttgg gcaaggggtc gctggtattc gtgcagggca   14700
agattcggaa taccaagtac gagaaggacg gccagacggt ctacgggcac gacttcattg   14760
ccgataaggt ggattatctg gacaccaagg caccaggcgg gtcaaatcag gaataagggc   14820
acattgcccc ggcgtgagtc ggggcaatcc cgcaaggagg gtgaatgaat cggacgtttg   14880
accggaaggc atacaggcaa gaactgatcg acgcggggtt ttcgccgag gatgccgaaa    14940
ccatcgcaag ccgcaccgtc atgcgtgcgc ccgcgaaac cttccagtcc gtcggctcga    15000
tggtccagca agctacgccc aagatcgagc gacacgact caactgctcc ccccgctccc    15060
tgcccgcgcc atcggccgcc gtggagcgtt cgcgtcgtct cgaacaggag gcggcaggtt   15120
tggcgaagtc gatgaccatc gacacgcgag gaactatgac gaccaagaag cgaaaaccg    15180
ccggcgagga cctggcaaaa caggtcagcg aggccaagca ggccgcgttg ctgaaacaca   15240
cgaagcagca gatcaaggaa atgcagcttt ccttgttcga tattcgccg tggccggaca    15300
cgatcgagc gatgccaaac gacacgtgcc gctctgccct gttcaccacg gccaacaaga   15360
aaatcccgcg cgaggcgctg caaaacaagg tcatttttcca cgtcaacaag acgtgaaga    15420
tcacctacac cggcgtcgag ctgcgggccg acgatgacga actggtgtgg cagcaggtgt   15480
tggagtacgg gaagcgcacc cctatcgcg agccgatcac cttcacgttc tacgagcttt    15540
gccaggacct gggctggtcg atcaatggcc ggtattacac gaaggccgag gaatgcctgt   15600
cgcgcctaca ggcgacgcg atgggcttca cgcgcatcgg ccgttggatg gtgaatcgg    15660
tgtcgctgct gcaccgcttc cgcgtcctgg accgtgcaa gaaaacgtcc cgttgccagg    15720
tcctgatcga cgaggaaatc gtcgtgctgt tgctggcga ccactacacg aaattcatat    15780
gggagaagta ccgcaagctg tcgccgacgg cccgacggat gttcgactat ttcagctcgc   15840
accgggagcc gtaccgctc aagctggaaa ccttccgcct catgtgcgga tcggattcca    15900
cccgcgtgaa gaagtggcgc gagcaggtcg gcgaagcctg cgaagagttg cgaggcagcg   15960
```

```
gcctggtgga acacgcctgg gtcaatgatg acctggtgca ttgcaaacgc tagggccttg   16020
tggggtcagt tccggctggg ggttcagcag ccagcgcttt actggcattt caggaacaag   16080
cgggcactgc tcgacgcact tgcttcgctc agtatcgctc gggacgcacg gcgcgctcta   16140
cgaactgccg ataaacagag gattaaaatt gacaattcaa tggcaaggac tgccagcgct   16200
gccattttg gggtgaggcc gttcgcggcc gagggggcca gccccctgggg ggatgggagg   16260
cccgcgttag cgggccggga gggttcgaga aggggggca cccccttcg gcgtgcgcgg   16320
tcacgcgcac agggcgcagc cctggttaaa aacaaggttt ataaatattg gtttaaaagc   16380
aggttaaaag acaggttagc ggtggccgaa aaacgggcgg aaacccttgc aaatgctgga   16440
ttttctgcct gtggacagcc cctcaaatgt caataggtgc gccctcatc tgtcagcact   16500
ctgcccctca agtgtcaagg atcgcgcccc tcatctgtca gtagtcgcgc ccctcaagtg   16560
tcaataccgc agggcactta tccccaggct tgtccacatc atctgtggga aactcgcgta   16620
aaatcaggcg ttttcgccga tttgcgaggc tggccagctc cacgtcgccg gccgaaatcg   16680
agcctgcccc tcatctgtca acgccgcgcc gggtgagtcg gcccctcaag tgtcaacgtc   16740
cgccccctcat ctgtcagtga gggccaagtt tccgcgaggg tatccacaac gccggcggcc   16800
gcggtgtctc gcacacggct tcgacgcgt ttctggcgcg tttgcagggc catgacggc   16860
cgccagccca gcggcgaggg caaccagccc ggtgagcgtc gcaaaggcgc tcggtcttgc   16920
cttgctcgtc gagatctggg gtcgatcagc cggggatgca tcaggccgac agtcggaact   16980
tcgggtcccc gacctgtacc attcggtgag caatggatag gggagttgat atcgtcaacg   17040
ttcacttcta agaaaatagc gccactcagc ttcctcagcg gctttatcca gcgatttcct   17100
attatgtcgg catagttctc aagatcgaca gcctgtcacg gttaagcgag aaatgaataa   17160
gaaggctgat aattcggatc tctgcgaggg agatgatatt tgatcacagg cagcaacgct   17220
ctgtcatcgt tacaatcaac atgctaccct ccgcgagatc atcgtgttt caaacccggc   17280
agcttagttg ccgttcttcc gaatagcatc ggtaacatga gcaaagtctg ccgccttaca   17340
acggctctcc cgctgacgcc gtcccggact gatgggctgc ctgtatcgag tggtgatttt   17400
gtgccgagct gccggtcggg gagctgttgg ctggctggtg gcaggatata ttgtggtgta   17460
aacaaattga gcttagaca acttaataac acattgcgga cgttttttaat gtactggggt   17520
ggttttttctt ttccaccagtg agacgggcaa cagctgattg cccttcaccg cctggcctg   17580
agagagttgc agcaagcggt ccacgctggt ttgccccagc aggcgaaaat cctgtttgat   17640
ggtggttccg aaatcggcaa aatcccttat aaatcaaaag aatagcccga gatagggttg   17700
agtgttgttc cagtttggaa caagagtcca ctattaaaa acgtggactc caacgtcaaa   17760
gggcgaaaaa ccgtctatca gggcgatggc ccactacgtg aaccatcacc caaatcaagt   17820
ttttgggggt cgaggtgccg taaagcacta aatcggaacc ctaaagggag ccccgattt   17880
agagcttgac ggggaaagcc ggcgaacgtg gcgagaaagg aagggaagaa agcgaaagga   17940
gcgggcgcca ttcaggctgc gcaactgttg ggaaggg                           17977
```

```
SEQ ID NO: 37           moltype = DNA   length = 17931
FEATURE                 Location/Qualifiers
misc_feature            1..17931
                        note = pBYR11eM-h6D8ZE3
source                  1..17931
                        mol_type = other DNA
                        organism = synthetic construct
SEQUENCE: 37
cgatcggtcg attcatagaa gattagattt tcatagtat tttttaaag taaaccttta     60
actacggtta ggacactttt aagttaaatt taatttgaac ccttaaatta atttttaaaa   120
tagataaata tcaatcatcc tgatatgctt ttgaaaaaat gaatgagaaa gatgattcaa   180
ttaaggccac attttaatca tgactaaaat aatatacagt ataatttcat atatatttgc   240
tttaaaaaaa aattgacaat ccattcgttt ctagcaataa atttcttcaa ccacaaatat   300
attaaagata actacggcat agaaacaaaa atctatgaag aattttttgta tacttcatat   360
gaaattaaaa aaaacttcat tgaacatcaa aataataata ataatcataa actcctcaat   420
atttatattc ctagcttctt gaattaaatt gtttacatat tcaacgatgt aaaaaattat   480
ttctctatct attttcctta tatcatgcat ggtttcatat atcaaagg ataaaagcaa    540
tctatgtaaa ttatctcact ttattaagtt ttctatctga attattgaga acgtagattt   600
cttttttgcac tatcccccaa taattagcaa acacacccta gactagattt gttttgctaa   660
cccaattgat attaattata tatgattaat atttatatgt aattgaatt ggtaataaa    720
atgcatctgg ttcatcaaag aattataaag acacgtgaca ttcatttagg ataagaaata   780
tggatgatct ctttctctta ttcagataat tagtaattac acataacaca caactttgat   840
gcccacatta tagtgattag catgtcacta tgtgtgcatc cttttatttc atacattaat   900
taacttggcc aatccagaag atggacaagt ctagggtcac attgcagggt actctagctt   960
actcgccttc ttttccggaag gtttgagtac cttcagggca tcctcttgat acatttactttt  1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc gtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga cttcgtcag   1380
gaagtttgaa gggagaagtt gtacctcctg atcctccatc ccaacgttca ctgttagctt   1440
gttccctagc gtcgttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttcacgat gctcctcgtg ggtggggtc catctttggg accactgtcg gcagaggcat    1740
cttcaacgat ggccttttcct ttatcgcaat gatggcattt gtaggagcca ccttcctttt   1800
ccactatctt cacaataaag tgacagatag ctgggcaatg gaatccgagg aggtttccgg   1860
atattaccccct tgttgaaaaaa gtctcaattg cccttttggtc ttctgagact gtatcttccg  1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
```

```
cgccctgagt gcttgcggca gcgtgaagct ggcgcgccgc tctagcagaa ggcatgttgt    2220
tgtgactccg aggggttgcc tcaaactcta tcttataacc ggcgtggagg catggaggca    2280
agggcatttt ggtaatttaa gtagttagtg gaaaatgacg tcatttactt aaagacgaag    2340
tcttgcgaca agggggggccc acgccgaatt ttaatattac cggcgtggcc ccaccttatc    2400
gcgagtgctt tagcacgagc ggtccagatt taaagtagaa aagtcccgc ccactagggt    2460
taaaggtgtt cacactataa aagcatatac gatgtgatgg tatttgatgg agcgtatatt    2520
gtatcaggta tttccgtcgg atacgaatta ttcgtacgac cctcctgcag gtcaacatgg    2580
tggagcacga cacacttgtc tactccaaaa atatcaaaga tacagtctca gaagaccaaa    2640
gggcaattga gacttttcaa caaagggtaa tatcccgaaa cctcctcgga ttccattgaa    2700
cagctatctg tcactttatt gtgaagatag tggaaaagga aggtggctcc tacaaatgcc    2760
atcattgcga taaaggaaag gccatcgttg aagatgcctc tgccgacagt ggtcccaaag    2820
atggaccccc acccacgagg agcatcgtgg aaaaagaaga cgttccaacc acgtcttcaa    2880
agcaagtgga ttgatgtgat aacatggtgg agcacgacac acttgtctac tccaaaaata    2940
tcaaagatac agtctcagaa gaccaaaggg caattgagac ttttcaacaa agggtaatat    3000
ccggaaacct cctcggattc cattgccag ctatctgtca ctttattgtg aagatagtgg    3060
aaaaggaagg tggctcctac aaatgccatc attgcgataa aggaaaggcc atcgttgaag    3120
atgcctctgc cgacagtggt cccaaagatg accccccacc cacgaggagc atcgtggaaa    3180
aagaagacgt tccaaccacg tcttcaaagc aagtggattg atgtgatatc tccactgacg    3240
taagggatga cgcacaatcc cactatcctt cgcaagaccc ttcctctata taggaagtt    3300
catttcattt ggagaggacc tcgagaaaca aacaaaatca acaaatatag aaaataacgc    3360
atttccaatt ctttgaaatt tctgcaacat ctagaacaat gggatggtct tgcatctac    3420
tcttttcttgt tgcaactgct acaggtgtcc actctgatgt tcagcttctc gagtctggag    3480
gtggtcttgt gcaacctgga ggttccttga gactctcctg tgcagcttca gggtttgact    3540
tcagtaggta ctggatgagt tgggttcgtc aagctcctgg gaaaggacta aatggattg    3600
gagagatcaa tccagattca agtaccatca actatactcc atctctgaag gatcgcttca    3660
ccatttccag agacaatgcc aagaacacgt tgtatcttca gatgaacagc ttgaggactg    3720
aagcacacagc cttgtactac tgcacaagac agggctatgg ctacaactac tggggtcaag    3780
gcaccactgt cacagtgtct tcagctagca ccaaaggtcc atcggtcttt ccactggcac    3840
cttcttccaa gagtacttct ggaggcacag ctgcactggg ttgtcttgtc aaggactact    3900
ttccagaacc tgttacggtt tcgtgaact caggtgctct gaccagtgga gtgcacacct    3960
ttccagctgt tcttcagtcc tcaggattgt attctcttag cagtgttgtg actgttccat    4020
cctcaagctt gggcactcag acctacatct gcaatgtgaa tcacaaaccc agcaacacca    4080
aggttgacaa gaaagttgag cccaagtctt gtgacaagac tcatacgtgt ccaccgtgcc    4140
cagcacctga acttcttgga ggaccgtcag tcttcttgtt tcctccaaag cctaaggata    4200
ccttgatgat ctccaggact cctgaagtca catgtgtagt tgtggatgtg agccatgaag    4260
atcctgaggt gaagttcaac tggtatgtgg atggtgtgga agtgcacaat gccaagacaa    4320
agccgagaga ggaacagtac aacagcacgt acagggttgt ctcagttctc actgttctcc    4380
atcaagattg gttgaatggc aaagagtaca agtgcaaggt ctccaacaaa gccctcccag    4440
cccccattga gaagaccatt tccaaagcga aagggcagcc ccgtgaacca caagtgtaca    4500
cacttcctcc atctcgcgat gaactgacca gaaccaggt cagcttgact tgcctggtga    4560
aaggcttcta tcccctctgac atagctgtag agtgggagag caatgggcaa ccggagaaca    4620
actacaagac tacacctccc gttctcgatt ctgacggctc cttcttcctc tacagcaagc    4680
tcacagtgga caagagcagg tggcaacaag ggaatgtctt ctcatgctcc gtgatgcatg    4740
aggctcttca caatcactac acacagaaga gtctctcctg tctcccgggt aaaggagtg    4800
gcggatcagg tggagcggt tcaggcggag gtggatccga ggcttcaatt tcagacatgg    4860
ctagtgacag ccgttgccca acacaaggtg aagcctacct tgacaagcaa tcagacactc    4920
aatatgtgtg caagagaaca ttggtggaca gaggttgggg aaacgggatgt ggacttttcg    4980
gtaagggaag cctcgtgaca tgcgctaaat tcgcttgctc cactagtcat aacactcctg    5040
tttacaagct ggacatatct gaggcaactc aataagagct cgaagtgaca tcacaaagtt    5100
gaaggtaata aagccaaatt aattaagaca ttttcataat gatgtcaaga atgcaaagca    5160
aattgcataa ctgcctttat gcaaaacatt aatataaa aaattataaa gaactgcgct    5220
ctctgcttct tattttctta gcttcattta ttagtcacta gctgttcaga atttcagta    5280
tcttttgata ttactaagaa cctaatcaca caatgtatat tctatgcag gaaaagcaga    5340
atgctgagct aaaagaaagg cttttttccat tttcgagaga caatgagaaa agaagaagaa    5400
gaagaagaag aagaagaaga agaaaagagt aaataataaa gccccacagg aggcgaagtt    5460
cttgtagctc catgttatct aagttattga tattgtttgc cctatatttt attttctgtca    5520
ttgtgtatgt tttgttcagt ttcgatcctcc ttgcaaaatg cagagattat gagatgaata    5580
aactaagtta tattattata cgtgttaata ttctcctcct ctctctagct agccttttgt    5640
tttctctttt tcttatttga ttttcttttaa atcaatccat tttaggagag ggcaggagag    5700
tgatccagca aaacatgaag attagaagaa acttccctct tttttttcct gaaaacaatt    5760
taacgtcgag atttatctct ttttgtaatg gaatcatttc tacagttatg acgaattctc    5820
gattaaaaat cccaattata tttggtctaa tttagttggg tattgagtaa aacaaattcg    5880
aaccaaacca aaatataaat atatagttttt tatatatg cctttaagac ttttttataga    5940
atttcttta aaaaatctc agaaatattt gcgactcttc tggcatgtaa tattcgtta    6000
aatatgaagt gctccatttt tattaacttt aaataattgg ttgtacgatc actttcttat    6060
caagtgttac taaaatgcgt caatctcttt gttcttccat attcatatgt caaaatctat    6120
caaaattctt atatatcttt ttcgaatttg aagtgaaatt tcgataattt aaaattaaat    6180
agaacatatc attattagg tatcatattg atttttatac ttaattacta aatttggtta    6240
actttgaaag tgtacatcaa cgaaaaatta gtcaaacgac taaaataaat aaatatcatg    6300
tgttattaag aaaattctcc tataagaata ttttaataga tcatatgttt gtaaaaaaaa    6360
ttaattttta ctaacacata tatttactta tcaaaaattt gacaaagtaa gattaaaata    6420
atattcatct aacaaaaaaa aaccagaaa atgctgaaaa cccggcaaaa ccgaccaat    6480
ccaaaccgat atagttggtt tggtttgatt tgatataaa ccgaaccaac tcggtccatt    6540
tgcaccccta atcataatag ctttaatatt tcaagatatt attaagttaa cgttgtcaat    6600
atcctggaaa ttttgcaaaa tgaatcaagc ctatatggct gtaatgaa ttaaagca    6660
gctcgatgtg gtggtaatat gtaatttact tgattctaaa aaaatatccc aagtattaat    6720
aatttctgct aggaagaagg ttagctacga tttacagcaa agccagaata caagaaccca    6780
taaagtgatt gaagctcgaa atatacgaag gaacaaatat ttttaaaaaa atacgcaatg    6840
acttggaaca aagaaaagtg atatattttt tgttcttaaa caagcatccc ctctaaagaa    6900
```

```
tggcagtttt cctttgcatg taactattat gctcccttcg ttacaaaaat ttttggactac  6960
tattgggaac ttcttctgaa aatagtggta ccgagtgtac ttcaagtcag ttggaaatca  7020
ataaaatgat tattttatga atatatttca ttgtgcaagt agatagaaat tacatatgtt  7080
acataacaca cgaaataaac aaaaaaacac aatccaaaac aaacacccca aacaaaataa  7140
cactatatat atcctcgtat gaggagaggc acgttcagtg actcgacgat tcccgagcaa  7200
aaaaagtctc cccgtcacac atatagtggg tgacgcaatt atcttcaaag taatccttct  7260
gttgacttgt cattgataac atccagtctt cgtcaggatt ccaaagaatt atagaaggga  7320
tcggtcaaca tggtggagca cgacacactt gtctactcca aaaatatcaa agatacagtc  7380
tcagaagacc aaagggcaat tgagacttttt caacaaaggg taatatccgg aaacctcctc  7440
ggattccatt gcccagctat ctgtcacttt attgtgaaga tagtggaaaa ggaaggtggc  7500
tcctacaaat gccatcattg cgataaagga aaggccatcg ttgaagatgc ctctgccgac  7560
agtggtccca aagatggacc cccacccacg aggagcatcg tggaaaaaga agacgttcca  7620
accacgtctt caaagcaagt ggattgatgt gataacatgg tggagcacga cacacttgtc  7680
tactccaaaa atatcaaaga tacagtctca gaagaccaaa gggcaaattga gacttttcaa  7740
caaagggtaa tatccggaaa cctcctcgga ttccattgcc cagctatctg tcactttatt  7800
gtgaagatag tggaaaagga aggtggctcc tacaaatgcc atcattgcga taaggaaag  7860
gccatcgttg aagatgcctc tgccgacagt ggtcccaaag atggaccccc acccacgagg  7920
agcatcgtgg aaaaagaaga cgttccaacc acgtcttcaa agcaagtgga ttgatgtgat  7980
atctccactg acgtaaggga tgacgcacaa tcccactatc cttcgcaaga cccttcctct  8040
atataaggaa gttcatttca tttggagagg acctcgagaa acaaacaaaa tcaacaaata  8100
tagaaaataa cgcatttcca attctttgaa atttctgcaa catctagaac aatgggatga  8160
tcttgcatca ttctcttctt ggtagccaca gctacagggtg tccactccga tgttttgatg  8220
actcaaagcc ctctctcact tcctgtgact cttggacagc ccgcatccat atcttgcaga  8280
tctagtcaga gtattgttca tagtaacggc aacacctact tggaatggta tctgcagaaa  8340
ccaggccagt ctccaaagct tctgatctac aaggcttcca atcgtttctc tggtgtccca  8400
gacaggttta gtggcagtgg atcaggcact gacttcacat tgaagatcag cagagttgag  8460
gctgaagatg cgggagtgta ctattgtctt caaggttcac atgttccgtc aacgtttgga  8520
ggtgggacca aagtggagat caagactgtt gcggcgccat ctgtcttcat ctttcctcca  8580
tctgatgaac aactcaagtc tggaactgct tctgttgtgt gccttctgaa caacttctat  8640
cctagagaag ccaaagtaca gtggaaggtt gacaatgctc ttcaatcagg taactcccag  8700
gagagtgtca cagagcaaga ttccaaggat tccacctaca gcctctcaag taccttgacg  8760
ttgagcaagg cagactatga gaaacacaaa gtgtacgcat gcgaagtcac tcatcagggc  8820
ctgtcatcac ccgtgacaaa gagcttcaac agggagagt gttaggtacc gagctcgaag  8880
tgacatcaca aagttgaagg taataaagcc aaattaatta agacatttc ataatgatgt  8940
caagaatgca aagcaaattg cataactgcc tttatgcaaa acattaatat aatataaatt  9000
ataaagaact gcgctctctg cttcttattt tcttagcttc atttattagt cactagctgt  9060
tcagaatttt cagtatcttt tgatattact aagaacctaa tcacacaatg tatattctta  9120
tgcaggaaaa gcagaatgct gagctaaaag aaaggctttt tccattttcg agagacaatg  9180
agaaaagaag aagaagaaga agaagaaaga aagaagaaa agagtaaata ataaagcccc  9240
acaggaggcg aagttcttgt agctccatgt tatctaagtt attgatattg tttgccctat  9300
attttatttc tgtcattgtg tatgtttttgt tcagtttcga tctccttgca aaatgcagag  9360
attatgagat gaataaacta agtatatta ttatacgtgt taatattctc ctcctctctc  9420
tagctagcct tttgttttct cttttttctta tttgattttc tttaaatcaa tccattttag  9480
gagagggcca gggagtgatc cagcaaaca tgaagattag aagaaacttc cctcttttt  9540
ttcctgaaaa caatttaacg tcgagattta tctcttttttg taatggaatc atttctacag  9600
ttatgacgaa ttgtacatca acgaaaaatt agtcaaacga ctaaaataaa taaatatcat  9660
gtgttattaa gaaaattctc ctataagaat attttaaatag atcatatgtt tgtaaaaaaa  9720
attaattttt actaacacat atatttactt atcaaaaatt tgacaaagta agattaaat  9780
aatattcatc taacaaaaaa aaaaaccagaa aatgctgaaa acccggcaaa accgaaccaa  9840
tccaaaccga tatagttggt ttggtttgat tttgatataa accgaaccaa ctcggtccat  9900
ttgcaccccct aatcataata gctttaatat ttcaagatat tattaagtta acgttgtcaa  9960
tatcctggaa attttgcaaa atgaatcaag cctatatggc tgtaatatga atttaaaagc  10020
agctcgatgt ggtggtaata tgtaatttac ttgattctaa aaaaatatcc caagtattaa  10080
taatttctgc taggaagaag gttagctacg atttacagca aagccagaat acaaagaacc  10140
ataaagtgat tgaagctcga aaatatacgaa ggaacaaata tttttaaaaa aatacgcaat  10200
gacttggaac aaaagaaagt gatatatttt ttgttcttaa acaagcatcc cctctaaaga  10260
atggcagttt tcctttgcat gtaactatta tgctcccttc gttacaaaaa ttttggacta  10320
ctattgggaa cttcttctga aaatagtggt accgagtgta cttcaagtca gttggaaatc  10380
aataaaatga ttattttatg aatatatttc atttgtgcaag tagatagaaa ttacatatgt  10440
tacataacac acgaaataaa caaaaaaca caatccaaaa caaacacccc aaacaaaata  10500
acactatata tatcctcgta tgaggagagg cacgttcagt gactcgacga ttcccgagca  10560
aaaaaagtct ccccgtcaca catatagtgg gtgacgcaat tatcttcaaa gtaatccttc  10620
tgttgacttg tcattgataa catccagtct tcgtcaggat tgcaaagaat tatagaaggg  10680
atcccacctt ttatttctt ctttttttcca tatttagggt tgacagtgaa atcagactgg  10740
caacctatta attgcttcca caatgggacg aacttgaagg ggatgtcgtc gatgatatta  10800
taggtggcgt gttcatcgta gttggtgaag tcgatggtcc cgttccagta gttgtgtcgc  10860
ccgagacttc tagcccaggt ggtctttccg gtacgagttg gtccgcagat gtagaggctg  10920
gggtgtctga ccccagtcct tccctcatcc tggttagatc ggcatcgatg tcaaggtcag  10980
attgtgcttg atcgtaggag acaggatgta tgaaagtgta ggcatcgatg cttacatgat  11040
ataggtgcgt ctctctccag ttgtgcagat cttcgtggca gcggagatct gattctgtga  11100
agggcgacac gtactgctca ggtgtggag gaaataattt gttggctgaa tattccagcc  11160
attgaagctt tgttgcccat tcatgaggga actcttcttt gatcatgtca agatactcct  11220
ccttagacgt tgcagtctgg ataatagttc gccatcgtgc gtcagatttg cgaggagaca  11280
ccttatgatc tcggaaatct cctctgtttt taatatctcc gtcctttgat atgtaatcaa  11340
ggacttgttt agagtttcta gctggctgga tattagggtg atttccttca aaatcgaaaa  11400
aagaaggatc cctaatacaa ggttttttat caagctggat aagagcatga tagtgggtag  11460
tgccatcttg atgaagctca gaagcaacac caaggaagaa aataagaaaa ggtgtgagtt  11520
tctcccagag aaactggaat aaatcatctc tttgagatga gcacttgggg taggtaagga  11580
aaacatattt agattggagt ctgaagttct tgctagcaga aggcatgttg ttgtgactcc  11640
```

```
gaggggttgc ctcaaactct atcttataac cggcgtggag gcatggaggc aagggcattt    11700
tggtaattta agtagttagt ggaaaatgac gtcattact taaagacgaa gtcttgcgac    11760
aagggggggcc cacgccgaat tttaatatta ccggcgtggc cccaccttat cgcgagtgct  11820
ttagcacgag cggtccagat ttaaagtaga aaagttcccg cccactaggg ttaaaggtgt   11880
tcacactata aaagcatata cgatgtgatg gtatttgatg gagcgtatat tgtatcaggt   11940
atttccgtcg gatacgaatt attcgtacgg ccggaccggt cccctaggcc ggccaattcg   12000
agatcggccg cggctgagtg gctccttcaa tcgttgcggt tctgtcagtt ccaaacgtaa    12060
aacgcttgt cccgcgtcat cggcgggggt cataacgtga ctcccttaat tctccgctca    12120
tgatcagatt gtcgtttccc gccttcagtt taaactatca gtgtttgaca ggatatattg   12180
gcgggtaaac ctaagagaaa agagcgttta ttagaataat cggatattta aaagggcgtg   12240
aaaaggttta tccgttcgtc catttgtatg tgcatgccaa ccacagggtt ccccagatct   12300
ggcgccggcc agcgagacga gcaagattgg ccgccgcccg aaacgatccg acagcgcgcc   12360
cagcacaggt gcgcaggcaa attgcaccaa cgcatacagc gccagcagaa tgccatagtg   12420
ggcggtgacg tcgttcgagt gaaccagatc gcgcaggagg cccggcagca ccggcataat   12480
caggccgatg ccgacagcgt cgagcgcgac agtgctcaga attacgatca ggggtatgtt   12540
gggtttcacg tctggcctcc ggagactgtc atacgcgtaa aaaggccgcg ttgctggcgt   12600
ttttccatag gctccgcccc cctgacgagc atcacaaaaa tcgacgctca agtcagaggt   12660
ggcgaaaccc gacaggacta taaagatacc aggcgtttcc ccctggaagc tccctcgtgc   12720
gctctcctgt tccgaccctg ccgcttaccg gatacctgtc cgcctttctc ccttcgggaa   12780
gcgtggcgct ttctcatagc tcacgctgta ggtatctcag ttcggtgtag gtcgttcgct   12840
ccaagctggg ctgtgtgcac gaaccccccg ttcagcccga ccgctgcgcc ttatccggta   12900
actatcgtct tgagtccaac ccggtaagac acgacttatc gccactggca gcagccactg   12960
gtaacaggat tagcagagcg aggtatgtag gcggtgctac agagttcttg aagtggtggc   13020
ctaactacgg ctacactaga aggacagtat ttggtatctg cgctctgctg aagccagtta   13080
ccttcggaaa aagagttggt agctcttgat ccggcaaaca aaccaccgct ggtagcggtg   13140
gttttttttgt ttgcaaagcag cagattacgc gcagaaaaaa aggatctcaa gaagatcctt  13200
tgatcttttc tacggggtct gacgctcagt ggaacgaaaa ctcacgttaa gggattttgg   13260
tcatgagatt atcaaaaagg atcttcacct agatcctttt aaattaaaaa tgaagtttta   13320
aatcaatcta aagtatatat gagtaaactt ggtctgcagt tgccatgttt tacggcagtg   13380
agagcagaga tagcgctgat gtccggcggt gcttttgccg ttacgcacca ccccgtcagt   13440
agctgaacag gagggacagc tgatagacac agaagccact ggagcacctc aaaaacacca   13500
tcatacacta aatcagtaag ttggcagcat cacccataat tgtggtttca aaatcggctc   13560
cgtcgatact atgttatacg ccaactttga aaacaacttt gaaaaagctg ttttctggta   13620
tttaaggttt tagaatgcaa ggaacagtga attggagttc gtcttgttat aattagcttc   13680
ttggggtatc tttaaatact gtagaaaaga ggaaggaaat aataaatggc taaaatgaga   13740
atatcaccgg aattgaaaaa actgatcgaa aaataccgct gcgtaaaaga tacgaaagga   13800
atgtctcctg ctaaggtata taagctgtgg ggagaaaatg aaaacctata tttaaaaatg   13860
acggacagcc ggtataaagg gaccacctat gatgtggaac gggaaaagga catgatgcta   13920
tggctgaag gaaagctgcc tgttccaaag gtcctgcact ttgaacggca tgatggctgg   13980
agcaatctgc tcatgagtga ggccgatggc gtcctttgct cggaagagta tgaagatgaa   14040
caaagccctg aaaagattat cgagctgtat gcggagtgca tcaggctctt tcactccatc   14100
gacatatcgg attgtcccta tacgaatagc ttagacagcc gcttagccga attggattac   14160
ttactgaata acgatctggc cgatgtgatt gcgaaaact ggaagaagaa cactccattt    14220
aaagatccgc gcgagctgta tgattttta aagacggaaa agcccgaaga ggaacttgtc   14280
ttttcccacg gcgacctggg agacagcaac atctttgtga aagatggcaa agtaagtggc   14340
tttattgatc ttgggagaag cggcagggcg gacaagtggt atgacattgc cttctgcgtc   14400
cggtcgatca gggaggatat cggggaagaa cagtatgtcg agctatttt tgacttactg   14460
gggatcaagc ctgattggga gaaaataaaa tattatattt tactggatga attgttttag   14520
tacctagatg tggcgcaacg atgccggcga caagcaggag cgcaccgact tcttccgcat   14580
caagtgtttt ggctctcagg ccgaggccca cggcaagtat ttgggcaagg ggtcgctggt   14640
attcgtgcag ggcaagattc ggaataccaa gtacgagaag gacggccaga cggtctacgg   14700
gaccgacttc attgccgata aggtggatta tctggacacc aaggcaccag gcgggtcaaa   14760
tcaggaataa gggcacattg ccccggcgtg agtcggggca atcccgcaag gagggtgaat   14820
gaatcggacg tttgaccgga aggcatacag gcaagaactg atcgacgcgg ggttttccgc   14880
cgaggatgcc gaaaccatcg caagccgcac cgtcatgcgt gcgccccgcg aaaccttcca   14940
gtccgtcggc tcgatggtcc agcaagctac ggccaagatc gagcgcgaca gcgtgcaact   15000
ggctcccccct gccctgcccg cgccatcggc cgccgtggag cgttcgcgtc gtctcgaaca   15060
ggaggcggca ggtttggcga agtcgatgac catcgacacg cgaggaacta tgacgaccaa   15120
gaagcgaaaa accgccggcg aggacctggc aaaacaggtc agcgaggcca agcaggccgc   15180
gttgctgaaa cacacgcaagc agcagatcaa ggaaatgcag ctttccttgt tcgatattgc   15240
gccgtggccg gacacgatgc gagcgatgcc aaacgacacg gcccgctctg ccctgttcac   15300
cacgcgcaac aagaaaatcc gcgcgcgagc gctgcaaaac aaggtcattt tccacgtcaa   15360
caaggacgtg aagatcacct acaccggcgt cgagctgcgg gccgacgatg acgaactggt   15420
gtggcagcag gtgttggagt acgcgaagcg caccctatc ggcgagccga tcacctcac    15480
gttctacgag ctttgccagg acctgggctg tcgatcaat ggccggtatt acacgaaggc    15540
cgaggaatgc ctgtcgcgcc tacaggcgac ggcgatgggc ttcacgtccg accgcgttgg   15600
gcacctgaa tcggtgtcgc tgctgcaccg cttccgcgtc ctggaccgtg caagaaaac    15660
gtcccgttgc caggtcctga tcgacgagga aatcgtcgtg ctgtttgctg gcgaccacta   15720
cacgaaattc atatgggaga agtaccgcaa gctgtcgccg acggcccgac ggatgttcga   15780
ctatttcagc tcgcaccggg agccgtaccc gctcaagctg gaaaccttcc ggcctcatgt   15840
cggatcggat tccacccgcg tgaagaagtg gcgcgagcag gtcggcgaag cctgcgaaga   15900
gttgcgaggc agcggcctgg tggaacacgc ctgggtcaat gatgacctgg tgcattgcaa   15960
acgctagggc cttgtgggt cagttccggc tggggggttca gcagcagcg ctttactggc    16020
atttcaggaa caagcgggca ctgctcgacg cacttgcttc gctcagtatc gtcgggacg    16080
cacggcgcgc tctacgaact gccgataaac agaggattaa aattgacaat tcaatgcaa    16140
ggactgccag cgctgccatt tttggggtga ggccgttcgc ggccgagggg cgcagccct    16200
gggggatgg gaggcccgcg ttagcggcc gggagggttc gagaaggggg ggcaccccc     16260
ttcggcgtgc gcggtcacgc gcacagggcg cagccctggt taaaaacaag gtttataat    16320
attggtttaa aagcaggtta aaagacaggt tagcggtggc cgaaaaacgg gcggaaaccc   16380
```

```
ttgcaaatgc tggattttct gcctgtggac agcccctcaa atgtcaatag gtgcgcccct    16440
catctgtcag cactctgccc ctcaagtgtc aaggatcgcg cccctcatct gtcagtagtc    16500
gcgcccctca agtgtcaata ccgcagggca cttatcccca ggcttgtcca catcatctgt    16560
gggaaactcg cgtaaaatca ggcgttttcg ccgatttgcg aggctggcca gctccacgtc    16620
gccggccgaa atcgagcctg cccctcatct gtcaacgccg cgccgggtga gtcggcccct    16680
caagtgtcaa cgtccgcccc tcatctgtca gtgagggcca agttttccgc gaggtatcca    16740
caacgccggc ggccgcggtg tctcgcacac ggcttgacg gcgtttctgg cgcgtttgca     16800
gggccataga cggccgccag cccagcggcg agggcaacca gcccggtgag cgtcgcaaag    16860
gcgctcggtc ttgccttgct cgtcgagatc tggggtcgat ggccgcggga tgcatcaggc    16920
cgacagtcgg aacttcgggt ccccgacctg taccattcgg tgagcaatgg ataggggagt    16980
tgatatcgtc aacgttccact tctaaagaaa tagcgccact cagcttcctc agcggcttta    17040
tccagcgatt tcctattatg tcggcatagt tctcaagatc gacagcctgt cacgttaag     17100
cgagaaatga ataagaaggc tgataattcg gatctctgcg agggagatga tattgatca     17160
caggcagcaa cgctctgtca tcgttacaat caacatgcta ccctccgcga gatcatccgt    17220
gtttcaaacc cggcagctta gttgccgttc ttccgaatag catcggtaac atgagcaaag    17280
tctgccgcct tacaacggct ctcccgctga cgccgtcccg gactgatggg ctgcctgtat    17340
cgagtggtga ttttgtgccg agctgccggt cggggagctg ttggctggct ggtggcagga    17400
tatattgtgg tgtaaacaaa ttgacgctta gacaacttaa taacacattg cggacgtttt    17460
taatgtactg gggtggtttt tctttcacc agtgagacgg gcaacagctg attgcccttc     17520
accgcctggc cctgagagag ttgcagcaag cggtccacgc tggtttgccc cagcaggcga    17580
aaatcctgtt tgatggtggt tccgaaatcg gcaaaatccc ttataaatca aagaatagc     17640
ccgagatagg gttgagtgtt gttccagttt ggaacaagga tccactatta aagaacgtgg    17700
actccaacgt caaagggcga aaaaccgtct atcaggcga tggcccacta cgtgaaccat     17760
cacccaaatc aagttttttg gggtcgaggt gccgtaaagc actaaatcgg aaccctaaag    17820
ggagcccccg atttagagct tgacggggaa agccggcgaa cgtggcgaga aggaaggga    17880
agaaagcgaa aggagcgggc gccattcagg ctgcgcaact gttgggaagg g             17931
```

```
SEQ ID NO: 38         moltype = DNA   length = 17686
FEATURE               Location/Qualifiers
misc_feature          1..17686
                      note = pBYR11eMa-BAZE3-Hgp371
source                1..17686
                      mol_type = other DNA
                      organism = synthetic construct
SEQUENCE: 38
cgatcggtcg attcatagaa gattagattt tcatagtat tttttaaag taaaccttta      60
actacggtta ggacactttt aagttaaatt taatttgaac ccttaaatta attttaaaa    120
tagataaata tcaatcatcc tgatatgctt ttgaaaaat aatatacagt ataatttcat atatatttga   180
ttaaggccac attttaatca tgactaaaat aatatacagt taatttcat atatatttga    240
tttaaaaaaa aattgacaat ccattcgttt ctagcaataa atttcttcaa ccacaaatat    300
attaaagata actacggcat agaaacaaaa atctatgaag aattttttgta tacttcatat    360
gaaattaaaa aaaacttcat tgaacatcaa aataataata ataatcataa actcctcaat    420
atttatattc ctagcttctt gaattaaatt gtttacatat tcaacgatgt aaaaaattat    480
ttctctatct attttcctta tatcatgcat ggtttcacat atatcaaagg ataaaagcaa    540
tctatgtaaa ttatctcact ttattaagtt ttctatctga attattgaga acgtagattt    600
cttttttgcac tatccccccaa taattagcaa acacaccta gactagattt gttttgctaa     660
cccaattgat attaattata tatgattaat attatatgt aggtgaatt ggttaataaa     720
atgcatctgg ttcatcaaag aattataaag acacgtgaca ttcatttagg ataagaaata   780
tggatgatct ctttctctta ttcagataat tagtaattac acataacaca caactttgat   840
gcccacatta tagtgattag catgtcacta tgtgtgcatc cttttatttc atacattaat    900
taacttggcc aatccagaag atggacaagt ctagggtaac attgcagggt actctagtt    960
actcgccttc ttttttcgaag gtttgagtac cttcagggca tcctcttgat acattactt   1020
ccacttcgat tggggcaagc tgtagcagtt cttgcttaga ccgaattgcc atctcacaga  1080
gatgctgaag agttcgcgac cctccagaaa cggtgatact aactcctcga aaccgaatac  1140
tataggtaca tccgatctgg tcgaaaccga aaaatcgaga tgctgcatag ttaaccgaat  1200
ctcccgtcca agatccaagg actctgtgca gtgaagcttc cgtcctgtcg tatctgagat  1260
atctcttaaa tacaactttc ccgaaacccc agctttcctt gaaacaagg ggattatctt   1320
gattcgaatt cgtctcatcg ttatgtagcc gccactcagt ccaactcgga ctttcgtcag  1380
gaagtttgaa gggagaagtt gtacctcctg atcctccatc ccaacgttca ctgttagctt  1440
gttccctagc gtcgtttcct tgtatagctc gttccatgaa ttgtaaatag taattgtaat  1500
gttgtttgtt gtttgttgtt gttggtaatt gttgtaaaaa tacgctctcc aaatgaaatg  1560
aacttcctta tatagaggaa gggtcttgcg aaggatagtg ggattgtgcg tcatcccta    1620
cgtcagtgga gatatcacat caatccactt gctttgaaga cgtggttgga acgtcttctt   1680
tttccacgat gctcctcgtg ggtggggtc catcttttgg accactgtcg gcagaggcat    1740
cttcaacgat ggcctttcct ttatcgcaat gatggcattt gtaggagcca cttcctttt     1800
ccactatctt cacaataaag tgacagatag ctgggcaatg gaatccgagg aggtttccgg  1860
atattaccct ttgttgaaaa gtctcaattg ccctttggtc ttctgagact gtatcttga   1920
tattttgga gtagacaagt gtgtcgtgct ccaccatgtt ctggcaattc cggttcgctt  1980
gctgtccata aaaccgccca gtctagctat cgccatgtaa gccactgtca agctacctgc   2040
tttctctttg cgcttgcgtt ttcccttgtc cagatagccc agtagctgac attcatccgg   2100
ggtcagcacc gtttctgcgg actggctttc tacgtgttcc gcttcctta gcagcccttg    2160
cgccctgagt gcttgcggca gcgtgaagct ggcgcgccgc tctagcagaa gcatgttgt    2220
tgtgactccg agggggttgcc tcaaactcta tcttataacc ggcgtggagg catggaggca  2280
aggggcattt ggtaatttaa gtagtagtg tcatttactt aaagacgaag                2340
tcttgcgaca aggggggccc acgccgaatt taatattac cggcgtggcc ccaccttatc     2400
gcgagtgctt tagcacgagc ggtccagatt taaagtagaa aagttccgcc ccactagggt    2460
taaaggtgtt cacactataa aagcatatac gatgtgatgg tatttgataa agcgtatatt    2520
gtatcaggta tttccgtcgg atacgaatta ttcgtacgac cctcctgcag gtcaacatgg    2580
tggagcacga cacacttgtc tactccaaaa atatcaaaga tacagtctca gaagaccaaa    2640
```

```
gggcaattga gacttttcaa caaagggtaa tatccggaaa cctcctcgga ttccattgcc    2700
cagctatctg tcactttatt gtgaagatag tggaaaagga aggtggctcc tacaaatgcc    2760
atcattgcga taaaggaaag gccatcgttg aagatgcctc tgccgacagt ggtcccaaag    2820
atggacccccc acccacgagg agcatcgtgg aaaagaaga cgttccaacc acgtcttcaa    2880
agcaagtgga ttgatgtgat aacatggtgg agcacgacac acttgtctac tccaaaaata    2940
tcaaagatac agtctcagaa gaccaaaggg caattgagac ttttcaacaa agggtaaat    3000
ccggaaacct cctcggattc cattgcccag ctatctgtca ctttattgtg aagatagtgg    3060
aaaaggaagg tggctcctac aaatgccatc attgcgataa aggaaaggcc atcgttgaag    3120
atgcctctgc cgacagtggt cccaaagatg gaccccccacc cacgaggagc atcgtggaa    3180
aagaagacgt tccaaccacg tcttcaaagc aagtggattg atgtgatatc tccactgacg    3240
taagggatga cgcacaatcc cactatcctt cgcaagaccc ttcctctata taaggaagtt    3300
catttcattt ggagaggacc tcgagaaaca aacaaaatca acaaatatag aaaataacgc    3360
atttccaatt ctttgaaatt tctgcaacat ctagaacaat ggctaacaag cacctctcat    3420
tgtctctctt ccttgtgctc cttggtcttt ctgcttctct tgcttctggt aagggcgtgt    3480
catactcctt gtgtaccgct gccttcacat tcaccaagat cccggctgaa acactcccacg   3540
gaaccgttac cgtgaggtc caatacgccg gtacagatgg accttgcaag gttccagctc    3600
agatggcggt ggacatgcaa actcttaccc cagttgaag gttgattacc gctaaccccg    3660
ttatcactga aagcactgag aactctaaga tgatgttgga acttgatcca ccattcggtg    3720
actcttacat tgtcattggt gtgggagaga agaagatcac ccaccactgg cacaggagtg    3780
gtagcactag tggtcattga ggaggttctg gtggttctgg aggttcagga tccgatgttc    3840
agcttcttga gtctggaggt ggtcttgtgc aacctggagg ttccttgaga ctctcctgtg    3900
cagcttcagg gtttgacttc agtaggtact ggatgagttg ggtcgtcaa acttgatctc    3960
aaggactaga atggattgga gagatcaatc cagattcaag taccatcaac tatactccat    4020
ctctgaagga tcgcttcacc atttccagag acaatgccaa gaacacgttg tatcttcaga    4080
tgaacagctt gaggactgaa gacacagcct tgtactactg cacaagacag ggctatggct    4140
acaactactg gggtcaaggc accactgtca cagtgtcttc agctagcacc aaaggtccat    4200
cggtctttcc actggcacct tcttccaaga gtacttctgg aggcacagct gcactggggtt    4260
gtcttgtcaa ggactacttt ccagaactgt tacggtttc gtggaactca ggtgctctga    4320
ccagtggagt gcacacctt ccagctgttc ttcagtcctc aggattgtat tctcttagca    4380
gtgttgtgac tgttccatcc tcaagcttgg gcactcagac ctacatctgc aatgtgaatc    4440
acaaacccag caacaccaag gttgacaaga aagttgagcc caagtcttgt gacaagactc    4500
atacgtgtcc accgtgccca gcacctgaac ttcttggagg accgtcagtc ttcttgtttc    4560
ctccaaagcc taaggatacc ttgatgatct ccaggactcc tgaagtcaca tgtgtagttg    4620
tggatgtgag ccatgaagat cctgaggtga agttcaactg gtatgtggat ggtgtggaag    4680
tgcacaatgc caagacaaag ccgagagagg aacagtacaa cagcacgtac aggggttgtc    4740
cagttctcac tgttctccat caagattggt tgaatggcaa agagtacaag tgcaaggtct    4800
ccaacaaagc cctcccagcc cccattgaga agaccatttc caaagcgaaa gggcaaccccc   4860
gtgaaccaca agtgtacaca cttcctccat ctcgcgatga actgaccaag aaccaggtca    4920
gcttgacttg cctggtgaaa ggcttctatc cctctgacat agctgtagag tgggagagca    4980
atgggcaacc ggagaacaac tacaagacta cacctcccgt tctcgattct gacggctcct    5040
tcttcctcta cagcaagctc acagtggaca gagcaggtg gcaacaaggg aatgtcttct    5100
catgctccgt gatgcatgag gctcttcaca atcactacac acagaagagt ctctccttgt    5160
ctccgggtaa aggaggtggc ggatcaggtg gaggcggttc aggggatccc ata           5220
acactcctgt ttacaagctg gacatatctg aggcaactca ataagagctc gaagtgacat    5280
cacaaagttg aagtaataa agccaaatta attaagacat tttcataatg atgtcaagaa    5340
tgcaaagcaa attgcataac tgcctttatg caaaacatta atataatata aattataaag    5400
aactgcgctc tctgcttctt attttcttag cttcatttat tagtcactag ctgttcagaa    5460
tttcagtat cttttgatat tactaagaac ctaatcacac aatgtatatt cttatgcagg    5520
aaaagcagaa tgctgagcta aagaaaggc tttttccatt ttcgagagac aatgagaaa    5580
gaagaagaag aagaagaaga agaagaagaa gaaagagta ataataaag ccccacagga    5640
ggcgaagttc ttgtagctcc atgttatcta agttattgat attgtttgcc ctatatttta    5700
tttctgtcat tgtgtatgtt ttgttcagtt tcgatctcct tgcaaatgc agagattatg    5760
agatgaataa actaagttat attattatac gtgttaatat tctcctcctc tctctagcta    5820
gccttttgtt ttctcttttt cttatttgat tttcttaaa tcaatccatt ttaggagagg    5880
gccagggagt ggtccagcaa aacatgaaga ttagaagaaa cttccctctt tttttttcctg   5940
aaaacaattt aacgtcgaga tttatctctt tttgtaatgg aatcatttct acagttatga    6000
cgaattgtac atcaacgaaa aattagtcaa acgactaaaa taaataaata tcatgtgtta    6060
ttaagaaaat tctcctataa gaatatttta atagatcata tgtttgtaaa aaaattaat    6120
ttttactaac acatatattt acttatcaaa aatttgacaa agtaagatta aaataatatt    6180
catctaacaa aaaaaaaacc agaaaatgct gaaaacccgg caaaaccgaa ccaatccaaa    6240
ccgatatagt tggtttggtt tgattttgat ataaaccgaa ccaactcggt ccatttgcac    6300
ccctaatcat aatagcttta atatttcaag atattattaa gttaacgttg tcaatatcct    6360
ggaaatttttg caaaatgaat caagcctata tggctgtaat atgaatttaa aagcagctcg    6420
atgtggtggt aatatgtaat ttacttgatt ctaaaaaaat atcccaagta ttaataattt    6480
ctgctaggaa gaaggttagc tacgatttac agcaaagcca gaatacaaag aaccataaag    6540
tgattgaagc tcgaaatata cgaaggaaca aatattttta aaaaaatacg caatgacttg    6600
gaacaaaaga aagtgatata tttttttgttc ttaaacaagc atccctctca aagaatggca    6660
gttttccttt gcatgtaact attatgctcc cttcgttaca aaaatttttgg actactattg    6720
ggaacttctt ctgaaaatag tggtaccgag tgtacttcaa gtcagttgaa aatcaataaa    6780
atgattattt tatgaatata tttcattgtg caagtagaaa gaaattacat atgttacata    6840
acacacgaaa taaacaaaaa aacacaatcc aaaacaaaca ccccaaacaa aataacacta    6900
tatatatcct cgtatgagga gaggcacgtt cagtgactcg acgattcccg agcaaaaaaa    6960
gtctcccgt cacacatata gtgggtgacg caattatctt caaagtaatc cttctgttga    7020
cttgtcattg ataacatcca gtcttcgtca ggattccaaa gaattataga agggatcggt    7080
caacatggtg gagcacgaca cacttgtcta ctccaaaaat atcaaagata cagtctcaga    7140
agaccaaagg gcaattgaga cttttcaaca aagggtaata tccggaaacc tcctcggatt    7200
ccattgccca gctatctgtc actttattgt gaagatagtg gaaaggaag gtggctccta    7260
caaatgccat cattgcgata aaggaaaggc catcgttgaa gatgcctctg ccgacagtgg    7320
tcccaaagat ggaccccccac ccacgaggag catcgtggaa aagaagacg ttccaaccac    7380
```

```
gtcttcaaag caagtggatt gatgtgataa catggtggag cacgacacac ttgtctactc    7440
caaaaatatc aaagatacag tctcagaaga ccaaagggca attgagactt ttcaacaaag    7500
ggtaatatcc ggaaacctcc tcggattcca ttgcccagct atctgtcact ttattgtgaa    7560
gatagtggaa aaggaaggtg gctcctacaa atgccatcat tgcgataaag gaaaggccat    7620
cgttgaagat gcctctgccg acagtggtcc caaagatgga cccccaccca cgaggagcat    7680
cgtggaaaaa gaagacgttc caaccacgtc ttcaaagcaa gtggattgat gtgatatctc    7740
cactgacgta agggatgacg cacaatccca ctatccttcg caagacccct cctctatata    7800
aggaagttca tttcatttgg agaggacctc gagaaacaaa caaaatcaac aaatatagaa    7860
aataacgcat ttccaattct ttgaaatttc tgcaacatct agaacaatgg gatggtcttg    7920
catcattctc ttcttggtag ccacagctac aggtgtccac tccgatgttt tgatgactca    7980
aagccctctc tcacttcctg tgactcttgg acagcccgca tccatatctt gcagatctag    8040
tcagagtatt gttcatagta acggcaacac ctacttggaa tggtatctgc agaaaccagg    8100
ccagtctcca aagcttctga tctacaaggc ttccaatcgt ttctctggtg tcccagacag    8160
gtttagtggc agtggatcag ggactgactt cacattgaaa atcagcagag ttgaggctga    8220
agatgcggga gtgtactatt gtcttcaagg ttcacatgtt ccgtcaacgt ttggaggtgg    8280
gaccaaagtg gagatcaaga ctgttgcggc gccatctgtc ttcatctttc ctccatctga    8340
tgaacaactc aagtctggaa ctgcttctgt tgtgtgcctt ctgaacaact tctatcctag    8400
agaagccaaa gtacagtgga aggttgacaa tgctcttcaa tcaggtaact cccaggagag    8460
tgtcacagag caagattcca aggattccac ctacagcctc tcaagtacct tgacgttgag    8520
caaggcagac tatgagaaac acaaagtgta cgcatgcgaa gtcactcatc agggcctgtc    8580
atcacccgtg acaaagagct tcaacagggg agagtgttag gtaccgagct cgaagtgaca    8640
tcacaaagtt gaaggtaata aagccaaatt aattaagaca ttttcataat gatgtcaaga    8700
atgcaaagca aattgcataa ctgccttat gcaaaacatt aatataatat aaattataaa    8760
gaactgcgct ctctgcttct tattttctta gcttcattta ttagtcacta gctgttcaga    8820
attttcagta tcttttgata ttactaagaa cctaatcaca caatgtatat tcttatgcag    8880
gaaaagcaga atgctgagct aaaagaaagg cttttttccat tttcgagaga caatgagaaa    8940
agaagaagaa gaagaagaag aagaagaaga agaaagagt aaataataaa gccccacagg    9000
aggcgaagtt cttgtagctc catgttatct aagttattga tattgtttgc cctatatttt    9060
atttctgtca ttgtgtatgt tttgttcagt ttcgatctcc ttgcaaaatg cagagattat    9120
gagatgaata aactaagtta tattattata cgtgttaata ttctcctcct ctctctagct    9180
agccttttgt tttctctttt tcttatttga tttttcttaa atcaatccat tttaggagag    9240
ggccagggag tgatccagca aaacatgaag attagaagaa acttccctct ttttttttcct    9300
gaaaacaatt taacgtcgag atttatctct ttttgtaatg gaatcatttc tacagttatg    9360
acgaattgta catcaacgaa ataattagtca aacgactaaa taaataaat atcatgtgtt    9420
attaagaaaa ttctcctata agaatatttt aatagatcat atgtttgtaa aaaaaattaa    9480
tttttactaa cacatatatt tacttatcaa aaatttgaca aagtaagatt aaaataat    9540
tcatctaaca aaaaaaaaac cagaaaatgc tgaaaacccg gcaaaaccga accaatccaa    9600
accgatatag ttggtttggt ttgattttga tataaaccga accaactcgg tccatttgca    9660
cccctaatca taatagctt aatattttcaa gatattatta agttaacgtt gtcaatatcc    9720
tggaaatttt gcaaaatgaa tcaagcctat atggctgtaa tatgaattta aaagcagctc    9780
gatgtggtgg taatatgtaa tttacttgat tctaaaaaaa tatcccaagt attaataatt    9840
tctgctagga agaaggttag ctacgattta cagcaaagcc agaatacaaa gaaccataaa    9900
gtgattgaag ctcgaaatat acgaaggaac aaatattttt aaaaaaatac gcaatgactt    9960
ggaacaaaag aaagtgatat atttttttgtt cttaaacaag catccccctct aaagaatggc   10020
agttttcctt tgcatgtaac tattatgctc ccttcgttac aaaaattttg gactactatt   10080
gggaacttct tctgaaaata gtggtaccga gtgtacttca agtcagttgg aaatcaataa   10140
aatgattatt ttatgaatat atttcattgt gcaagtagat agaaattaca tatgttacat   10200
aacacacgaa ataaacaaaa aaacacaatc caaaacaaac accccaaaca aaataacact   10260
atatatatcc tcgtatgagg agaggcacgt tcagtgactc gacgattccc gagcaaaaaa   10320
agtctccccg tcacacatat agtgggtgac gcaattatct tcaaagtaat ccttctgttg   10380
acttgtcatt gataacatcc agtcttcgtc aggattgcaa agaattatag aagggatccc   10440
acctttatt ttcttctttt ttccatattt agggttgaca gtgaaatcag actggcaacc   10500
tattaattgc ttccacaatg ggacgaactt gaaggggatg tcgtcgatga tattataggt   10560
ggcgtgttca tcgtagttgg tgaagtcgat ggtcccgttc cagtagttgt gtcgcccgag   10620
acttctagcc caggtggtct ttccggtacg agttggtccg cagatgtaga ggctggggtg   10680
tctgacccca gtccttccct catcctggtt agatcggcca tccactcaag gtcagattgt   10740
gcttgatcgt aggagacagg atgtatgaaa gtgtaggcat cgatgcttac atgatatagg   10800
tgcgtctctc tccagttgtg cagatcttcg tggcagcgga gatctgattc tgtgaagggc   10860
gacacgtact gctcaggttg tggaggaaat aaatttgttg ctgaatattc cagccattga   10920
agctttgttg cccattcatg agggaactct tctttgatca tgtcaagata ctcctcctta   10980
gacgttgcag tctggataat agttcgccat cgtcgtcag atttgcgagg agacaccttta   11040
tgatctcgga aatctcctct ggttttaata tctccgtcct ttgatatgta atcaaggact   11100
tgtttagagt ttctagctgg ctggatatta gggtgatttc cttcaaaatc gaaaaagaa   11160
ggatccctaa tacaaggttt tttatcaagc tggataagag catgatagtg ggtagtgcca   11220
tcttgatgaa gctcagaagc aacaccaagg aagaaaataa gaaaaggtgt gagtttctcc   11280
cagagaaact ggaataaatc atctcttttga gatgagcact tggggtaggt aaggaaaaca   11340
tatttagatt ggagtctgaa gttcttgcta gcagaaggca tgttgttgtg actccgaggg   11400
gttgcctcaa actctatctt ataaccggcg tggaggcatg gaggcaaggg cattttggta   11460
atttaagtag ttagtggaaa atgacgtcat ttacttaaag acgaagtctt gcgacaaggg   11520
gggcccacgc cgaattttaa tattaccggc gtggccccac cttatcgcga gtgctttagc   11580
acgagcggtc cagatttaaa gtagaaaagt tcccgcccac tagggttaaa ggtgttcaca   11640
ctataaaagc atatacgatg tgatggtatt tgatggagcg tatattgtat caggtatttc   11700
cgtcggatac gaattattcg tacggccgga ccggtccct aggccggcca attcgagatc   11760
ggccgcggtc gagtggctcc ttcaatcgtt gcggttctgt cagttccaaa gctaaaacgg   11820
cttgtcccgc gtcatcggcg ggggtcataa cgtgactccc ttaattctcc gctcatgatc   11880
agattgtcgt ttcccgcctt cagtttaaac tatcagtgtt tgacaggata tattggcggg   11940
taaacctaag agaaagagc gtttattaga ataatcggat atttaaaagg gcgtgaaaag   12000
gtttatccgt tcgtccattt gtatgtgcat gccaaccaca gggttcccca gatctggcgc   12060
cggccagcga gacgagcaag attggccgcc gcccgaaacg atccgacagc gcgcccagca   12120
```

```
caggtgcgca ggcaaattgc accaacgcat acagcgccag cagaatgcca tagtgggcgg  12180
tgacgtcgtt cgagtgaacc agatcgcgca ggaggcccgg cagcaccggc ataatcaggc  12240
cgatgccgac agcgtcgagc gcgacagtgc tcagaattac gatcaggggt atgttgggtt  12300
tcacgtctgg cctccggaga ctgtcatacg cgtaaaaagg ccgcgttgct ggcgtttttc  12360
cataggctcc gccccctga cgagcatcac aaaaatcgac gctcaagtca gaggtggcga  12420
aacccgacag gactataaag ataccaggcg tttccccctg gaagctccct cgtgcgctct  12480
cctgttccga ccctgccgct taccggatac ctgtccgcct ttctcccttc gggaagcgtg  12540
gcgctttctc atagctcacg ctgtaggtat ctcagttcgg tgtaggtcgt tcgctccaag  12600
ctgggctgtg tgcacgaacc ccccgttcag cccgaccgct gcgccttatc cggtaactat  12660
cgtcttgagt ccaacccggt aagacgac ttatcgccac tggcagcagc cactggtaac  12720
aggattagca gagcgaggta tgtaggcggt gctacagagt tcttgaagtg gtggcctaac  12780
tacggctaca ctagaaggac agtatttggt atctgcgctc tgctgaagcc agttaccttc  12840
ggaaaaagag ttggtagctc ttgatccggc aaacaaacca ccgctggtag cggtggtttt  12900
tttgtttgca agcagcagat tacgcgcaga aaaaaaggat ctcaagaaga tcctttgatc  12960
ttttctacgg ggtctgacgc tcagtggaac gaaaactcac gttaagggat tttggtcatg  13020
agattatcaa aaaggatctt cacctagatc cttttaaatt aaaaatgaag ttttaaatca  13080
atctaaagta tatatgagta aacttggtct gcagttgcca tgtttacgg cagtgagagc  13140
agagatagcg ctgatgtccg gcggtgcttt tgccgttacg caccacccg tcagtagctg  13200
aacaggaggg acagctgata gacacagaag ccactggagc acctcaaaaa caccatcata  13260
cactaaatca gtaagttggc agcatcaccc ataattgtgg tttcaaaatc ggctccgtcg  13320
atactatgtt atacgccaac tttgaaaaca actttgaaaa agctgttttc tggtatttaa  13380
ggttttagaa tgcaaggaac agtgaattgg agttcgtctt gttataatta gcttcttggg  13440
gtatctttaa atactgtaga aaagaggaag gaaataataa atggctaaaa tgagaatatc  13500
accggaattg aaaaaactga tcgaaaaata ccgctgcgta aaagatacgg aaggaatgtc  13560
tcctgctaag gtatataagc tggtgggaga aaatgaaaac ctatatttaa aaatgacgga  13620
cagccggtat aaagggacca cctatgatgt ggaacgtgaa aaggacatga tgctatggct  13680
ggaaggaaag ctgcctgttc caaaggtcct gcactttgaa cggcatgatg gctggagcaa  13740
tctgctcatg agtgaggccg atggcgtcct ttgctcggaa gagtatgaag atgaacaaag  13800
ccctgaaaag attatcgagc tgtatgcgga gtgcatcagg ctctttcact ccatcgacat  13860
atcggattgt ccctatacga atagcttaga cagccgctta gccgaattgg attacttact  13920
gaataacgat ctggccgatg tggattgcga aaactgggaa gaagacactc catttaaaga  13980
tccgcgcgag ctgtatgatt ttttaaagac ggaaaagccc gaagaggaac ttgtcttttc  14040
ccacggcgac ctgggagaca gcaacatctt tgtgaaagat ggcaaagtaa gtggctttat  14100
tgatcttggg agaagcggga gggcggacaa gtggtatgac attgccttct gcgtccggtc  14160
gatcaggagg gatatcgggg aagaacagta tgtcgagctc tttttttgact tactgaggat  14220
caagcctgat tgggagaaaa taaaatatta tattttactg gatgaattgt tttagtacct  14280
agatgtggcg caacgatgcc ggcgacaagc aggagcgcac cgacttcttc cgcatcaagt  14340
gttttggctc tcaggccgag gcccacggca agtatttggg caaggggtcg ctggtattcg  14400
tgcagggcaa gattcggaat accaagtacg agaaggacgg ccagacggtc tacgggaccg  14460
acttcattgc cgataaggtg gattatctgc acaccaaggc accaggcggg tcaaatcagg  14520
aataagggca cattgccccg gcgtgagtcg gggcaatccc gcaaggaggg tgaatgaatc  14580
ggacgtttga ccggaaggca tacaggcaag aactgatcga cgcggggttt ccgccgagg  14640
atgccgaaac catcgcaagc cgcaccgtca tgcgtgccgc ccgcgaaacc ttccagtccg  14700
tcggctcgat ggtccagcaa gctacggcca agatcgagcg cgacagcgtg caactggctc  14760
cccctgccct gcccgcgcca tcggccgccg tggagcgttc gcgtcgtctc gaacgaggag  14820
cggcaggttt ggcgaagtcg atgaccatcg acacgcgagg aactatgacg accaagaagc  14880
gaaaaaccgc cggcgaggac ctggcaaaac aggtcagcga ggcaagcag gccgcgttgc  14940
tgaaacacac gaagcagcag atcaaggaaa tgcagctttc cttgttcgat attgcgccgt  15000
ggccggacac gatgcgagcg atgccaaacg acacggcccg ctctgccctg ttcaccacgc  15060
gcaacaagaa aatcccgcgc gaggcgctgc aaaacaaggt catttccac gtcaacaagg  15120
acgtgaagat cacctacacc ggcgtcgaagc tgcgggccga cgatgacgaa ctggtgtgc  15180
agcaggtgtt ggagtacgcg aagcgcaccc ctatcggcga gccgatcacc ttcacgttct  15240
acgagctttg ccaggacctg ggctggtcga tcaatggccg gtattacacg aaggccgagg  15300
aatgcctgtc gcgcctacag gcgacggcga tgggcttcac gtccgaccgc gttgggcacc  15360
tggaatcggt gtcgctgctg caccgcttcc gcgtcctgga ccgtgcaag aaaacgtccc  15420
gttgccaggt cctgatcgac gaggaaatcg tcgtgctgtt tgctggcgac cactacacga  15480
aattcatatg ggagaagtac cgcaagctgt cgccgacggc ccgacggatg ttcgactatt  15540
tcagctcgca ccgggagccg taccgctca agctggaaac cttccgcctc atgtgcggat  15600
cggattccac ccgcgtgaag aagtggccg agcagtcgg cgaagctgc gaagagttga  15660
gaggcagcgg cctggtggaa cacgcctggg tcaatggaca cctggtgcat tgcaaacgct  15720
agggccttgt ggggtcagtt ccggctgggg gttcagcagc cagcgcttta ctggcatttc  15780
aggaacaagc gggcactgct cgacgcactt gcttcgctca gtatcgctcg ggacgcacgg  15840
cgcgctctac gaactgccga taaacagagg attaaaattg acaattcaat ggcaaggact  15900
gccagcgctg ccatttttgg ggtgaggccg ttcgcgggca gggtcgagg cccctgggga  15960
gatgggaggc ccgcgttagc gggccggag ggttcgagaa gggggggcac cccccttcgg  16020
cgtgcgcggt cacgcgcaca gggcgcagcc ctggttaaaa acaagtttta aatattgg  16080
tttaaaagca ggttaaaaga caggttagcg gtggccgaaa aacgggcgga aaccttgca  16140
aatgctggat tttctgccct tggacagccc ctcaaatgtc aataggtgcg ccctcatct  16200
gtcagcactc tgccctcaa gtgtcaagga tcgcgcccct catctgtccg tagtcgcc  16260
cctcaagtgt caataccgca gggcacttat ccccaggctt gtccacatca tctgtgggaa  16320
actcgcgtaa aatcaggcgt tttgccgat ttgcgaggct ggccagctcc acgtcgccgg  16380
ccgaaatcga gcctgcccct catctgtcaa cgccgcgccg ggtgagtcgg ccctcaagt  16440
gtcaacgtcc gcccctcatc tgtcagtgag ggccaagttt ccgcgaggt atccacaacg  16500
ccggcgtccg cggtgtctcg cacacggctt gcaggcgct tctggcgtt ttgcagggga  16560
atagacggcc gccagccag cggcgagggc aaccagcccg tgagcgtcg caaaggcgct  16620
cggtcttgcc ttgctcgtcg agatctgggg tcgatcagcc ggggatgcat caggccgaca  16680
gtcggaactt cgggtccccg acctgtacca ttcggtgagc aatggatagg ggagttgata  16740
tcgtcaacgt tcacttctaa agaaaatagcg ccactcagct tcctcagcgg ctttatccag  16800
cgatttccta ttatgtcggc atagttctca agatcgacag cctgtcacgg ttaagcgaga  16860
```

-continued

```
aatgaataag aaggctgata attcggatct ctgcgaggga gatgatattt gatcacaggc   16920
agcaacgctc tgtcatcgtt acaatcaaca tgctaccctc cgcgagatca tccgtgtttc   16980
aaacccggca gcttagttgc cgttcttccg aatagcatcg gtaacatgag caaagtctgc   17040
cgccttacaa cggctctccc gctgacgccg tcccggactg atgggctgcc tgtatcgagt   17100
ggtgattttg tgccgagctg ccggtcgggg agctgttggc tggctggtgg caggatatat   17160
tgtggtgtaa acaaattgac gcttagacaa cttaataaca cattgcggac gtttttaatg   17220
tactggggtg gttttctttt caccagtga gacgggcaac agctgattgc ccttcaccgc    17280
ctggccctga gagagttgca gcaagcggtc cacgctggtt tgcccagca ggcgaaaatc    17340
ctgtttgatg gtggttccga aatcggcaaa atccctata aatcaaaaga atagcccgag    17400
atagggttga gtgttgttcc agtttggaac aagagtccac tattaaagaa cgtggactcc    17460
aacgtcaaag ggcgaaaaac cgtctatcag ggcgatggcc cactacgtga accatcaccc    17520
aaatcaagtt ttttgggtc gaggtgccgt aaagcactaa atcggaaccc taaagggagc    17580
ccccgattta gagcttgacg gggaaagccg gcgaacgtgg cgagaaagga agggaagaaa    17640
gcgaaggag cgggcgccat tcaggctgcg caactgttgg gaaggg                   17686

SEQ ID NO: 39           moltype = AA  length = 16
FEATURE                 Location/Qualifiers
REGION                  1..16
                        note = linker sequence
source                  1..16
                        mol_type = protein
                        organism = synthetic construct
SEQUENCE: 39
GGSGGSGGSG GSGGSG                                                   16

SEQ ID NO: 40           moltype = AA  length = 12
FEATURE                 Location/Qualifiers
REGION                  1..12
                        note = linker sequence
source                  1..12
                        mol_type = protein
                        organism = synthetic construct
SEQUENCE: 40
GTGGGGSGGG GS                                                       12

SEQ ID NO: 41           moltype = DNA  length = 14
FEATURE                 Location/Qualifiers
misc_feature            1..14
                        note = linker sequence
source                  1..14
                        mol_type = other DNA
                        organism = synthetic construct
SEQUENCE: 41
ggsggsgssg gsgg                                                     14

SEQ ID NO: 42           moltype = AA  length = 15
FEATURE                 Location/Qualifiers
REGION                  1..15
                        note = linker sequence
source                  1..15
                        mol_type = protein
                        organism = synthetic construct
SEQUENCE: 42
SGGSGGSGGS GGSGS                                                    15

SEQ ID NO: 43           moltype = DNA  length = 14314
FEATURE                 Location/Qualifiers
misc_feature            1..14314
                        note = pBYR2eK2M-HBcheL2ic
source                  1..14314
                        mol_type = other DNA
                        organism = synthetic construct
SEQUENCE: 43
cgatcggtcg attcatagaa gattagattt ttcatagtat ttttttaaag taaaccttta    60
actacggtta ggacactttt aagttaaatt taatttgaac ccttaaatta atttttaaaa   120
tagataaata tcaatcatcc tgatatgctt ttgaaaaaat gaatgagaaa gatgattcaa   180
ttaaggccac attttaatca tgactaaaat aatatacagt ataatttcat atatatttgc   240
tttaaaaaaa aattgacaat ccattcgttt ctagcaataa atttcttcaa ccacaaatat   300
attaaagata actacggcat agaaacaaaa atctatgaag aattttttgta tacttcatat   360
gaaattaaaa aaaacttcat tgaacatcaa aataataata ataatcataa actcctcaat   420
attatattc ctagcttctt gaattaaatt gtttacatat tcaacgatgt aaaaaaattat   480
ttctctatct atttttccta tatcatgcat ggtttcacat atatcaaagg ataaaagcaa   540
tctatgtaaa ttatctcact ttattaagtt ttctatctga attattgaga acgtagattt   600
cttttttgcac tatccccaa taattagcaa aacacactta gactagattt gtttttgctaa   660
cccaattgat attaattata tatgattaat atttatatgt atatggaatt ggttaataaa   720
atgcatctgg ttcatcaaag aattataaag acacgtgaca ttcatttagg ataagaaata   780
tggatgatct cttctctctta ttcagataat tagtaattac acataacaca aactttgat    840
gcccacatta tagtgattag catgtcacta tgtgtgcatc cttttatttc atacattaat   900
taacttggcc aatccagaag atggacaagt ctagggtcac attgcaggt actctagctt   960
```

```
actcgccttc ttttcgaag gtttgagtac cttcagggca tcctcttgat acattacttt    1020
ccacttcgat tggggcaagc tgtagcagtt cttgcttaga ccgaattgcc atctcacaga    1080
gatgctgaag agttcgcgac cctccagaaa cggtgatact aactcctcga aaccgaatac    1140
tataggtaca tccgatctgg tcgaaaccga aaaatcgaga tgctgcatag ttaaccgaat    1200
ctcccgtcca agatccaagg actctgtgca gtgaagcttc cgtcctgtcg tatctgagat    1260
atctcttaaa tacaactttc ccgaaacccc agctttcctt gaaaccaagg ggattatctt    1320
gattcgaatt cgtctcatcg ttatgtagcc gccactcagt ccaactcgga cttcgtcag    1380
gaagtttgaa gggagaagtt gtacctcctg atcctccatc ccaacgttca ctgttagctt    1440
gttccctagc gtcgtttcct tgtatagctc gttccatgga ttgtaaatag taattgtaat    1500
gttgttttgt gtttgttgtt gttggtaatt gttgtaaaaa tacgctctcc aaatgaaatg    1560
aacttcctta tatagaggaa gggtcttgcg aaggatagtg ggattgtgcg tcatcccta    1620
cgtcagtgga gatatcacat caatccactt gctttgaaga cgtggttgga acgtcttctt    1680
tttccacgat gctcctcgtg ggtggggtc catctttggg accactgtcg gcagaggcat    1740
cttcaacgat ggcctttcct ttatcgcaat gatggcattt gtaggagcca ccttccttt    1800
ccactatctt cacaataaag tgacagatag ctgggcaatg aatccgagg aggtttccgg    1860
atattaccct ttgttgaaaa gtctcaattg ccctttggtc ttctgagact gtatctttga    1920
tatttttgga gtagacaagt gtgtcgtgct ccaccatgtt ctggcaattc cggttcgctt    1980
gctgtccata aaaccgccca gtctagctat cgccatgtaa gcccactgca agctacctgc    2040
tttctctttg cgcttgcgtt ttccttgtc cagatagccc agtagctgac attcatccgg    2100
ggtcagcacc gtttctgcgg actggctttc tacgtgttcc gcttcctta gcagcccttg    2160
cgccctgagt gcttgcggca gcgtgaagct ggcgcgccgc tctagcagaa ggcatgttgt    2220
tgtgactccg aggggttgcc tcaaactcta tcttataacg gccgtggagg catgaggca    2280
agggcatttt ggtaatttaa gtagttagtg gaaaatgacg tcatttactt aaagacgaag    2340
tcttgcgaca aggggggccc acgccgaatt ttaatattac cggcgtggcc ccaccttatc    2400
gcgagtgctt tagcacgagc ggtccagatt taaagtagaa aagttccgc ccactagggt    2460
taaaggtgtt cacactataa aagcatatac gatgtgatag tatttgatgg agcgtatatt    2520
gtatcaggta tttccgtcgg atacgaatta ttcgtacgac cctcctgcag gtcaacatgg    2580
tggagcacga cacacttgtc tactccaaaa atatcaaaga tacagtctca gaagaccaaa    2640
gggcaattga gacttttcaa caaagggtaa tatccggaaa cctcctcgga ttccattgcc    2700
cagctatctg tcactttatt gtgaagatag tggaaaagga aggtggctcc tacaaatgcc    2760
atcattgcga taaggaaag gccatcgttg aagatgcctc tgccgacagt ggtcccaaag    2820
atggaccccc acccacgagg agcatcgtgg aaaaagaaga cgttccaacc acgtcttcaa    2880
agcaagtgga ttgatgtgat aacatggtgg agcacgacac acttgtctac tccaaaaata    2940
tcaaagatac agtctcagaa gaccaaaggg caattgagac ttttcaacaa agggtaatat    3000
ccggaaacct cctcggattc cattgcccag ctatctgtca ctttattgtg aagatagtgg    3060
aaaaggaagg tggctcctac aaatgccatc attgcgataa aggaaaggcc atcgttgaag    3120
atgcctctgc cgacagtggt cccaaagatg gaccccacc cacgaggagc atcgtggaaa    3180
aagaagacgt tccaaccacg tcttcaaagc aagtggattg atgtgatatc tccactacg    3240
taaggatga cgcacaatcc cactatcctt cgcaagaccc ttcctctata taaggaagtt    3300
catttcattt ggagaggacc tcgagaaaca aacaaaatca acaaatatag aaaataacgc    3360
atttccaatt ctttgaaatt tctgcaacac catggacatt gacccttaca agaatttgg    3420
agctactgtg gagcttctca gcttttttgcc ttctgacttc tttccttctg tcagggatct    3480
ccttgacact gcctcagctc tttataggga agccttggag tctcctgagc attgctcatc    3540
tcaccatact gcactcaggc aagccattct ctgctgggga gaattgatga ctcttgctac    3600
ctgggtgggt aacaatctag aggatccagc atccagagat cttgttgtta actatgttaa    3660
tactaatgtg ggtttgaaga tcaggcaact cttgtggttt catatatctt gccttacttt    3720
tggaagagag actgtacttg aatatttggt tctcttttgga gtgtggatta gaactcctcc    3780
agcctataga ccaccaaatg cccctatctt gtcgactctt ccagaaacta ctgttgttgg    3840
aggttctggt ggatcaggag gttccggtgg ttctggaggt tccggaatgg acattgaccc    3900
ttacaaagaa tttggagcta ctgtggagct ctcagctttt tgccttctg acttctttcc    3960
ttctgtcagg gatctccttg acactgcctc agctctttat agggaagcct tggagtctcc    4020
tgagcattgc tcacctcacc atactgcact caggcaagcc attctctgct ggggagaatt    4080
gatgactctt gctacctggg tgggtaacaa tctagaggt accggtgag gcggttcagg    4140
cggaggtgga tccgcaaccc aactttacaa gacttgcaaa caggctggaa catgtccacc    4200
tgacattatc ccaaaggtgg aagaaagac cattgctgat cagatcctcc agtatggatc    4260
aatgggtgtg tctcttggtg gacttggaat tggaacagga agtggtacag gaggaaggac    4320
tggttacatc ccattgggaa caagacctcc aacagcaca gatacactgg caccagttag    4380
acctcctcta acagtagatc cagttggacc atctgatcca tctatcgtgt cccttgtaga    4440
ggagacctct ttcattgatg ctggtgcccc aactagtgga ggttctggag gatctggttc    4500
tggtggaggt tctggtggag atccagcatc cagagatctt gttgttaact atgttaatac    4560
taatgtgggt ttgaagatca ggcaactctt gtggtttcat atatcttgcc ttactttgg    4620
aagagagact gtacttgaat atttggtctc ttttggagtg tggattagaa ctcctccagc    4680
ctatagacca ccaaatgccc tatcttgtc gactcttcca gaaactactg ttgttcgaag    4740
aagggacagg ggcagatccc ctagacgtag aactccccagc cctagaagaa ggagatcccc    4800
atctcctagg cgtagataag agctcgaagt gacatcacaa agttgaaggt aataaagcca    4860
aattaattaa gacattttca taatgatgtc aagaatgcaa agcaaattgc ataactgcct    4920
ttatgcaaaa cattaatata atataaatta taaagaactg cgctctctgc ttcttatttt    4980
cttagcttca tttattagtc actagctgtt cagaatttc agtatctttt gatattacta    5040
agaacctaat cacacaatgt atatcttat gcaggaaaaa cagaatgctg agctaaaaga    5100
aaggcttttt ccattttcga gagacaatga gaaaagaaga agaagaagaa gaagaagaag    5160
aagaagaaaa gagtaaataa taaagcccca caggaggcga agttcttgta gctccatgtt    5220
atctaagtta ttgatattgt ttgccctata ttttattct gtcattgtgt atgttttgtt    5280
cagtttcgat ctccttgcaa aatgcagaga ttatgagatg aataaactaa gttatattat    5340
tatacgtgtt aatattctcc tcctctctct agctagctct ttgtttttctc ttttcttat    5400
ttgattttct ttaaatcaat ccatttagg agagggccag ggagtgatcc agcaaaacat    5460
gaagattaga agaacttcc ctctttttttt tcctgaaaac aatttaacgt cgagatttat    5520
ctcttttgt aatggaatca tttctacagt tatgacgaat tctcgattaa aaatcccaat    5580
tatatttggt ctaatttagt ttggtattga gtaaaacaaa ttcgaaccaa accaaaatat    5640
aaatatatag ttttttatata tatgcccttta agacttttta tagaatttc tttaaaaaat    5700
```

```
atctagaaat atttgcgact cttctggcat gtaatatttc gttaaatatg aagtgctcca   5760
tttttattaa ctttaaataa ttggttgtac gatcactttc ttatcaagtg ttactaaaat   5820
gcgtcaatct cttttgttctt ccatattcat atgtcaaaat ctatcaaaat tcttatatat   5880
cttttttcgaa tttgaagtga aatttcgata atttaaaatt aaatagaaca tatcattatt   5940
taggtatcat attgatttt atacttaatt actaaatttg gttaactttg aaagtgtaca    6000
tcaacgaaaa attagtcaaa cgactaaaat aaataaatat catgtgttat taagaaaatt   6060
ctcctataag aatattttaa tagatcatat gtttgtaaaa aaaattaatt tttactaaca   6120
catatattta cttatcaaaa atttgacaaa gtaagattaa aataatattc atctaacaaa   6180
aaaaaaacca gaaaatgctg aaaacccggc aaaaccgaac caatccaaac cgatatagtt   6240
ggtttggttt gattttgata taaaccgaac caactcggtc catttgcacc cctaatcata   6300
atagctttaa tatttcaaga tattattaag ttaacgttgt caatatcctg gaaatttgc    6360
aaaatgaatc aagcctatat ggctgtaata tgaatttaaa agcagctcga tgtggtggta   6420
atatgtaatt tacttgattc taaaaaaata tcccaagtat taataatttc tgctaggaag   6480
aaggttagct acgatttaca gcaaagccag aatacaaaga accataaagt gattgaagct   6540
cgaaatatac gaaggaacaa atattttaa aaaaatacgc aatgacttgg aacaaaagaa     6600
agtgatatat tttttgttct taaacaagca tcccctctaa agaatggcag ttttcctttg   6660
catgtaacta ttatgctccc ttcgttacaa aaattttgga ctactattgg gaacttcttc   6720
tgaaaatagt ggtaccgagt gtacttcaag tcagttggaa atcaataaaa tgattatttt   6780
atgaatatat ttcattgtgc aagtagatag aaattacata tgttacataa cacacgaaat   6840
aaacaaaaaa acacaatcca aaacaaacac cccaaacaaa ataacactat atatatcctc   6900
gtatgaggag aggcacgttc agtgactcga cgattcccga gcaaaaaaag tctccccgtc   6960
acacatatag tgggtgacgc aattatcttc aaagtaatcc ttctgttgac ttgtcattga   7020
taacatccag tcttcgtcag gattgcaaag aattatagaa gggatcccac cttttatttt   7080
cttctttttt ccatatttag ggttgacagt gaaatcagac tggcaaccta ttaattgctt   7140
ccacaatggg acgaacttga aggggatgtc gtcgatgata ttataggtgg cgtgttcatc   7200
gtagttggtg aagtcgatgg tcccgttcca cgtagttgtgt cgcccgagac ttctagccca   7260
ggtggtctttt ccgtacgag ttggtccgca gatgtagagg ctggggtgtc tgaccccagt    7320
ccttccctca tcctggttag atcggccatc cactcaaggt cagattgtgc ttgatcgtag   7380
gagacaggat gtatgaaagt gtaggcatcg atgcttacat gatataggtg cgtctctctc   7440
cagttgtgca gatcttcgtg gcagcggaga tctgattctg tgaagggcga cacgtactgc   7500
tcaggttgtg gaggaaataa tttgttggct gaatattcca gccattgaag ctttgttgcc   7560
cattcatgag ggaactcttc tttgatcatg tcaagatact cctccttaga cgttgcagtc   7620
tggataatag ttcgccatcg tgcgtcagat ttgcgaggag acaccttatg atctcggaaa   7680
tctcctctgg ttttaatatc tccgtccttt gatatgtaat caaggacttg tttagagttt   7740
ctagctggct ggatattagg gtgatttcct tcaaaatcga aaaagaagg atccctaata    7800
caaggttttt tatcaagctg gataagagca tgatagtggg tagtgccatc ttgatgaagc   7860
tcagaagcaa caccaaggaa gaaaataaga aaaggtgtga gttctccca gagaaactgg    7920
aataaatcat ctctttgaga tgagcacttg gggtaggtaa ggaaaacata tttagattgg   7980
agtctgaagt tcttgctagc agaaggcatg ttgttgtgac tccgagggt tgcctcaaac    8040
tctatcttat aaccggcgtg gaggcatgga ggcaagggca ttttggtaat ttaagtagtt   8100
agtggaaaat gacgtcattt acttaaagac gaagtcttgc gacaagggg gcccacgccg    8160
aattttaata ttaccggcgt ggccccacct tatcgcgagt gctttagcac gagcggtcca   8220
gatttaaagt agaaaagttc ccgcccacta gggttaaagg tgttcacact ataaaagcat   8280
atacgatgtg atggtatttg atggagcgta tattgtatca ggtatttccg tcggatacga   8340
attattcgta cggccggacc ggtccccctag gccggccaat tcgagatcgg ccgcggctga   8400
gtggctcctt caatcgttgc ggttctgtca gttccaaacg taaaacgct tgtcccgcgt     8460
catcgcggg ggtcataacg tgactcccctt aattctccgc tcatgatcag attgtcgttt    8520
cccgccttca gtttaaacta tcagtgtttg acaggatata ttggcgggta aacctaagag   8580
aaaaagagcgt ttattagaat aatcggatat ttaaaagggc gtgaaaaggt ttatccgttc   8640
gtccattgt atgtgcatgc caaccacagg gttccccaga tctggcgccg gccagcgaga    8700
cgagcaagat tggccgccgc ccgaaacgat ccgacacggc ccagcaca ggtgcgcagg     8760
caaattgcac caacgcatac agcgccagca gaatgccata gtgggcggtg acgtcgttcg   8820
agtgaaccag atcgcgcagg aggccccggca gcaccggcat aatcaggccg atgccgacag   8880
cgtcgagcgc gacagtgctc agaattacga tcagggggtat gttgggttttc acgtctggcc   8940
tccggagact gtcatacgcg taaaaaggcc gcgttgctgg cgttttttcca taggctccgc   9000
cccccctgacg agcatcacaa aaatcgacgc tcaagtcaga ggtggcgaaa cccgacagga   9060
ctataaagat accaggcgtt tccccctgga agctccctcg tgcgctctcc tgttccgacc   9120
ctgccgctta ccggatacct gtccgccttt ctcccttcgg gaagcgtggc gctttctcat   9180
agctcacgct gtaggtatct cagttcggtg taggtcgttc gctccaagct gggctgtgtg   9240
cacgaacccc ccgttcagcc cgaccgctgc gccttatccg gtaactatcg tcttgagtcc   9300
aacccggtaa gacacgactt atcgccactg gcagcagcca ctggtaacag gattagcaga   9360
gcgaggtatg taggcggtgc tacagagttc ttgaagtggt ggcctaacta cggctacact   9420
agaaggacag tatttggtat ctgcgctctg ctgaagccag ttaccttcgg aaaaagagtt   9480
ggtagctctt gatccggcaa acaaaccacc gctggtaagc ggtggttttt tgtttgcaag   9540
cagcagatta cgcgcagaaa aaaaggatct caagaagatc ctttgatctt ttctacgggg   9600
tctgacgctc agtggaacga aaactcacgt taagggattt tggtcatgag attatcaaaa   9660
aggatcttca cctagatcct tttaaattaa aaatgaagtt ttaaatcaat ctaaagtata   9720
tatgagtaaa cttggtctgc agttgccatg ttttacggca gtgagagcag agatagcgct   9780
gatgtccggc ggtgcttttg ccgttacgca ccaccccgtc agtagctgaa caggagggac   9840
agctgataga cacagaagcc actgagcac ctcaaaaaca ccatcataca ctaaatcagt    9900
aagttggcag catcacccat aattgtgtt tcaaatcgg ctccgtcgat actatgttat     9960
acgccaactt tgaaacaac tttgaaaaag ctgttttctg gtatttaagg ttttagaatg     10020
caaggaacag tgaattggag ttcgtcttgt tataattagc ttcttggggt atctttaaat   10080
actgtagaaa agaggaagga aataataaat ggctaaaatg acggaattgaa                    10140
aaaactgatc gaaaaatacc gctgcgtaaa agatacggaa ggaatgtctc ctgctaaggt   10200
atataagctg gtgggagaaa atgaaaacct atatttaaaa atgacggaca gccggtataa   10260
agggaccacc tatgatgtgg aacgggaaaa ggacatgatg ctatggctgg aaggaaagct   10320
gcctgttcca aaggtcctgc actttgaacg gcatgatggc tggagcaatc tgctcatgag   10380
tgaggccgat ggcgtccttt gctcggaaga gtatgaagat gaacaaagcc ctgaaaagat   10440
```

```
tatcgagctg tatgcggagt gcatcaggct ctttcactcc atcgacatat cggattgtcc    10500
ctatacgaat agcttagaca gccgcttagc cgaattggat tacttactga ataacgatct    10560
ggccgatgtg gattgcgaaa actgggaaga agacactcca tttaaagatc cgcgcgagct    10620
gtatgatttt ttaaagacgg aaaagcccga agaggaactt gtcttttccc acggcgacct    10680
gggagacagc aacatctttg tgaaagatgg caaagtaagt ggctttattg atcttgggag    10740
aagcggcagg gcggacaagt ggtatgacat tgccttctgc gtccggtcga tcagggagga    10800
tatcggggaa gaacagtatg tcgagctatt ttttgactta ctggggatca agcctgattg    10860
ggagaaaata aaatattata ttttactgga tgaattgttt tagtacctag atgtggcgca    10920
acgatgccgg cgacaagcag gagcgcaccg acttcttccg catcaagtgt tttggctctc    10980
aggccgaggc ccacgcaag tatttgggca aggggtcgct ggtattcgtg cagggcaaga    11040
ttcggaatac caagtacgag aaggacggcc agacggtcta cgggaccgac ttcattgccg    11100
ataaggtgga ttatctggac accaaggcac caggcgggtc aaatcaggaa taagggcaca    11160
ttgccccggc gtgagtcggg gcaatcccgc aaggagggtg aatgaatcgg acgtttgacc    11220
ggaaggcata caggcaagaa ctgatcgacg cggggttttc cgccgaggat gccgaaacca    11280
tcgcaagccg caccgtcatg cgtgcgcccc gcgaaacctt ccagtccgtc ggctcgatgt    11340
tccagcaagc tacgccaag atcgagcgcg acagcgtgca actggctccc cctgccctgc    11400
ccgcgccatc ggccgccgtg gagcgttcgc gtcgtctcga acaggaggcg gcaggtttgg    11460
cgaagtcgat gaccatcgac acgcgaggaa ctatgacgac caagaagcga aaaaccgccg    11520
gcgaggacct ggcaaaacag gtcagcgagg ccaagcaggc cgcgttgctg aaacacacga    11580
agcagcagat caaggaaatg cagctttcct tgttcgatat tgcgccgtgg ccggacacga    11640
tgcgagcgat gccaaacgac acggcccgct ctgcccgtt caccacgcgc aacaagaaaa    11700
tccccgcgcga ggcgctgcaa aacaaggtca ttttccacgt caacaaggac gtgaagatca    11760
cctacaccgg cgtcgagctg cgggccgacg atgacgaact ggtgtggcag caggtgttgg    11820
agtacgcgaa gcgcacccct atcggcgagc cgatcacctt cacgttctac gagctttgcc    11880
aggacctggg ctggtcgatc aatggccggt attacacgaa ggccgaggaa tgcctgtcgc    11940
gcctacaggc gacggccgt ggcttcacgt ccgaccggt tgggcacctg gaatcggtgt    12000
cgctgctgca ccgcttccgc gtcctggacc gtgcaagaa aacgtcccgt tgccaggtcc    12060
tgatcgacga ggaaatcgtc gtgctgtttg ctggcgacca ctacacgaaa ttcatatggg    12120
agaagtaccg caagctgtcg ccgacggccc gacggatgtt cgactatttc agctcgcacc    12180
gggagccgta cccgctcaag ctggaaacct tccgcctcat gtgcggatcg gattccaccc    12240
gcgtgaagaa gtggcgcgag caggtcggcg aagcctgcga agagttgcga ggcagcggcc    12300
tggtggaaca cgcctgggtc aatgatgacc tggtgcattg caaacgctag ggccttgtgg    12360
ggtcagttcc ggctggggt tcagcagcca gcgctttact ggcatttcag gaacaagcgg    12420
gcactgctcg acgcacttgc ttcgctcagt atcgctcggg acgcacggcg cgctctacga    12480
actgccgata aacagaggat taaaattgac aattcaatgg caaggactgc cagcgctgcc    12540
attttttgggg tgaggccgtt cgcggccgag gggcgcagcc cctgggggga tgggaggccc    12600
gcgttagcgg gccgggaggg ttcgagaagg ggggcaccc cccttcggcg tgcgcggtca    12660
cgcgcacagg gcgcagccct ggttaaaaac aaggtttata aatattggtt taaaagcagg    12720
ttaaaagaca ggttagcggt ggccgaaaaa cgggcggaaa ccccttgcaaa tgctggattt    12780
tctgcctgtg gacagcccct caaatgtcaa taggtgcgcc cctcatctgt cagcactctg    12840
ccccctcaagt gtcaaggatc gcgcccctca tctgtcagta gtcgcgcccc tcaagtgtca    12900
ataccgcagg gcacttatcc ccaggcttgt ccacatcatc tgtgggaaac tcgcgtaaaa    12960
tcaggcgttt tcgccgattt gcgaggctgg ccagctccac gtcgccggcc gaaatcgagc    13020
ctgcccctca tctgtcaacg ccgcgccggg tgagtcggcc cctcaagtgt caacgtccgc    13080
ccctcatctg tcagtgaggg ccaagttttc cgcgaggtat ccacaacgcc ggcggccgcg    13140
gtgtctcgca cacggcttcg acggcgtttc tggcgcgttt gcagggccat agacggccgc    13200
cagcccaggc gcgagggcaa ccagcccggt gagcgtccga aaggcgctcg gtcttgcctt    13260
gctcgtcgag atctgggtc gatcagccgg ggatgcatca ggccgacagt cggaacttcg    13320
ggtccccgac ctgtaccatt cggtgagcaa tggataggg agttgatatc gtcaacgttc    13380
acttctaaag aaatagcgcc actcagcttc ctcagcggct ttatccagcg atttcctatt    13440
atgtcggcat agttctcaag atcgacagcc tgtcacggtt aagcgagaaa tgaataaaa    13500
ggctgataat tcggatctct gcgagggaga tgatatttga tcacaggcag caacgctctg    13560
tcatcgttac aatcaaacatg ctaccctccg cgagatcatc cgtgtttcaa acccggcagc    13620
ttagttgccg ttcttccgaa tagcatcggt aacatgagca aagtctgccg ccttacaacg    13680
gctctcccgc tgacgccgtc ccggactgat gggctgcctg tatcgagtgg tgattttgtg    13740
ccgagctgcc ggtcggggag ctgttggctg gctggtggca ggatatattg tggtgtaaac    13800
aaattgacgc ttagacaact taataacaca ttgcggacgt ttttaatgta ctgggggtggt    13860
ttttcttttc accagtgaga cgggcaacag ctgattgccc ttcaccgcct ggccctgaga    13920
gagttgcagc aagcggtcca cgctggtttg cccccagcagg cgaaaatcct gtttgatggt    13980
ggttccgaaa tcggcaaaat ccccttataaa tcaaagaat agcccgagat aggggttgagt    14040
gttgttccag tttggaacaa gagtccacta ttaaagaacg tggactccaa cgtcaaaggg    14100
cgaaaaaccg tctatcaggg cgatggccca ctacgtgaac catcacccaa atcaagttttt    14160
ttggggtcga ggtgccgtaa agcactaaat cggaacccta aagggagccc ccgatttaga    14220
gcttgacggg gaaagccggc gaacgtggcg agaaaggaag ggaagaaagc gaaaggagcg    14280
ggcgccattc aggctgcgca actgttggga aggg                                  14314

SEQ ID NO: 44         moltype = DNA  length = 18066
FEATURE               Location/Qualifiers
misc_feature          1..18066
                      note = pBYR11eMa-h6D8-L2
source                1..18066
                      mol_type = other DNA
                      organism = synthetic construct
SEQUENCE: 44
cgatcggtcg attcatagaa gattagattt tcatagtat tttttaaag taaacctta    60
actacggtta ggcacttttt aagttaaatt taatttgaac ccttaaatta attttttaaaa   120
tagataaata tcaatcatcc tgatatgctt ttgaaaaaat gaatgagaaa gatgattcaa   180
ttaaggccac atttttaatca tgactaaaat aatatacagt ataatttcat atatatttgc   240
tttaaaaaaa aattgacaat ccattcgttt ctagcaataa atttcttcaa ccacaaatat   300
```

```
attaaagata actacggcat agaaacaaaa atctatgaag aatttttgta tacttcatat   360
gaaattaaaa aaaacttcat tgaacatcaa ataataata ataatcataa actcctcaat   420
atttatattc ctagcttctt gaattaaatt gtttacatat tcaacgatgt aaaaaattat   480
ttctctatct attttcctta tatcatgcat ggtttcacat atatcaaagg ataaaagcaa   540
tctatgtaaa ttatctcact ttattaagtt ttctatctga attattgaga acgtagattt   600
cttttttgcac tatcccccaa taattagcaa aacacaccta gactagattt gttttgctaa   660
cccaattgat attaattata tatgattaat atttatatgt atatgaatt ggttaataaa   720
atgcatctgg ttcatcaaag aattataaag acacgtgaca ttcatttagg ataagaaata   780
tggatgatct cttttctctta ttcagataat tagtaattac acataacaca caactttgat   840
gcccacatta tagtgattag catgtcacta tgtgtgcatc ctttttatttc atacattaat   900
taacttggcc aatccagaag atggacaagt ctagggtcac attgcagggt actctagctt   960
actcgccttc tttttcgaag gtttgagtac cttcagggca tcctcttgat acattacttt  1020
ccacttcgat tggggcaagc tgtagcagtt cttgcttaga ccgaattgcc atctcacaga  1080
gatgctgaag agttcgcgac cctccagaaa cggtgatact aactcctcga aaccgaatac  1140
tataggtaca tccgatctgg tcgaaaccga aaaatcgaga tgctgcatag ttaaccgaat  1200
ctcccgtcca agatccaagg actctgtgca gtgaagcttc cgtcctgtcg tatctgagat  1260
atctcttaaa tacaactttc ccgaaacccc agctttcctt gaaaccaagg ggattatctt  1320
gattcgaatt cgtctcatcg ttatgtagcc gccactcagt ccaactcgga ctttcgtcag  1380
gaagtttgaa gggagaagtt gtacctcctg atcctccatc ccaacgttca ctgttagctt  1440
gttccctagc gtcgtttcct tgtatagctc gttccatgga ttgtaaatag taattgtaat  1500
gttgtttgtt gtttgttgtt gttggtaatt gttgtaaaaa tacgctctcc aaatgaaatg  1560
aacttcctta tatagaggaa gggtcttgcg aaggatagtg ggattgtgcg tcatccctta  1620
cgtcagtgga gatatcacat caatccactt gctttgaaga cgtggttgga acgtcttctt  1680
tttccacgat gctcctcgtg ggtggggtc catctttggg accactgtcg gcagaggcat  1740
cttcaacgat ggccttttcct ttatcgcaat gatggcattt gtaggagcca ccttcctttt  1800
ccactatctt cacaataaag tgacagatag ctgggcaatg gaatccgagg aggtttccgg  1860
atattcccct ttgttgaaaa gtctcaattg ccctttggtc ttctgagact gtatctttga  1920
tattttgga gtagacaagt gtgtcgtgct ccaccatgtt ctggcaattc cggttcgctt  1980
gctgtccata aaaccgccca gtctagctat cgccatgtaa gcccactgca agctacctgc  2040
tttctctttg cgcttgcgtt ttcccttgtc cagatagccc agtagctgac attcatccgg  2100
ggtcagcacc gtttctgcgg actggctttc tacgtgttcc gcttccttta gcagcccttg  2160
cgccctgagt gcttgcggca gcgtgaagct ggcgcgccgc tctagcagaa ggcatgttgt  2220
tgtgactccg aggggttgcc tcaaactcta tcttataacc ggcgtggagg catggaggca  2280
agggcatttt ggtaatttaa gtagttagtg gaaaatgacg tcatttactt aaagacgaag  2340
tcttgcgaca aggggggccc acgccgaatt ttaatattac cggcgtggcc ccaccttatc  2400
gcgagtgctt tagcacgagc ggtccagatt taaagtagaa aagttcccgc ccactagggt  2460
taaaggtgtt cacactataa aagcatatac gatgtgatgg tatttgatgg agcgtatatt  2520
gtatcaggta tttccgtcgg atacgaatta ttcgtacgac cctcctgcag gtcaacatgg  2580
tggagcacga cacacttgtc tactccaaaa atatcaaaga tacagtctca gaagaccaaa  2640
gggcaattga gacttttcaa caaagggtaa tatccggaaa cctcctcgga ttccattgcc  2700
cagctatctg tcactttatt gtgaagatag tggaaaagga aggtggctcc tacaaatgcc  2760
atcattgcga taaaggaaag gccatcgttg aagatgcctc tgccgacagt ggtcccaaag  2820
atggaccccc acccacgagg agcatctggg aaaaagagaa cgttccaacc acgtcttcaa  2880
agcaagtgga ttgatgtgat aacatggtgg agcacgacac acttgtctac tccaaaaata  2940
tcaaagatac agtctcagaa gaccaaaggg caattgagac ttttcaacaa agggtaatat  3000
ccggaaacct cctcggattc cattgcccag ctatctgtca ctttattgtg aagatagtgg  3060
aaaaggaagg tggctcctac aaatgccatc attgcgataa aggaaaggcc atcgttgaag  3120
atgcctctgc cgacagtggt cccaaagatg gaccccacc cacgaggagc atcgtggaaa  3180
aagaagacgt tccaaccacg tcttcaaagc aagtggattg atgtgatatc tccactgacg  3240
taagggatga cgcacaatcc cactatcctt cgcaagaccc ttcctctata taggaagttt  3300
catttcatttt ggagaggacc tcgagaaaca aacaaaatca acaaatatag aaataaccgc  3360
atttccaatt ctttgaaatt tctgcaacat ctagaacaat gggatggtct tgcatcatac  3420
tcttttcttgt tgcaactgct acaggtgtcc actctgatgt tcagcttctc gagtctggag  3480
gtggtcttgt gcaacctgga ggttccttga gactctcctg tgcagcttca gggtttgact  3540
tcagtaggta ctggatgagt tgggttcgtc aagctcctgg gaaaggacta gaatggattg  3600
gagagatcaa tccagattca agtaccatca actatactcc atctctgaag gatcgcttca  3660
ccatttccag agacaatgcc aagaacacgt tgtatcttca gatgaacagc ttgaggactg  3720
aagcacagc cttgtactac tgcacaagac agggctatgg ctacaactac tggggtcaag  3780
gcaccactgt cacagtgtct tcagctagca ccaaaggtcc atcggtcttt cccactggcca  3840
cttcttccaa gagtacttct ggaggcacag ctgcactggg ttgtcttgtc aaggactact  3900
ttccagaacc tgttacggtt tcgtggaact caggtgctct gaccagtgga gtgcacacct  3960
ttccagctgt tcttcagtcc tcaggattgt attctcttag cagtgttgtg actgttccat  4020
cctcaagctt gggcactcag acctacatct gcaatgtgaa tcacaaaccc agcaacacca  4080
aggttgacaa gaaagttgag cccaagtctt gtgacaaagc tcatacgtgt ccaccgtgcc  4140
cagcacctga acttcttgga ggaccgtcag tcttccttgtt tcctccaaag cctaaggata  4200
ccttgatgat ctccaggact cctgaagtca catgtgtagt tgtggatgtg agccatgaag  4260
atcctgaggt gaagttcaac tggtatgtgg atggtgtgga agtgcacaat gccaagacaa  4320
agccgagaga ggaacagtac aacagcacgt acaggggttgt ctcagtttctc actgttctgc  4380
atcaagattg gttgaatggc aaagagtaca agtgcaaggt ctccaacaaa gccctcccag  4440
cccccattga gaagaccatt tccaaagcga aagggcaacc cgtgaaccca caagtgtaca  4500
cacttcctcc atctcgcgat gaactgacca gaaccaggt cagcttgact tgcctggtga  4560
aaggcttcta tccctctgac atagctgtag agtgggagag caatgggcaa ccggagaaca  4620
actacaagac tacctctccc gttctcgatt ctgacggctc cttcttcctc tacagcaagc  4680
tcaccgtgga caagagcagg tggcaacaag ggaatgtctt ctcatgctcc gtgatgcatg  4740
aggctcttca caatcactac acacagaaga gtctctcctt gtctccgggt aaggagtg  4800
gcggatcagg tggagcggt tcaggcggag gtggatccgc aacccaactt acaagactt   4860
gcaaacaggc tggaacatgt ccacctgaca ttatccaaa ggtggaaggga aagaccattg   4920
ctgatcagat cctccagtat ggatcaatgg gtgtgttctt tggtgacttg gaattggaa   4980
caggaagtgg tacaggagga aggactggtt acatcccatt gggaacaaga cctccaacag   5040
```

```
ctacagatac actggcacca gttagacctc ctctaacagt agatccagtt ggaccatctg   5100
atccatctat cgtgtccctt gtagaggaga cctctttcat tgatgctggt gccccaacta   5160
gtcataacac tcctgtttac aagctggaca tatctgaggc aactcaataa gagctcgaag   5220
tgacatcaca aagttgaagg taataaagcc aaattaatta agacattttc ataatgatgt   5280
caagaatgca aagcaaattg cataactgcc tttatgcaaa acattaatat aatataaatt   5340
ataaagaact gcgctctctg cttcttattt tcttagcttc atttattagt cactagctgt   5400
tcagaatttt cagtatcttt tgatattact aagaacctaa tcacacaatg tatattctta   5460
tgcaggaaaa gcagaatgct gagctaaaag aaaggctttt tccattttcg agagacaatg   5520
agaaaagaag aagaagaaga agaagaagaa gaagaagaaa agagtaaata ataaagcgat   5580
acaggaggcg aagttcttgt agctccatgt tatctaagtt attgatattg tttgccctat   5640
attttatttc tgtcattgtg tatgttttgt tcagtttcga tctccttgca aaatgcagag   5700
attatgagat gaataaacta agttatatta ttatacgtgt taatattctc ctcctctctc   5760
tagctagcct tttgttttct cttttcttta tttgattttc tttaaatcaa tccattttag   5820
gagagggcca gggagtgatc cagcaaaaca tgaagattaa aagaaacttc cctctttttt   5880
ttcctgaaaa caatttaacg tcgagattta tctcttttg taatggaatc atttctacag   5940
ttatgacgaa ttctcgatta aaaatcccaa ttatatttgg tctaatttag tttggtattg   6000
agtaaaacaa attcgaacca aaccaaaata taaatatata gttttatat atatgccttt    6060
aagactttt atagaatttt cttaaaaaaa tatctagaaa tatttgcgac tcttctggca   6120
tgtaatattt cgttaaatat gaagtgctcc attttatta acttaaata attggttgta    6180
cgatcacttt cttatcaagt gttactaaaa tgcgtcaatc tctttgttct tccatattca   6240
tatgtcaaaa tctatcaaaa ttcttatata tcttttttcga atttgaagtg aaatttcgat   6300
aatttaaaat taaatagaac atatcattat ttaggtatca ttattgatttt tatacttaat   6360
tactaaattt ggttaacttt gaaagtgtac atcaacgaaa aattagtcaa acgactaaaa   6420
taaataaata tcatgtgtta ttaagaaaat tctcctataa gaatatttta atagatcata   6480
tgtttgtaaa aaaattaat ttttactaac acatatattt acttatcaaa aatttgacaa    6540
agtaagatta aaataatatt catctaacaa aaaaaaaacc agaaaatgct gaaaacccgg   6600
caaaaccgaa ccaatccaaa ccgatatagt tggtttggtt tgattttgat ataaaccgaa   6660
ccaactcggt ccatttgcac ccctaatcat aatagcttta atatttcaag atattattaa   6720
gttaacgttg tcaatatcct ggaaattttg caaaatgaat caagcctata tggctgtaat   6780
atgaatttaa aagcagctcg atgtggtggt aatatgtaat ttacttgatt ctaaaaaaat   6840
atcccaagta ttaataattt ctgctaggaa gaaggttagc tacgattac agcaaagcca    6900
gaatacaaag aaccataaag tgattgaagc tcgaaatata cgaaggaaca aatattttta   6960
aaaaatacg caatgacttg gaacaaaaga aagtgatata ttttttgttc ttaaacaagc    7020
atcccctcta aagaatggca gttttccttt gcatgtaact attatgctcc cttcgttaca   7080
aaaattttgg actactattg ggaacttctt ctgaaaatag tggtaccgag tgtacttcaa   7140
gtcagttgga aatcaataaa atgattattt tatgaatata tttcattgtg caagtagata   7200
gaaattacat atgttacata acacacgaaa taaacaaaaa aacacaatcc aaaacaaaca   7260
ccccaaacaa aataacacta tatatatcct cgtatgagga gaggcacgtt cagtgactcg   7320
acgattcccg agcaaaaaaa gtctcccccgt cacacatata gtgggtgacg caattatctt   7380
caaagtaatc cttctgttga cttgtcattg ataacatcca gtcttcgtca ggattccaaa   7440
gaattataga agggatcggt caacatggtg gagcacgaca cacttgtcta ctccaaaaat   7500
atcaaagata cagtctcaga agaccaaagg gcaattgaga ctttcaaca aagggtaata    7560
tccggaaacc tcctcggatt ccattgccca gctatctgtc acttattgt gaagatagtg    7620
gaaaaggaag gtggctccta caaatgccat cattgcgata aaggaaaggc catcgttgaa   7680
gatgcctctg ccgacagtgg tcccaaagat ggaccccac ccacgaggag catcgtggaa    7740
aaagaagacg ttcaaccac gtcttcaaag caagtggatt gatgtgataa catggtggag   7800
cacgacaca ttgtctactc caaaaatatc aaagatacgt tctcagaaga ccaaagggca    7860
attgagactt ttcaacaaag ggtaatatcc ggaaacctcc tcggattcca ttgcccagct   7920
atctgtcact ttattgtgaa gatagtggaa aaggaaggtg gctcctacaa atgccatcat   7980
tgcgataaag gaaaggccat cgttgaagat gcctctgccg acagtggtcc caaagatgga   8040
cccccacccca cgaggagcat cgtggaaaaa gaagacgttc aaaagcaa     8100
gtggattgat gtgatatctc cactgacgta agggatgacg cacaatccca ctatccttcg   8160
caagacccttt cctctatata aggaagttca tttcatttgg agaggacctc gagaaacaaa   8220
caaaatcaac aaatatagaa aataacgcat ttccaattct ttgaaatttc tgcaacatct   8280
agaacaatgg gatggtcttg catcattctc ttcttggtag ccacagctac aggtgtccac   8340
tccgatgttt tgatgactca aagccctctc tcacttcctg tgactcttgg acagcccgca   8400
tccatatctt gcagatctag tcagagtatt gttcatagta acggcaacac ctacttggaa   8460
tggtatctgc agaaaccagg ccagtctcca aagcttctga tctacaaggc ttccaatcgt   8520
ttctctggtg tcccagacag gtttagtggc agtggatcag ggactt cacattgaag       8580
atcagcagag ttgaggctga agatgcggga gtgtactatt gtcttcaagg ttcacatgtt   8640
ccgtcaacgt ttggaggtgg gaccaaagtg gagatcaaga ctgttgcggc gccatctgtc   8700
ttcatctttc ctccatctga tgaacaactc aagtctggaa ctgcttctgt tgtgtgcctt   8760
ctgaacaact tctatcctag agaagccaaa gtacagtgga aggttgacaa tgctcttcaa   8820
tcaggtaact cccaggagag tgtcacagag caagattcca ctacagcctc   8880
tcaagtacct tgacgttgag caaggcagac tatgagaaac acaaagtgta cgcatgcgaa   8940
gtcactcatc agggcctgtc atcacccgtg acaaagagct tcaacagggg agagtgttag   9000
gtaccgagct cgaagtgaca tcacaaagtt gaaggtaata aagccaaatt aattaagaca   9060
ttttcataat gatgtcaaga atgcaaagca aattgcataa ctgcctttat gcaaaacatt   9120
aatataataa aaattataaa gaactgcgct ctctgcttct tatttt ctta gcttcattta    9180
ttagtcacta gctgttcaga ttttcagta tcttttgata ttactaagaa cctaatcaca    9240
caatgtatat tcttatgcag gaaaagcaga atgctgagct aaaagaaagg cttttt ccat   9300
tttcgagaga caatgagaaa agaagaagaa gaagaagaag aagaagaaga gaaaagagt    9360
aaataataaa gccccacagg aggcgaagtt cttgtagctc catgttatct aagttattga   9420
tattgttgc cctatatttt attt ctgtca ttgtgtatgt tttgttcagt ttcgatctcc    9480
ttgcaaaatg cagagattat gagatgaata aactaagtta tattattata cgtgttaata   9540
ttctcctcct ctctctagct agccttttgt tttctctttt tcttatttga ttttctttaa   9600
atcaatccat tttaggagag ggccaggag tgatccagca aaacatgaag attagaagaa    9660
acttccctct ttttttcct gaaaacaatt taacgtcgag atttatctct ttttgtaatg    9720
gaatcatttc tacagttatg acgaattgta catcaacgaa aaattagtca aacgactaaa   9780
```

```
ataaataaat atcatgtgtt attaagaaaa ttctcctata agaatatttt aatagatcat    9840
atgtttgtaa aaaaaattaa ttttttactaa cacatatatt tacttatcaa aaatttgaca    9900
aagtaagatt aaaataatat tcatctaaca aaaaaaaaac cagaaaatgc tgaaaacccg    9960
gcaaaaccga accaatccaa accgatatag ttggtttggt ttgattttga tataaaccga   10020
accaactcgg tccatttgca cccctaatca taatagcttt aatattcaa gatattatta   10080
agttaacgtt gtcaatatcc tggaaatttt gcaaaatgaa tcaagcctat atggctgtaa   10140
tatgaattta aaagcagctc gatgtggtgg taatatgtaa tttacttgat tctaaaaaaa   10200
tatcccaagt attaataatt tctgctagga agaaggttag ctacgattta cagcaaagcc   10260
agaatacaaa gaaccataaa gtgattgaag ctcgaaatat acgaaggaac aaatattttt   10320
aaaaaaatac gcaatgactt ggaacaaaag aaagtgatat atttttttgtt cttaaacaag   10380
catccctct aaagaatggc agttttcctt tgcatgtaac tattatgctc ccttcgttac   10440
aaaaattttg gactactatt gggaacttct tctgaaaata gtggtaccga gtgtacttca   10500
agtcagttgg aaatcaataa aatgattatt ttatgaatat atttcattgt gcaagtagat   10560
agaaattaca tatgttacat aaacacgaa ataaacaatc caaaacaaac   10620
acccaaaca aaataacact atatatatcc tcgtatgagg agaggcacgt tcagtgactc    10680
gacgattccc gagcaaaaaa agtctccccg tcacacatat agtgggtgac gcaattatct    10740
tcaaagtaat ccttctgttg acttgtcatt gataacatcc agtcttcgtc aggattgcaa    10800
agaattatag aagggatccc acctttatt tctttctttt ttccatattt aggttgaca    10860
gtgaaatcag actggcaacc tattaattgc ttccacaatg ggacgaactt gaaggggatg    10920
tcgtcgatga tattataggt ggcgtgttca tcgtagttgg tgaagtcgat ggtcccgttc    10980
cagtagttgt gtcgcccgag acttctagcc caggtggtct ttccggtacg agttggtccg    11040
cagatgtaga ggctgggtg tctgacccca gtccttcct catcctggtt agatcggcca    11100
tccactcaag gtcagattgt gcttgatcgt aggagacagg atgtatgaaa gtgtaggcat    11160
cgatgcttac atgatatagg tgcgtctctc tccagttgtg cagatcttcg tggcagcgga    11220
gatctgattc tgtgaagggc gacacgtact gctcaggttg tggaggaaat aatttgttgg    11280
ctgaatattc cagccattga agctttgttg cccattcagg agggaactct tcttttgatca   11340
tgtcaagata ctcctcctta gacgttcag tctggataat agttcgccat cgtgcgtcag    11400
atttgcgagg agacaccta tgatctcgga aatctcctct ggtttttaata tctccgtcct    11460
ttgatatgta atcaaggact tgtttagagt ttctagctgg ctggatatta gggtgattc    11520
cttcaaaatc gaaaaaagaa ggatccctaa tacaaggttt tttatcaagc tggataagag    11580
catgatagtg ggtagtgcca tcttgatgaa gctcagaagc aacaccaagg aagaaaataa    11640
gaaaaggtgt gagtttctcc cagagaaact ggaataaatc atctctttga gatgagcact    11700
tggggtaggt aaggaaaaca tatttagatt ggagtctgaa gttcttgcta gcagaaggca    11760
tgttgttgtg actccgaggg gttgcctcaa actctatctt ataaccggcg tggaggcatg    11820
gaggcaaggg cattttggta atttaagtag ttagtggaaa atgacgtcat ttacttaaag    11880
acgaagtctt gcgacaaggg gggcccacgc cgaattttaa tattaccggc gtggccccac    11940
cttatcgcga gtgctttagc acgagcggtc cagatttaaa gtagaaaagt tcccgcccac    12000
tagggttaaa ggtgttcaca ctataaaagc atatacgatg tgatggtatt tgatggagcg    12060
tatattgtat caggtatttc cgtcggatac gaattattca tacggccgga ccggtcccct    12120
aggccggcca attcgagatc ggccgcggct gagtggctcc ttcaatcgtt gcggttctgt    12180
cagttccaaa cgtaaaacgg cttgtcccgc gtcatcggcg ggggtcataa cgtgactccc    12240
ttaattctcc gctcatgatc agattgtcgt ttcccgcctt cagtttaaac tatcagtgtt    12300
tgacaggata tattggcggg taaacctaag agaaaagagc gtttattaga ataatcggat    12360
atttaaaagg gcgtgaaaag gtttatccgt tcgtccattt gtatgtgcat gccaaccaca    12420
gggttcccca gatctggcgc cggccagcga gacgagcaag attggccgcc gcccgaaacg    12480
atccgacagc gcgcccagca caggtgcgca ggcaaattgc accaacgcat acagcgccag    12540
cagaatgcca tagtgggcgg tgacgtcgtt cgagtgaacc agatcgcgca ggaggcccgg    12600
cagcaccggc ataatcaggc cgatgccgac agcgtcgagc gcgacagtgc tcagaattac    12660
gatcaggggt atgttgggtt tcacgtctgg cctccggaga ctgtcatacg cgtaaaaagg    12720
ccgcgttgct ggcgttttc cataggctcc gcccccctga cgagcatcac aaaaatcgac    12780
gctcaagtca gaggtggcga aacccgacag gactataaag ataccaggcg tttcccctg    12840
gaagctccct cgtgcgctct cctgttccga ccctgccgct taccggatac ctgtccgcct    12900
ttctcccttc gggaagcgtg gcgctttctc atagctcacg ctgtaggtat ctcagttcgg    12960
tgtaggtcgt tcgctccaag ctgggctgtg tgcacgaacc cccgttcag cccgaccgct    13020
gcgccttatc cggtaactat cgtcttgagt ccaacccggt aagacacga ttatcgccac    13080
tggcagcagc cactggtaac aggattagca gagcgaggta tgtaggcggt gctacagagt    13140
tcttgaagtg gtggcctaac tacggctaca ctagaaggac agtatttggt atctgcgctc    13200
tgctgaagcc agttaccttc ggaaaaagag ttggtagctc ttgatccggc aaacaaacca    13260
ccgctggtag cggtggtttt tttgtttgca agcagcagat tacgcgcaga aaaaaggat    13320
ctcaagaaga tccttttgatc ttttctacgg gtctgacgc tcagtggaac gaaaactcac    13380
gttaagggat tttggtcatg agattatcaa aaaggatctt cacctagatc cttttaaatt    13440
aaaaatgaag ttttaaatca atctaaagta tatatgagta aacttggtct gcagttgcca    13500
tgttttacgg cagtgagagc agagatacg ctgatgtccg gcggtgcttt tgccgttacg    13560
caccacccg tcagtagctg aacaggaggg acagctagta acagcagaag ccactggag    13620
acctcaaaaa caccatcata cactaaatca gtaagttggc agcatcaccc ataattgtgg    13680
tttcaaaatc ggctccgtcg atactatgtt atacgccaac tttgaaaaca actttgaaaa    13740
agctgttttc tggtatttaa ggtttagaa tgcaaggaac agtgaattgg agttcgtctt    13800
gttataatta gcttcttggg gtatctttaa atactgtaga aagagaag gaaataataa    13860
atggctaaaa tgagaatatc accggaattg aaaaaactga tcgaaaaata ccgctgcgta    13920
aaagatacgg aaggaatgtc tcctgctaag gtatataagc tggtgggaga aaatgaaaac    13980
ctatatttaa aaatgacgga cagccggtat aaagggacca cctatgatgt ggaacgggaa    14040
aaggacatga tgctatggct ggaaggaaag ctgcctgttc caaggtcct gcactttgaa    14100
cggcatgatg gctgagcaa tctgctcatg agtgaggccg atggcgtcct ttgctcggaa    14160
gagtatgaag atgaacaaag ccctgaaaag atatcggcaa tgtatgcgga gtcatcagg    14220
ctctttcact ccatcgacat atcggattgt ccctatacga atagcttaga cagccgctta    14280
gccgaattgg attacttact gaataacgat ctggccgatg tggattgcga aaactggaa    14340
gaagacactc catttaaaga tccgcgcgag ctgtatgatt ttttaaagac ggaaaagccc    14400
gaagaggaac ttgtctttc ccacggcgac ctgggagaca gcaacatctt tgtgaaagat    14460
ggcaaagtaa gtggctttat tgatcttggg agaagcggca gggcggacaa gtggtatgac    14520
```

```
attgccttct gcgtccggtc gatcaggag gatatcgggg aagaacagta tgtcgagcta   14580
tttttgact tactggggat caagcctgat tgggagaaaa taaaatatta tatttactg    14640
gatgaattgt tttagtacct agatgtggcg caacgatgcc ggcgacaagc aggagcgcac  14700
cgacttcttc cgcatcaagt gttttggctc tcaggccgag gcccacggca agtatttggg  14760
caagggtcg ctggtattcg tgcagggcaa gattcggaat accaagtacg agaaggacgg   14820
ccagacggtc tacgggaccg acttcattgc cgataaggtg gattatctgg acaccaaggc  14880
accaggcggg tcaaatcagg aataagggca cattgccccg gcgtgagtcg ggcaatccc   14940
gcaaggaggg tgaatgaatc ggacgtttga ccggaaggca tacaggcaag aactgatcga  15000
cgcggggttt tccgccgagg atgccgaaac catcgcaagc cgcaccgtca tgcgtgcgcg  15060
ccgcgaaacc ttccagtccg tcggctcgat ggtccagcga gctacggcca agatcgagcg  15120
cgacagcgtg caactggctc cccctgcccct gcccgcgcca tcgccgccg tggagcgttc   15180
gcgtcgtctc gaacaggagg cggcaggttt ggcgaagtcg atgaccatcg acacgcgagg  15240
aactatgacg accaagaagc gaaaaaccgc cggcgaggac ctggcaaaac aggtcagcga  15300
ggccaagcag gccgcgttgc tgaaacacac gaagcagcag atcaaggaaa tgcagcttc   15360
cttgttcgat attgcgccgt ggccggacac gatgcgagcg atgccaaacg acacggcccg  15420
ctctgccctg ttcaccacgc gcaacaagaa atcccgcgc gaggcgctgc aaaacaaggt   15480
catttttccac gtcaacaagg acgtgaagat cacctacacc ggcgtcgagc tgcgggccga  15540
cgatgacgaa ctggtgtggc agcaggtgtt ggagtacgcg aacgcaccc ctatcggcga   15600
gccgatcacc ttcacgttct acgagctttt ccaggacctg ggctggtcga tcaatgccg   15660
gtattacacg aaggccgagg aatgcctgtc gcgcctacag gcgacggcga tgggcttcac  15720
gtccgaccgc gttgggcacc tggaatcggt gtcgctgctg caccgcttcc gcgtcctgga  15780
ccgtgccaag aaaacgtccc gttgccaggt cctgatcgac gaggaaatcg tcgtgctgtt  15840
tgctggcgac cactcacgga aattcatatg ggagaagtac cgcaagctgt cgccgacggc  15900
ccgacggatg ttcgactatt tcagctcgca ccgggagccg tacccgctca agctggaaac  15960
cttccgcctc atgtgcggat cggattccac ccgcgtgaag aagtggcgcg agcaggtcgg  16020
cgaagcctgc gaagagttgc gaggcagcgg cctggtcgaa cacgcctggt tcaatgatga  16080
cctggtgcat tgcaaacgct agggccttgt ggggtcagtt ccggctgggg gttcagcagc  16140
cagcgcttta ctggcatttc aggaacaagc gggcactgct cgacgcactt gcttcgctca  16200
gtatcgctcg ggacgcacgg cgcgctctac gaactgccga taaacagagg attaaaattg  16260
acaattcaat ggcaaggact gccagcgctg ccatttttgg ggtgaggccg ttcgcggccg  16320
agggcgcag ccctgggggg gatgggaggc ccgcgttagc gggcggggag ggttcgagaa   16380
gggggcgcac cccccttcgg cgtgcgcggt cacgcgcaca gggcgcagcc ctggttaaaa  16440
acaaggttta taaatattgg tttaaaagca ggttaaaaga caggttagcg gtggccgaaa  16500
aacgggcgga aaccccttgca aatgctggat ttttctgcctg tggacagcca tccaaatgtc  16560
aataggtgcg ccctcatct gtcagcactc tgccctcaca gtgtcaagga tcgcgccct   16620
catcgtcag tagtcgcgcc cctcaagtgt caataccgca gggcacttat cccaggctt    16680
gtccacatca tctgtgggaa actcgcgtaa aatcaggcgt tttcgccgat ttgcgaggct   16740
ggccagctcc acgtcgccgg ccgaaatcga gcctgccccct catctgtcaa cgccgcgccg   16800
ggtgatgcg ccccctcaagt gtcaacgtcc gcccctcatc tgtcagtgag ggcaagttt    16860
tccgcgaggt atccacaacg ccggcggccg cggtgtctcg cacacggctt cgacggcgtt  16920
tctggcgt ttgcagggcc atagacggcc gccagcccag cggcgaggggc aaccagcccg    16980
gtgagcgtcg caaaggcgct cggtcttgcc ttgctcgtcg atctggggg tcgatcagcc   17040
ggggatgcat caggccgaca gtcggaactt cgggtcccg acctgtacca tcggtgagg    17100
aatggatagg ggagttgata tcgtcaacgt tcacttctaa agaaatagcg ccactcagct  17160
tcctcagcgg ctttatccag cgatttccta ttatgtcggc atagttctca agatcgcacag  17220
cctgtcacgg ttaagcgaga atgaataag aaggctgata ttcggatct ctgcgaggga    17280
gatgatattt gatcacaggc agcaacgctc tgtcatcgtt acaatcaaca tgctaccctc   17340
cgcgagatca tccgtgtttc aaaccccggca gcttagttgc cgttcttccg aatagcatcg  17400
gtaacatgag caaagtctgc cgccttacaa cggctctccc gctgacgccg tcccggactg  17460
atgggctgcc tgtatcgagt ggtgattttg tgccgagctg ccggtcgggg agctgttggc  17520
tggctggtga caggatatat tgtggtgtaa acaaattgac gcttagacaa cttaataaca  17580
cattgcggac gtttttaatg tactggggtg gttttttcttt tcaccagtga cacgggcaac  17640
agctgattgc ccttcaccgc ctggccctga gagagttgca gcaagcggtc cacgctggtt  17700
tgccccagca ggcgaaaatc ctgtttgatg gtggttccga aatcggcaaa atcccttata  17760
aatcaaaaga atagcccgag atagggttga gtgttgttcc agtttggaac aagagtccac  17820
tattaaagaa cgtggactcc aacgtcaaag ggcgaaaaac cgtctatcag ggcgatggcc  17880
cactacgtga accatcaccc aaatcaagtt tttggggtc gaggtgccgt aaagcactaa   17940
atcggaaccc taaagggagc ccccgattta gagcttgacg ggaaagccg gcgaacgtgg   18000
cgagaaagga agggaagaaa gcgaaaggag cgggcgccat tcaggctgcg caactgttgg   18060
gaaggg                                                             18066
```

SEQ ID NO: 45          moltype = DNA   length = 14156
FEATURE                Location/Qualifiers
misc_feature           1..14156
                       note = pBYe3R2K2Mc-BAZsE6H
source                 1..14156
                       mol_type = other DNA
                       organism = synthetic construct
SEQUENCE: 45

```
cgatcggtcg attcatagaa gattagattt tcatagtat ttttttaaag taaacccttta    60
actacggtta ggacactttt aagttaaatt taatttgaac ccttaaatta attttttaaa   120
tagataaata tcaatcatcc tgatatgctt ttgaaaaaat gaatgagaaa gatgattcaa   180
ttaaggccac atttttaatca tgactaaaat aatatacagt ataatttcat atatatttgc  240
tttaaaaaaa aattgacaat ccattcgttt ctagcaataa atttcttcaa cccacaaatat 300
attaaagata actacggcat agaaacaaaa atctatgaag aatttttgta tacttcatat   360
gaaattaaaa aaacttcat tgaacatcaa aataataata ataatcataa actcctcaat   420
atttatattc ctagcttctt gaattaaatt gtttacatat tcaacgatgt aaaaaattat   480
ttctctatct atttttcctta tatcatgcat ggtttcacat atatcaaagg ataaaagcaa  540
tctatgtaaa ttatctcact ttattaagtt ttctatctga attattgaga acgtagattt   600
```

```
cttttttgcac tatcccccaa taattagcaa aacacaccta gactagattt gttttgctaa    660
cccaattgat attaattata tatgattaat atttatatgt atatggaatt ggttaataaa    720
atgcatctgg ttcatcaaag aattataaag acacgtgaca ttcatttagg ataagaaata    780
tggatgatct ctttctctta ttcagataat tagtaattac acataacaca caactttgat    840
gcccacatta tagtgattag catgtcacta tgtgtgcatc cttttatttc atacattaat    900
taacttggcc aatccagaag atggacaagt ctagggtcac attgcagggt actctagctt    960
actcgccttc ttttttcgaag gtttgagtac cttcagggca tcctcttgat acattacttt   1020
ccacttcgat tgggcaagc tgtagcagtt cttgcttaga ccgaattgcc atctcacaga    1080
gatgctgaag agttcgcgac cctccagaaa cggtgatact aactcctcga aaccgaatac   1140
tataggtaca tccgatctgg tcgaaaccga aaaatcgaca tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatcccctta  1620
cgtcagtgga gatatcacat caatccactt gctttgaaga cgtggttgga acgtcttctt   1680
tttccacgat gctcctcgtg ggtgggggtc catctttggg accactgtcg cgagaggcat   1740
cttcaacgat ggccttttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tattttggga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggcttc tacgtgttcc gcttccttta gcagccccttg   2160
cgccctgagt gcttgcggca gcgtgaagct ggcgcgccgc tctagcagaa ggcatgttgt   2220
tgtgactccg agggggttgcc tcaaactcta tcttataacc ggcgtggagg catgcaggca   2280
agggcatttt ggtaatttaa gtagttagtg gaaaatgacg tcatttactt aaagacgaag   2340
tcttgcgaca aggggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgatgg agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagttga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gaccccccacc cacgaggagc atcgtggaaa   3180
aagaagacgt tccaaccacg tcttcaaagc aagtggattg atgtgatatc tccactacg    3240
taagggatga cgcacaatcc cactatcctt cgcaagaccc ttcctctata taggaagtt    3300
catttcattt ggagaggacc tcgagaaaca aacaaaatca acaaatatag aaaataacgc   3360
atttccaatt cttttgaaatt tctgcaacat ctagaacaat ggctaacaag cacctctcat   3420
tgtctctctt ccttgtgctc cttggtcttt ctgcttctct tgcttctggt atcaggtgca   3480
ttggagtgag caacagggac tttgtggaag gtatgtcagg tggaacttgg gttgatgttg   3540
tgttggaaca tgggggttgt gtcaccgtga tggcccagga caaaccgact gtcgacattg   3600
agttggttac aacaacggtc agcaacatgg ccgaggttag atcctactgc tatgaggctt   3660
caattcaga catggctagt gacagccgtt gcccaacaca aggtgaagcc taccttgaca   3720
agcaatcaga cactcaatat gtgtgcaaga gaacattggt ggacagaggt tggggaaacg   3780
gatgtgact tttcggtaag gaagcctcg tgacatgcgc taaattcgct tgctccaaga    3840
agatgccgg aaaagactca cagccagaga acctcgagta ccggattatg ttgtcagttc   3900
atggttccca gcacagcgga atgatcgtta atgacacagt acatgaaact gatgagaata   3960
gagccaaggt tgagattaca cctaactcac caagagccga agccaccctc ggaggtttcg   4020
gaagcttggg acttgattgt gaaccgagga caggccttga cttttcagat ttgtactact   4080
tgactatgaa taacaagcac tggttggttc acaaggaatg gttccacgac attccattgc   4140
cttggcacgc tggtgctgac accggaactc cacactggaa caacaaagag gcactcgtgg   4200
aattcaagga cgcccatgcc aagaggcaaa ctgtcgtggt tcttggtact caagaaggag   4260
ccgttcacac agcccttgct ggtgctctcg aggctgagat ggatggtgct aagggaaggc   4320
tttcctctgg ccacttgaaa tgtcgtttga agatggataa gcttagattg aagggcgtgt   4380
catactcctt gtgtaccgct gccttcacat tcaccaagat cccggctgaa acactccacg   4440
gaaccgttac cgtggaggtc caatacgccg gtacagatgg accttgcaag gttccagctc   4500
agatggcggt ggacatgcaa actcttaccc cagttggaag gttgattacc gctaaccccg   4560
ttatcactga aagcactgag aactctaaga tgatgttgga acttgatcca ccattcgtgt   4620
actcttacat tgtcattggt gtgggagaga agaagatcac ccaccactgg cacaggagtg   4680
gtagcactag tcaccatcac catcaccatt aagagcctga agtgacatca caaagttgaa   4740
ggtaataaag ccaaattaat taagacattt tcataatgat gtcaagaatg caaagcaaat   4800
tgcataactg cctttatgca aaacattaat ataatataaa ttataaagaa ctgcgctctc   4860
tgcttcttat tttcttagct tcatttatta gtcactagct gttcagaatt tcagtatctt   4920
tttgatatta ctaagaacct aatcacacaa tgtatattct tatgcaggaa aagcagaatg   4980
ctgagctaaa agaaaggctt tttccatttt cgagagacaa tgagaaaaga agaagaagaa   5040
gaagaagaag aagaagaaga aaagagtaaa taataaagcc ccacaggagg cgaagttctt   5100
gtagctccat gttatctaag ttattgatat tgtttgccct atattttatt tctgtcattg   5160
tgtatgtttt gttcagtttc gatctccttg caaaatgcag agattatgag atgaataaac   5220
taagttatat tattatacgt gttaatattc tcctcctctc tctagctagc cttttgtttt   5280
ctcttttttct tatttgatt tctttaaatc aatccatttt aggagagggc cagggagtga   5340
```

```
tccagcaaaa catgaagatt agaagaaact tccctctttt ttttcctgaa acaatttaa    5400
cgtcgagatt tatctctttt tgtaatggaa tcatttctac agttatgacg aattgtccgc    5460
aaaaatcacc agtctctctc tacaaatcta tctctctcta tttttctcca gaataatgtg    5520
tgagtagttc ccagataagg gaattagggt tcttataggg tttcgctcat gtgttgagca    5580
tataagaaac ccttagtatg tatttgtatt tgtaaaatac ttctatcaat aaaattctta    5640
attcctaaaa ccaaaatcca gtgaccctaa aaccaaaatc cagtgacgaa ttctcgatta    5700
aaaatcccaa ttatatttgg tctaatttag tttggtattg agtaaaacaa attcgaacca    5760
aaccaaaata taaatatata gttttttatat atatgccttt aagactttt atagaatttt     5820
cttaaaaaa tatctaggta catcaacgaa aaattagtca aacgactaaa ataaataaat     5880
atcatgtgtt attaagaaaa ttctcctata agaatatttt aatagatcat atgtttgtaa    5940
aaaaaattaa ttttttactaa cacatatatt tacttatcaa aaatttgaca aagtaagatt    6000
aaaataatat tcatctaaca aaaaaaaaac cagaaaatgc tgaaacccg gcaaaaccga     6060
accaatccaa accgatatag ttggtttggt ttgatttga tataaccga accaactcgg      6120
tccatttgca cccctaatca taatagcttt aatatttcaa gatattatta agttaacgtt    6180
gtcaatatcc tggaaatttt gcaaaatgaa tcaagcctat atggctgtaa tatgaattta    6240
aaagcagctc gatgtggtgg taatatgtaa tttacttgat tctaaaaaa tatcccaagt     6300
attaataatt tctgctagga agaaggttag ctacgattta cagcaaagcc agaatacaaa    6360
gaaccataaa gtgattgaag ctcgaaatat acgaaggaac aaatatttt aaaaaaatac     6420
gcaatgactt ggaacaaaag aaagtgatat atttttttgtt cttaaacaag catcccctct    6480
aaagaatggc agtttccctt tgcatgtaac tattatgctc ccttcgttac aaaaattttg    6540
gactactatt gggaacttct tctgaaaata gtggtaccga gtgtacttca agtcagttgg    6600
aaatcaataa aatgattatt ttatgaatat atttcattgt gcaagtagat agaaattaca    6660
tatgttacat aacacacgaa ataaacaaaa aaacacaatc caaacaaac accccaaaca     6720
aaataacact atatatatcc tcgtatgagg agagcacgt tcagtgactc gacgattccc      6780
gagcaaaaaa agtctccccg tcacacatat agtgggtgac gcaattatct tcaaagtaat    6840
ccttctgttg acttgtcatt gataacatcc agtcttcgtc aggattgcaa agaattatag    6900
aagggatccc acctttttat ttcttctttt ttccatattt agggttgaca gtgaaatcag    6960
actggcaacc tattaattgc ttccacaatg ggacgaactt gaaggggatg tcgtcgatga    7020
tattataggt ggcgtgttca tcgtagttgg tgaagtcgat ggtcccgttc cagtagttgt    7080
gtcgcccgag acttctagcc caggtggtct ttccggtacg agttggtccg cagatgtaga    7140
ggctggggtg tctgaccccca gtccttccct catcctggtt agatcggcca tccactcaag    7200
gtcagattgt gcttgatcgt aggagacagg atgtatgaaa gtgtaggcat cgatgcttac    7260
atgatatagg tgcgtctctc tccagttgtg cagatcttcg tggcagcgga gatctgattc    7320
tgtgaagggc gacacgtact gctcaggttg tggaggaaat aatttgttgg ctgaatattc    7380
cagccattga agctttgttg cccattcatg agggaactct tctttgatca tgtcaagata    7440
ctcctcctta gacgttgcag tctggataat agttcgccat cgtgcgtcag atttgcgagg    7500
agacaccta tgatctcgga aatctcctct ggttttaata tctccgtcct ttgatatgta     7560
atcaaggact tgtttagagt ttctagctgg ctggatatta gggtgatttc cttcaaaatc    7620
gaaaaagaa ggatccctaa tacaaggttt tttatcaagc tggataagag catgatagtg     7680
ggtagtgcca tcttgatgaa gctcagaagc aacaccaagg aagaaaataa gaaaaggtgt    7740
gagtttctcc cagagaaact ggaataaatc atctctttga gatgagcact tggggtaggt    7800
aaggaaaaca tatttagatt ggagtctgaa gttcttgcta gcagaaggca tgtggttgtg    7860
actccgaggg gttgcctcaa actctatctt ataaccggcg tggaggcatg gaggcaaggg    7920
cattttggta atttaagtag ttagtggaaa atgacgtcat ttacttaaag acgaagtctt    7980
gcgacaaggg gggcccacgc cgaatttaaa tattaccggc gtggcccac cttatcgcga     8040
gtgctttagc acgagcggtc cagatttaaa gtagaaaagt tcccgcccac tagggttaaa    8100
ggtgttcaca ctataaaagc atatacgatg tgatggtatt ggtggagcg tatattgtat     8160
caggtatttc cgtcggatac gaattattcg tacggccgga ccgtcccct aggccggcca     8220
attcgagatc ggccgcggct gagtggctcc ttcaatcgtt gcggttctgt cagttccaaa    8280
cgtaaaacgc cttgtcccgc gtcatcggcg ggggtcataa cgtgactccc ttaattctcc    8340
gctcatgatc agattgtcgt ttcccgcctt cagtttaaac tatcagtgtt tgacaggata    8400
tattggcggg taaacctaag agaaaagagc gtttattaga ataatcggat atttaaaagg    8460
gcgtgaaaag gtttatccgt tcgtccatttt gtatgtgcat gccaaccaca gggttcccca   8520
gatctggcgc cggccagcga gacgagcaag attggccgcc gcccgaaacg atccgacagc    8580
gcgcccagca caggtgcgca ggcaaattgc accaacgcat acagcgccag cagaatgcca    8640
tagtgggcgg tgacgtcgtt ggagtgaacc agatcgcgca ggaggccgg cagcaccggc     8700
ataatcaggc cgatgccgac agcgtcgagc gcgacagtgc tcagaattac gatcaggggt    8760
atgttgggtt tcacgtctgg cctccggaga ctgtcatacg cgtaaaaagg ccgcgttgct    8820
ggcgttttc cataggctcc gccccctga cgagcatcac aaaaatcgac gctcaagtca      8880
gaggtggcga aacccgacag gactataaag ataccaggcg tttccccctg gaagctccct    8940
cgtgcgctct cctgttccga ccctgccgct taccggatac ctgtccgcct ttctcccttc    9000
gggaagcgtg gcgctttctc atagctcacg ctgtaggtat ctcagttcgg tgtaggtcgt    9060
tcgctccaag ctgggctgtg tgcacgaacc cccgttcag cccgaccgct gcgccttatc     9120
cggtaactat cgtcttgagt ccaacccggt aagacacga ttatcgccac tggcagcagc     9180
cactggtaac aggattagca gagcgaggta tgtaggcggt gctacagagt tcttgaagtg    9240
gtggcctaac tacggctaca ctagaaggac agtatttggt atctgcgctc tgctgaagcc    9300
agttaccttc ggaaaaagag ttggtagctc ttgatccgc aaacaaacca ccgctggtag     9360
cggtggtttt tttgtttgca agcagcagat tacgcgcaga aaaaaaggat ctcaagaaga    9420
tcctttgatc ttttctacgg ggtctgacgc tcagtggaac gaaaactcac gttaagggat    9480
tttggtcatg agattatcaa aaaggatctt cacctagatc cttttaaatt aaaaatgaag    9540
ttttaaatca atctaaagta tatatgagta aacttggtct gcagttgcca tgttttacgg    9600
cagtgagagc agagatagcg ctgatgtccg gcggtgcttt tgccgttacg caccaccccg    9660
tcagtagctg aacaggaggg acagctgata gacacagaag ccactggagc acctcaaaaa    9720
caccatcata cactaaatca gtaagttggc agcatcacca taattgtgg tttcaaaatc     9780
ggctccgtcg atactatgtt atacgccaac tttgaaaaca actttgaaaa agctgtttc     9840
tggtatttaa ggtttagaa tgcaaggaac agtgaattgg agtcgtctt gttataatta     9900
gcttcttggg gtatctttaa atactgtaga aagaggaag gaaataataa atggctaaaa     9960
tgagaatatc accggaattg aaaaaactga tcgaaaaata ccgctgcgta aaagatacgg   10020
aaggaatgtc tcctgctaag gtatataagc tggtgggaga aaatgaaaac ctatatttaa   10080
```

```
aaatgacgga cagccggtat aaagggacca cctatgatgt ggaacgggaa aaggacatga   10140
tgctatggct ggaaggaaag ctgcctgttc caaaggtcct gcactttgaa cggcatgatg   10200
gctggagcaa tctgctcatg agtgaggccg atggcgtcct ttgctcggaa gagtatgaag   10260
atgaacaaag ccctgaaaag attatcgagc tgtatgcgga gtgcatcagg ctctttcact   10320
ccatcgacat atcggattgt ccctatacga atagcttaga cagccgctta gccgaattgg   10380
attacttact gaataacgat ctggccgatg tggattgcga aaactgggaa gaagacactc   10440
catttaaaga tccgcgcgag ctgtatgatt ttttaaagac ggaaaagccc gaagaggaac   10500
ttgtcttttc ccacggcgac ctgggagaca gcaacatctt tgtgaaagat ggcaaagtaa   10560
gtggctttat tgatcttggg agaagcggca gggcggacaa gtggtatgac attgccttct   10620
gcgtccggtc gatcagggag gatatcgggg aagaacagta tgtcgagcta tttttttgact  10680
tactggggat caagcctgat tgggagaaaa taaaatatta tattttactg gatgaattgt   10740
tttagtacct agatgtggcg caacgatgcc ggcgacaagc aggagcgcac cgacttcttc   10800
cgcatcaagt gttttggctc tcaggccgag gcccacggca agtatttggg caaggggtcg   10860
ctggtattcg tgcagggcaa gattcggaat accaagtacg agaaggaccg ccagacggtc   10920
tacgggaccg acttcattgc cgataaggtg gattatctgg acaccaaggc accaggcggg   10980
tcaaatcagg aataagggca cattgccccg gcgtgagtcg gggcaatccc gcaaggaggg   11040
tgaatgaatc ggacgtttga ccggaaggca tacaggcaag aactgatcga cgcggggttt   11100
tccgccgagg atgccgaaac catcgcaagc cgcaccgtca tgcgtgcgcc ccgcgaaacc   11160
ttccagtccg tcggctcgat ggtccagcaa gctacggcca agatcgagcg cgacagcgtg   11220
caactggctc cccctgccct gcccgcgcca tcggccgccg tggagcgttc gcgtcgtctc   11280
gaacaggagg cggcaggttt ggcgaagtcg atgaccatcg acacgcgagg aactatgacg   11340
accaagaagc gaaaaaccgc cggcaaggac ctggcaaaac aggtcagcga ggccaagcag   11400
gccgcgttgc tgaaacacac gaagcagcag atcaaggaaa tgcagctttc cttgttcgat   11460
attgcgccgt ggccggacac gatgcgagcg atgccaaacg cacgcccg ctctgccctg     11520
ttcaccacgc gcaacaagaa aatcccgcgc gaggcgctgc aaaacaaggt cattttccac   11580
gtcaacaagg acgtgaagat caccta cacc ggcgtcgagc tgcgggccga cgatgacgaa   11640
ctggtgtggc agcaggtgtt ggagtacgcg aagcgcaccc ctatcggcga gccgatcacc   11700
ttcacgttct acgagctttg ccaggacctg ggctggtcga tcaatggccg gtattacacg   11760
aaggccgagg aatgcctgtc gcgcctacag gcgacggcga tgggcttcac gtccgaccgc   11820
gttgggcacc tggaatcggt gtcgctgctg caccgcttcc gcgtcctgga ccgtggcaag   11880
aaaacgtccc gttgccaggt cctgatcgac gaggaaatcg tcgtgctgtt tgctggcgac   11940
cactacacga aattcatatg ggagaagtac cgcaagctgt cgccgacggc ccgacggatg   12000
ttcgactatt tcagctcgca ccgggagccg tacccgctca agctggaaac cttccgcctc   12060
atgtgcggat cggattccac ccgcgtgaag aagtggcgcg agcaggtcgg cgaagcctgc   12120
gaagagttgc gaggcagcgg cctggtggaa cacgcctggg tcaatgatga cctggtgcat   12180
tgcaaacgct agggccttgt ggggtcagtt ccggctgggg gttcagcagc cagcgcttta   12240
ctggcatttc aggaacaagc gggcactgct cgacgcactt gcttcgctca gtatcgctcg   12300
ggacgcacgg cgcgctctac gaactgccga taaacagagg attaaaattg acaattcaat   12360
ggcaaggact gccagcgctg ccattttttgg ggtgaggccg ttcgcggccg aggggcgcag  12420
ccctgggg gatgggaggc ccgcgttagc gggccgggag ggttcgagaa gggggggcac     12480
ccccttcgg cgtgcgcggt cacgcgcaca gggcgcagcc ctggttaaaa acaaggttta    12540
taaatattgg tttaaaagca ggttaaaaga caggttagcg gtggccgaaa aacgggcgga   12600
aaccccttgca aatgctggat tttctgcctg tggacagccc ctcaaatgtc aataggtgcg  12660
ccctcatct gtcagcactc tgcccctcaa gtgtcaagga tcgcgcccct catctgtcag    12720
tagtcgcgcc cctcaagtgt caataccgca gggcacttat ccccaggctt gtccacatca   12780
tctgtgggaa actcgcgtaa aatcaggcgt tttcgccgat ttgcgaggct ggccagctcc   12840
acgtcgccgg ccgaaatcga gcctgccct catctgtcaa gggcgtcgcg ggtgagtcgg    12900
cccctcaagt gtcaacgtcc gcccctcatc tgtcagtgag gccaagttt tccgcgaggt    12960
atccacaacg ccggcggccg cggtgtctcg cacacggctt cgacgcgtt tctggcgcgt    13020
ttgcagggcc atagacggcc gccagcccag cggcgagggc aaccagcccg gtgagcgtcg   13080
caaaggcgct cggtcttgcc ttgctcgtcg agatctgtcg tcgatcagcc ggggatgcat   13140
caggccgaca gtcggaactt cgggtccccg acctgtacca ttcggtgagc aatggatagg   13200
ggagttgata tcgtcaacgt tcacttctaa agaaatagcg ccactcagct tcctcagcgg   13260
ctttatccga cgatttccta ttatgtcggc atagttctca agatcgacag cctgtcacgg   13320
ttaagcgaga aatgaataag aaggctgata attcggatct ctgcgaggga gatgatattt   13380
gatcacaggc agcaacgctc tgtcatcgtt acaatcaaca tgctaccctc cgcgagatca   13440
tccgtgtttc aaacccggca gcttagttgc cgttcttccg aatagcatcg gtaacatgag   13500
caaagtctgc cgccttacaa cggctctccc gctgacgccg tcccgactg atgggctgcc    13560
tgtatcgagt ggtgatttg tgccgagctg ccggtcgggg agctgttggc tggctggtgg    13620
caggatatat tgtggtgtaa acaaattgac gcttagacaa cttaataaca cattgcggac   13680
gttttaatg tactggggtg gtttttcttt tcaccagtga gacgggcaac agctgattgc    13740
ccttcaccgc ctgccctga gagagttgca gcaagcggtc cacgctggtt tgccccagca    13800
ggcgaaaatc ctgtttgatg gtggttccga aatcggcaaa atcccttata aatcaaaaga   13860
atagcccgag atagggttga gtgttgttcc agtttggaac aagagtccac tattaaagaa   13920
cgtggactcc aacgtcaaag ggcgaaaaac cgtctatcag ggcgatggcc cactacgtga   13980
accatcaccc aaatcaagtt ttttggggtc gaggtgccgt aaagcactaa atcggaaccc   14040
taaagggagc ccccgattta gagcttgacg gggaaagccg gcgaacgtgg cgagaaagga   14100
agggaagaaa gcgaaaggag cgggcgccat tcaggctgcg caactgttgg gaaggg       14156
```

UNIVERSAL VACCINE PLATFORM

RELATED APPLICATIONS

This application is a continuation of U.S. patent application Ser. No. 17/367,296, filed Jul. 2, 2021, which is a continuation of U.S. patent application Ser. No. 16/404,698, filed May 6, 2019, which claims the benefit of and priority to U.S. provisional patent application 62/667,414, filed May 4, 2018, and U.S. provisional patent application 62/821,599, filed Mar. 21, 2019, the contents of each of which are incorporated herein by reference in their entireties.

STATEMENT REGARDING FEDERALLY SPONSORED RESEARCH OR DEVELOPMENT

This invention was made with government support under R33 AI101329 and U19 AI062150 awarded by the National Institutes of Health. The government has certain rights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 217,522-byte XML file named "Seq_List.xml" created on Mar. 21, 2024.

TECHNICAL FIELD

The disclosure relates to vaccine platform comprising a virus-like particle (VLP) formed from hepatitis B core antigens and/or a recombinant immune complex (RIC).

BACKGROUND

Documentation on using inoculation as a strategy to provide protection against smallpox dates as early as hundreds of years before common era. These early reports of inoculation involved exposure to tissue diseased with smallpox (powered smallpox scabs or fluid from smallpox pustule). After Edward Jenner's report that inoculation with pus from a cowpox sore became widely accepted in the late 18th century, vaccine researchers turn to inoculants with reduced virulence. With improved understanding of the genetic makeup of pathogens and advancements in bioengineering, vaccination strategies moved away from attenuated vaccination or inactivated vaccination where an actual pathogen was used. Instead, recombinant proteins that induce an antigenic response against a pathogen without the risk of an infection developing have become focus of vaccination strategies. Some of the efforts in recombinant vaccine development have focused on the design of and evaluating the effectiveness of recombinant immune complexes (RICs) and virus-like particles (VLPs) against pathogens that currently lack an effective or efficient vaccine.

Recombinant immune complexes (RICs), fundamentally, are composed of immunoglobulin molecules specific for a desired antigen that are fused to the same antigen that the antibody is specific for (Chargelegue et al., 2005). Specifically, the parts of an RIC are an antibody, linked via its C-terminus, to an antigen that is followed by an epitope tag for the antibody. This allows for the binding region of one antibody to bind to the antigen recombinantly fused to another antibody, resulting in the formation of large, highly immunogenic antibody-antigen complexes (Chargelegue et al., 2005). RICs can be engineered into 'universal vaccine platforms' through the use of antibodies specific for an epitope tag, which allows for the same antibody to be used regardless of the antigen so long as the antibody's corresponding epitope tag is expressed on the antigen (Mason et al., 2016) (FIG. 1). Thus, RIC can potentiate the immunogenicity of a given antigen. However, the requirement that the antigen needs to be fused to the C-terminus of the antibody of the RIC prevents antigens with inaccessible N-termini to easily be used in a RIC without disrupting native antigenic conformation.

RICs take advantage of existing immunological mechanisms by utilizing antibodies' natural interaction with Fcγ receptors (Fridman, 1991; Van den Hoecke et al., 2017), which results in the phagocytosis and processing of the RICs and the target antigens contained within. Additionally, the increased concentration of antigens within the RIC can allow for increased B cell-receptor cross-linking, increasing B cell stimulation and activation (Avalos & Ploegh, 2014). Thus, RICs can mimic a natural immune complex and effect activation of the immune system. RICs have been evaluated as treatment platforms for diseases like Ebola fever (Phoolcharoen et al., 2011) and tuberculosis (Pepponi et al., 2014) as well as vaccine platforms for HIV (Hioe et al., 2009) and Dengue fever (Kim et al., 2015).

Virus-like particles (VLPs) are non-infectious, protein-based nanoparticles derived from virus capsids that self-assemble into virus-like structures and can be modified to recombinantly express vaccine antigens, making them an adaptable vaccine platform for combatting a myriad of diseases (Rohovie et al., 2017). One of the VLP vaccines against human papillomavirus have been commercially available in the United States since the 2006 approval of Merck & Co.'s Gardasil, and more recently, potent, VLP-based vaccines have been shown significant efficacy against diseases like Zika virus (Yang et al., 2017), norovirus (Diamos & Mason, 2018), and even influenza (Pushko et al., 2017; Ramirez et al., 2018), each of which make use of the hepatitis B core antigen (HBcAg) as the platform for their VLPs.

HBcAg offers several advantages as a vaccine platform: it is both a T-cell dependent and T-cell independent antigen (Milich et al., 1986), it preferentially evokes a Th1 response instead of a Th2 response like other hepatitis B antigens (Milich et al., 1995), is a potent activator of macrophages (Cooper et al., 2005), and can be used effectively to present heterologous antigens without compromising the assembly or integrity of the HBc VLP (Schodel et al., 1992). Delivering HBcAg VLPs with non-HBc antigens at the c/el loop of HBc α-helical spike, a region also known as the 'major insertion region' (MIR), has been shown to evoke immune responses to both the HBcAg and the inserted antigen (Whitacre et al., 2009). To form VLPs, HBcAg monomers first assemble into dimers, which in turn form full VLPs when expressed in eukaryotes (Pumpens et al., 2001; Mechtcheriakova et al., 2006). This technique has been refined to allow for larger proteins to be expressed through the use of the 'tandem core' approach, which involves fusing two HBcAg reading frames together, which enables the expression of foreign antigens on both, neither, or only one of the MIRs of the HBc tandem core (Peyret et al., 2015) (FIG. 2). Opting to express foreign antigens on only one of the two spike regions of the HBc dimer reduces the steric hindrance between foreign antigens, which consequently increases the maximum size of the potential foreign antigens that can be included in the VLP (Peyret et al., 2015).

VLPs offer several advantages over more traditional vaccination approaches. To start, they can self-assemble to resemble the structure of their native virus, providing the immune system with a more authentic target and consequently improving VLPs' immunogenicity (Chackerian, 2014). Further, because they lack genomic information, they are unable to replicate, improving the safety of any VLP delivered as a vaccine. Additionally, owing to their fundamental nature of being solely a recombinant protein, they are able to be produced at much faster rates than live-attenuated and inactivated viruses, as there is no need to use production systems, like eggs, that would support virus replication. This simultaneously lowers the cost and opens the doors to a wide variety of different production methods that can be chosen based on the needs for glycosylation, folding, speed, etc. desired for any given VLP.

One of hindrances of recombinant vaccines include difficulties in economically producing sufficient amounts of these recombinant proteins. One approach to answering this need is the use of plants as a production vector for recombinant vaccines (Favre, 2018). The production of valuable and viable biopharmaceuticals and vaccine antigens in plants is well-documented as being a cost-effective alternative to other means of biopharmaceutical production (Streatfield et al., 2001; Fischer & Emans, 2000; Tiwari et al., 2009; Rybicki, 2010). Plants can be grown abundantly and cheaply, providing a large source of inexpensive biomass without the need for costly bioreactors used by traditional fermentation-based systems (Chen and Davis 2016). Recent economic analyses have found substantial cost reductions for biological products made in plant-based systems compared to traditional systems (Tuse et al. 2014; Nandi et al. 2016). Furthermore, unlike mammalian systems, plants do not harbor animal pathogens, and have limited potential for contamination with bacterial endotoxins.

The use of geminiviral vectors has been demonstrated to significantly increase the yield of proteins expressed in plants systems. Geminiviral vectors allow for the insertion of desired genes into a self-replicating plant virus vector (Davies & Stanley, 1989; Stanley, 1993), which facilitates the production of vaccine antigens in plants (Chen et al., 2011). Geminiviral replication proteins amplify gene expression through the use of cellular DNA replication machinery in the nucleus, where the DNA uses soluble histones to form a 'viral minichromosome' (separate of the host genome) (Hefferon, 2014; Paprotka et al., 2015). This amplification of genes of interest is achieved through the inclusion of geminiviral replicon elements in the expression cassette. Specifically, the inclusion of the genes Rep and Rep A, as well as geminiviral short and long intergenic regions, in cis allows for the genes of interest to be amplified once delivered into the plant (Lazarowitz & Shepherd, 2008; Hefferon, 2014). Delivery of the expression cassette containing both the genes of interest and geminiviral replicon elements is enhanced through the use of the hypervirulent EHA105 strain of *Agrobacterium tumefaciens*, which can be used to transfer an expression cassette flanked by the left and right border sequences of the *A. tumefaciens* Ti plasmid into plants.

Plants are prime candidates for producing recombinant vaccines, as their glycosylation patterns can be modified to improve vaccine efficacy. For instance, some biopharmaceutical production methods inadvertently fucosylate their products, which can be counterintuitive as fucose inhibits binding of various targets by Fc gamma RIII receptors, which decreases the efficacy of antibody-based therapeutics (Shields et al., 2002). However, engineering plants to feature knocked out fucosylation pathways, as well as upregulated GnGn glycosylation (which increases binding to Fcγ RIIIA receptors (Maverakis et al., 2015), can increase the efficacy of plant-expressed biopharmaceuticals. Specifically, GnGn *N. benthamiana* plants have been engineered to produce human N-glycosylation by downregulating the endogenous β1,2-xylosylation (XylT) and α1,3-fucosyltransferase (FucT) genes (Strasser et al., 2008). This is key, as fucosylation inhibits FcγR recognition which reduces the efficacy of immunoglobulin-based treatments (Niwa et al., 2005), and β1,2-xylosylation and core α1,3-fucose are absent from humans entirely, which could provoke unwanted immune responses against non-GnGn plant-produced therapeutics. The lack of α1,6-fucose, which is normally present in humans but not in plants, may actually be beneficial, as the lack of fucose improves antibody-dependent cellular cytotoxicity (Shields et al., 2002), making GnGn plants the optimal production system for plant-produced biopharmaceuticals and a viable production vector for a universal influenza A vaccine.

SUMMARY

The disclosure relates to compositions and methods for vaccination against viruses. The vaccination compositions include a virus-like particle (VLP) and a recombinant immune complex (RIC). The methods relate to increasing the immunogenicity of virus antigens, and methods of generating an immune response in a mammalian subject, e.g., an immune response against human papillomavirus, influenza virus, and zika virus. The methods of increasing the immunogenicity of virus antigens comprise presenting virus antigens to an immune system on a VLP or a RIC. Accordingly, in some aspects, the disclosure relates to the VLPs and RICs described herein. The methods of generating an immune response in a mammalian subject against human papillomavirus, influenza virus, and zika virus comprise administering to a subject a VLP presenting an antigen from these viruses and/or at least one RIC comprising an antigen from these viruses. In some aspects, the methods of generating an immune response in a mammalian subject against human papillomavirus (HPV), influenza virus, and zika virus comprises administering to the mammalian subject a composition comprising the VLP and the RIC.

In certain embodiments, the VLPs described herein comprise a first hepatitis B virus core antigen (HBcAg) monomer, a second HBcAg monomer, and a first fragment of a virus protein, wherein the first fragment of a virus protein is linked to the major insertion region of the second HBcAg monomer. The first HBcAg monomer and the second HBcAg monomer forms a HBcAg dimer, which forms the VLP core. In some aspects, the first fragment of the virus protein is linked between amino acid residue 77 and amino acid residue 78 of the second HBcAg monomer.

In certain embodiments, the RIC comprises an immunoglobulin heavy chain, an epitope tag that can bind to the immunoglobulin heavy chain, and a second fragment of a virus protein. In some aspects, the second fragment of the virus protein is linked to the C-terminus of the immunoglobulin heavy chain, which forms a C-RIC. Thus, in some embodiments, the epitope tag is linked to the C-terminus of the second fragment of the virus protein. While in other aspects, the second fragment of the virus protein is linked to the N-terminus of the immunoglobulin heavy chain, which forms a N-RIC. In such embodiments, the epitope tag is linked to the C-terminus of the immunoglobulin heavy chain. In some embodiments, the RIC further comprises an immunoglobulin light chain.

In certain embodiments of the RIC, the epitope tag is an ebola antigen. In such embodiments, the epitope tag is preferably the 6D8 epitope tag and the immunoglobulin heavy chain of the RIC is preferably the immunoglobulin heavy chain of humanized 6D8 monoclonal antibody.

Certain vaccination compositions are configured for vaccination against multiple subtypes of HPV, and they comprise the virus protein HPV minor capsid protein L2 (GenBank Accession No. AGH32604.1). In such compositions, the first fragment of the virus protein comprises at least 100 continuous amino acid residues from the first 200 amino acid residues from the N-terminus of HPV minor capsid protein L2. In certain embodiments, the first fragment of the virus protein comprises residues 14-122 of HPV16 minor capsid protein L2. In some aspects, the second fragment of the virus protein comprises at least 8 continuous amino acids from the first 200 amino acid residues from the N-terminus of HPV minor capsid protein L2. In certain embodiments, the second fragment of the virus protein comprises at least one peptide sequence from the HPV minor capsid protein L2 selected from the group consisting of: amino acid residues 17-36, amino acid residues 56-75, amino acid residues 65-85, and amino acid residues 96-115.

In certain vaccination compositions configured for vaccination against influenza virus, the virus protein is the ectodomain of influenza matrix protein 2 and the first fragment of the virus protein and the second fragment of the virus protein comprises the amino acid sequence SLLTE-VETPIRNEWGCRCNDSSD (SEQ ID NO. 9). In certain embodiments, first fragment of the virus protein and the second fragment of the virus protein comprises the amino acid sequence set forth in SEQ ID NO. 10.

In particular vaccination compositions configured for vaccination against zika virus, the virus protein is selected from the group consisting of: zika virus E protein domain 3 protein (ZE3), zika virus fusion loop antigen (ZE), and zika virus soluble envelope protein (Zse). In some aspects, the first fragment of the virus protein and the second fragment of the virus protein comprise amino acid residues 591-696 of GenBank Accession No. AMC13911.1. In other aspects, the first fragment of the virus protein and the second fragment of the virus protein comprise amino acid residues 352-412 of GenBank Accession No. AMC13911.1.

BRIEF DESCRIPTION OF THE DRAWINGS

FIG. 3B depicts a vector map for a plant expression plasmid encoding a HPV VLP presenting residues 14-122 of HPV minor capsid protein L2. The nucleic acid sequence of pBYR2eK2M-HBcheL2ic is set forth in SEQ ID NO. 43. FIG. 3D depicts a vector map for a plant expression plasmid encoding a HPV RIC comprising residues 14-122 of HPV minor capsid protein L2. The nucleic acid sequence of pBYR11eMa-h6D8-L2 is set forth in SEQ ID NO. 44.

FIG. 4a shows leaves of *Nicotinana benthamiana* were agroinfiltrated with VLP vectors and imaged under visible light at 4-5 DPI to monitor tissue cell death. FIG. 4B depicts the SDS-PAGE and western blot of homogenized and clarified agroinfiltrated leaf tissue. Arrows indicate VLP bands. FIG. 4C depicts western blot analysis of soluble and insoluble samples from RIC agroinfiltrated leaves.

FIGS. 5A-5E depict, in accordance with certain embodiments, the purification of fully assembled HPV L2 VLP and RIC. FIG. 5A depicts the sucrose gradient sedimentation profile of crude extracts of leaf tissue agroinfiltrated with either L2-fused or unfused HBche. Following sedimentation through 10%-20%-30%-40%-50% sucrose layers, fractions were analyzed by SDS-PAGE, using ImageJ software to quantify the band intensity. FIG. 5B depicts SDS-PAGE of pooled material from either sucrose gradient purified VLP or protein G affinity purified RIC. Far right lane shows western blot analysis of purified RIC with anti-L2 as probe. FIGS. 5C and 5D depict electron microscopy of dialyzed peak sucrose fractions after negative staining with 0.5% uranyl acetate, bar=20 nm. FIG. 5E shows C1q binding of HBche-L2 RIC. Purified human IgG (left) or purified HBche-L2 RIC (right) were used at 0.5 mg/ml (1:1) and 3-fold serial dilutions.

FIG. 6 depicts, in accordance with certain embodiments, L2-specific IgG titers in mice receiving VLP or RIC. Balb/c mice were immunized subcutaneously, using alum as adjuvant, with three doses of either PBS, L2, VLP, RIC, or VLP/RIC mixed 1:1. Except for the PBS control group, each dose delivered 5 µg total L2 and was administered in three-week intervals. Blood samples were collected before each dose and analyzed for L2-specific antibodies by endpoint titer ELISA. The y-axis shows the geometric mean titers (GMT) and error bars show 95% confidence intervals. Two stars () indicates p values <0.05 and three stars (*) indicates p values <0.001.

FIG. 7, in accordance with certain embodiments, compares IgG1 and IgG2a production of mice receiving VLP or RIC in accordance with certain embodiments. Serum samples after the final dose were diluted as indicated and analyzed by ELISA specific for IgG1 or IgG2a antibodies. Columns represent means±the standard error from 8 serum samples. The inset table shows the relative ratio of IgG2a to IgG1 for each group as compared to L2 alone.

FIG. 8, in accordance with certain embodiments, compares in vitro neutralization of HPV pseudovirons with L2, VLP, RIC, or VLP/RIC. Sera of mice immunized with L2, VLP, RIC, or VLP/RIC were diluted and used to neutralize HPV16 pseudovirons before infection of 293FT cells. Infectivity is shown as relative luminesce; diminished luminescence is evidence of impaired infection of 293FT cells. Horizontal lines indicate the group mean. () indicates p value <0.005; (*) indicates p value <0.001.

FIG. 9A shows a simplified schematic of the vector, while FIG. 9B shows expression vector map. Pin2 3' is the 3' end of the Pin2 gene's promoter. The p19 gene encodes the p19 protein of the tomato bushy stunt virus, a suppressor of post-translational gene silencing (Chen et al., 2011). The TMV 5' UTR is a viral translational enhancer that is spurred on by the binding of HSP101, which recruits the translational initiation factors eIF4G and eIF3 (Gaille 2002, Diamos et al., 2016). P35s is a viral promoter sequence. NbPsaK2T (Nb=*N. benthamiana*, PsaK=photosystem I reaction center subunit, T=truncated) 1-63 5' UTR is used as a leader sequence and is directly upstream of the initiation codon; previous work in this laboratory found that this was the optimal 5' UTR for expressing vaccine antigens in plants in a comparison of 23 5' UTRs (Diamos et al., 2016). The human IgG 6D8 Heavy Chain gene (shown as Human IgG 6D8 Heavy Chain H2IS in FIG. 9B) encodes the heavy chain of the humanized anti-ebola antibody specific for ebola glycoprotein epitope 6D8, while the 6D8-K3 gene encodes the antibody's light chain. This is linked by a glycine-serine linker to dimeric 2×M2e, with each copy of M2e being linked to the other by a glycine-serine linker. 6D8 (gp 357-371) is the ebola glycoprotein epitope 6D8, which serves as the epitope binding tag for this RIC. Ext-3' FL is the extensin gene's 3' flanking region, which was used as a terminator and was previously found through research in this laboratory to enhance protein production relative to other more common terminators (Diamos et al., 2016). The Rb7 MAR (matrix attachment region) increases the likelihood and magnitude of transgene expression in plants (Halweg et al., 2005). C1/C2 encodes the geminiviral bean yellow dwarf virus (BeYDV) Rep/RepA proteins, which require the BeYDV LIR and SIR to function properly, as the LIR contains a bi-directional promoter and stem-loop structure essential for the initiation of rolling-circle replication and the SIR is the origin of C-strand synthesis and supplies termination and polyadenylation signals (Chen et al., 2011). The Rep/RepA proteins facilitate the formation of a transgene-containing 'viral minichromosome' within the plant cells' nuclei and subsequently enhances protein expression (Chen et al., 2011). Finally, the T-DNA left and right borders are the borders of the expression cassette that is transferred to the cells of the plant by *Agrobacterium tumefaciens.*

FIGS. 10A-10B depict, in accordance with certain embodiments, the vector encoding the M2e-VLP, pBYR2eK2M-HBcheM2e. FIG. 10A shows a simplified schematic of the vector, while FIG. 10B shows expression vector map. The vector uses many of the same elements as the M2e-RIC vector, pBYR11eMa-h6D8M2e (FIGS. (A-9B), but features HBc1-149, HBc1-77, and HBc78-176 genes encoding the heptatis B core antigen assembled in a 'tandem core' fashion, in the place of the human IgG heavy and light chain sequences and ACT3a 3' as a stabilizing agent of mRNAs that increases the lifespan of the transcript (Diamos & Mason, 2018).

FIGS. 11A-11B depict, in accordance with certain embodiments, Coomassie staining of RIC plant extract showing successful expression of M2e-RIC. The approximate size of the M2e RIC is 164 kDa, with the heavy chain-2×M2e-h6D8 fusion being roughly 57 kDa in size and the anti-6D8 light chain being roughly 25 kDa in size. In FIG. 11A, samples were run under non-reducing conditions, with the bands of the size of the RIC being clearly present in the elutions from the protein G resin and the removal of other contaminants post-acid precipitation and post-chromatography being evident. Bands of a larger size than the expected 164 kDa could indicate immune complex formation. For FIG. 11B, all samples were run under reducing conditions (indicated by a '-R', with the exception of an IgG standard, which was run under both reducing and non-reducing conditions. The heavy chain of the RIC, when reduced, has a greater size than that of the IgG standard's, which is due to the heavy chain of the RIC being fused to the M2e dimer and 6D8 epitope tag, which adds an additional 7 kDa to its size. Additionally, the light chains of the IgG standard and the RIC groups are of the same size, indicating that the 2×M2e and epitope tag were not expressed on the light chain of the RIC.

FIGS. 12A-12B depict, in accordance with certain embodiments, western blotting of RIC and VLP samples. For FIG. 12A, the gel was run concurrently with gel in FIG. 11A and samples were run under non-reducing conditions. The samples were probed with anti-h6D8 antibody, and a clear signal is seen in both the crude and the elution fractions, demonstrating the presence of the epitope tag. Bands are present at the expected 164 kDa range, and larger bands may suggest immune complex formation. For FIG. 12B, samples of the M2e-RIC, M2e-VLP, and an anti-M2e antibody, MAb65, were run under both reducing and non-reducing conditions. The samples were probed with MAb65 to confirm the presence of M2e, and the detection antibody was anti-human light chain. A single band is present in the M2e-RIC reducing conditions group that is around the expected size of the M2e-RIC's heavy chain-2×M2e-epitope tag fusion. Because the samples were run under reducing conditions, no band of the heavy chain's size would have appeared if it did not contain M2e, as the anti-human light chain probe would not have bound to the heavy chain on its own. The probe did bind to the light chains of the M2e RIC and MAb65 further down the gel (not pictured). Additionally, bands are present in both samples of the VLP, confirming the presence of M2e in the VLP.

FIG. 13, shows, in accordance with certain embodiments, an exemplary Transmission Electron Microscopy image of M2e-VLP. Of the formation of VLPs indicated by this image, the particle in the upper-right quartile shows the clearest indication of proper virus-like particle formation.

FIGS. 14A-14C depict, in accordance with certain embodiments, mouse antibody titers post-vaccination. Total anti-M2e antibody titers were higher, on average, in mice that received both the M2e-RIC and the M2e VLP vaccines than in mice that received only the M2e-VLP vaccine (Dose 1: $1.17*10^4$ vs $6.25*10^3$; Dose 2: $1*10^6$ vs $3.8*10^5$; Dose 3: $4.43*10^6$ vs $2.25*10^6$, respectively. IgG2a to IgG1 ratios, however, were higher in the group receiving only the M2e-VLP vaccine compared to the group receiving both vaccines. Although dilutions were different for IgG1 and IgG2a titer ELISAs, preventing direct comparison, the VLP/RIC group demonstrated IgG2a:IgG1 ratios that were 64% lower relative to those of the VLP-alone group when the ratio of IgG2a to IgG1 is arbitrarily set at 1.0.

FIGS. 15A-15B show, in accordance with certain embodiments, an analysis of cytokine production in mouse splenocytes. Splenocyte analysis revealed that the combination VLP/RIC vaccine induced lower levels of both IL-4 and IFN-7 when compared to both unvaccinated and the VLP alone group.

FIGS. 21A-21D depict, in accordance with certain embodiments, purification of ZE3 C-RIC and N-RIC. Following protein G column chromatography of the ZE3 C-RIC and N-RIC, samples of the C-RIC elutions were analyzed by an SDS-PAGE gel stained with Coomassie (FIG. 21A) and by a western blot probed anti-human IgG+HRP (FIG. 21B). Samples of the N-RIC were also analyzed by an SDS-PAGE gel stained with Coomassie (FIG. 21C) and a western blot probed anti-human IgG (Fc only)+HRP (FIG. 21D). Both reducing and non-reducing conditions were tested. Abbreviations: R, reducing conditions, and NR, non-reducing conditions FIGS. 22A-22B depict, in accordance with certain embodiments, partial purification of the ZE3 VLP. After sucrose gradient sedimentation, a fraction was analyzed on an SDS-PAGE gel stained with Coomassie (FIG. 22A) and a western blot probed with a polyclonal rabbit anti-Zika envelope antibody and detected with a goat anti-rabbit+HRP antibody (FIG. 22B).

FIGS. 23A-23B depict, in accordance with certain embodiments, purification of a recombinant immune complex where the domain III of the zika virus E protein (K591-T696 of Accession No. AMC13911, labeled ZE3 in the figure) or the zika soluble ectodomain E protein (amino acids 291-693, labeled ZsE in the figure) is linked to the antibody at the N-terminus of its heavy chain. The Western blot results showed appropriate assembly of both the ZsE N-RIC and ZDIII N-RIC (FIG. 23A). FIG. 23B depicts Coomassie-stained gel with purified recombinant immune complex having the domain III of the zika virus E protein (K591-T696 of Accession No. AMC13911, labeled ZE3 in the figure) linked to the antibody at the N-terminus of its heavy chain (ZE3 N-RIC) under reducing (R) and non-reducing (NR) conditions.

FIG. 24 depicts, in accordance with certain embodiments, an image of ZE3 VLP obtained though electron microscopy.

FIGS. 25A-25B depict, in accordance with certain embodiments, purification and partial purification of a recombinant immune complex with the zika soluble ectodomain E protein (amino acids 291-693, labeled ZsE in the figure) as the antigen linked to the antibody (ZEFL62 RIC). A sample of protein-G purified ZEFL62 RIC was analyzed on an SDS-PAGE gel stained with Coomassie (FIG. 25A). After sucrose gradient sedementation of the ZEFL62 VLP, a fraction was analyzed on an SDS-PAGE gel stained with Coomassie (FIG. 25B).

Even if the universal vaccine platform described herein is insufficient fully protect recipients after a single dose, the composition comprising the described VLP and RIC could be used as an adjuvant. For example, the composition for generating an immune response against multiple strains of influence virus could be administered as an adjuvant to existing flu vaccines to increase the efficacy of the existing vaccines from season to season. The immunogenicity of the RICs, VLPs, and the universal vaccine platform described herein can be enhanced through the use of glycoengineered plants to glycosylate the vaccines in favorable patterns (Shields et al., 2002; Maverakis et al., 2015)). Accordingly, in some aspects, the disclosure relates to methods of producing the described VLP and/or RIC in plants using a plant expression vector, for example, a geminivirus-based vector. The production of the vaccines in plants further compounds the reduction of the economic cost of the vaccine. In some implementations, the immunogenicity of the RICs, VLPs, and the universal vaccine platform described herein, even if they are produced by plant, may be further enhanced by co-administration with a vaccine adjuvant. Vaccine adjuvants commonly used with current vaccinations include, for example, alum (composed of aluminum salts), MF59 (an oil-in-water emulsion of squalene oil), ASO4 (a combination of alum and monophosphoryl lipid A), and ASO3 (an oil-in-water emulsion of α-tocopherol, squalene, and polysorbate 80).

Virus-Like Particles

The VLPs described herein have a virus core formed from hepatitis B virus core antigen (HBcAg). Upon expression, HBcAg self-aggregate to form a VLP. The target antigen for inducing a desired immune response in a subject is linked to HBcAg and is presented upon VLP formation to an organism's immune system. In preferred embodiments, the target antigen is linked to HBcAg at its major insertion region (MIR), which is located at the tip of the α-helical spike. In some aspects, the target antigen is displayed on the surface of the VLP through the production of a fusion protein where the target antigen is inserted into the HBcAg protein between residues 77 and 78 of the HBcAg protein.

In some aspects, the VLPs are formed from coexpression of wildtype HBcAg proteins and HBcAg with the targeted antigen linked at its MIR to create mosaics. In other aspects, the VLPS are formed with a split core, where the HBcAg protein is expressed as distinct N- and C-terminal portions, which allows assembly of structural dimers even in the absence of covalent linkage. In yet other aspects, the VLPS are formed with a tandem core where two HBcAgs are joined together by a flexible linker to give a single fused dimer protein. In such embodiments, a target antigen may be linked to the MIR of just one of the HBcAgs or both. In some aspects, different target antigens may be linked to each of the MIRs in the tandem core.

Figure 2:
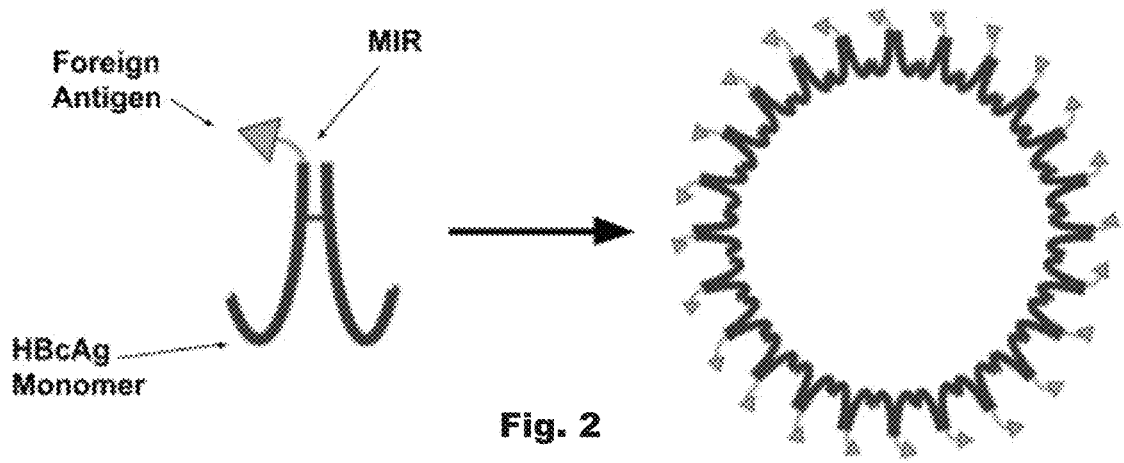
FIG. 2 is an exemplary diagram showing the assembly of virus-like particles (VLPs) with a core of hepatitis B core antigen (HBcAg) using the tandem core approach.

In some embodiments, the VLPs described herein comprise two HBcAg monomers that are linked to form a HBcAg dimer, which self-aggregates to form the VLP (FIG. 2). In a preferred embodiment, at least one of the HBcAg monomers in the HBcAg dimer is linked to the target antigen at its MIR. In some aspects, the other HBcAg monomer in the HBcAg dimer does not have a target antigen linked to its MIR.

In certain embodiments of an expression cassette encoding a VLP disclosed herein, the target antigen with flanking linker regions is inserted into the tip of the α-helical spike of an HBc gene copy that is fused to another copy of HBc lacking the target antigen. In preferred embodiments, the linker regions are glycine serine linker sequences.

Recombinant Immune Complexes

Figure 1:
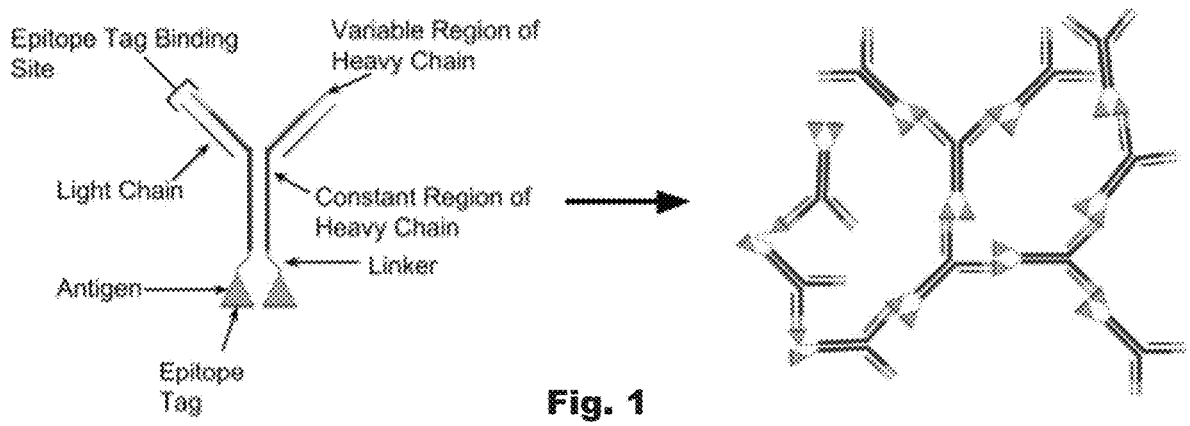
FIG. 1 depicts an exemplary diagram of universal recombinant immune complex (RIC) targeting an antigen. In this example, the antigen is linked to the C-terminus of the immunoglobulin heavy chain. The epitope tag of one immunoglobulin is bound to the binding site of other immunoglobulins, forming complexes that contain the target antigen.

The RICs described herein comprise an immunoglobulin heavy chain, an epitope tag that can bind to the immunoglobulin heavy chain, and a target antigen. In some aspect, the immunoglobulin heavy chain is a camelid immunoglobulin. In certain embodiments, the RIC further comprises an immunoglobulin light chain. Thus, in some aspects, the RIC comprises a standard antibody (two heavy chains and two light chains joined to form a "Y" shaped molecule), an antigen, and an epitope tag that is recognized by the antibody (FIG. 1). The antibody binds to the epitope tags on other antibody fusions and forms a complex. In some embodiments, the RIC comprises human IgG 6D8, and the epitope tag is ebola glycoprotein epitope 6D8.

RICs described herein include conventional RICs where the target antigen is linked to the C-terminus of the immunoglobulin heavy chain and the epitope tag is linked to the other end of the target antigen (also referred to herein as "C-RIC"). The recombinant immune complex is produced by fusing a target antigen to the C-terminus of the heavy chain of an immunoglobulin that binds specifically to the antigen, wherein the co-expression of this fusion protein with the light chain of the antibody produces a fully formed immunoglobulin that is self-reactive, and results in the creation of an immune complex due to the bivalent binding capacity of the immunoglobulin. However, antigens with inaccessible N-termini cannot be easily used in the RIC platform without disrupting native antigenic conformation. Also described herein is a novel design of RIC where the target antigen is linked to the N-terminus of the immunoglobulin heavy chain and the epitope tag is linked to C-terminus of the immunoglobulin heavy chain (also referred to herein as "N-RIC").

In certain embodiment of an expression vector encoding RICs, the expression vector comprises a expression cassette encoding the immunoglobulin heavy chain, the target antigen, and the epitope tag. In some aspects, the expression vector further comprises a second expression cassette encoding the immunoglobulin light chain.

Human Papilloma Virus Vaccine Compositions

In some embodiments, the disclosure relates to vaccine compositions that target multiple subtypes of HPV and methods of generating an immune response in a mammalian subject against multiple subtypes of HPV.

Papillomaviruses are an ancient and diverse group of viruses, and over 200 subtypes currently known to infect humans (Doorbar et al. 2015). Diverse human papillomavirus (HPV) subtypes are responsible for considerable disease burden worldwide, necessitating safe, cheap, and effective vaccines. HPV is the most common pathogen sexually transmitted disease, with more than 15 HPV oncogenic types responsible for oropharyngeal and anogenital cancers that result in significant morbidity and mortality worldwide (Crow 2012). Currently available prophylactic HPV vaccines target the L1 capsid protein, which self-assembles into highly immunogenic VLPs (Kirnbauer et al. 1992). Because neutralizing epitopes found on L1 are not broadly conserved among HPV types, multiple L1 proteins must be included in vaccine preparations to protect against multiple HPV types. The most broadly protective vaccine approved to date, Garadasil-9, provides protection against HPV types 6, 11, 18, 31, 33, 45, 52, 58. However cross-protection with other HPV types is minimal, and the complex formulation of the vaccine makes it cost-prohibitive for much of the world (Brown et al. 2009; Wheeler et al. 2009; Mariani and Venuti 2010; Vesikari et al. 2015).

The HPV minor capsid protein L2 is a promising candidate to create broadly protective HPV vaccines, though it is poorly immunogenic by itself. Unlike L1, neutralizing epitopes on the N-terminus of L2 are broadly conserved, and L2 antibodies can provide protection against multiple HPV subtypes (Kondo et al. 2007; Gambhira et al. 2007b; Alphs et al. 2008; Schellenbacher et al. 2017). However, as L2 is unable to form VLPs, it is poorly immunogenic by itself, necessitating strategies to enhance L2 antibody production. Accordingly, there is a need for improved HPV vaccine designs using L2.

A successful vaccine based on HPV minor capsid protein L2 has yet to be confirmed. However, as shown in FIGS. 3 and 4, the VLP and RIC based on HPV minor capsid protein L2 described herein, when administered alone or together generates an immune response in the subject against HPV minor capsid protein L2. Specifically, the immune response generated by the administration of the described VLP and/or RIC based on HPV minor capsid protein L2, reduce infectivity of HPV16 (FIG. 5). When the described VLP is administered with the described RIC, a synergistic increase in the immune response produced against HPV minor capsid protein L2 takes place. Accordingly, the disclosure relates a VLP based on HPV minor capsid protein L2, a RIC based on HPV minor capsid protein L2, related vaccine compositions for target multiple subtypes of HPV, and methods of generating an immune response against multiple subtypes of HPV.

As referenced herein, the term "fragments of HPV minor capsid protein L2" refers to fragments from the highly conserved N-terminal region of the minor capsid protein L2 of human papillomaviruses. In certain embodiments, the high conserved N-terminal region of the HPV minor capsid protein L2 refers to an amino sequence corresponding to the first 200 amino acid residues of the L2 protein based on the amino acid sequence of HPV16 minor capsid protein L2, for example, residues 14-120 or residues 14-122. In some aspects, the amino acid sequence of the highly conserved N-terminal region of the L2 protein is the sequence set forth in Gene Accession CAC51368.1. As the N-terminus of the L2 protein is highly conserved across HPVs, the amino acid sequence of the highly conserved N-terminal region of the L2 protein may refer to the corresponding region in other HPVs. In some aspects, the corresponding nucleic acid sequence encoding the high conserved N-terminal region of the HPV minor capsid protein L2 is set forth in residues 1-473 of GenBank Accession No. KC330735. In other aspects, the corresponding nucleic acid sequence encoding the high conserved N-terminal region of the HPV minor capsid protein L2 may be a functionally equivalent version of nucleic acids 1-473 of GenBank Accession No. KC330735, where the translated product of the nucleic acid sequence has an amino acid sequence with at least 55%, at least 60%, at least 75%, at least 80%, at least 85%, at least 90%, at least 95%, at least 97%, or at least 99% identity to the first 200 amino acid of the sequence set forth in Gene Accession CAC51368.1.

The amino acid positions of HPV minor capsid protein L2 referenced herein are based on the amino acid sequence of HPV16 minor capsid protein L2 (Accession No. AGH32604.1). Due to the high level of conservation, the immune response generated from RIC and VLP targeting HPV minor capsid protein L2, even if the antigenic fragments are based on the amino acid sequence of HPV16 minor capsid protein L2 would also be an immune response that targets a variety of HPV subtypes aside from HPV16.

In certain embodiments, the vaccine composition comprises a VLP assembled with a fragment of HPV minor capsid protein L2 selected from the first 200 amino acid residues from the N-terminus of HPV minor capsid protein L2 and a recombinant immune complex (RIC) comprising, as antigenic portion, an amino acid sequence of at least 8 continuous amino acids from the first 200 amino acid residues from the N-terminus of HPV minor capsid protein L2.

In certain implementations of the method of generating an immune response in a mammalian subject against HPV, which are also methods of increasing the immunogenicity of HPV minor capsid protein L2, the method comprises administering to the mammalian subject a RIC comprising an HPV minor capsid protein L2 antigenic fragment, wherein the HPV minor capsid protein L2 antigenic fragment comprises an amino acid sequence of at least 8 continuous amino acids from the first 200 amino acid residues from the N-terminus of HPV minor capsid protein L2. In some implementations, the RIC is administered with a VLP displaying a fragment of HPV minor capsid protein L2. In some aspects, the VLP comprises a hepatis B virus core, for example the HBcAg protein. In certain implementations, the VLP and the RIC are administered to the mammalian subject in two vaccination events, wherein each vaccination event comprises administration of one dose of the VLP and one dose of the RIC. In some aspects, the two vaccination events are separated by a period of at least 14 day, at least 21 days, at least 28 days, at least 35 days, at least 42 days, at least 49 days, at least 56 days, about three weeks, about four weeks, about five week, about six weeks, about seven weeks, or about eight weeks. As used herein, the term "about" refers to ±3 days, ±2 days, or ±1 day. The methods of administering the VLP and RIC may be any established methods of vaccination in the prior art. In some instances, the VLP and RIC are administered subcutaneously. In some implementations, the VLP and RIC are administered with an adjuvant, for example, Imject® Alum (Thermo Scientific, Rockford, TL).

a. Virus-Like Particle with HPV Minor Capsid Protein L2

The VLPs of the disclosure include embodiments where fragments of HPV minor capsid protein L2 displayed on the surface of viral core, for example a hepatitis B core (HBc). In some aspects, the VLPs of the disclosure also refer to fragments of HPV minor capsid protein L2 fused to fragments of HPV major capsid protein L i, which can self-assemble into a VLP. In certain embodiments, the VLPs have a core comprising the HBcAg protein and the fragment of HPV minor capsid protein L2 is displayed on the surface of HBc VLP. In some implementations, the fragment of HPV minor capsid protein L2 is displayed on the surface of HBc VLP through the production of a fusion protein where the HPV fragment is insert into the HBcAg protein between residues 77 and 78 of the HBcAg protein. In some embodiments, the fragment of HPV minor capsid protein L2 with flanking linker regions is inserted into the tip of the α-helical spike of an HBc gene copy that is fused to another copy of HBc lacking the L2 insert.

As the N-terminus of HPV minor capsid L2 protein is known to contain cross-neutralizing epitopes, the VLPs of the disclosure display fragments of HPV minor capsid protein L2 comprising at least 100 continuous amino acid residues from the first 200 amino acid residues from the N-terminus of the HPV minor capsid protein L2. In some implementations, the VLPs display at least 100 continuous amino acid residues from the amino acid residues 11-200 of the HPV16 minor capsid protein L2, for example, amino acid residues 11-128, amino acid residues 14-120, or amino acid residues 14-122 of HPV16 minor capsid protein L2. In certain embodiments, the fragments of HPV minor capsid protein L2 comprise about 105, 106, 107, 108, 109, 110, 120, 130, 140, 150, 160, 170, 180, 190, 200, 210, 220, 230, or 240 amino acid residues. In some aspects, the fragments of HPV minor capsid protein L2 is a string of several epitopes of HPV minor capsid protein L2.

In some embodiments of an expression cassette for producing the HPV VLP, the expression cassette comprises a DNA sequence encoding amino acid residues 1-149 of HBcAg, a linker $(G_2S)_5G$, amino acid residues 1-77 of HBcAg, a linker $GT(G_4S)_2$, amino acid residues 14-122 of HPV16 minor capsid protein L2, a linker (GGS)$_2$GSSGGSGG, and amino acid residues 78-176 of HBcAg.

The HBc VLPs are potently immunogenic in mice, generating very consistent and high antibody titers directed against HPV L2 (>1,000,000) (FIG. 6), which is as high as those seen with L1 vaccines.

b. Recombinant Immune Complex with HPV Minor Capsid Protein L2

The HPV RIC comprises an immunoglobulin heavy chain and a fragment of HPV minor capsid protein L2 wherein the fragment of HPV minor capsid protein L2 is genetically fused to the immunoglobulin heavy chain. In some embodiments, the HPV RIC is a C—RIC or N-RIC.

In some embodiments, the fragment of HPV minor capsid protein L2 is inserted into the gene encoding humanized mAb 6D8 heavy chain, resulting in 6D8 epitope-tagged fragment of HPV minor capsid protein L2. Accordingly, the RIC further comprises an ebola antigenic fragment, in particular, the GP1 protein. In one aspect, the humanized mAb 6D8 heavy chain is produced from substituting the H2 chain of mouse monoclonal antibody 6D8 with the human constant region sequences for gamma type 1 chain.

In some embodiments, the antigenic fragment of HPV minor capsid protein L2 comprises an amino acid sequence of at least 8, at least 9, at least 10, at least 11, at least 12, at least 15, at least 20, at least 25, at least 30, at least 40, at least 50, at least 60, at least 70, at least 80, at least 90, at least 100, or at least 110 continuous amino acids from the first 200 amino acid residues from the N-terminus of HPV minor capsid protein L2.

In some embodiments, the RIC comprises at least one peptide sequence from HPV minor capsid protein L2 selected from the group consisting of: amino acid residues 17-31, amino acid residues 17-36, amino acid residues 56-75, amino acid residues 65-85, and amino acid residues 96-115. In one embodiment, the fragment of HPV minor capsid protein L2 genetically fused to an immunoglobulin has an amino acid sequence consisting of amino acid residues 14-122. The RIC is potently immunogenic in mice, generating very consistent and high antibody titers directed against HPV L2 (>1,000,000).

c. Methods of Production

A plant-based transient expression system based on bean yellow dwarf virus was designed to produce the VLPs and RICs of the disclosure (see example vector in FIG. 3). In this system, the viral replication machinery is used to amplify the target gene to high copy number in the plant nucleus (Huang et al. 2009). After rigorous genetic optimization, the system is capable of producing very high levels of recombinant protein, up to 30-50% of the total soluble plant protein, in 4-5 days (Diamos et al. 2016). Using this system, milligram quantities of fully assembled and potently immunogenic HBc VLPs displaying fragments of HPV minor capsid protein L2 can be produced and purified through a simple one-step purification process (FIGS. 4A-4C and 6). Remarkably, all of the VLPs used for immunization in the Examples were derived from a single plant leaf, demonstrating the promise of plant-based recombinant expression systems.

Influenza Virus

In some embodiments, the disclosure relates to vaccine compositions that target multiple strains of the influenza virus (also referred to herein as "flu virus") and methods of generating an immune response in a mammalian subject against multiple strains of the flu virus.

Influenza is a deadly disease that poses a major threat to global health. Influenza is a historically and socially significant disease that is characterized by the sudden onset of a high fever, runny nose, fatigue, muscle pains, sneezing, coughing, and general malaise (World Health Organization, 2018). In a meta-analysis of six influenza seasons in the United States (from the 2010-2011 season to the 2015-2016 season), it was estimated that the number of influenza-related illnesses ranged from 9.2 million to 35.6 million per season, including 140,000 to 710,000 influenza-related hospitalizations (Rolfes et al., 2018). Further, the disease is also estimated to cost the U.S. economy anywhere from $6.3 to $25.3 billion annually (Putri et al., 2018). On a global scale, influenza-associated mortality typically ranges from 291, 243 to 645,832 influenza-associated respiratory deaths per year (Juliano et al., 2018), with most (>99%) deaths of children below the age of 5 years old occurring in developing countries. However, should a pandemic strain of influenza similar in severity to the 1918 Spanish Flu pandemic occur, the cost to human life could be catastrophic, which would simultaneously cripple the global economy; the World Bank estimates that such a pandemic would cost the global economy approximately 5% of its GDP in the pandemic's first year alone (Burns et al., 2006).

Due to the disease's impact around the world, there have been calls for substantial improvement in the methods used to estimate the global burden of influenza (e.g. including data on nonrespiratory complications of influenza infection, severe influenza case data, etc.) (Bresse et al., 2018), indicating that not only a potentially substantial number of cases are currently left unreported and unaccounted for within the literature, but that influenza may be a larger problem than is currently believed. While influenza vaccines lessen the annual impact of influenza on the world, it is of the utmost importance that vaccines with high rates of efficacy are developed in a timely manner.

Influenza is a member of the Orthomyxoviridae family of viruses, a group of single-stranded negative sense RNA viruses, and its genome is comprised of eight segments (McGeoch et al., 1976). There are four types influenza viruses: A, B, C, and D; though influenza C is not commonly associated with disease in most populations, being observed only in isolated, sporadic outbreaks in children younger than the age of six years old and elderly populations (Matsuzaki et al., 2006; Smith et al., 2016). Influenza D has been shown to only infect swine and cattle (Hause et al., 2014) (Smith et al., 2016). Influenza A and B, meanwhile, regularly circulate and cause disease in humans, with rates of influenza-related hospitalizations being higher in seasons where influenza A viruses dominate (Thompson et al., 2004). Influenza A is also more routinely the cause of epidemics and pandemics (Hay et al., 2001), as influenza A viruses have a higher mutation rate than influenza B viruses (Nobusawa & Sato, 2006) and consequently have a higher propensity to evade the protective immune response that influenza vaccines or infections confer. The high mutation rate of influenza A viruses, when compared to influenza B viruses, is partially due to influenza B viruses generally being limited to infecting humans (Hay et al., 2001). Meanwhile, influenza A viruses are able to infect a range of creatures, including, but not limited to, pigs, birds, and humans (Hay et al., 2001), increasing the likelihood of antigenic shift between human and zoonotic strains. Influenza A's association with high levels of hospitalization, seasonal epidemics, and global pandemics makes the need for a 'universal' influenza A vaccine that maintains its efficacy and protection from season to season, despite the virus' high rate of mutation, absolutely essential to preventing the influenza pandemics of the future.

The surface proteins of influenza A, the type most often associated with epidemics and pandemics, mutate at a very high frequency from season to season, reducing the efficacy of seasonal influenza vaccines. Over six influenza seasons in the U.S., from 2010 to 2016, it was determined that overall vaccination rates ranged from 42%-47% of the population, preventing anywhere from 1.6 million to 6.7 million illnesses, 790,000-3.1 million outpatient medical visits, 39,000-87,000 hospitalizations, and 3,000-10,000 influenza-related deaths (Rolfes et al., 2018). However, seasonal influenza vaccines are routinely associated with low rates of vaccine efficacy (VE); the U.S. Centers for Disease Control and Prevention (CDC) reported VEs of 56% for the 2012-2013 (Jackson et al., 2013), 61% for the 2013-2014 season (Flannery et al., 2014), 23% for the 2014-2015 season (Flannery et al., 2015), 48% for the 2015-2016 season (Jackson et al., 2017), and 48% for the 2016-2017 season (Flannery et al., 2017). Furthermore, during the 2017/2018 influenza season, VE against the circulating strain of influenza A (H3N2) was estimated to be as low as 25% in the United States (Centers for Disease Control and Prevention, 2018), 17% in Canada (Skowronski et al., 2018) and 10% in Australia (Sullivan et al., 2017) despite the 2017/2018 influenza vaccine containing influenza of the same subtype and clade. This was due, in part, to three mutations in hemagglutinin (HA), a protein on the influenza virus' surface.

The vulnerability of influenza vaccines to small mutations like those observed in the 2017/2018 strain's HA protein is due primarily to the vaccines' composition, which involve including three to four strains of inactivated or attenuated influenza virus. Predictions, and subsequent recommendations, are made by the scientific community on an annual basis as to which three to four strains will most likely be in circulation during that year's influenza season. Then, vaccines composed of the predicted strains are mass-produced, traditionally in eggs, and shipped before the influenza season starts. Due to the structure and behavior of the influenza virus, traditional methods of influenza vaccine production, as well as vaccine composition, it comes as no surprise that the influenza virus is regularly able to mutate in ways that reduce the VE of a given season's influenza vaccine.

The influenza A genome encodes at least ten proteins and up to 14 proteins through strain-dependent alternative splicing (Eisfeld et al., 2015; Suarez et al., 2016). The ten common influenza A proteins can be grouped into the surface proteins, which include hemagglutinin (HA), neuraminidase (NA), and the matrix 2 protein (M2); the internal proteins, which include the nucleoprotein (NP), the matrix 1 protein (M1), polymerase basic protein 1 (PB1), polymerase basic protein 2 (PB2), and polymerase acidic protein (PA); and the non-structural proteins 1 (NS1) and 2 (NS2) (Suarez et al., 2016). Segment 1 encodes PB2, segment 2 encodes PB1, segment 3 encodes PA, segment 4 encodes HA, segment 5 encodes NP, segment 6 encodes NA, segment 7 encodes both M1 and M2, and segment 8 encodes NS1 and NS2 (Inglis et al., 1976). HA and NA, in particular, are common targets of recombinant influenza vaccines, as HA's primary role is to facilitate viral entry into target cells through binding to sialic acid-containing receptors on the host cell (Skehel & Wiley, 2000) and NA promotes the release of newly-formed influenza virions through the removal of sialic acid residues on both the host cell and the nascent virion (Mitnaul et al., 2000). However, while the neutralization of either could provide protection against influenza A infection, HA and NA mutate frequently from season to season (Webster et al., 1982). This has led to the search for conserved, protective epitopes in not only HA (Kramer & Palese, 2019) and NA (Kosik et al., 2019), but also other influenza A proteins, so that a 'universal' influenza vaccine that is effective from season to season can be developed.

Certain regions of these proteins are conserved between strains of influenza A, making them attractive targets for the development of a 'universal' influenza vaccine. One of these regions can be found on influenza matrix 2 protein M2, which is a tetrameric integral membrane protein that, despite being found at low levels on influenza A virion, facilitates viral uncoating in its role as a proton channel (Lamb et al., 1985). The ectodomain of the influenza matrix 2 protein (M2e) has not changed significantly since it was first identified in 1933 (Fiers et al., 2004). This highly-conserved region of M2 is poorly immunogenic on its own, but when conjugated or fused to potent adjuvants or carriers, it becomes a potent target against influenza A (Mardanova & Ravin, 2018). M2 is expressed on the surface of infected cells at nearly the same rate as NA, but is incorporated into virions much less than NA, with only 14 to 68 molecules of M2 per virion versus 198-211 molecules of NA, suggesting that M2 is selectively excluded from forming virions (Lamb et al., 1985; Zebedee et al., 1988). Despite this, vaccines targeting M2e have demonstrated protection in several studies, with this protection having been determined to be due not to the prevention of infection, but instead through Fc-receptor dependent antibody-dependent cell cytotoxicity (ADCC) and alveolar macrophage antibody-dependent cell-mediated phagocytosis (ADCP) of infected cells (El Bakkouri et al., 2011). Additionally, it has been discovered that lung-resident Th17 CD4 T cells specific for M2e tetramers are broadly effective against influenza infection, indicating that the anti-M2e response is not limited only to antibody-dependent responses (Eliasson et al., 2018).

In clinical trials, vaccines targeting M2e have been well-tolerated, with studies investigating M2e expressed recombinantly on hepatitis B core antigen (HBc) (Fiers et al., 2009), even in the presence of anti-HBc antibodies, and fused to flagellin (Turley et al., 2011) demonstrating safety and efficacy. Several other clinical trials have been conducted around the world investigating M2e's potential as a vaccine antigen (Scorza et al., 2016) to varying degrees of success. However, to the best of our knowledge, no studies have attempted to express M2e recombinantly in a recombinant immune complex (RIC), a promising 'universal vaccine platform' that could boost the immunogenicity of M2e substantially and whose modularity could allow for the addition of other prominent and conserved influenza targets and adjuvants to adjust to whatever potential hurdles the influenza epidemics and pandemics of the future may have to offer.

In certain implementations of the method of generating an immune response in a mammalian subject against influenza virus, which are also methods of increasing the immunogenicity of M2e protein of influenza A virus, the method comprises administering to the mammalian subject a VLP presenting M2e. In some implementations, a RIC comprising M2e is also administered. In some aspects, RIC comprising M2e and VLP presenting M2e are co-administered. In some aspects, the RIC and the VLP are coadministered in a ratio of 1:1. In certain implementations, the VLP and the RIC are administered to the mammalian subject in three vaccination events, wherein each vaccination event comprises administration of one dose of the VLP and/or one dose of the RIC. In some aspects, two vaccination events are separated by a period of at least 14 day, at least 21 days, at least 28 days, at least 35 days, at least 42 days, at least 49 days, at least 56 days, about three weeks, about four weeks, about five week, about six weeks, about seven weeks, or about eight weeks. As used herein, the term "about" refers to ±3 days, ±2 days, or 1 day. The methods of administering the VLP and RIC may be any established methods of vaccination in the prior art. In some instances, the VLP and RIC are administered subcutaneously. In some implementations, the VLP and RIC are administered with an adjuvant.

As shown in Example 2 section d, recipients of the VLP+RIC exhibited endpoint anti-M2e antibody titers that were 2 to 3 times higher than mice that received the VLP alone. While IgG2a:IgG1 ratios were higher in mice vaccinated solely with the VLP, the higher overall titers are encouraging and demonstrate a degree of interaction between the RIC and VLP vaccines. Thus, the VLP presenting M2e and RICs comprising M2e are promising new universal influenza A vaccines. Additionally, co-delivering different types of recombinant vaccines could reduce the total number of vaccine doses needed to achieve a protective immune response.

a. Virus-Like Particle with M2e

The VLPs disclosed herein for generating an immune response against influenza viruses present M2e protein. In certain embodiments, the amino acid sequence of the M2e protein presented in the VLP is SLLTEVET-PIRNEWGCRCNDSSD (SEQ ID NO. 9). In preferred embodiments, the VLPs present a dimeric M2e protein, where two monomeric M2e proteins are linked with a linker sequence. In some aspects, the linker is a glycine serine linker sequence. In particular embodiments, the amino acid sequence of dimeric M2e protein presented by the VLPs is set forth in SEQ ID NO. 10.

b. Recombinant Immune Complex with M2e

The influenza virus RIC comprises an immunoglobulin heavy chain and M2e wherein the M2e is genetically fused to the immunoglobulin heavy chain. In certain embodiments, the amino acid sequence of the M2e protein presented in the RIC is SLLTEVETPIRNEWGCRCNDSSD (SEQ ID NO. 9). In certain embodiments, the influenza virus RIC comprises an immunoglobulin heavy chain linked to a M2e dimer. The M2e dimer is formed from a glycine serine linkage sequence linking two M2e proteins. In some embodiments, the influenza virus RIC is a C—RIC or N-RIC.

c. Methods of Production

It has been shown that M2e and M2e-containing vaccines has been able to be expressed effectively in plants (Nemchinov & Natilla, 2007). RICs comprising M2e and VLPs presenting M2e can be produced in plants using a geminiviral expression vector (see SEQ ID NOs. 19 and 20), and the VLPs and RICs can be extracted and purified from plants accordingly to methods established in the art.

Zika Virus Vaccine Compositions

In some embodiments, the disclosure relates to vaccine compositions that target zika virus and methods of generating an immune response in a mammalian subject against zika virus.

Zika virus (ZIKV) is a positive-sense single-stranded RNA virus that is a part of the genus Flavivirus and family Flaviviridae (Oliveira et al., 2017). Currently, the genus Flavivirus consists of fifty-three documented species along with a growing number of tentative species (Sim6n et al., 2017). These viruses produce a single polyprotein that is later cleaved into three structural proteins (C, prM and E) and seven nonstructural proteins (Oliveira et al., 2017). The prM (precursor transmembrane M) protein is proteolytically cleaved during virion maturation by a host cell protease to create the membrane (M) and pr protein. On a mature virus particle, a hundred and eighty copies of the envelope glycoprotein (E) and membrane (M) proteins can be found arranged in an icosahedral structure with 90 E dimers. This structure covers the viral surface (Boigard et al., 2017; Dai et al., 2016).

ZIKV is considered a global public health threat due to factors involving its spread and involvement with neonatal complications. From 2015-2017, Zika viral transmission has been reported in over 69 countries worldwide. In February 2016, the World Health Organization declared a Public Health Emergency of International Concern in response to the growing number of global Zika infections and the increasing amount of evidence suggesting links between Zika infection and congenital/neurological complications such as Guillain-Barre Syndrome and neonatal microcephaly (Rabaan et al., 2017; Wilder-Smith et al., 2018). Since then, there has been significant interest in developing vaccines and other therapeutic aids against the Zika virus. At this time, there are 45 vaccine candidates that were tested in non-clinical studies. Of the vaccine candidates that advanced past animal pre-clinical studies, several are in phase 1 human clinical trials and at least one is in phase 2 clinical trials ((NIAID); Durbin and Wilder-Smith, 2017; Wilder-Smith et al., 2018).

The main antigenic determinant of the virus is the envelope glycoprotein (E) since it is available on the surface of the mature virus particle and can be targeted by a number of neutralizing antibodies (Yang et al., 2018; Zhang et al., 2017). For this reason, many vaccine candidates utilize the ZIKV E protein ((NIAID)). One example is the experimental vaccine candidate currently in phase 2 clinical trials. This DNA vaccine candidate encodes the ZIKV wild type precursor transmembrane M (prM) and envelope (E) protein ((NIAID)). However, as of now, DNA vaccines are not licensed for human use and may have some risk of chromosomal integration via nonhomologous recombination (Barzon and Palu, 2017). Plant-produced, vaccines can potentially overcome safety and cost concerns associated with other ZIKV vaccine candidates, including inactivated virus, mRNA or DNA-based vaccines, and adenovirus-vectored vaccines. Plant expression systems are highly scalable and avoid many of the costs of traditional systems, such as expensive bioreactors, thereby allowing cheaper production of biological products (Alam et al., 2018; Tuse et al., 2014). Additionally, using a recombinant protein vaccine also removes the safety concerns of improperly inactivated virus, genomic insertion, and the development of immune responses to adenoviral vectors (Yang et al., 2018).

The E protein contains three structurally separate domains (Zhang et al., 2017). Of these domains, the E domain III (ZE3) is a promising target for vaccine development since it has been shown to contain a number of epitopes for neutralizing, type-specific monoclonal antibodies (Dai et al., 2016; Haiyan Zhao et al., 2016; Yang et al., 2017). Since neutralizing antibodies developed against approved vaccines for yellow fever virus and tick-borne encephalitis virus, both of which are closely related to ZIKV, appear to have a correlation with viral protection (Belmusto-Worn et al., 2005; Heinz et al., 2007), ZE3 is an important target. Furthermore, ZE3-specific antibodies do not show dengue virus antibody dependent enhancement (Stettler et al., 2016). Antibody-dependent enhancement occurs when non-neutralizing antibodies developed in response to one viral infection cross-reacts and forms complexes with another virus upon infection. These complexes bind to cells with Fc-gamma or complement-associated receptors and are taken up by myeloid cells. However, since the antibodies merely bind to and do not neutralize the virus, the severity of viral infection is enhanced (Taylor et al., 2015). Published work utilizing a subunit ZE3 protein vaccine candidate showed an absence of antibody dependent enhancement of dengue viral infection (Yang et al., 2017). This result, along with the presence of known, neutralizing antibody epitopes on ZE3, render this antigen a prime target for vaccination.

In certain implementations of the method of generating an immune response in a mammalian subject against zika virus, the method comprises administering to the mammalian subject a VLP presenting a zika virus antigen. In some implementations, a RIC comprising a zika virus antigen is also administered. In some aspects, RIC comprising a zika virus antigen and VLP presenting a zika virus antigen are co-administered. In some aspects, the RIC and the VLP are coadministered in a ratio of 1:1. In certain implementations, the VLP and the RIC are administered to the mammalian subject in three vaccination events, wherein each vaccination event comprises administration of one dose of the VLP and/or one dose of the RIC. In some implementations, the three vaccination events are performed within a period of 8 weeks. In some aspects, two vaccination events are separated by a period of at least 14 day, at least 21 days, at least 28 days, at least 35 days, at least 42 days, at least 49 days, at least 56 days, about three weeks, about four weeks, about five week, about six weeks, about seven weeks, or about eight weeks. As used herein, the term "about" refers to ±3 days, ±2 days, or ±1 day. The methods of administering the VLP and RIC may be any established methods of vaccination in the prior art. In some instances, the VLP and RIC are administered subcutaneously. In some implementations, the VLP and RIC are administered with an adjuvant.

a. Virus-Like Particle with Zika Virus Antigens

The VLPs disclosed herein for generating an immune response against zika viruses present an antigen selected from the group consisting of zika virus E protein domain 3 protein (ZE3), zika virus fusion loop antigen (ZE), and zika virus soluble envelope protein (Zse). In some aspects, the amino acid sequence of ZE3 is set forth in residues 591-696 of GenBank Accession No. AMC13911. In some aspects, the amino acid sequence of ZE is set forth in residues 352-412 of GenBank Accession No. AMC13911. In some aspects, the amino acid sequence of Zse is set forth in residues 291-693 of GenBank Accession No. AMC13911. In other aspects, the amino acid sequences of ZE3, ZE, and Zse may be functionally equivalent versions of corresponding regions of GenBank Accession No. AMC13911 from other strains of zika virus, for example, the corresponding sequences of ZE3, ZE, Zse in GenBank Accession Nos. AY632535, KU321639, KJ776791, KF383115, KF383116, KF383117, KF383118, KF383119, KF268948, KF268949, KF268950, EU545988, KF993678, JN860885, HQ234499, KU501215, KU501216, KU501217.

The zika virus VLPs can be produced in plants using a geminiviral expression vector (see SEQ ID NOs. 34 and 35), and the VLPs can be extracted and purified from plants accordingly to methods established in the art.

b. Recombinant Immune Complex with Zika Virus Antigens

The zika virus RIC comprises an immunoglobulin heavy chain and a zika virus antigen genetically fused to the immunoglobulin heavy chain. In some embodiments, the zika virus RIC is a C—RIC or N-RIC. The zika virus antigen is selected from the group consisting of zika virus E protein domain 3 protein (ZE3), zika virus fusion loop antigen (ZE), and zika virus soluble envelope protein (Zse). In some aspects, the amino acid sequence of ZE3 is set forth in residues 591-696 of GenBank Accession No. AMC13911. In some aspects, the amino acid sequence of ZE is set forth in residues 352-412 of GenBank Accession No. AMC13911. In some aspects, the amino acid sequence of Zse is set forth in residues 291-693 of GenBank Accession No. AMC13911. In other aspects, the amino acid sequences of ZE3, ZE, and Zse may be functionally equivalent versions of corresponding regions of GenBank Accession No. AMC13911 from other strains of zika virus, for example, the corresponding sequences of ZE3, ZE, Zse in GenBank Accession Nos. AY632535, KU321639, KJ776791, KF383115, KF383116, KF383117, KF383118, KF383119, KF268948, KF268949, KF268950, EU545988, KF993678, JN860885, HQ234499, KU501215, KU501216, KU501217.

The zika virus RICs can be produced in plants using a geminiviral expression vector (see SEQ ID NOs. 36-38), and the RICs can be extracted and purified from plants accordingly to methods established in the art.

ILLUSTRATIVE, NON-LIMITING EXAMPLE IN ACCORDANCE WITH CERTAIN EMBODIMENTS

The disclosure is further illustrated by the following examples that should not be construed as limiting. The contents of all references, patents, and published patent applications cited throughout this application, as well as the Figures, are incorporated herein by reference in their entirety for all purposes.

Example 1. Human Papillomavirus Vaccine Compositions a. Materials and Methods
i. Vector Construction
1. Virus-Like Particle As most broadly neutralizing HPV antibodies are derived from the highly conserved N-terminal region of L2, amino acids 14-122 of HPV16 L2 were used to create HBc VLPs. L2 with flanking linker regions was inserted into the tip of the α-helical spike of an HBc gene copy which was fused to another copy of HBc lacking the L2 insert. This arrangement allows the formation of HBc dimers that contain only a single copy of L2, increasing VLP stability (Peyret et al. 2015). This heterodimer is referred to as HBche-L2. A dicot plant-optimized HPV16 L2 coding sequence was designed based upon the sequence of GenBank Accession No. CAC51368.1 and synthesized in vitro using synthetic oligonucleotides by the method described (Stemmer et al., 1995). The plant-optimized L2 nucleotide sequence encoding residues 1-473 is posted at GenBank Accession No. KC330735. PCR end-tailoring was used to insert XbaI and SpeI sites flanking the L2 aa 14-122 using primers L2-14-Xba-F (SEQ ID NO. 1: CGTCTAGAGTCCGCAACC-CAACTTTACAAG) and L2-122-Spe-R (SEQ ID NO. 2: GGGACTAGTTGGGGCACCAGCATC). The SpeI site was fused to a sequence encoding a 6His tag, and the resulting fusion was cloned into a geminiviral replicon vector (Diamos, 2016) to produce pBYe3R2K2Mc-L2(14-122)6H.

The HBche heterodimer VLP system was adapted from Peyret et al (2015). Using the plant optimized HBc gene (Huang et al., 2009), inventors constructed a DNA sequence encoding a dimer comprising HBc aa 1-149, a linker $(G_2S)_5$ G (SEQ ID NO. 39), HBc aa 1-77, a linker $GT(G_4S)_2$ (SEQ ID NO. 40), HIPV-16 L2 aa 14-122, a linker $(GGS)_2$ GSSGGSGG (SEQ ID NO. 41), and HBc aa 78-176. The dimer sequence was generated using multiple PCR steps including overlap extensions and insertion of BamHI and SpeI restriction sites flanking the L2 aa 14-122, using primers L2-14-Bam-F (SEQ ID NO. 3: CAG-GATCCGCAACC CAACTTTACAAGAC) and L2-122-Spe-R (SEQ ID NO. 2). The HBche-L2 coding sequence was inserted into a geminiviral replicon binary vector pBYR2eK2M (FIG. 3), which includes the following elements: CaMV 35S promoter with duplicated enhancer (Huang et al., 2009), 5' UTR of N. benthamiana psaK2 gene (Diamos et al., 2016), intron-containing 3' UTR and terminator of tobacco extensin (Rosenthal et al, 2018), CaMV 35S 3' terminator (Rosenthal et al, 2018), and Rb7 matrix attachment region (Diamos et al., 2016).

2. Recombinant Immune Complex

The recombinant immune complex (RIC) vector was adapted from Kim et al., (2015). The HPV-16 L2 (aa 14-122) segment was inserted into the BamHI and SpeI sites of the gene encoding humanized mAb 6D8 heavy chain, resulting in 6D8 epitope-tagged L2. The heavy chain fusion was inserted into an expression cassette linked to a 6D8 kappa chain expression cassette, all inserted into a geminiviral replicon binary vector (FIG. 3, RIC vector). Both cassettes contain CaMV 35S promoter with duplicated enhancer (Huang et al., 2009), 5' UTR of N. benthamiana psaK2 gene (Diamos et al., 2016), intron-containing 3' UTR and terminator of tobacco extensin (Rosenthal et al, 2018), and Rb7 matrix attachment region (Diamos et al., 2016).

ii. Agroinfiltration of Nicotiana benthamiana Leaves

Binary vectors were separately introduced into Agrobacterium tumefaciens EHA105 by electroporation. The resulting strains were verified by restriction digestion or PCR, grown overnight at 30° C., and used to infiltrate leaves of 5- to 6-week-old N. benthamiana maintained at 23-25° C. Briefly, the bacteria were pelleted by centrifugation for 5 minutes at 5,000 g and then resuspended in infiltration buffer (10 mM 2-(N-morpholino)ethanesulfonic acid (MES), pH 5.5 and 10 mM $MgSO_4$) to $OD_{600}$=0.2, unless otherwise described. The resulting bacterial suspensions were injected by using a syringe without needle into leaves through a small puncture (Huang et al. 2004). Plant tissue was harvested after 5 DPI, or as stated for each experiment. Leaves producing GFP were photographed under UV illumination generated by a B-100AP lamp (UVP, Upland, CA).

iii. Protein Extraction

Total protein extract was obtained by homogenizing agroinfiltrated leaf samples with 1:5 (w:v) ice cold extraction buffer (25 mM sodium phosphate, pH 7.4, 100 mM NaCl, 1 mM EDTA, 0.1% Triton X-100, 10 mg/mL sodium ascorbate, 0.3 mg/mL PMSF) using a Bullet Blender machine (Next Advance, Averill Park, NY) following the manufacturer's instruction. To enhance solubility, homogenized tissue was rotated at room temperature or 4° C. for 30 minutes. The crude plant extract was clarified by centrifugation at 13,000 g for 10 minutes at 4° C. Necrotic leaf tissue has reduced water weight, which can lead to inaccurate measurements based on leaf mass. Therefore, extracts were normalized based on total protein content by Bradford protein assay kit (Bio-Rad) with bovine serum albumin as standard.

iv. SDS-PAGE and Western Blot

Clarified plant protein extract was mixed with sample buffer (50 mM Tris-HCl, pH 6.8, 2% SDS, 10% glycerol, 0.02% bromophenol blue) and separated on 4-15% polyacrylamide gels (Bio-Rad). For reducing conditions, 0.5M DTT was added, and the samples were boiled for 10 minutes prior to loading. Polyacrylamide gels were either transferred to a PVDF membrane or stained with Coomassie stain (Bio-Rad) following the manufacturer's instructions. For L2 detection, the protein transferred membranes were blocked with 5% dry milk in PBST (PBS with 0.05% tween-20) overnight at 4° C. and probed with polyclonal rabbit anti-L2 diluted 1:5000 in 1% PBSTM, followed by goat anti-rabbit horseradish peroxidase conjugate (Sigma). Bound antibody was detected with ECL reagent (Amersham).

v. Immunization of Mice and Sample Collection

All animals were handled in accordance to the Animal Welfare Act and Arizona State University IACUC. Female BALB/C mice, 6-8 weeks old, were immunized subcutaneously with purified plant-expressed L2 (14-122), HBche-L2 VLP, L2 RIC, or PBS mixed 1:1 with Imject® Alum (Thermo Scientific, Rockford, IL). In all treatment groups, the total weight of antigen was set to deliver an equivalent 5 µg of L2. Doses were given on days 0, 21, and 42. Serum collection was done as described (Santi et al. 2008) by submandibular bleed on days 0, 21, 42, and 63.

vi. Antibody Measurements

Mouse antibody titers were measured by ELISA. Bacterially-expressed L2 (amino acids 11-128) was bound to 96-well high-binding polystyrene plates (Corning), and the plates were blocked with 5% nonfat dry milk in PBST. After washing the wells with PBST (PBS with 0.05% Tween 20), the diluted mouse sera were added and incubated. Mouse antibodies were detected by incubation with polyclonal goat anti-mouse IgG-horseradish peroxidase conjugate (Sigma). The plate was developed with TMB substrate (Pierce) and the absorbance was read at 450 nm. Endpoint titers were taken as the reciprocal of the lowest dilution which produced an OD450 reading twice the background. IgG1 and IgG2a antibodies were measured with goat-anti mouse IgG1 or IgG2a horseradish peroxidase conjugate.

vii. Electron Microscopy

Purified samples of HBche or HBche-L2 were initially incubated on 75/300 mesh grids coated with formvar. Following incubation, samples were briefly washed twice with deionized water then negatively stained with 2% aqueous uranyl acetate. Transmission electron microscopy was performed with a Phillips CM-12 microscope, and images were acquired with a Gatan model 791 CCD camera.

viii. Statistical Analysis

The significance of vaccine treatments and virus neutralization was measured by non-parametric Mann-Whitney test using GraphPad prism software. Two stars () indicates p values <0.05. Three stars (*) indicates p values <0.001.

b. Design and Expression of HBc VLPs and RIC Displaying HPV16 L2

BeYDV plant expression vectors (FIG. 3) expressing either the target VLP HBche-L2, or L2 and HBche alone as controls, were agroinfiltrated into the leaves of *N. benthamiana* and analyzed for VLP production. After 4-5 days post infiltration (DPI), leaves displayed only minor signs of tissue necrosis, indicating that the VLP was well-tolerated by the plants (FIG. 4A). Leaf extracts analyzed by reducing SDS-PAGE showed an abundant band near the predicted size of 51 kDa for HBche-L2, just above the large subunit of rubisco (RbcL). HBche was detected around the predicted size of 38 kDa (FIG. 4B). Western blot probed with anti-L2 polyclonal serum detected a band for HBche-L2 at ~51 kDa (FIG. 4B). These results indicate that this plant system is capable of producing high levels of L2-containing HBc VLP.

To express L2-containing RIC, amino acids 14-122 of HPV16 L2 were fused with linker to the C-terminus of the 6D8 antibody heavy chain and tagged with the 6D8 epitope (Kim et al. 2015). A BeYDV vector (FIG. 3) expressing both the L2-fused 6D8 heavy chain and the light chain was agroinfiltrated into leaves of *N. benthamiana* and analyzed for RIC production. To create more homogenous human-type glycosylation, which has been shown to improve antibody Fc receptor binding in vivo, transgenic plants silenced for xylosyltransferase and fucosyltransferase were employed (Castilho and Steinkellner 2012). By western blot, high molecular weight bands >150 kDa suggestive of RIC formation were observed (FIG. 4C). Expression of soluble L2 RIC was lower than HBche-L2 due to relatively poor solubility of the RIC (FIG. 4C).

After rigorous genetic optimization, the *N. benthamiana* system is capable of producing very high levels of recombinant protein, up to 30-50% of the total soluble plant protein, in 4-5 days (Diamos et al. 2016). Using this system, we produced and purified milligram quantities of fully assembled and potently immunogenic HBc VLPs displaying HPV L2 through a simple one-step purification process (FIGS. 4A-4C and 6).

c. Purification and Characterization of HBche-L2 and L2 RIC

To assess the assembly of HBc-L2 VLP, clarified plant extracts containing either HBche-L2 or HBche were analyzed by sucrose gradient sedimentation. HBche-L2 sedimented largely with HBche, which is known to form VLP, though a small increase in density was observed with HBche-L2, perhaps due to the incorporation of L2 into the virus particle (FIG. 5A). To demonstrate particle formation, sucrose fractions were examined by electron microscopy. Both HBche and HBche-L2 formed ~30 nm particles, although the appearance of HBche-L2 VLP suggested slightly larger, fuller particles (FIGS. 5C and 5D). As most plant proteins do not sediment with VLP, pooling peak sucrose fractions resulted in >95% pure HBche-L2 (FIG. 5B), yielding sufficient antigen (>3 mg) for vaccination from a single plant leaf.

L2 RIC was purified from plant tissue by protein G affinity chromatography. By SDS-PAGE, an appropriately sized band was visible >150 kDa that was highly pure (FIG. 5B). Western blot confirmed the presence of L2 in this band, indicating proper RIC formation (FIG. 5B). L2 RIC bound to human complement C1q receptor with substantially higher affinity com-pared to free human IgG standard, suggesting proper immune complex formation (FIG. 5E).

d. Mouse Immunization with HBche-L2 and L2 RIC

Groups of Balb/c mice (n=8) were immunized, using alum as adjuvant, with three doses each of 5 μg L2 delivered as either L2 alone, HBche-L2 VLP, L2 RIC, or a combination of half VLP and half RIC. VLP and RIC, alone or combined, greatly enhanced antibody titers compared to L2 alone by more than an order of magnitude at all time points tested (FIG. 6). After one or two doses, the combined VLP/RIC treatment group outperformed both the VLP or RIC groups, reaching mean endpoint titers of >200,000, which represent a 700-fold increase over immunization with L2 alone (FIG. 6). After the third dose, both the VLP and combined VLP/RIC groups reached endpoint titers >1,300,000, a 2-fold increase over the RIC alone group. To determine the antibody subtypes produced by each treatment group, sera were assayed for L2-binding IgG1 and IgG2a. All four groups produced predominately IgG1 (FIG. 7, note dilutions). However, RIC and especially VLP-containing groups had an elevated ratio of IgG2a:IgG1 (>3-fold) compared to L2 alone (FIG. 7).

In vitro neutralization of HPV16 pseudovirions showed that the VLP and RIC groups greatly enhanced neutralization compared to L2 alone (FIG. 5, $p<0.001$). Additionally, VLP and RIC combined further enhanced neutralization activity ($5-fold, $p<0.05$) compared to either antigen alone, supporting the strong synergistic effect of delivering L2 by both platforms simultaneously.

In this study, by displaying amino acids 11-128 on the surface of plant-produced HBc VLPs, L2 antibody titers as high as those seen with L1 vaccines were generated (FIG. 6). Mice immunized with L2 alone had highly variable antibody titers, with titers spanning two orders of magnitude. By contrast, the other groups had much more homogenous antibody responses, especially the VLP-containing groups, which had no animals below an endpoint titer of 1:1,000,000 (FIG. 6). These results underscore the potential of HBc VLP and RIC to provide consistently potent immune responses against L2. Moreover, significant synergy of VLP and RIC systems was observed when the systems were delivered together, after one or two doses (FIG. 6). Since equivalent amounts of L2 were delivered with each dose, the enhanced antibody titer did not result from higher L2 doses. Rather, these data suggest that higher L2-specific antibody production may be due to augmented stimulation of L2-specific B cells by T-helper cells that were primed by RIC-induced antigen presenting cells. Although treatment with VLP and RIC alone reached similar endpoint titers as the combined VLP/RIC group after 3 doses, virus neutralization was substantially higher (>5-fold) in the combined group (FIG. 8). Together, these data indicate unique synergy exists when VLP and RIC are delivered together. Inventors have observed similarly significant synergistic enhancement of immunogenicity for a variety of other antigens.

Mice immunized with L2 alone had highly variable antibody titers, with titers spanning two orders of magnitude. By contrast, the VLP and VLP/RIC groups had much more homogenous antibody responses, with no animals below an endpoint titer of 1:1,000,000 (FIG. 6). These results underscore the potential of HBc VLP and RIC to provide consistently potent immune responses against L2.

Fc gamma receptors are present on immune cells and strongly impact antibody effector functions such as antibody-dependent cell-mediated cytotoxicity and complement-dependent cytotoxicity (Jefferis 2009). In mice, these interactions are controlled in part by IgG subtypes. IgG1 is associated with a Th2 response and has limited effector functions. By contrast, IgG2a is associated with a Th1 response and more strongly binds complement components (Neuberger and Rajewsky 1981) and Fc receptors (Radaev 2002), enhancing effector functions and opsonophagocytosis by macrophages (Takai et al. 1994). Immunization with L2 alone was found to produce low levels of IgG2a, however immunization with RIC and VLP produced significant increases in IgG2a titers. VLP-containing groups in particular showed a 3-fold increase in the ratio of IgG2a to IgG1 antibodies (FIG. 7). Importantly, production of IgG2a is associated with successful clearance of a plethora of viral pathogens (Coutelier et al. 1988; Gerhard et al. 1997; Wilson et al. 2000; Markine-Goriaynoff and Coutelier 2002).

Figures 4A, 4B, 4C:
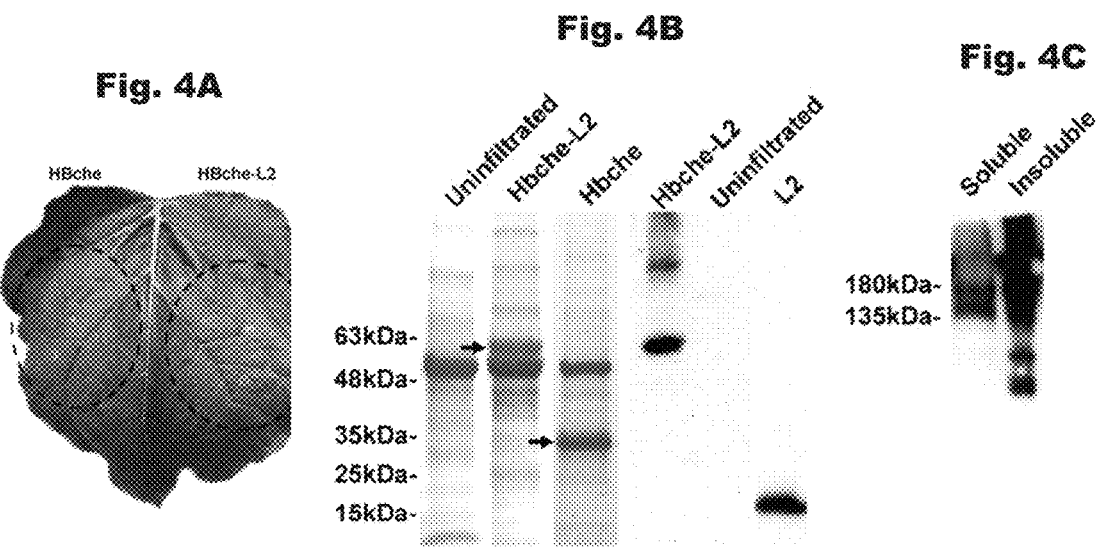
FIG. 4A-4C depict, in accordance with certain embodiments, the expression of VLP and RIC that display L2 antigen.
Figure 3A:
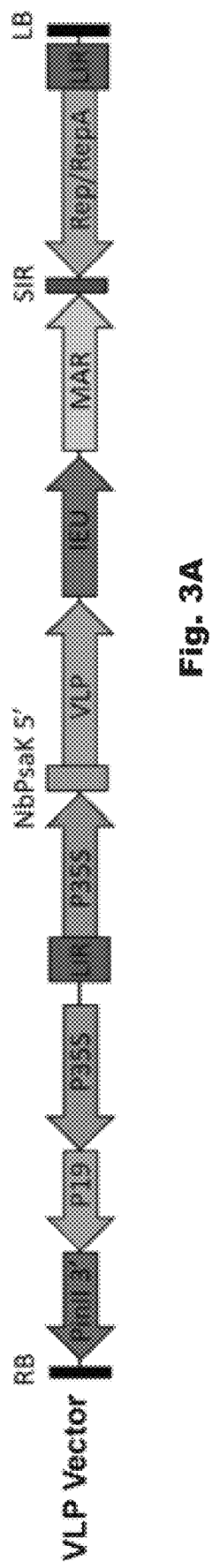
FIG. 3A-3D depict, in accordance with certain embodiments, schematic representation of exemplary BeYDV plant expression vectors used to express human papillomavirus (HPV) VLPs and RICs. For FIGS. 3A and 3C, the region between the two LIRs is circularized and amplified to high copy number in the plant nucleus, serving as transcription templates for the VLP and RIC, respectively. Abbreviations: RB, the *agrobacterium* right T-DNA border region; PinII3', the terminator from the potato proteinase inhibitor II gene; P19, the RNA silencing suppressor from tomato bushy stunt virus; P35S, the 35S promoter from cauliflower mosaic virus; LIR, the long intergenic region from BeYDV; NbPsaK 5', the truncated 5' UTR from NbPsaK; VLP, either L2-fused or unfused hepatitis B core antigen; Heavy-L2, the mAb 6D8 gamma (heavy) chain with C-terminal L2 fusion; Light, the 6D8 kappa (light) chain; IEU, the tobacco extensin terminator with intron; MAR, the rb7 matrix attachment region; SIR, the short intergenic region from BeYDV; Rep/RepA, the replication proteins from BeYDV; LB, the *agrobacterium* T-DNA left border region.
Figure 3B:
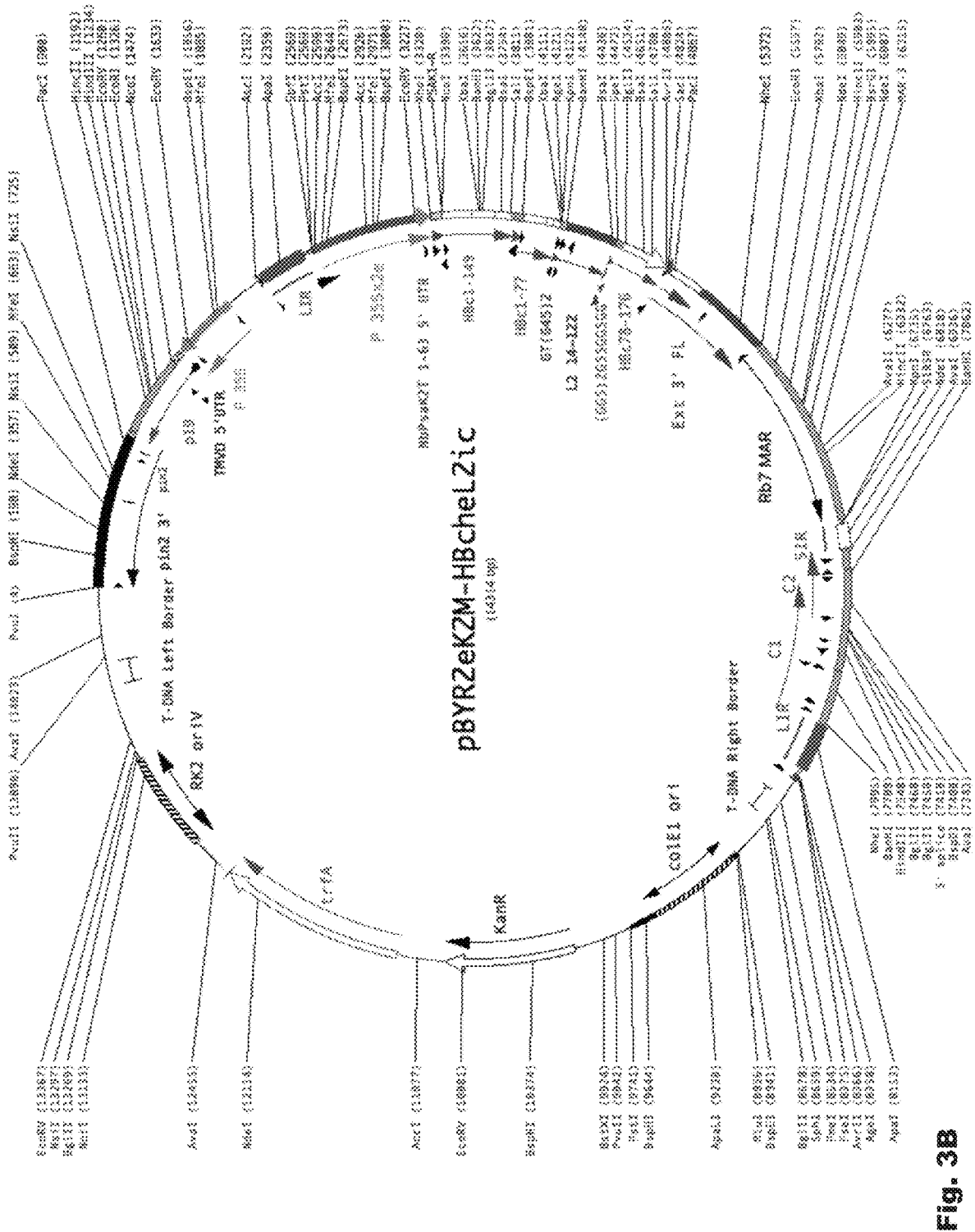
Figure 3C:
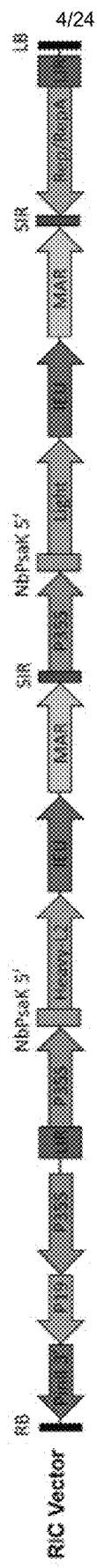
Figure 3D:
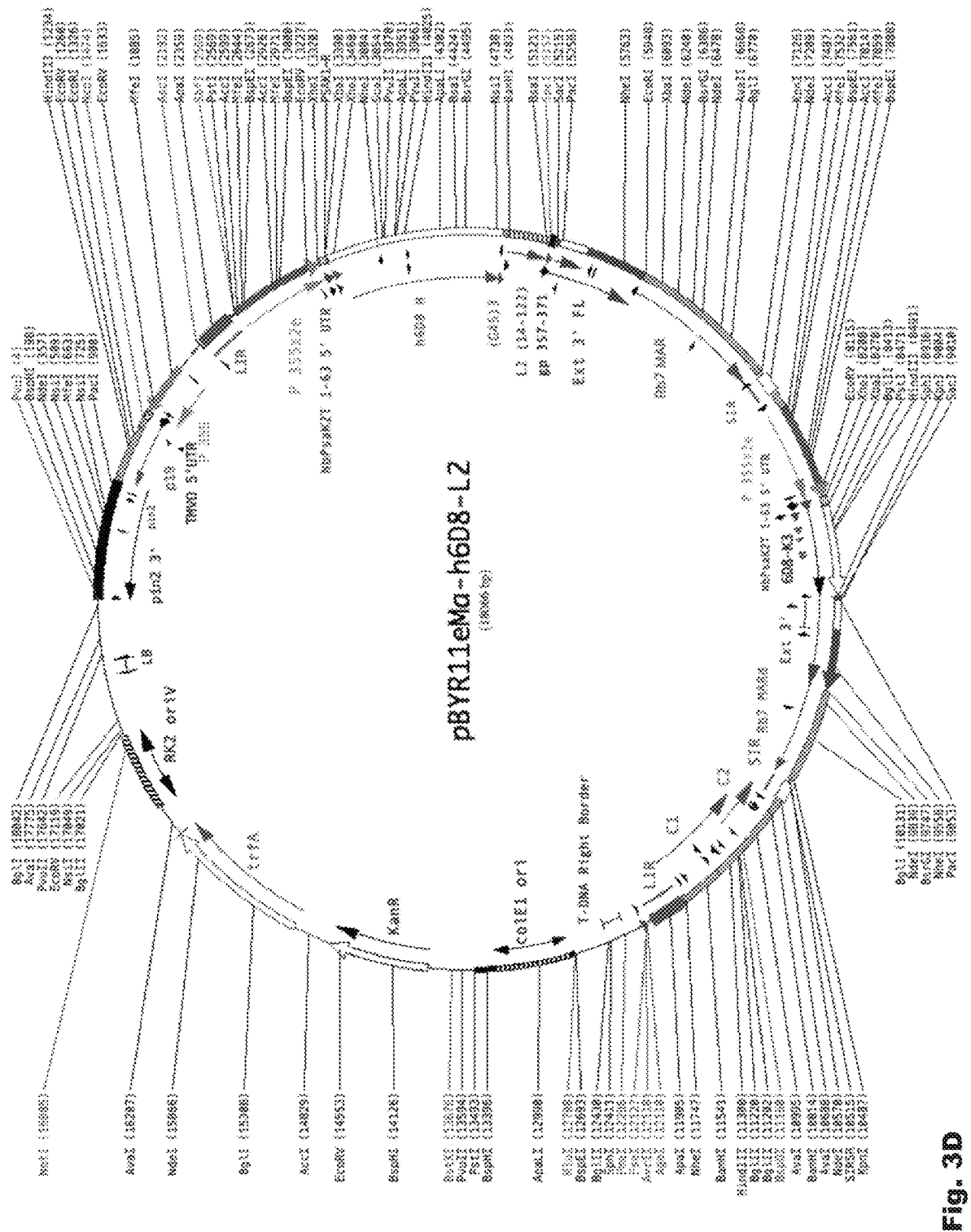

The glycosylation state of the Fc receptor also plays an important role in antibody function. Advances in glycoengineering have led to the development of transgenic plants with silenced fucosyl- and xylosyl-transferase genes capable of producing recombinant proteins with authentic human N-glycosylation (Strasser et al. 2008). Antibodies produced in this manner have more homogenous glycoforms, resulting in improved interaction with Fc gamma and complement receptors compared to the otherwise identical antibodies produced in mammalian cell culture systems (Zeitlin et al. 2011; Hiatt et al. 2014; Strasser et al. 2014; Marusic et al. 2017). As the known mechanisms by which RIC vaccines increase immunogenicity of an antigen depend in part on Fc and complement receptor binding, HPV L2 RIC were produced in transgenic plants with silenced fucosyl- and xylosyl-transferase. Consistent with these data, we found that L2 RIC strongly enhanced the immunogenicity of L2 (FIG. 6). However, yield suffered from insolubility of the RIC (FIG. 4C). We found that the 11-128 segment of L2 expresses very poorly on its own in plants and may be a contributing factor to poor L2 RIC yield. Importantly, we have produced very high yields of RIC with different antigen fusions. Thus, in some aspects, antibody fusion with a shorter segment of L2 could substantially improve the yield of L2 RIC.

e. Neutralization of HPV Pseudovirions

Neutralization of papilloma pseudoviruses (HPV 16, 18, and 58) with sera from mice immunized IP with HBc-L2 VLP and L2(11-128) showed neutralization of HPV 16 at titers of 400-1600 and 200-800, respectively (Table 1). More mice IP-immunized with HBc-L2 VLP had antisera that cross-neutralized HPV 18 and HPV 58 pseudoviruses, compared with mice immunized with L2(11-128). Anti-HBc-L2 VLP sera neutralized HPV 18 at titers of 400 and HPV 58 at titers ranging from 400-800 (Table 1), while anti-L2(11-128) sera neutralized HPV 18 at a titer of 200 and HPV 58 at a titer of 400 (Table 1). None of the sera from intranasal-immunized mice demonstrated neutralizing activity, consistent with lower anti-L2 titers for intranasal than for intraperitoneal immunized mice.

TABLE 1

L2-specific serum IgG and pseudovirus neutralization titers from IP immunized mice

| Immunogen | Serum IgG | Neutralization of Pseudoviruses | | |
| --- | --- | --- | --- | --- |
| | | HPV 16 | HPV 18 | HPV 58 |
| HBc-L2 | >50,000 | 400 | — | — |
| | ~70,000 | 1600 | 400 | 400 |
| | >80,000 | 1600 | 400 | 800 |
| L2 (11-128) | ~8000 | 200 | — | — |
| | ~12,000 | 400 | — | — |
| | ~50,000 | 800 | 200 | 400 |

Example 2. Influenza Vaccine Compositions a. Methods
i. Vector Construction

A codon-optimized sequence for the expression of a dimeric human consensus M2e protein (SLLTEVET-PIRNEWGCRCNDSSDGGSGGSLLTEVETPIRNEWGC-RCNDSSD, SEQ ID NO. 10) in *N. benthamiana* was designed (Neirynck et al., 1999; Blokhina et al., 2013; Mardanova et al., 2015; Krishnavajhala et al., 2018), and restriction sites for the restriction enzymes BamHI (New England Biolabs) and SpeI (New England Biolabs) and binding sites for the M13F and M13R primers flanking the BamHI and SpeI sites were added to the ends of the sequence to maximize compatibility with existing vectors. M2e monomers were linked by a glycine-serine linker to minimize interference of the linker with the protein and RIC as a whole. Tandem repeats of M2e increases the chance of cross-linking occurring in B cell receptors on B cells and also increases the chances of M2e being degraded and displayed by proteosomal digestion and MHC presentation. This increases the immunogenicity of the vaccine. 250 ng of the sequence was ordered from IDT (Integrated DNA Technologies, Coralville, IA) as a gBlock, which was promptly resuspended by centrifuging the geneblock for 5 seconds at 3,000 xg and resuspending the resulting pellet in TE buffer to a final concentration of 10 ng/µl. The geneblock was then amplified by high-fidelity PCR using M13F and M13R primers and run on a 1% agarose gel, with the resulting band being excised and the DNA contained within being isolated by dissolving the gel fragment in sodium iodide (a chaotropic salt that dissolves agarose) and heating for approximately 10 minutes. The DNA was precipitated out of the solution by mixing the solution with a small amount (7 µl) of silicon dioxide suspension, which binds DNA under high salt conditions. The solution was pelleted, washed with 50% ethanol/50 mM NaCl to remove NaI, and the DNA was eluted from the silicon dioxide with sterile water. Following this, the amplified M2e sequence was then digested with BamHI and SpeL. The vector backbone plasmid, pBYR11eMa-h6D8-L2, was digested with SbfI and SpeL for the vector fragment, and separately with SbfI and BamHI for the 2264 bp fragment. The three fragments were ligated using T4 DNA ligase (New England Biolabs) overnight in a 16° C. water bath.

The ligated plasmid was then precipitated using ammonium acetate and 2-propanol to increase purity and decrease the volume of the plasmid in solution (the precipitation allowed for a volume reduction from 20 µl to 3 µl, vastly increasing the concentration of the plasmid in solution). Following precipitation, 2 µl of the plasmid was electroporated into competent DH5α *E. coli*, which was allowed to grow in a 2 mL Eppendorf tube containing 500 µl YENB broth for one hour to allow the *E. coli* to recover. This 500 µl of broth was subsequently plated onto an LB+kanamycin plate and allowed to grow overnight in a 37° C. incubator. Ten colonies were selected and screened via PCR using the 6D8H-F and Ext3-R primers (Table 1) with the two colonies producing the brightest bands on the agarose gel being selected for plasmid preparation via lysis of the cells (using an EDTA-containing buffer to prevent DNAse activity) and precipitation of the plasmid through mixing with ammonium acetate and ethanol to precipitate the DNA. pBYR11eMa-h6D8M2e was isolated via centrifugation and resuspension in TE buffer. Isolated pBYR11eMa-h6D8M2e from the *E. coli* were Sanger sequenced in the region of the plasmid containing M2e to ensure sequence integrity.

To generate the plasmid encoding the VLP, pBYR2eK2M-HBcheM2e was constructed. pET-28b (Novalgen) and the M2e geneblock were digested with NcoI and XhoI. These fragments were ligated to generate the plasmid pET28b-M2e. Then, the plasmid pBY037P3-HbcheL2ic and the M2e gBlock were digested with BamHI and SpeI, with the fragments being ligated to form pBY037P3-HbcheM2e, which contained M2e fused to the MIR of an HBc monomer. pBY037P3-HbcheM2e was digested with NcoI and SpeI to obtain the 926 bp fragment. pBYR2eK2M-HbcheZE3 was digested with SbfI and SpeI for the vector fragment, and separately with SbfI and NcoI to obtain the 821 bp fragment with promoter and 5'UTR. These fragments were ligated together to form pBYR2eK2M-HbcheM2e, which contained the HBc dimer with M2e inserted into the second HBc monomer's MIR region.

Table 2 lists nucleotide sequences used in the construction of the vectors.

TABLE 2

Summary of nucleic acid sequence used.

| Name | Sequence from 5' to 3' |
|---|---|
| M2e gBlock, SEQ ID NO. 11 | GTAAAACGACGGCCAGTGGATCCTCTTTGC TTACCGAGGTTGAGACCCCTATTAGAAACG AGTGGGGTTGCAGATGTAACGATTCTTCCG ACGGaGGtTCTGGaggtTCCCTTTTGACTG AAGTgGAGACTCCAATcAGgAACGAATGGG GATGcAGATGCAACGACTCCTCTGACGGAG GTGGAactagtCATGGTCATAGCTGTTTCC |
| M2e-Nco-F Primer, SEQ ID NO. 12 | tagccatgGGATCCTCTTTGCTTACCG |
| M2e-Xho-R Primer, SEQ ID NO. 13 | tcgctcgagactagtTCCACCTCCGTC |
| 6D8H-F Primer, SEQ ID NO. 14 | TGAGGCTCTTCACAATCA |
| Ext3-R Primer, SEQ ID NO. 15 | CTTCTTCTTCTTCTTTTCTCATTGTC |
| Ext3i-R Primer, SEQ ID NO. 16 | CAATTTGCTTTGCATTCTTGAC |
| M13-F Primer, SEQ ID NO. 17 | GTAAAACGACGGCCAGT |
| M13-R Primer. SEQ ID NO. 18 | GGAAACAGCTATGACCATG | ii. Agroinfiltration

After verifying the presence of M2e in pBYR11eMa-h6D8M2e and pBYR2eK2M-HBcheM2e, the plasmids were electroporated into *Agrobacterium tumefaciens* EHA 105 cells, which were allowed to recover in 500 µl YENB broth for one hour. The cells were then plated on LB+kan plates and incubated at 28° C. for two days. Following this, cultures of the transformed *A. tumefaciens* were grown overnight at 28° C. on a shaker in YENB, rifampicin (2.775 µg/ml) and kanamycin (50 µg/ml). These cultures were PCR screened after which cultures identified to contain pBYR11 eMa-h6D8M2e and pBYR2eK2M-HBcheM2e were spun down and resuspended in 1× infiltration buffer to an OD of 0.260. Three GnGn *N. benthamiana* plants (Strasser et al., 2008) ranging from five to six weeks old were infiltrated (specifically in the leaves) with the *A. tumefaciens* suspensions (Huang and Mason, 2004) and allowed to grow at room temperature for five days. The plants were watered daily.

iii. Extraction and Purification of Recombinant Influenza A Vaccines

Five days after agroinfiltration, plant leaves were homogenized with an electric blender in ice cold buffer (100 mM tris, 50 mM NaCl, 10 mM EDTA, 2 mM PMSF, 0.1 Triton, pH=8.0). No significant necrosis was observed in any of the infiltrated or uninfiltrated leaves. The blended plant leaves were then stirred for 20 minutes at 4° C., after which the solution was filtered through four-ply miracloth to remove plant fibers. 1 ml of this solution was taken as a sample of 'crude extract' and frozen at −80° C. for later analysis. 1M phosphoric acid was then added to lower the pH of the extraction to 4.6 for one minute to precipitate plant proteins like RuBisCo, with 2M Tris Base being added to raise the pH of the sample back up to 7.6. The extraction was then centrifuged at 16,000×g for 20 minutes at 4° C. The supernatant was isolated and centrifuged for another 30 minutes at 16,000×g at 4° C. Then, the supernatant was again isolated and centrifuged for a final 10 minutes at 16,000×g at 4° C. to remove as much precipitated plant protein and other insoluble matter in the extraction as possible (as RICs are present in the soluble fraction). The supernatant was then run through vacuum filter sterilizers (pore size=0.45 micron) to remove any remnant bacteria that might have remained after centrifugation.

For the M2e-RIC, a protein G resin column (containing protein G conjugated to agarose beads) (Thermo Fisher Scientific, Waltham, MA, USA) was prepared by running the RIC extraction buffer through the column. The extraction was then run through the prepared column, after which the column was washed again with the RIC extraction buffer again to remove any final contaminants from the column. The RICs were then eluted from the column using a glycine solution (100 mM glycine, pH=2.5), with five 1.5 ml elutions being taken from the column and pH-neutralized using Tris base (100 µl of 1M Tris pH=8.0 in each elution). 50 µl aliquots from each elution were immediately frozen in a −80° C. freezer for later analysis to prevent the larger elutions from degrading due to frequent freezing and thawing. Additionally, small volumes from each elution were used in spectrophotometry to determine the concentration of RICs present in each elution.

For the M2e-VLP, a sucrose gradient and subsequent ultracentrifugation was used to purify the VLPs out of the plant extract as described herein elsewhere. Briefly, 6 mL of extract was centrifuged at 148,000×g for 2.5 hours at 4° C. through a 13 ml sucrose cushion gradient composed of layered 25% and 70% sucrose in phosphate-buffered saline (PBS). VLPs, which have a density between the density 25% and 70% sucrose, was extracted out of the cushion and dialyzed against PBS for further purification and to remove residual sucrose. The use of a sucrose cushion allows for more gentle purification of the VLPs and can increase the yield of the purification (Peyret et al., 2015). The purified M2e-VLPs were then analyzed via spectrophotometry and frozen at −80° C.

An Eppendorf BioPhotometer™ RS232c was used to determine the concentration of RICs within each elution. Using the Beer-Lambert Law ($A=F*b*c$, where A=absorbance, F=extinction coefficient, b=length of the path of the light in centimeters, and c=concentration), concentration can of the RIC can be determined by rearranging the equation to solve for 'c'. The extinction coefficient of human IgG is approximately 1.4 (Eisenberg, 1976), and with the length of the path of the light being 1 cm, $A_{280}$ values can be used to determine concentration.

iv. Western Blotting and Coomassie Staining

For the RIC, samples of crude extract, the extract post-filtration, the extract post-acid precipitation, the wash buffer, and five elutions, and a protein ladder standard (GOLDBIO BLUEstain) were run on two 10% SDS-PAGE gels (Bio-Rad) simultaneously under non-reducing conditions. Fresh SDS was added to the running buffer to maximize resolution. One gel was stained using Coomassie Brilliant Blue dye for an hour, after which the gel was destained overnight using deionized water.

The other gel was used to transfer proteins to a PVDF membrane for 20 minutes at 110V. The membrane was blocked in 5% PBSTM (1× phosphate-buffered saline (PBS) containing tween and 5% skim milk) overnight at 4° C., after which the membrane was rinsed in deionized water three times. Then, the membrane was rotated in a 37° C. incubator in a 1% PBSTM (1×PBS and tween and 1% skim milk) solution containing mouse anti-6D8 antibody (Wilson et al., 2000) at a 1:2000 dilution to detect the 6D8 epitope tag on the RIC (Phoolcharoen et al., 2011). Following this, the membrane was washed again in deionized water and incubated and rotated at 37° C. in a 1% PBSTM solution containing goat anti-mouse antibody conjugated to horseradish peroxidase (Sigma) at a 1:500 dilution for one hour. After this, the membrane was washed in deionized water and exposed to a mixture of developing reagents. The membrane was used to develop photosensitive film at an exposure time of 1 minute in the dark.

Additional SDS-PAGE gels were run under similar conditions and using an anti-M2e antibody, MAb 65 (Kolpe et al., 2018) as the primary antibody for western blotting and mouse-anti-kappa chain antibody as the secondary antibody. MAb 65 was expressed in plants and purified in-house. Both RICs and VLPs were probed for the presence of M2e.

v. Electron Microscopy

Purified samples of the M2e VLP were incubated on 75/300 mesh grids coated with formvar and washed twice with deionized water. The VLPs were then negatively stained with 2% aqueous uranyl acetate and analyzed using transmission electron microscopy (TEM). TEM was performed with a Phillips CM-12 microscope, and images were acquired with a Gatan model 791 CCD camera.

vi. Immunization of Mice

All mice were handled in compliance with ASU IACUC regulations and in accordance with the Animal Welfare Act. Groups of 6 female Balb/c mice, 6-8 weeks old, were immunized subcutaneously with three doses of antigen, each containing an equal mass of 5 µg of M2e presented on either VLPs or a 1:1 ratio of the M2e-RIC and M2e-VLP. Doses were administered in a 1:1 ratio with the alum adjuvant Imject Alum (Thermo Fisher Scientific, Waltham, MA). Doses were administered on day 0, 28, and 56, and serum collection was done as described (Santi et al., 2008) by submandibular bleed on days 0, 28, 56, and 86.

vii. Antibody Quantification

Mouse sera were analyzed via enzyme-linked immunosorbent assay (ELISA). 100 µl of a stock solution of 1 mg/ml synthetic monomeric human consensus M2e peptide (GenScript Biotech Corp., NJ) was diluted into 5.8 ml of 50 mM carbonate-bicarbonate buffer (15 mM $Na_2CO_3$, 35 mM $NaHCO_3$, pH=9.6) (Ebrahimi et al., 2012) to generate a 17 µg/ml solution of M2e peptide in carbonate buffer. 50 µl of this solution was used to coat each well of 96-well plates (850 ng/well) overnight at 4° C. Following this, plates were allowed to warm to room temperature for 20 minutes, after which the plates were rinsed thrice with PBST and blocked with 100 µl of 5% PBSTM per well at room temperature for 15 minutes. Mouse sera were diluted in 1% PBSTM to dilutions ranging from 1:50 to 1:6250 for dose one, 1:8,000 to 1:1,000,000 for dose two, and 1:40,000 to 1:5,000,000 for dose three. After blocking with 5% PBSTM, 50 µl of diluted mouse sera were added to each well and the plate was incubated overnight at 4° C. The following day, the plates were incubated at 37° C. for 20 minutes and then rinsed thrice with PBST. Following this, a mixture of goat anti-mouse IgG2a antibodies, goat anti-mouse IgG1 antibodies, goat anti-mouse kappa chain antibodies, and goat anti-mouse IgG antibodies, all conjugated to HRP (Santa Cruz Biotechnology Inc., TX) in 1% PBSTM was prepared. Each antibody was present in the solution at a 1:5700 dilution. This solution was used to detect the total antibody titers within each sera sample by adding 50 µl of the mixture to each well and subsequently incubating the plates at 37° C. for 1 hour. Furthermore, additional plates used to determine the titers of IgG2a and IgG1 within each sample. Plates were rinsed five times with PBST and incubated for 45 minutes with 50 µl of TMB (3,3',5,5'-Tetramethylbenzidine) being added to each well. After this, the TMB-HRP reaction was stopped through the addition of HCl and the absorbance of the plates were read using a Molecular Devices SpectraMax 340PC Microplate Reader at 450 nm. Endpoint titers were calculated using GraphPad Prism (GraphPad Sofware, Inc.) to calculate the geometric mean of the ELISA results to determine geometric mean titers.

viii. Analysis of Cytokine Production in Mice

Mouse splenocytes were removed and homogenized via mashing in a 70 µm nylon strainer with the plunger of a 3 ml syringe. The strainer and plunger were then washed using 13 ml of RPMI complete (RPMI, 10% heat-inactivated PBS, 1% P/S/G) into a microcentrifuge tube to collect cells. Cells were then centrifuged for 5 mins at 1200 RPM at 4° C., with the supernatant being removed thereafter and the cells being resuspended in 2 ml red cell lysis buffer (ACK) and incubated for 2 minutes at room temperature. The cells were then quenched in 8 ml RPMI complete and centrifuged again for 5 minutes at 1200 RPM at 4° C. The cell pellet was then washed twice with 10 ml RPMI complete and subsequently resuspended in 2 ml RPMI.

Figure 9A:
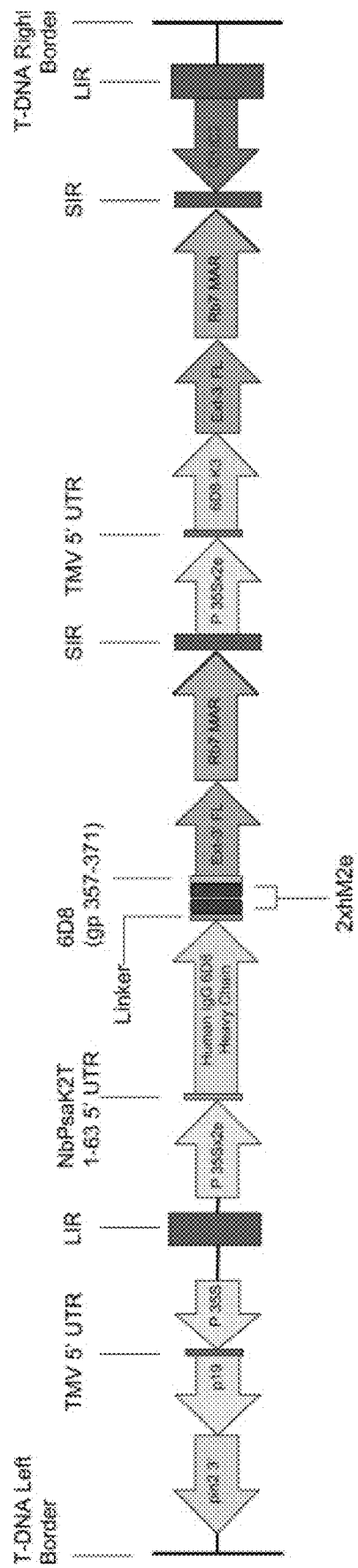
FIGS. 9A-9B depict, in accordance with certain embodiments, the vector encoding the M2e-RIC, pBYR11eMa-h6D8M2e.
Figure 9B:
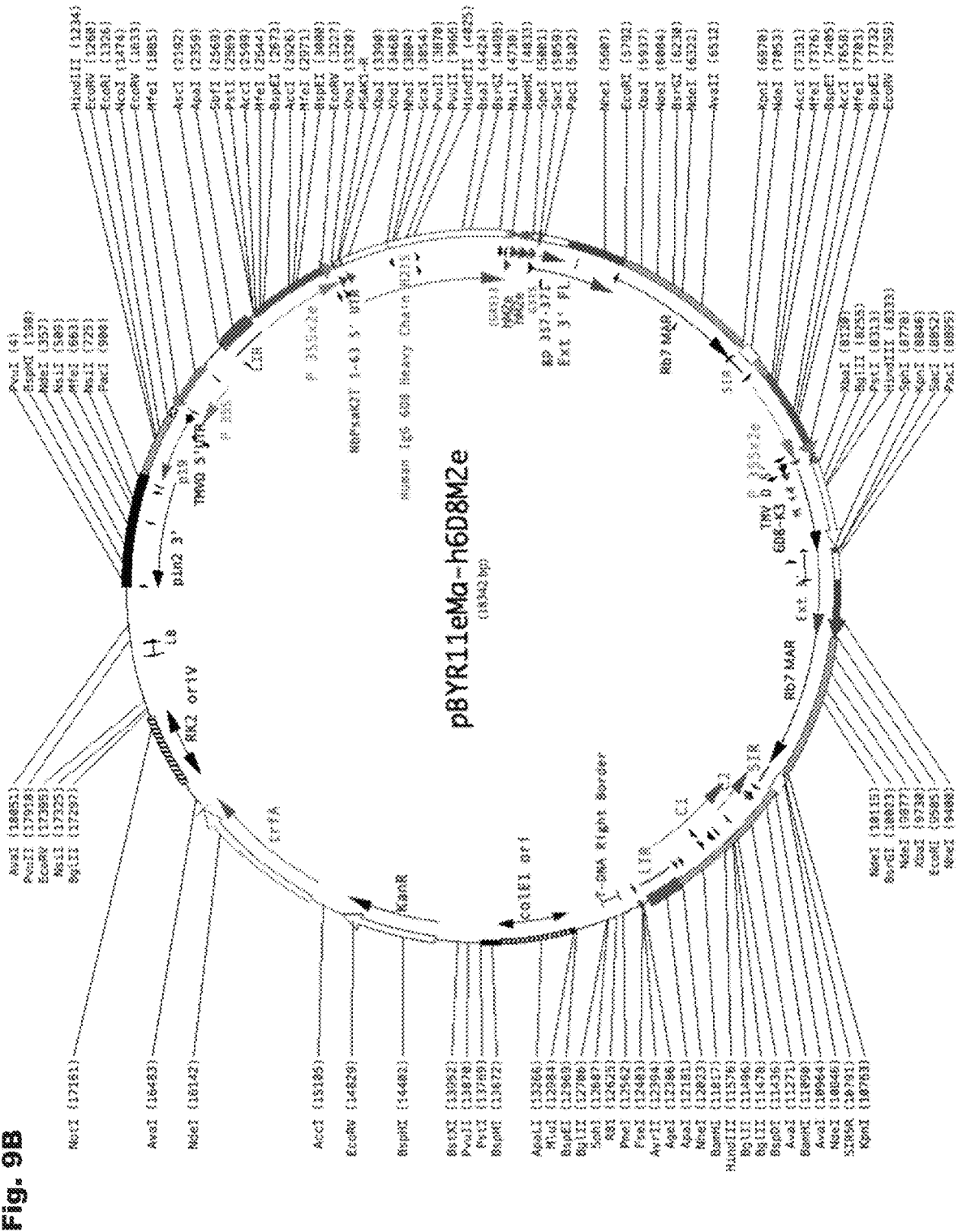

Splenocytes were then plated in 96-well round bottom plates at a concentration of 106 cells per well. The plate was then centrifuged and the splenocytes were resuspended in 180 µl of assay media (RPMI complete, 1.11 ng/ml human IL-2, 5.5 µl/ml GolgiPlug (BD Biosciences-US)). Splenocytes were then exposed to either 20 µl of 10 µg/ml synthetic M2e peptide (GenScript Biotech Corp., NJ), 20 µl of RPMI complete, or 20 µl PMI/ionomycin) and incubated at 37° C. for 5 hours. Following incubation, cells were pelleted at 1300 rpm for 3 minutes, the supernatant was removed, and cells were washed with 1× fluorescence-activated cell sorting (FACS) buffer. Cells were stained with anti-CD8 (1:100) and anti-CD4 (1:100) in 100 µl FACS buffer and incubated for 30 minutes at 4° C., after which cells were washed twice with FACS buffer to remove excess unbound stain. The cells were then fixed and permeabilized through resuspension in 100 µl of Fixation/Permeabilization solution (BD Biosciences, USA). Cells were then stained for intracellular cytokines using 50 µl of staining solution; CD4 responses were assayed via staining in a solution containing 1:100 dilutions of anti-IL-4, anti-IL-21, and anti-IFN-γ in Permeabilization/Wash buffer (BD Biosciences, USA). while CD8 responses were assayed via staining with a solution containing 1:100 dilutions of anti-IL-2, anti-TNFα, and anti-IFN-γ in Permeabilization/Wash buffer. Cells were then washed twice with Permeabilization/Wash buffer, resuspended in 200 µl FACS buffer, and analyzed via FACS using an LSR Fortessa (FIG. 9).

b. Construction of Recombinant Influenza Vaccines

Figure 10A:
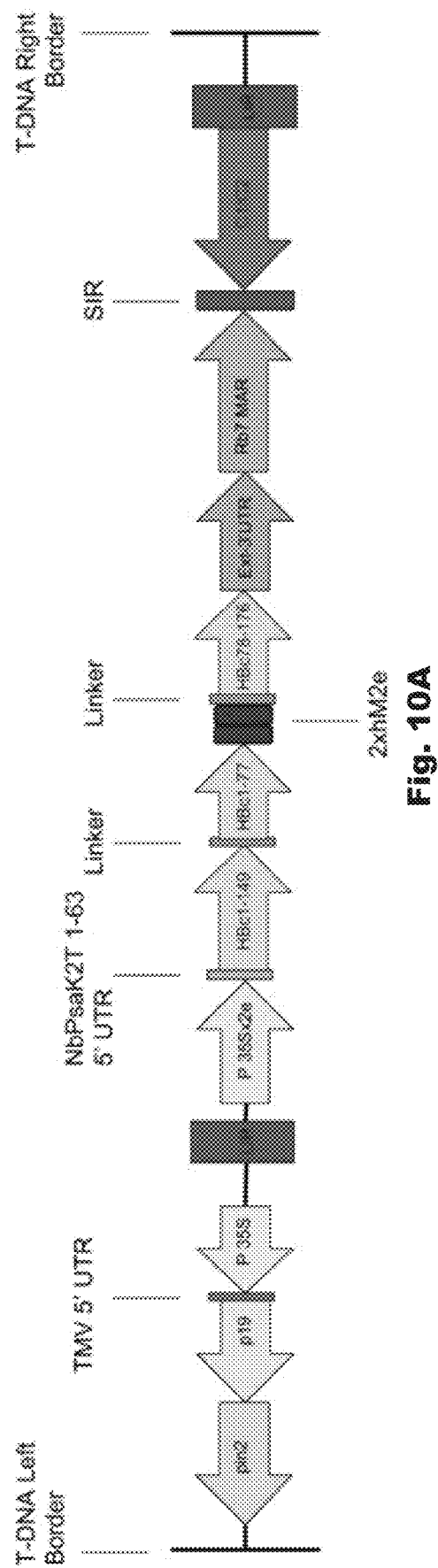
Figure 10B:
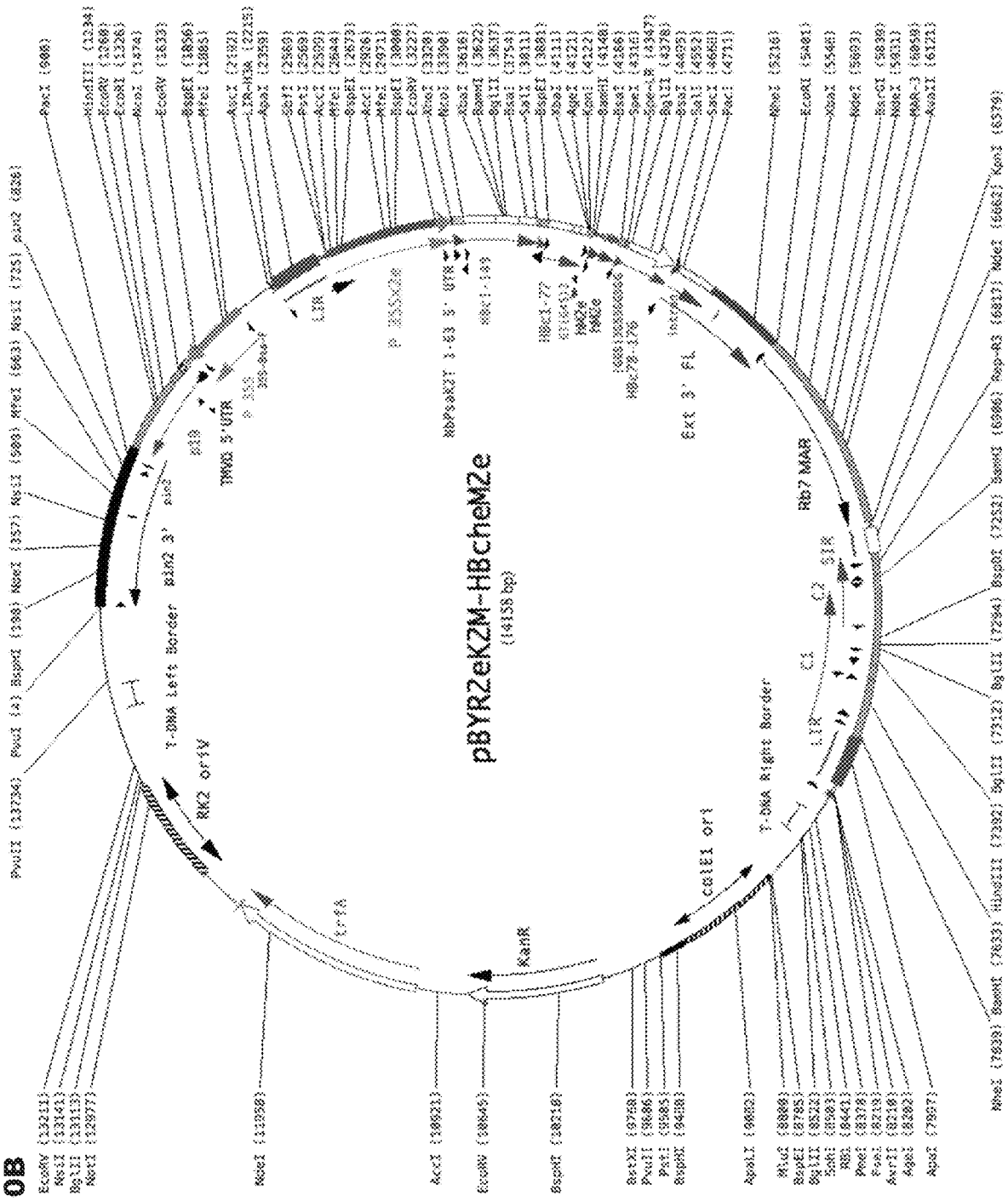

Two recombinant universal influenza A vaccines were developed and expressed using *Agrobacterium tumefaciens*-mediated transfer of geminiviral vectors into glycoengineered *Nicotiana benthamiana* plants (Strasser et al., 2008). The vaccines, using both the recombinant immune complex (RIC) and hepatitis B core antigen (HbcAg) virus-like particles (VLP) as vaccine platforms to boost immunogenicity, presented a consensus sequence of the ectodomain of the matrix 2 protein of human influenza A, M2e (SLLTEVETPIRNEWGCRCNDSSD, SEQ ID NO. 9). The antigen was constructed as a dimer, with a 2×GGS linker linking the two copies of M2e together to minimize steric hindrance and other unwanted interactions between the two copies, codon-optimized for expression in *Nicotiana benthamiana*, and inserted into the C-terminal end of the human IgG 6D8 heavy chain gene encoded in pBYR11eMa-h6D8M2e (FIGS. 9A-9B) and into the MIR of the C-terminal copy of the tandem dimer HBcAg encoded in pBYR2eK2M-HBcheM2e (FIGS. 10A-10B), both geminiviral vector plasmids containing several elements to enhance transcription and protein expression.

c. Production of the M2e-RIC and M2e-VLP in Plants

After the expression and purification of the recombinant vaccines via protein G chromatography for the RIC and sucrose gradient purification and dialysis for the VLP, samples were characterized via SDS-PAGE and subsequent Coomassie Brilliant Blue staining and western blotting (FIGS. 11 and 12). The RIC was probed using anti-6D8 antibody and anti-M2e antibody while the VLP was probed solely with anti-M2e antibody. Samples were compared to a standard protein ladder, with the RIC being further compared to an IgG standard to elucidate the suspected differences between the heavy chains and the light chains of the RIC and the standard. Samples probed with the anti-M2e probe demonstrated a clear signal, indicating that both the RIC and the VLP contained the M2e antigen. Further, RICs probed with the anti-6D8 epitope tag demonstrated the presence of the epitope tag. Signal above the expected 164 kDa could be interpreted as suggesting the presence of complex formation, though additional studies to characterize the structure of the RIC binding to other RICs would be necessary to determine whether these bands are indicative of complex formation of aggregation driven by other, unexpected factors. Regardless, the results of these characterization studies confirmed the presence of the target antigen, M2e, and other characteristics of the vaccines. Furthermore, M2e-VLPs were analyzed using TEM, with the images generated confirming the structure of VLP (FIG. 13).

d. Analysis of Mouse Sera and Splenocytes

Two groups of five BALB/c mice were immunized with either the M2e-VLP alone or a combination of the M2e-RIC and the M2e-VLP at days 0, 28, and 56, with bleeds at 0, 28, 56, and 86. Mouse sera was analyzed via ELISA, with total antibody titers being measured after each bleed, and IgG1, and IgG2a titers being measured at the conclusion of day 63. Total antibody titers were consistently 2-3 times higher at all time points in the M2e-RIC/M2e-VLP combination group, though the ratio of IgG2a to IgG1, was lower in the combination group relative to the group that received the M2e-VLP alone (FIGS. 14A-14C).

Both IgG1 and IgG2a play important roles in viral immunity against influenza; in one study, mice with high expression of IgG1 had lower lung viral titers and high influenza virus neutralization, but lower survival rate when challenged with significantly high doses of influenza virus (Huber et al., 2006). Mice that had both isotypes fared the best, though it was noted that mice that had low IgG1 expression and high IgG2a had the same survival rates as those that had equivalent expression of both IgG1 and IgG2a (Huber et al., 2006). This could be due to IgG2a antibodies' propensity to stimulate complement activation much more effectively than IgG1 in mice (Neuberger & Rajewsky, 1981). The data presented suggest that, if mice were challenged with high doses of influenza, those that received the VLP only would have better outcomes than those receiving both groups.

Figure 15A:
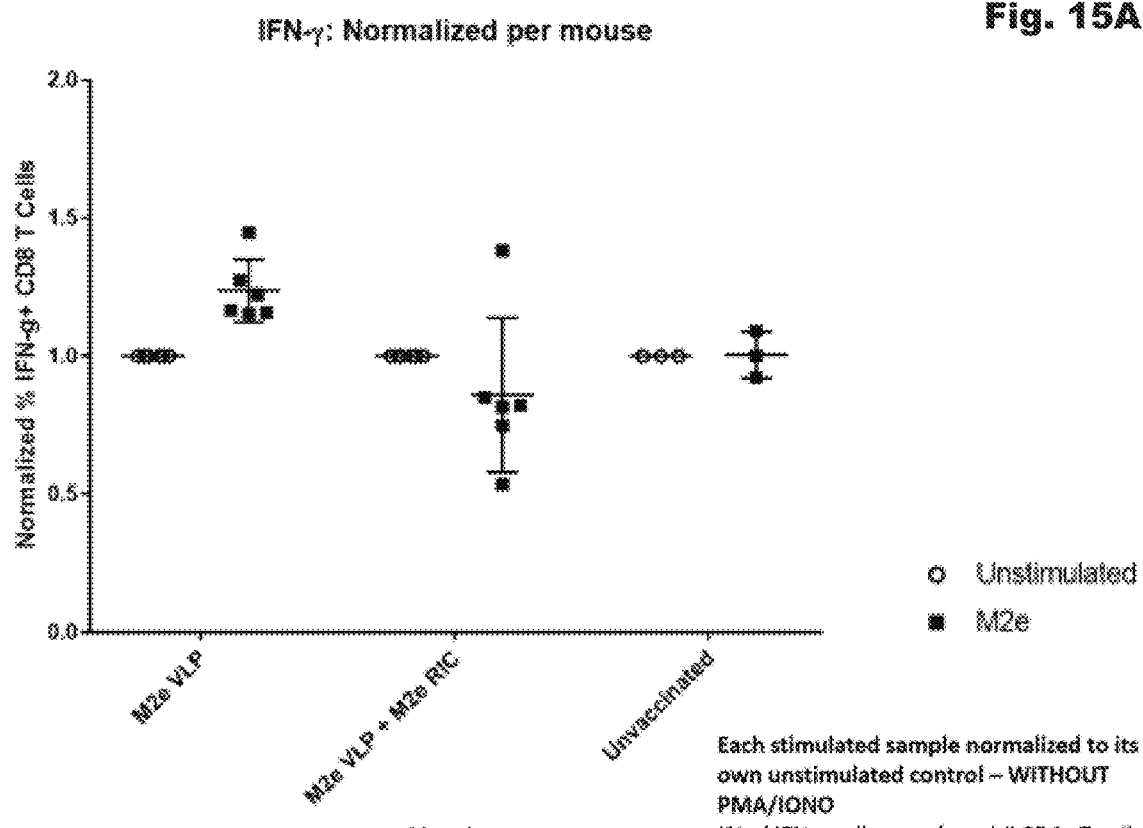
Figure 15B:
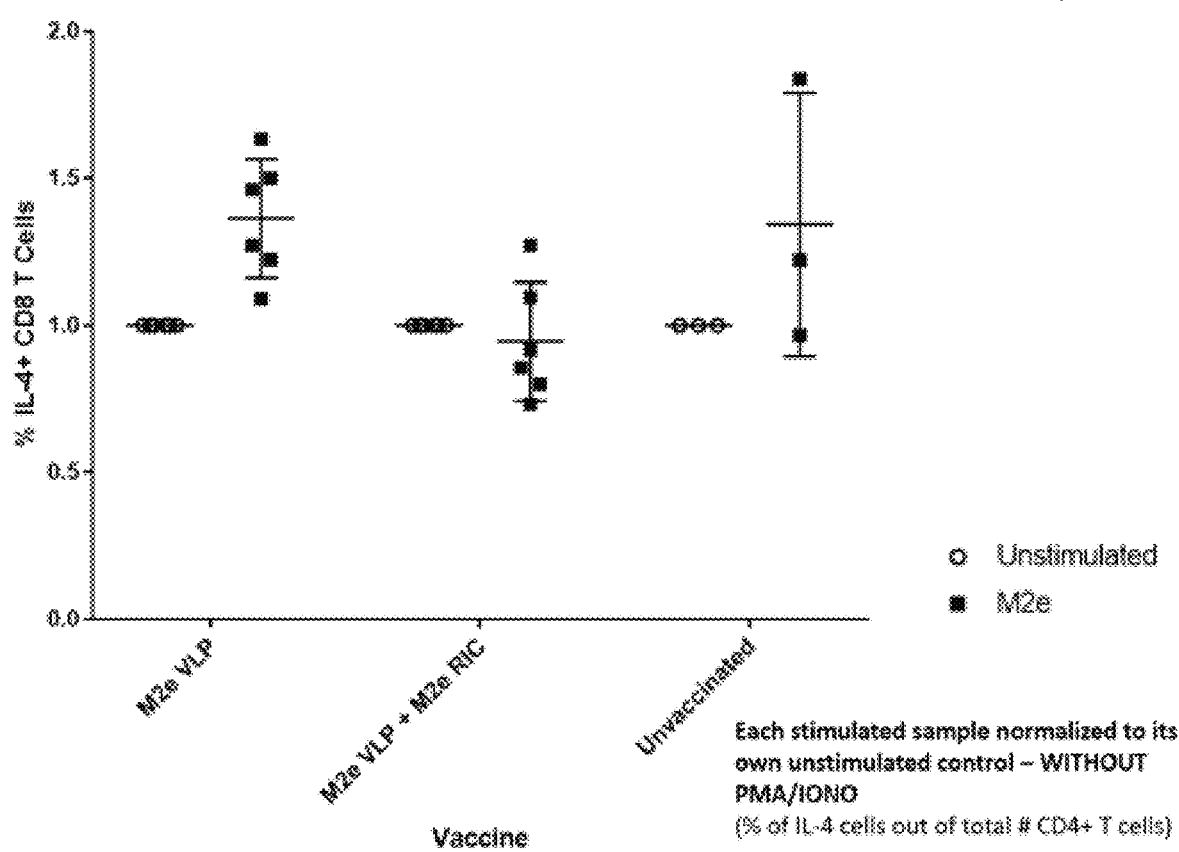
Figure 16:
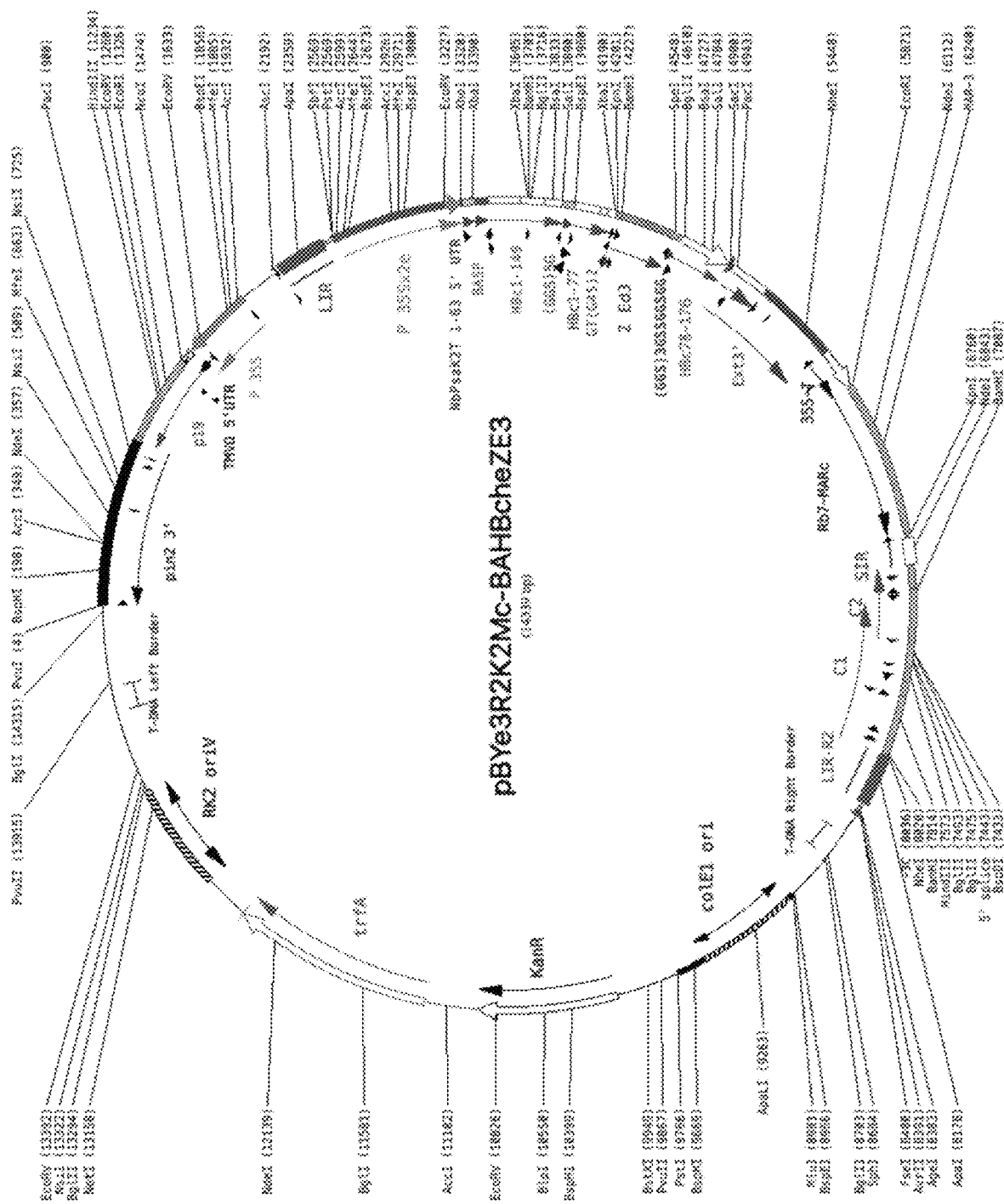
FIG. 16 depicts, in accordance with certain embodiments, a vector map for a plant expression plasmid encoding a zika virus VLP presenting domain III of the zika virus E protein (K591-T696 of Accession No. AMC13911) (ZE3 VLP). The nucleic acid sequence of pBYe3R2K2Mc-BAHBcheZE3 is set forth in SEQ ID NO. 34.
Figure 17:
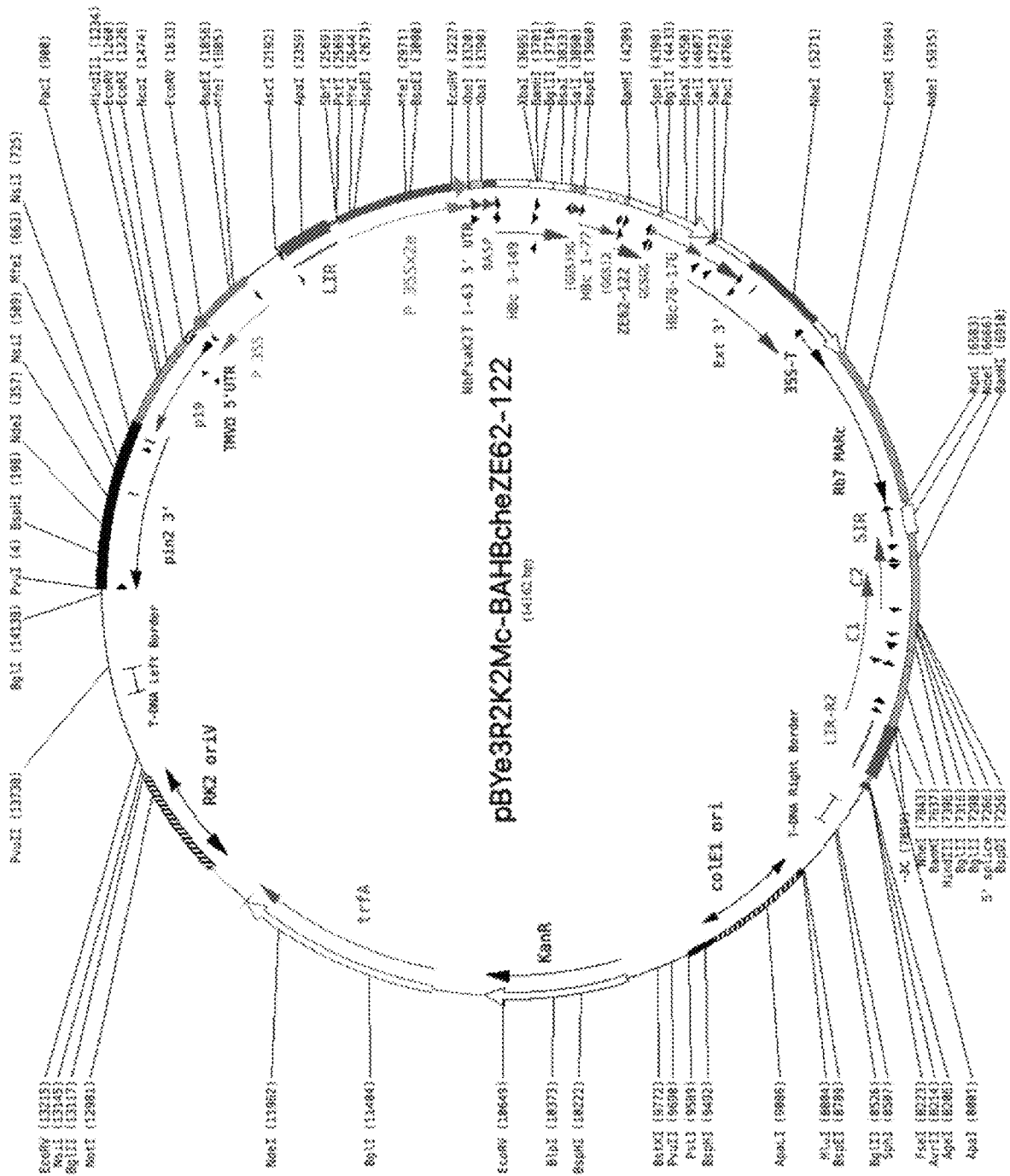
FIG. 17 depicts, in accordance with certain embodiments, a vector map for a plant expression plasmid encoding a zika virus VLP presenting the zika virus fusion loop antigen (E352-S412 of Accession No. AMC13911). The nucleic acid sequence of pBYe3R2K2Mc-BAHBcheZE62-122 is set forth in SEQ ID NO. 35.
Figure 18:
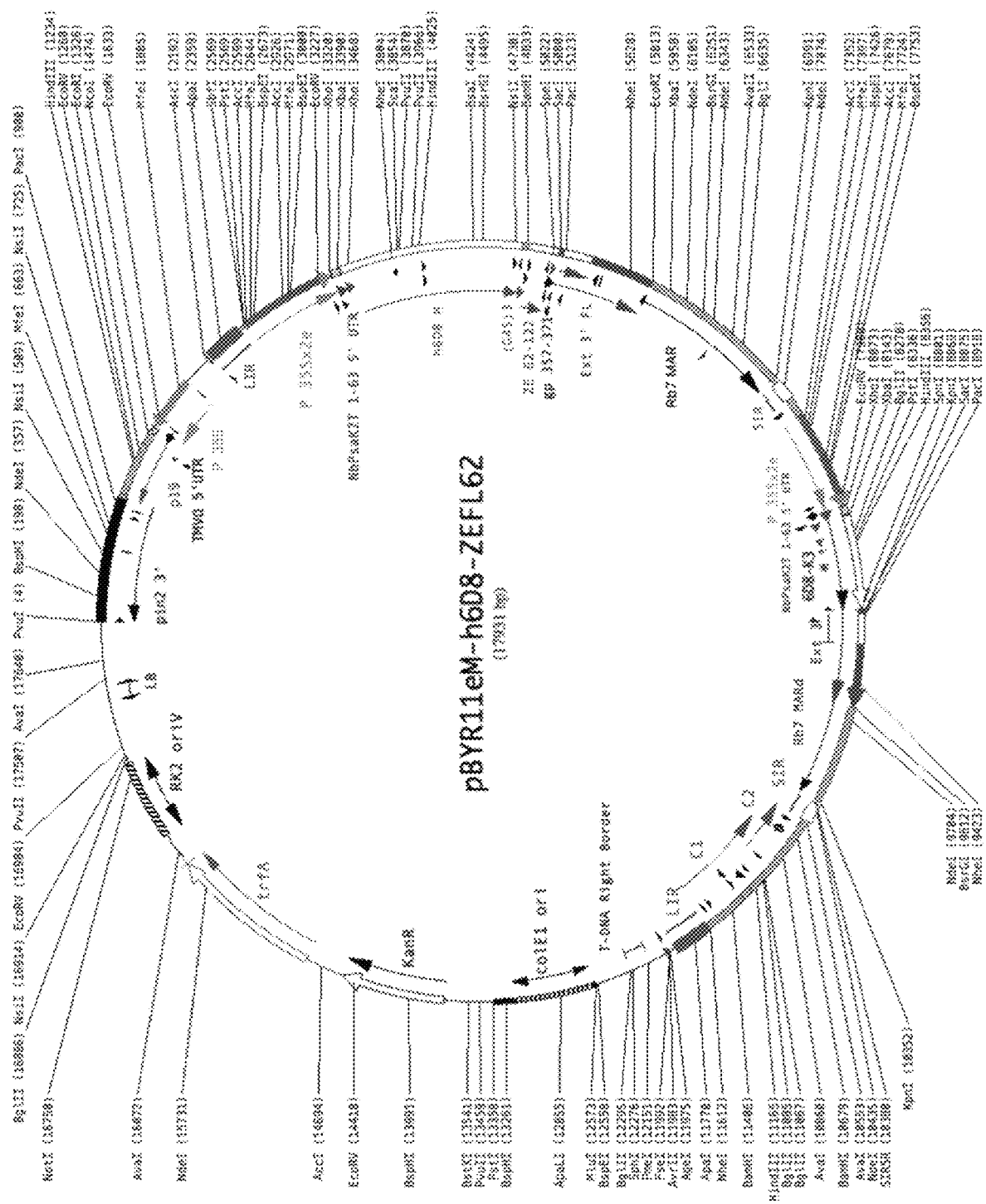
FIG. 18 depicts, in accordance with certain embodiments, a vector map for a plant expression plasmid encoding a zika virus RIC where the zika virus fusion loop antigen (E352-S412 of Accession No. AMC13911) is linked to the h6D8 antibody at the N-terminus of its heavy chain. The nucleic acid sequence of pBYRIleM-h6D8-ZEFL62 is set forth in SEQ ID NO. 36.
Figure 19:
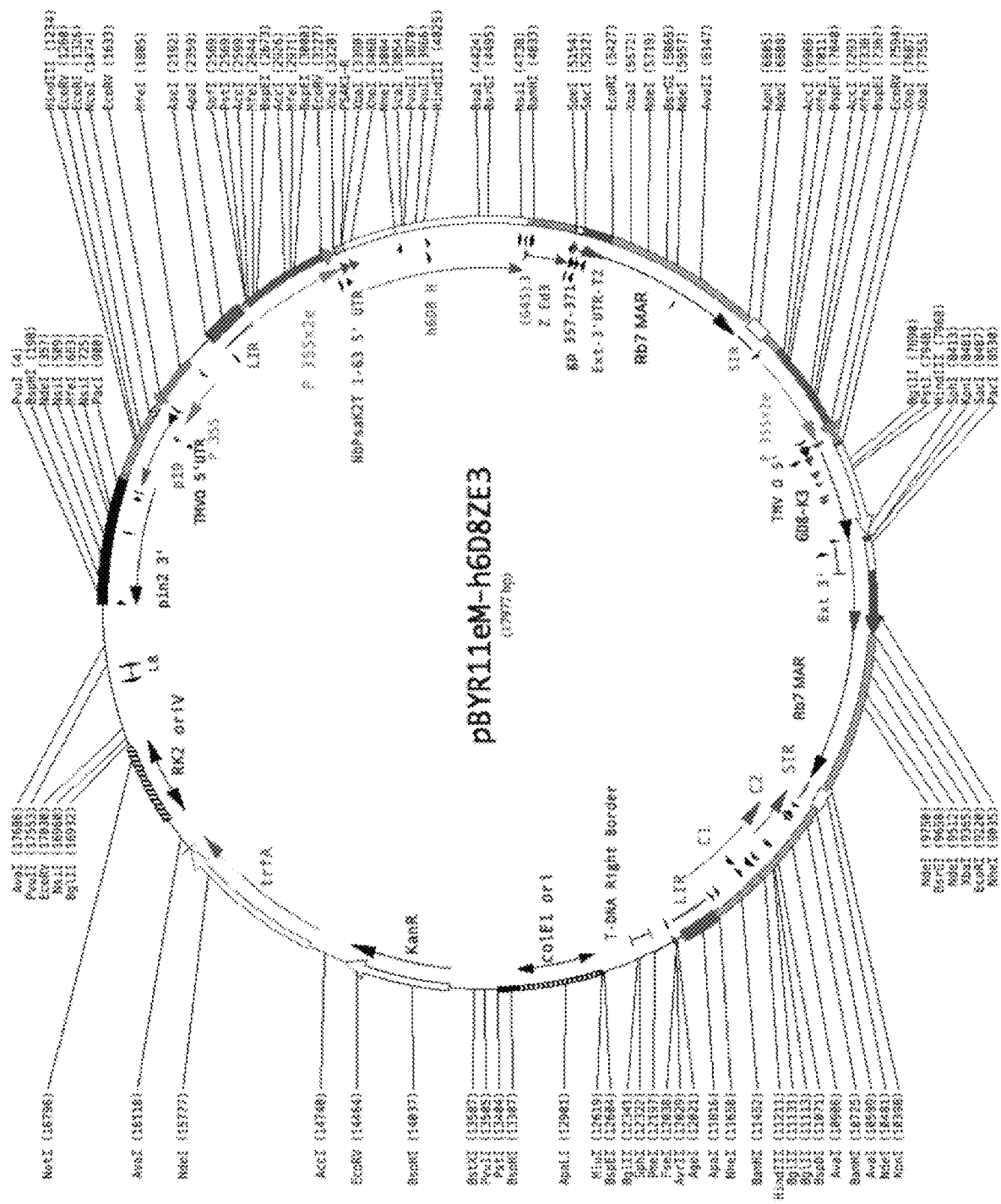
FIG. 19 depicts, in accordance with certain embodiments, a vector map for a plant expression plasmid encoding a zika virus RIC where the domain III of the zika virus E protein (K591-T696 of Accession No. AMC13911) is linked to the h6D8 antibody at the N-terminus of its heavy chain. The nucleic acid sequence of pBYRIleM-h6D8ZE3 is set forth in SEQ ID NO. 37.
Figure 20:
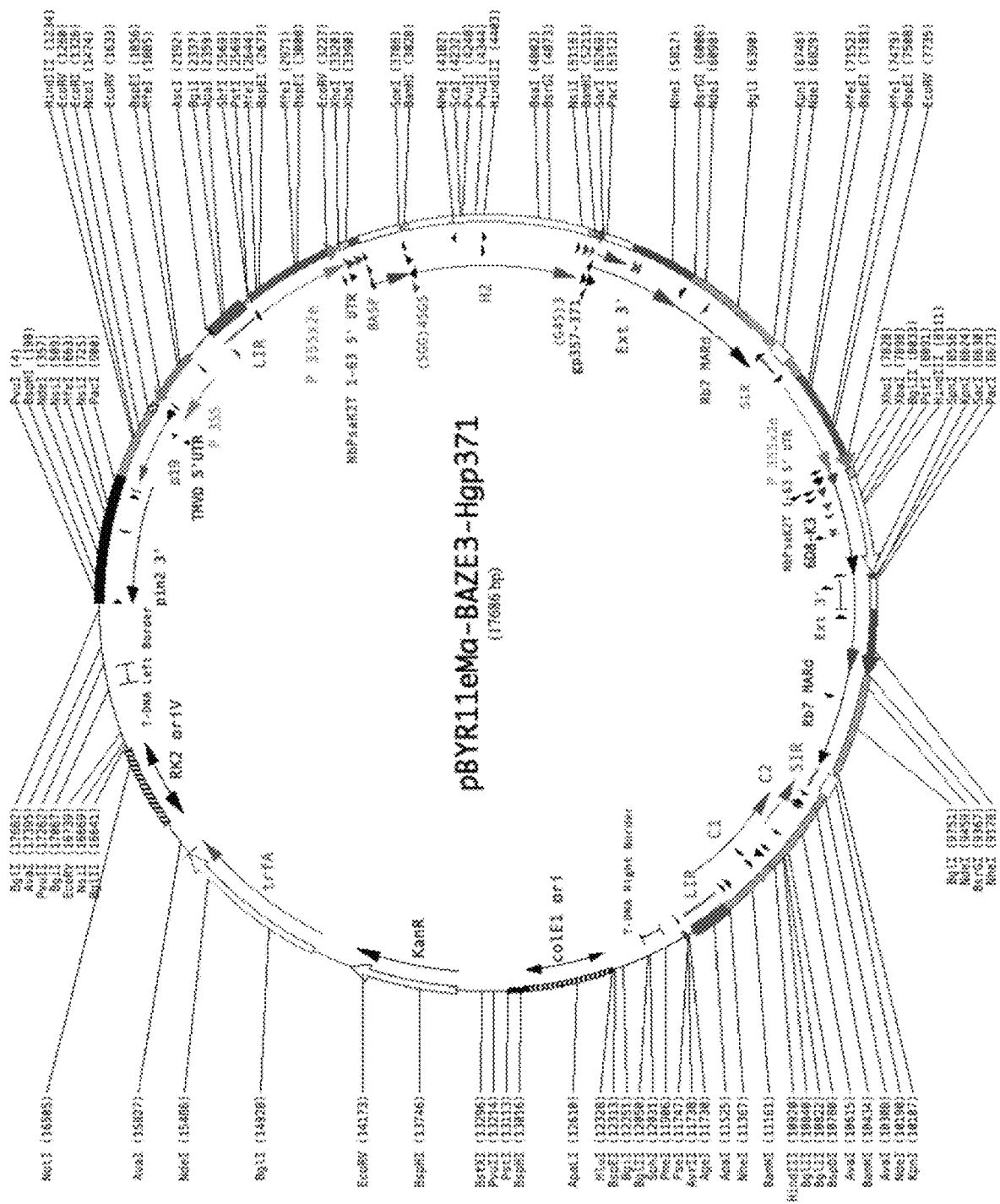
FIG. 20 depicts, in accordance with certain embodiments, a vector map for a plant expression plasmid encoding a zika virus RIC where the C-terminus of domain III of the zika virus E protein (K591-T696 of Accession No. AMC13911) is linked to the N-terminus of the heavy chain of h6D8 antibody. The C-terminus of the heavy chain of the antibody is linked to the 6D8 epitope tag. The nucleic acid sequence of pBYRIleMa-BAZE3-Hgp371 is set forth in SEQ ID NO. 38.
Figure 26:
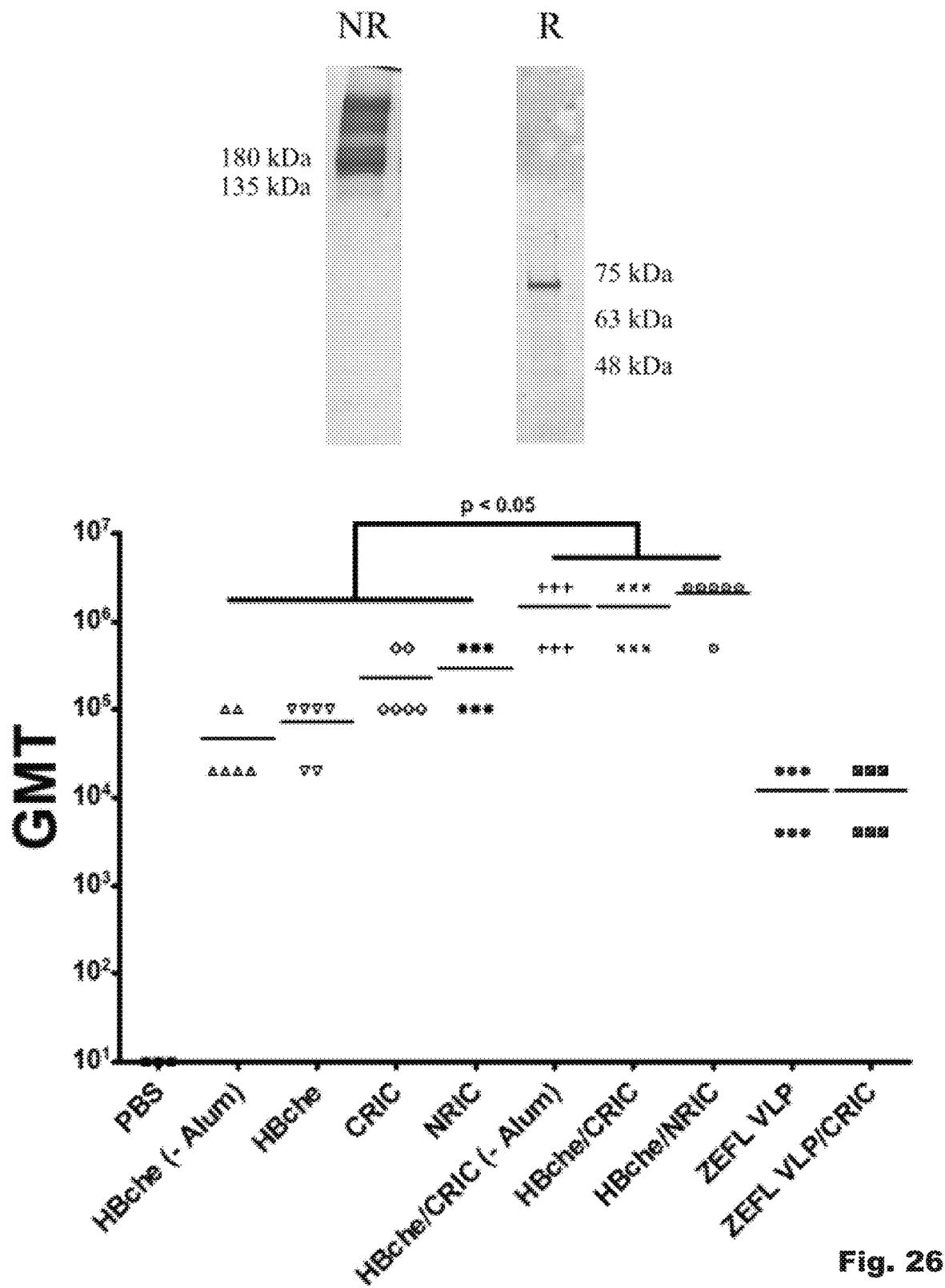
FIG. 26 depicts, in accordance with certain embodiment, IgG titers of mice after the second dose treatment with zika virus antigen. BALB/c mice (6 per group) were immunized subcutaneously with ZE3 N-terminal RIC, ZE3 C-terminal RIC, HBche-ZE3 VLP (abbreviated HBche), ZEFL RIC, and ZEFL HBche-VLP either alone or in various combinations of RIC and VLP mixed 1:1. Two groups, HBche-ZE3 alone and the HBche-ZE3+C-RIC, were not given alum as an adjuvant in order to test the effect of an adjuvant on the antibody titers elicited by the experimental groups. Except for the PBS control group, each dose delivered 4 µg total ZE3. The dose for the ZEFL-containing groups delivered 4 µg of ZEFL. Blood samples, collected after the second dose, were analyzed for ZIKV-specific antibodies by endpoint titer ELISA. The y-axis shows the geometric mean titers (GMT). Combination groups of the ZE3 VLP and RIC, delivered with or with alum, had higher antibody titers (approximately a 14-fold difference) than the HBche-ZE3 VLP delivered with or without adjuvant. Abbreviations: HBche, HBche-ZE3 and—Alum, without alum. Non-parametric Mann-Whitney test was used to evaluate significance of the differences indicated; $p<0.05$.
Figure 27:
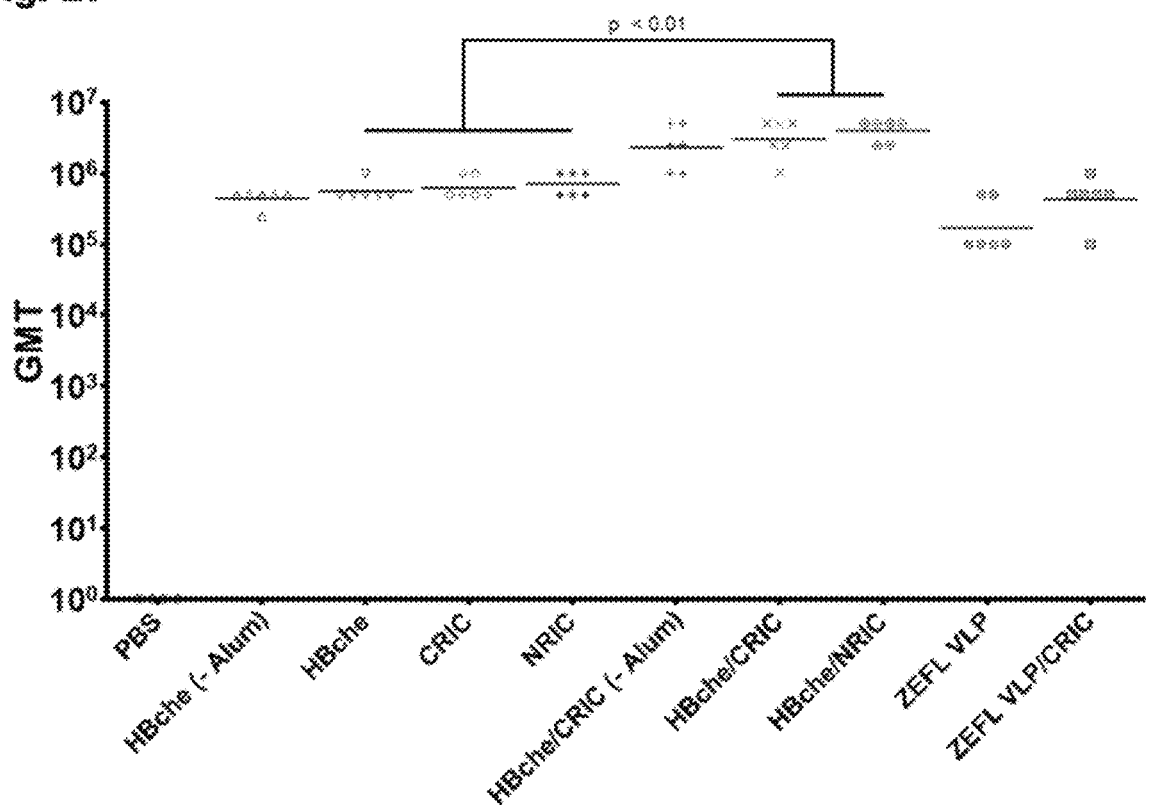
FIG. 27 depicts, in accordance with certain embodiments, IgG titers of mice after the third dose of treatment with zika virus antigen. Total anti-ZE3 IgG titers were measured by ELISA after the third dose. Geometric mean titers (GMT) were calculated for each group and are indicated by the horizontal line for each group, as well as indicated numerically in the table. Individual data points indicate the titer obtained with serum of each mouse. Non-parametric Mann-Whitney test was used to evaluate significance of the differences indicated; $p<0.01$.
Figure 28:
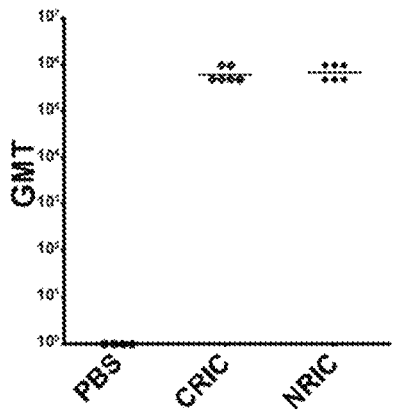
FIG. 28 depicts, in accordance with certain embodiments, compares the total antibody titer (terminal bleed) of mice treated with a recombinant immune complex with the domain III of the zika virus E protein (K591-T696 of Accession No. AMC13911, labeled ZE3 in the figure) is linked to the antibody at the N-terminus (NRIC) or C-terminus (CRIC) of its heavy chain. Six Balb/C mice were given three doses of either ZDIII N-RIC or RIC over an 8-week period. Serum samples were collected and the antibody titers determined by ELISA. The terminal bleed serum samples were collected a little over a month after the third dose. The ELISA results showed that both the N-RIC and C-RIC produced comparable antibody titers.
Figure 29:
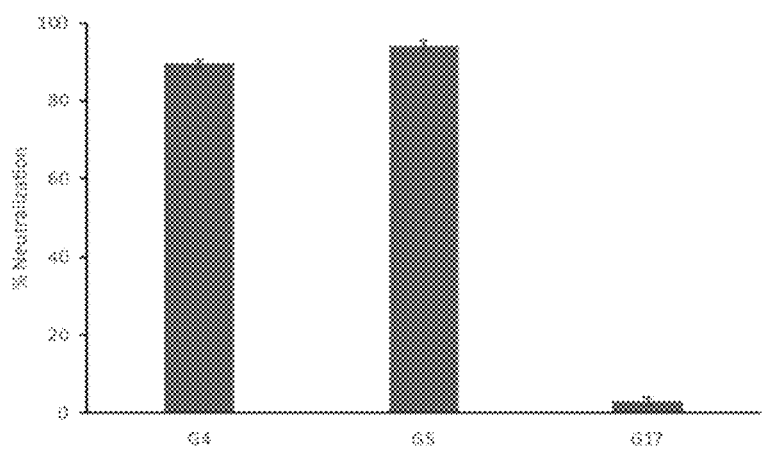
FIG. 29 depicts, in accordance with certain embodiments, a plaque reduction neutralization test conducted with live zika virus. Similar neutralization activity was seen following immunization with either N-RIC or C-RIC.
Figure 30:
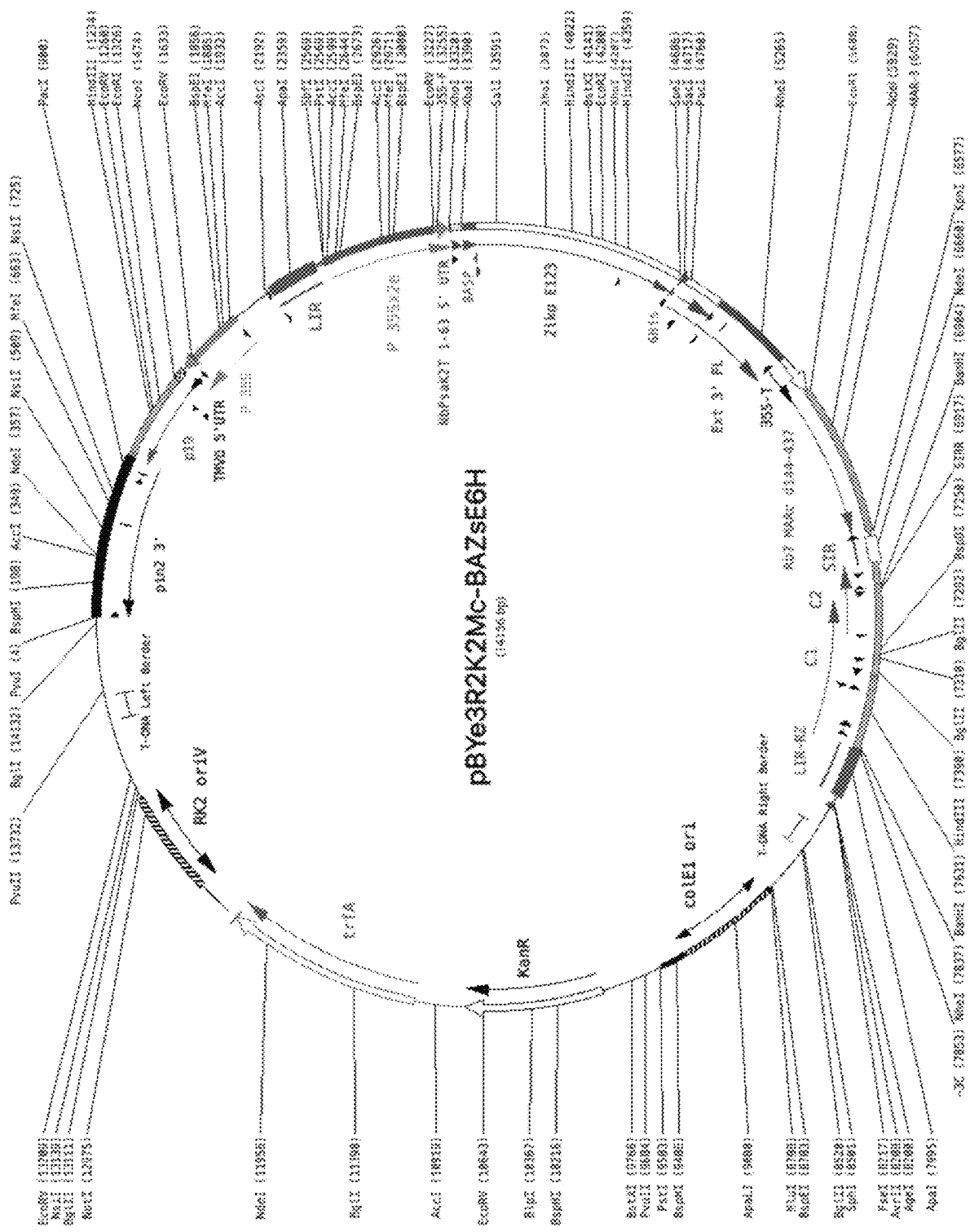
FIG. 30 depicts, in accordance with certain embodiments, a vector map for a plant expression plasmid encoding the zika soluble ectodomain E protein (Liu et al., 2005; Zhou et al., 2012). While consensus sequences are useful to a point, including multiple conserved, immunogenic antigens in the design of universal influenza vaccines would make the vaccine more effective for a longer period of time.

Splenocyte analysis revealed that mice vaccinated with the M2e-VLP had higher levels of IFN-γ and IL-4 positive splenocytes when stimulated with synthetic M2e peptide than mice vaccinated with both vaccines. Interestingly, mice receiving the combination vaccine had, on average, lower proportions of IFN-γ and IL-4 positive splenocytes post-stimulation than both pre-stimulation cells and cells from unvaccinated mice (FIGS. 15A-15B). Th1 cytokines, like IFN-7, induce isotype switching to IgG2a, and Th2 cytokines, like IL-4, a cytokine associated with deleterious effects on viral clearance due to its mediation of down-regulation of antiviral cytokine expression (Sharma et al., 1996), induce isotype switching to IgG1 (Mossman & Coffman, 1989). Thus, the fact that IL-4 production increased to a level higher than that of IFN-γ after stimulation with M2e peptide suggests that the mice receiving the VLP alone may have been undergoing an isotype switch to a Th2-biased phenotype.

Example 3. N-Terminal Recombinant Immune Complex

Although conventional RICs consists of an antibody, linked via its C-terminus, to an antigen that is followed by an epitope tag for the antibody, the versatility of the RIC platform can be expanded by fusing antigens to the N-terminus of the antibody in an RIC. Thus, antigens with inaccessible N-termini can now be easily used in RICs.

a. Vector Creation and Expression of N-RIC

A bean yellow dwarf expression vector containing dual-expression cassettes was used to create the N-RIC (Kim et al., 2015).

One cassette contained the antigenic coding sequence (either Zika soluble envelope protein (ZsE) or domain zika virus domain III protein (ZDIII)) fused via a short linker to the standard RIC antibody heavy chain that was in turn linked to the antibody epitope tag. The second cassette contained the antibody light chain. Following confirmation of the recombinant plasmid by PCR and restriction digests, the plasmid was transformed into *Agrobacterium tumefaciens* strain EHA105 and confirmed by PCR.

Agro cultures were grown overnight in YENB+appropriate antibiotics for selection and used for infiltration of 4- to 6-week-old *N. benthamiana* plants.

b. Confirmation of N-RIC Assembly/Purification

The leaves of transformed *N. benthamiana* were harvested 4-5 days post infiltration, and the extracted protein were used for a Western blot. The Western blot results showed appropriate assembly of both the ZsE N-RIC and ZDIII N-RIC (FIG. 23A). The ZDIII construct had higher yield, so it was chosen for further study. Following a large-scale infiltration of the ZDIII N-RIC construct, Protein G affinity chromatography was used to purify the construct. The 75 grams of leaf material used for the purification yielded over 4 mg of highly purified material.

Accordingly, an antigen (of various sizes) can be fused to the N-terminus of the RIC antibody.

c. Mice Immunization Trials

Immunization with ZDIII as both the N-RIC and C-RIC had highly comparable immune responses in mice as measured by total antibody titers and a plaque reduction neutralization test with live Zika virus. To test whether the ZDIII N-RIC produces a comparable immune response as a standard RIC (C-RIC), a mouse immunization trial was conducted with both the ZDIII N-RIC construct and a previously created ZDIII C-RIC. Six Balb/C mice were given three doses of either ZDIII N-RIC or RIC over an 8-week period. Serum samples were collected and the antibody titers determined by ELISA. The terminal bleed serum samples were collected a little over a month after the third dose. The ELISA results showed that both the N-RIC and C-RIC produced comparable antibody titers. A plaque reduction neutralization test conducted with live ZIKV virus showed that similar neutralization activity was seen following immunization with either RIC configuration.

Example 4. Zika Virus Vaccine Compositions a. Methods i. Vector Construction

The maps of all expression vectors are provided in FIGS. 16-20, and the sequences are provided in SEQ ID Nos. 34-38. Table 3 lists the oligonucleotide used.

TABLE 3

| Oligo name | Sequence (5' to 3') | SEQ ID NO. |
|---|---|---|
| 35S-F | AATCCCACTATCCTTCGC | 21 |
| BASP-G-Bsa-R | GCGGTCTCCACCAGAAGCA AGAGAAGC | 22 |
| Ext3-R | CTTCTTCTTCTTCTTTTCT CATTGTC | 15 |
| H2-Bam-F | GTCGGATCCGATGTTCAGC TTCTTGAGTCTGGAG | 23 |
| HBc176-Sac-R | GCGAGCTCTTATCTACGCC TAGGAGATGGGGA | 24 |
| HBc-Bsa-F | GCGGTCTCGTGGTATGGAC ATTGACCCTTACA | 25 |
| LIR-H3A | AAGCTTGTTGTTGTGACTC CGAG | 26 |
| Spe-L-Bam-F | CTAGTGGTGGATCAGGAGG TTCTGGTGGTTCTGGAGGT TCAG | 27 |
| Spe-L-Bam-R | GATCCTGAACCTCCAGAAC CACCAGAACCTCCTGATCC ACCA | 28 |
| ZE3-Bam-F | GCGGGATCCAAGGGCGTGT CATACTCC | 29 |
| ZE3-Bsa-F | GGGGTCTCGTGGTAAGGGC GTGTCATACTC | 30 |
| ZE3-Spe-R | CCGACTAGTGCTACCACTC CTGTG | 31 |

TABLE 3-continued

| Oligo name | Sequence (5' to 3') | SEQ ID NO. |
|---|---|---|
| ZEE62-Bam-F | GAGGGATCCGAGGCTTCAA TTTCAGACATG | 32 |
| ZES122-Spe-R | GGGACTAGTGGAGCAAGCG AATTTAGC | 33 |

1. pBYRIleM-h6D8ZE3 (ZE3 C-Terminal RIC)

A recombinant immune complex consisting of the humanized 6D8 mAb (h6D8) linked via the heavy chain C-terminus to the ZE3 antigen which is in turn linked to the 6D8 epitope tag. This construct is very similar to pBYR11eMa-h6D8-L2.

The coding DNA sequence of ZIKV E protein (GenBank Accession No. AMC13911) was synthesized with optimized *N. benthamiana* codons (Integrated DNA Technologies, Iowa, USA). DNA encoding E protein domain III (ZE3, amino acids K591-T696) was PCR end-tailored to contain a BamHI site at 5' and SpeI site at 3' with primers ZE3-Bam-F and ZE3-Spe-R (Table 3), digested with BamHI and SpeI, and ligated with pBYR11eMa-h6D8-L2 digested BamHI/SpeI to yield pBYR11 eM-h6D8ZE3.

2. pBYR11eMa-BAZE3-Hgp371 (ZE3 N-Terminal RIC)

A recombinant immune complex consisting of the humanized h6D8 Ebola mAb fused via the heavy chain N-terminus to the C-terminus of the ZE3 antigen. The C-terminus of the antibody is linked to the 6D8 epitope tag.

The construct was assembled by ligation of six DNA fragments:

pBYR11 eMa-h6D8-L2 was digested SbfI-XhoI for the vector fragment.

A DNA sequence encoding the promoter, 5'UTR and barley alpha amylase signal peptide (BASP) was amplified from template pBYR2eK2M-6HplcCnetB (Hunter et al., 2019) with primers LIR-H3A and BASP-G-Bsa-R and then digested with SbfJ and BsaI.

The ZE3 coding sequence was PCR end-tailored using primers ZE3-Bsa-F and ZE3-Spe-R, and the product was digested with BsaI and SpeI.

pLIT-L-BamH2 was digested SpeI and BsaI to obtain the 1016 bp fragment containing a linker and 5' end of the heavy chain sequence. pLIT-L-BamH2 was made thus: The template pBYR11eMa-h6D8-L2 was amplified by PCR with the primers H2-Bam-F and Ext3-R, digested with BamHI and SacI, and ligated with pLITMUS28 (New England Biolabs) digested likewise. A DNA segment encoding the linker "$(SGG)_4SGS$" (SEQ ID NO. 42) was produced by annealing the oligonucleotides Spe-L-Bam-F and Spe-L-Bam-R, which was ligated with pLIT-BamH2 digested with SpeI and BamHI to make pLIT-L-BamH2.

pKS-HH-gp371 (Kim et al., 2015) containing a DNA sequence encoding the epitope-tagged h6D8 heavy chain was digested with BsaI and SacI to obtain the 467 bp fragment.

pBYR11eMa-h6D8-L2 was digested SacI and XhoI to obtain the 2559 bp fragment containing the Ext 3' region, Rb7 MAR, SIR, and 35S promoter.

3. pBYe3R2K2Mc-BAHBcheZE3 (HBche-ZE3 VLP)

A virus-like particle formed by using the Hepatitis B virus core (HBc) with the ZE3 antigen inserted via two linkers into the second of two tandemly-linked HBc copies.

The final construct was assembled by ligation of five fragments:

pBY-R2-GFP (Diamos & Mason, 2018b) was digested XhoI-ClaI to obtain the vector fragment, which contains a single nt mutation at position −3 from the C1 start codon.

The barley alpha amylase signal peptide (BASP) was fused to the N-terminus of the HBc coding sequence, by construction of pLIT-BAHBc. A DNA sequence encoding the 5' UTR and BASP was amplified from template pBYR2eK2M-6HplcCnetB (Hunter et al., 2019) with primers 35S-F and BASP-G-Bsa-R, and the product digested with XhoI and BsaI to obtain the 146 bp fragment. The HBc coding sequence was amplified by PCR from template pBYR2eK2M-HBche using primers HBc-Bsa-F and HBc176-Sac-R, and the product digested with BsaI and SacI. The two digested PCR products were ligated with pLITMUS28 (New England Biolabs) digested XhoI-SacI to make pLIT-BAHBc, which was digested XhoI-SalI to obtain the 570 bp fragment.

pBYR2eK2M-HBcheL2ic was digested SalI-KpnI to obtain the 311 bp fragment encoding the C-terminal part of the first HBc monomer, the segment linking HBc monomers 1 and 2, and the N-terminal part of the second HBc monomer.

A subclone was made from pBYR2eK2M-HBcheL2ic, named pUC-HBc176iL2c, containing DNA encoding a linker, the L2 antigen, a second linker, and HBc amino acids 78-176. The ZE3 BamHI-SpeI fragment (321 bp) was inserted into the BamHI-SpeI sites of pUC-HBc176iL2c to make pUC-HBc176iZE3, which was digested KpnI-SacI to obtain the 699 bp fragment) encoding an N-terminal linker, ZE3, a C-terminal linker, and HBc amino acids 78-176.

pBYR2e3K2Mc-GFP (Diamos & Mason, 2018a) was digested SacI-ClaI to obtain a 2533 bp segment containing the Ext 3', 35S 3', MARc, SIR, and the C2 coding DNA.

4. pBYRIIeM-h6D8-ZEFL62 (ZEFL RIC)

A recombinant immune complex consisting of the h6D8 mAb linked via its heavy chain C-terminus to the Zika virus fusion loop antigen (Zika E E352-S412), with a C-terminal 6D8 epitope tag.

A DNA segment encoding Zika E E352-S412 was amplified by PCR of the E protein plant-optimized gene using primers ZEE62-Bam-F and ZES122-Spe-R, and the product digested with BamHI and SpeI. The resulting 189 bp fragment was inserted to replace the ZE3 sequence in pBY-RIIeM-h6D8ZE3 at BamHI and SpeI, to produce pBY-RIIeM-h6D8-ZEFL62.

5. pBYe3R2K2Mc-BAHBcheZE62-122 (HBche-ZEFL VLP)

Similar to the HBche-ZE3 VLP with the Zika virus fusion loop antigen replacing the ZE3 antigen.

The construct was assembled by ligation of fragments:
pBYe3R2K2Mc-BAHBcheZE3 was digested XhoI-SpeI for the vector fragment.
pBYe3R2K2Mc-BAHBcheZE3 was digested XhoI-SalI to obtain the 570 bp fragment.
pBYe3R2K2Mc-BAHBcheZE3 was digested SalI-BamHI to obtain the 337 bp fragment.
pBYR11eM-h6D8-ZEFL62 was digested BamHI-SpeI to obtain the 189 bp fragment encoding Zika E E352-S412.

ii. Agroinfiltration of *Nicotiana benthamiana* Leaves

BeYDV plant expression vectors for each construct were introduced into *Agrobacterium tumefaciens* EHA105 via electroporation. The resulting strains were verified by restriction digestion or PCR, grown overnight at 30 C, and used to infiltrate leaves of 5- to 6-week-old *N. benthamiana* maintained at 23-25° C. For the RICs, a vector expressing both the ZE3-fused 6D8 heavy chain and the light chain was agroinfiltrated into *N. benthamiana* leaves. The vector was similar to that previously described in (Kim et al., 2015) with the ZIKV Domain III as the antigen instead of the DENV antigen. Transgenic *N. benthamiana* plants that have been silenced for xylosyltransferase and fucosyltransferase enzymes were used since these plants produce a highly homogenous, human-like glycosylation pattern that can improve in vivo Fc receptor binding (Castilho and Steinkellner, 2012).

Briefly, the bacteria were pelleted by centrifugation for 8 minutes at 5,000 g and then resuspended in infiltration buffer (10 mM 2-(N-morpholino)ethanesulfonic acid (MES), pH 5.5 and 10 mM MgSO4) to $OD_{600}$=0.2, unless otherwise described. The resulting bacterial suspensions were injected by using a syringe without needle into leaves through a small puncture (Huang et al. 2004). Plant tissue was harvested after 5 days post infiltration (DPI), or as stated for each experiment.

iii. C-RIC Purification 4-5 days post infiltration, the leaves were harvested and extracted in ice-cold, 1:2 w/v buffer at pH 7.4 (100 mM Tris-HCl, 50 mM NaCl, 10 mM EDTA, 0.1% Triton, 10 mg/mL sodium ascorbate, and 0.3 mg/mL PMSF). The remainder of the protein G column chromatography purification protocol was conducted as described.

iv. N-RIC Purification

The infiltration, extraction, and protein G purification for the N-terminal ZE3 RIC was conducted according to the same protocol as described for the C-RIC. The only change was that the extraction buffer used for the N-RIC purification was at pH 9.5 instead of pH 8.

v. ZEFL RIC

The infiltrated leaf material was extracted in ice-cold, 1:2 w/v buffer at pH 9.5 (100 mM Tris-HCl, 50 mM NaCl, 10 mM EDTA, 7M urea, 10 mg/mL sodium ascorbate, and 0.3 mg/mL PMSF). The rest of the protocol was conducted as written in the C-RIC purification. The only change was that the extract was diluted 1:1 in cold, pH 9.5 extraction buffer before loading the extract onto the column for protein G purification. This was done in order to lower the urea concentration so that the ZEFL RIC could bind to the protein G resin. This buffer was the same one used earlier for the extraction process. In addition, at this step, 1M phosphoric acid was added to set the pH of the extract to pH 7.5 in order to allow for optimal binding to the resin.

vi. SDS-PAGE and Western Blot

Samples from the purified RIC elutions were mixed with SDS sample buffer (50 mM Tris-HCl, pH 6.8, 2% SDS, 10% glycerol, 0.02% bromophenol blue) and separated on 4-15% polyacrylamide gels (Bio-Rad). For reducing conditions, 300 mM DTT was added, and the samples were boiled for 10 minutes prior to loading. Polyacrylamide gels were either transferred to a PVDF membrane or stained with Coomassie stain (Bio-Rad) following the manufacturer's instructions. For ZE3 detection, the protein transferred membranes were blocked with 5% dry milk in PBST (PBS with 0.05% tween-20) overnight at 4° C., washed with PBST (3 washes, 5 minutes each), and probed with appropriate antibodies.

The C-RIC samples were detected with goat anti-human IgG (Southern Biotech) antibody that was conjugated with horseradish peroxidase (HRP) (Southern Biotech). The N-RIC samples were detected by mouse anti-human IgG (Fc-only) antibody conjugated with HRP (Southern Biotech). Bound antibody was detected with Pierce ECL western Blotting Substrate according to the manufacturer's instructions (ThermoFisher Scientific).

vii. HBche-ZE3 VLP

The vector containing the HBche-ZE3 VLP construct was agroinfiltrated into the leaves of 4-6-week-old *N. benthamiana* plants. At 4-5 DPI, the leaves were harvested, extracted in ice-cold, 1:2 w/v buffer at pH 7.4 (100 mM Tris-HCl, 50 mM NaCl, 10 mM EDTA, 0.1% Triton, 10 mg/mL sodium ascorbate, and 0.3 mg/mL PMSF), and analyzed by sucrose gradient sedimentation.

viii. Electron Microscopy

To obtain the images of the HBche-ZE3 VLP, samples of HBche-ZE3 VLP partially purified by sucrose gradient sedimentation were initially incubated on 75/300 mesh grids coated with formvar. After incubation, the samples were washed twice with deionized water then negatively stained with 2% aqueous uranyl acetate. The transmission electron microscopy was performed with a Phillips CM-12 microscope. The images were acquired with a Gatan model 791 CCD camera.

ix. HBche-ZEFL VLP

Through agroinfiltration, the vector containing the HBche-ZEFL VLP was delivered into the leaves of 4- to 6-week-old *N. benthamiana* plants. At 4-5 DPI, the leaves were harvested, extracted in ice-cold, 1:2 w/v buffer at pH 7.4 (100 mM Tris-HCl, 50 mM NaCl, 10 mM EDTA, 0.1% Triton, 10 mg/mL sodium ascorbate, and 0.3 mg/mL PMSF), and analyzed by sucrose gradient sedimentation. After the sucrose gradient sedimentation, samples of the sucrose fractions were run on a Coomassie-stained gel. Upon reducing conditions, a band at the appropriate size was visible (FIG. 22A).

x. Immunization of Mice and Sample Collection

Female BALB/C mice (6-8 weeks old) were immunized subcutaneously with the following constructs: purified plant-expressed ZE3 N-terminal RIC (N-RIC), ZE3 C-terminal RIC (C-RIC), HBche-ZE3 VLP, ZEFL RIC, and ZEFL HBche-VLP. The antigens were either delivered alone or in various combinations of RIC and VLP mixed at a ratio of 1:1. Most groups were given antigen mixed 1:1 with Imject Alum (Thermo Scientific, Rockford, IL) prior to immunization. However, two groups, HBche-ZE3 alone and the HBche-ZE3+C-RIC, were not given alum as an adjuvant in order to test the effect of alum on the response elicited by the delivered vaccine antigens. All groups contained 6 mice. For the ZE3-containing groups, the total dose of antigen was set to deliver an equivalent 4 μg of ZE3. For the ZEFL-containing groups, the total dose of antigen was 2 μg. Doses were given on days 0, 28, and 56. Serum collection was done as described (Santi et al., 2008) by submandibular bleed on days 0, 28, and 56, and 86. All animals were handled in accordance to the Animal Welfare Act and Arizona State University IACUC.

xi. Antibody Measurements

Mouse antibody titers were measured by ELISA. Zika soluble ectodomain E (ZsE) protein (amino acids 291-693, 6-His tagged) was produced by agro-infiltration delivery of expression vector pBYe3R2K2Mc-BAZsE6H into leaves of *N. benthamiana* and purified by metal affinity chromatography. ZsE was bound to 96-well high-binding polystyrene plates (Corning). After the plates were blocked with 5% nonfat dry milk in PBST (PBS with 0.05% tween-20), the wells were washed with PBST. Then, the diluted mouse sera from the terminal bleed were added, and the plate incubated at 37 C for 1 hour. Mouse antibodies were detected by incubation with polyclonal goat anti-mouse IgG-horseradish peroxidase conjugate (Sigma). The plate was developed with TMB substrate (Pierce) and the absorbance was read at 450 nm. Endpoint titers were taken as the reciprocal of the lowest dilution which produced an OD450 reading twice the background. IgG1 and IgG2a antibodies were measured with goat-anti mouse IgG1 or IgG2a horseradish peroxidase conjugate (Southern Biotech). Statistical analysis and determination of signification between the various vaccine treatment was done by non-parametric Mann-Whitney tests using GraphPad prism software. The results, which are displayed in FIGS. 5 and 6, show the endpoint titers after the second and after the terminal bleed.

b. C-RIC, N-RIC production

After purification by protein G affinity, C—RIC and N-RIC samples were examined by SDS-PAGE and western blot. Staining with Coomassie Brilliant Blue showd the C-RIC sample was highly pure and that the protein displayed expected molecular mass under nonreducing conditions (~178 kDa) and reducing conditions (~65.4 kDa and 25 kDa bands) (FIG. 21A). A western blot, probed for the presence of IgG, also showed bands at the appropriate size (FIG. 21B).

Likewise, a Coomassie-stained gel containing samples of the purified N-RIC material showed appropriately sized bands under both reducing and non-reducing conditions that signified correctly assembled RICs (FIG. 21C). Under reducing conditions, the expected band sizes were ~65.4 kDa and 25 kDa bands. A fully-formed RIC was expected to show a band around 178 kDa. A western blot of the purified samples that was probed for the antibody Fc region also showed bands at the expected size (FIG. 21D).

c. HBche-ZE3 VLP Production

Samples of the sucrose gradient preparations were run on a Coomassie-stained gel. Upon reducing conditions, bands at the appropriate size were visible (FIG. 22A). A western blot with the HBche-ZE3 VLP was probed with a rabbit polyclonal anti-Zika virus envelope protein antibody (GeneTex) and detected by goat anti rabbit plus HRP (SeraCare) (FIG. 22B). To show formation of virus-like particles, the sucrose gradient fractions were further analyzed by electron microscopy (FIG. 24). The sucrose gradient fractions containing the target VLP were combined and dialyzed against 1×PBS for use in the mouse immunization trials.

d. ZEFL-RIC and ZEFL VLP Production

The ZEFL-RIC and ZEFL VLP were purified and examined by SDS-PAGE with Coomassie staining (FIG. 25). Expected molecular masses for nonreduced ZEFL-RIC and reduced ZEFL VLP were observed.

e. Mouse Immunization Study

BALB/c mice (6 per group) were immunized subcutaneously with ZE3 N-terminal RIC (N-RIC), ZE3 C-terminal RIC (C-RIC), HBche-ZE3 VLP (HBche-ZE3), ZEFL RIC, and ZEFL HBche-VLP either alone or in various combinations of RIC and VLP mixed 1:1. After the second dose (FIG. 26), the combination groups of HBche-ZE3+C-RIC delivered either with or without alum adjuvant had roughly a 14-fold increase in anti-ZE3 IgG antibody titers when compared to the groups containing the HBche-ZE3, delivered with or without adjuvant. In addition, there was a 6-fold increase in antibody titers of the VLP/RIC combination groups compared to the groups containing either C-RIC or N-RIC alone. These data show that co-delivery of the RIC and VLP produced substantially increased antibody titers when compared to delivery of either VLP alone or RIC alone. Furthermore, since there was an insignificant difference between the HBche-ZE3 VLP groups and the HBche-ZE3 VLP+C-RIC groups that were delivered with or without adjuvant, the use of alum adjuvant does not seem to affect the synergistic effect seen by the co-delivery of the VLP and RIC. The C-RIC and N-RIC groups had similar titers with no statistically significant difference.

These trends continued with the antibody titers measured after the third dose (FIG. 27, Table 4 lists the mean titer counts for each treatment group). Once again, both the C-RIC and N—RIC groups showed highly similar antibody titers. Delivery of either RIC resulted in mean endpoint antibody titers that were greater than 100,000. However, the co-delivery of either C-RIC or N-RIC with the HBche-ZE3 VLP produced increased antibody titers greater than 1,000,000, a 10-fold increase when compared to the RIC-only groups. This strongly suggests that there is a synergistic effect seen when the HBche-ZE3 is co-delivered with either the C-RIC or N-RIC. The antibody titers of the groups without alum were slightly lower than the corresponding groups that were delivered with alum. However, this difference was not statistically significant.

TABLE 4

Mean titer after three doses.

| Group | Mean titer |
|---|---|
| PBS | 0 |
| HBc | 600,000 |
| HBche-alum | 450,000 |
| HBche | 550,000 |
| CRIC | 700,000 |
| NRIC | 750,000 |
| HBc/CRIC | 3,500,000 |
| HBche/CRIC-alum | 2,800,000 |
| HBche/CRIC | 3,500,000 |
| HBche/NRIC | 4,000,000 |
| zE-Fc: | 2,000,000 |
| FL VLP | 250,000 |
| FL VLP/RIC | 500,000 |

The ZEFL-containing groups performed equally well after dose 2 with no statistical significance seen between the titers elicited by either the ZEFL VLP alone or the ZEFL VLP+ZEFL RIC group. After dose three, a slight but statistically insignificant increase in antibody titers was observed in the combination group.

REFERENCES CITED (NIAID), N.I. of A. and I.D. VRC 705: A Zika Virus DNA Vaccine in Healthy Adults and Adolescents (DNA).

Alam, A., Jiang, L., Kittleson, G. A., Steadman, K. D., Nandi, S., Fuqua, J. L., Palmer, K. E., Tuse, D., and McDonald, K. A. (2018). Technoeconomic Modeling of Plant-Based Griffithsin Manufacturing. Front. Bioeng. Biotechnol. 6, 102.

Ali, S. T., Cowling, B. J., Lau, E. H., Fang, V. J., & Leung, G. M. (2018). Mitigation of Influenza B Epidemic with School Closures, Hong Kong, 2018. Emerging infectious diseases, 24(11), 2071.

Alphs, H. H., Gambhira, R., Karanam, B., Roberts, J. N., Jagu, S., Schiller, J. T., et al. (2008). Protection against heterologous human papillomavirus challenge by a synthetic lipopeptide vaccine containing a broadly cross-neutralizing epitope of L2. Proc. Natl. Acad. Sci. U.S.A 105, 5850-5. doi:10.1073/pnas.0800868105.

Atsmon, J., Kate-Ilovitz, E., Shaikevich, D., Singer, Y., Volokhov, I., Haim, K. Y., & Ben-Yedidia, T. (2012). Safety and immunogenicity of multimeric-001-a novel universal influenza vaccine. Journal of clinical immunology, 32(3), 595-603.

Avalos, A. M., & Ploegh, H. (2014). Early BCR events and antigen capture, processing, and loading on MHC class II on B cells. Frontiers in immunology, 5, 92.

Bajtay, Z., Csomor, E., Sándor, N., and Erdei, A. (2006). Expression and role of Fc- and complement-receptors on human dendritic cells. in Immunology Letters, 46-52. doi:10.1016/j.imlet.2005.11.023.

Barzon, L., and Palù, G. (2017). Current views on Zika virus vaccine development. Expert Opin. Biol. Ther. 17, 1185-1192.

Belmusto-Worn, V. E., Sanchez, J. L., Mccarthy, K., Nichols, R., Bautista, C. T., Magill, A. J., Pastor-Cauna, G., Echevarria, C., Laguna-Torres, V. A., Samame, B. K., et al. (2005). RANDOMIZED, DOUBLE-BLIND, PHASE III, PIVOTAL FIELD TRIAL OF THE COMPARATIVE IMMUNOGENICITY, SAFETY, AND TOLERABILITY OF TWO YELLOW FEVER 17D VACCINES (ARILVAX™ AND YF-VAX) IN HEALTHY INFANTS AND CHILDREN IN PERU.

Bianchi, E., Liang, X., Ingallinella, P., Finotto, M., Chastain, M. A., Fan, J., . . . & Manger, W. (2005). Universal influenza B vaccine based on the maturational cleavage site of the hemagglutinin precursor. Journal of virology, 79(12), 7380-7388.

Blokhina, E. A., Kuprianov, V. V., Stepanova, L. A., Tsybalova, L. M., Kiselev, O. I., Ravin, N. V., & Skryabin, K. G. (2013). A molecular assembly system for presentation of antigens on the surface of HBc virus-like particles. Virology, 435(2), 293-300.

Boigard, H., Alimova, A., Martin, G. R., Katz, A., Gottlieb, P., and Galarza, J. M. (2017). Zika virus-like particle (VLP) based vaccine. PLoS Negl. Trop. Dis. 11, e0005608.

Bresee, J., Fitzner, J., Campbell, H., Cohen, C., Cozza, V., Jara, J., . . . & Lee, V. (2018). Progress and remaining gaps in estimating the global disease burden of influenza. Emerging infectious diseases, 24(7), 1173.

Brown, A. L., Francis, M. J., Hastings, G. Z., Parry, N. R., Barnett, P. V, Rowlands, D. J., et al. (1991). Foreign epitopes in immunodominant regions of hepatitis B core particles are highly immunogenic and conformationally restricted. Vaccine 9, 595-601.

Brown, D. R., Kjaer, S. K., Sigurdsson, K., Iversen, O., Hernandez-Avila, M., Wheeler, C. M., et al. (2009). The Impact of Quadrivalent Human Papillomavirus (HPV; Types 6, 11, 16, and 18) L1 Virus-Like Particle Vaccine on Infection and Disease Due to Oncogenic Nonvaccine HPV Types in Generally HPV-Naive Women Aged 16-26 Years. J. Infect. Dis. 199, 926-935. doi:10.1086/597307.

Burns, A., Van der Mensbrugghe, D., & Timmer, H. (2006). Evaluating the economic consequences of avian influenza. World Bank.

Caini, S., Alonso, W. J., Balmaseda, A., Bruno, A., Bustos, P., Castillo, L., . . . & Kusznierz, G. F. (2017). Characteristics of seasonal influenza A and B in Latin America: Influenza surveillance data from ten countries. PloS one, 12(3), e0174592.

Castilho A, Steinkellner H. Glyco-engineering in plants to produce human-like N-glycan structures. Biotechnol J 2012; 7:1088-98. doi:10.1002/biot.201200032.

Centers for Disease Control and Prevention. (2018, November 02). Summary of the 2017-2018 Influenza Season.

Chackerian, B. (2007). Virus-like particles: flexible platforms for vaccine development. Expert review of vaccines, 6(3), 381-390.

Chargelegue, D., Drake, P. M. W., Obregon, P., Prada, A., Fairweather, N., and Ma, J. K. C. (2005). Highly immunogenic and protective recombinant vaccine candidate expressed in transgenic plants. Infect. Immun. 73, 5915-5922. doi:10.1128/IAI.73.9.5915-5922.2005.

Chen Q, Davis K R. The potential of plants as a system for the development and production of human biologics. F1000Research 2016; 5:912. doi:10.12688/f1000research.8010.1.

Chen, Q., He, J., Phoolcharoen, W., & Mason, H. S. (2011). Geminiviral vectors based on bean yellow dwarf virus for production of vaccine antigens and monoclonal antibodies in plants. Human vaccines, 7(3), 331-338.

Cooper, A., Tal, G., Lider, O., & Shaul, Y. (2005). Cytokine induction by the hepatitis B virus capsid in macrophages is facilitated by membrane heparan sulfate and involves TLR2. The Journal of Immunology, 175(5), 3165-3176.

Coutelier, J. P., van der Logt, J. T., Heessen, F. W., Vink, A., and van Snick, J. (1988). Virally induced modulation of murine IgG antibody subclasses. J Exp Med 168, 2373-2378. doi:10.1084/jem.168.6.2373.

Crow, J. M. (2012). HPV: The global burden. Nature 488, S2-S3. doi:10.1038/488S2a.

Dai, L., Song, J., Lu, X., Deng, Y.-Q., Musyoki, A. M., Cheng, H., Zhang, Y., Yuan, Y., Song, H., Haywood, J., et al. (2016). Structures of the Zika Virus Envelope Protein and Its Complex with a Flavivirus Broadly Protective Antibody. Cell Host Microbe 19, 696-704.

Davies, J. W., & Stanley, J. (1989). Geminivirus genes and vectors. Trends in Genetics, 5, 77-81.

de Jong, J. M. H., Schuurhuis, D. H., Ioan-Facsinay, A., van der Voort, E. I. H., Huizinga, T. W. J., Ossendorp, F., et al. (2006). Murine Fc receptors for IgG are redundant in facilitating presentation of immune complex derived antigen to CD8+ T cells in vivo. Mol. Immunol. 43, 2045-2050. doi:10.1016/j.molimm.2006.01.002.

Diamos A G, Mason H S (2018) Chimeric 3' Flanking Regions Strongly Enhance Gene Expression in Plants. Plant Biotechnol J., 2018 Apr. 10. doi: 10.1111/pbi.12931. [Epub ahead of print] PMID: 29637682.

Diamos A G, Mason H S (2018). Modifying the replication of geminiviral vectors reduces cell death and enhances expression of biopharmaceutical proteins in Nicotiana benthamiana leaves. Front Plant Sci. 9:1974. doi: 10.3389/fpls.2018.01974. eCollection 2018. PMID: 30687368

Diamos, A. G., & Mason, H. S. (2018). High-level expression and enrichment of norovirus virus-like particles in plants using modified geminiviral vectors. Protein expression and purification.

Diamos, A. G., Rosenthal, S. H., & Mason, H. S. (2016). 5' and 3' untranslated regions strongly enhance performance of geminiviral replicons in Nicotiana benthamiana leaves. Frontiers in plant science, 7, 200.

Diamos, A. G., Larios, D., Brown, L., Kilbourne, J., Kim, H. S., Saxena, D., Palmer, K. E., and Mason, H. S. (2019). Vaccine synergy with virus-like particle and immune complex platforms for delivery of human papillomavirus L2 antigen. 37, 137-144.

Doorbar, J., Egawa, N., Griffin, H., Kranjec, C., and Murakami, I. (2015). Human papillomavirus molecular biology and disease association. Rev. Med. Virol. 25, 2-23. doi:10.1002/rmv.1822.

Dreyfus, C., Laursen, N. S., Kwaks, T., Zuijdgeest, D., Khayat, R., Ekiert, D. C., ... & van der Vlugt, R. (2012). Highly conserved protective epitopes on influenza B viruses. Science, 337(6100), 1343-1348.

Durbin, A., and Wilder-Smith, A. (2017). An update on Zika vaccine developments. Expert Rev. Vaccines 16, 781-787.

Ebrahimi, S. M., Dabaghian, M., Tebianian, M., & Jazi, M. H. Z. (2012). In contrast to conventional inactivated influenza vaccines, 4×M2e. HSP70c fusion protein fully protected mice against lethal dose of H1, H3 and H9 influenza A isolates circulating in Iran. Virology, 430(1), 63-72.

Eichelberger, M. C., Morens, D. M., & Taubenberger, J. K. (2018). Neuraminidase as an influenza vaccine antigen: a low hanging fruit, ready for picking to improve vaccine effectiveness. Current opinion in immunology, 53, 38-44.

Eisenberg, R. (1976). The specificity and polyvalency of binding of a monoclonal rheumatoid factor. Immunochemistry, 13(4), 355-359.

Eisfeld, A. J., Neumann, G., & Kawaoka, Y. (2015). At the centre: influenza A virus ribonucleoproteins. Nature Reviews Microbiology, 13(1), 28.

El Bakkouri, K., Descamps, F., De Filette, M., Smet, A., Festjens, E., Birkett, A., ... & Saelens, X. (2011). Universal vaccine based on ectodomain of matrix protein 2 of influenza A: Fc receptors and alveolar macrophages mediate protection. The Journal of Immunology, 186(2), 1022-1031.

Eliasson, D. G., Omokanye, A., Schon, K., Wenzel, U. A., Bernasconi, V., Bemark, M., ... & Fiers, W. (2018). M2e-tetramer-specific memory CD4 T cells are broadly protective against influenza infection. Mucosal immunology, 11(1), 273.

Ellebedy, A. H., Krammer, F., Li, G. M., Miller, M. S., Chiu, C., Wrammert, J., ... & Edupuganti, S. (2014). Induction of broadly cross-reactive antibody responses to the influenza HA stem region following H5N1 vaccination in humans. Proceedings of the National Academy of Sciences, 111(36), 13133-13138.

Favre, B. C. (2018). The Development of a Plant-Expressed M2e-Based Universal Influenza Vaccine (Honors thesis). Retrieved from the Barrett, The Honors College Thesis/Creative Project Collection.

Fiers, W., De Filette, M., Birkett, A., Neirynck, S., & Jou, W. M. (2004). A "universal" human influenza A vaccine. Virus research, 103(1), 173-176.

Fiers, W., De Filette, M., El Bakkouri, K., Schepens, B., Roose, K., Schotsaert, M., ... & Saelens, X. (2009). M2e-based universal influenza A vaccine. Vaccine, 27(45), 6280-6283.

Fischer, R., & Emans, N. (2000). Molecular farming of pharmaceutical proteins. Transgenic research, 9(4-5), 279-299.

Flannery, B., Chung, J. R., Thaker, S. N., Monto, A. S., Martin, E. T., Belongia, E. A., ... & Nowalk, M. P. (2017). Interim estimates of 2016-17 seasonal influenza vaccine effectiveness-United States, February 2017. MMWR. Morbidity and mortality weekly report, 66(6), 167.

Flannery, B., Clippard, J., Zimmerman, R. K., Nowalk, M. P., Jackson, M. L., Jackson, L. A., ... & Gaglani, M. (2015). Early estimates of seasonal influenza vaccine effectiveness-United States, January 2015. MMWR. Morbidity and mortality weekly report, 64(1), 10.

Flannery, B., Thaker, S. N., Clippard, J., Monto, A. S., Ohmit, S. E., Zimmerman, R. K., ... & Belongia, E. A. (2014). Interim estimates of 2013-14 seasonal influenza vaccine effectiveness-United States, February 2014. Morbidity and Mortality Weekly Report, 63(7), 137-142.

Fridman, W. H. (1991). Fc receptors and immunoglobulin binding factors. The FASEB journal, 5(12), 2684-2690.

allie, D. R. (2002). The 5'-leader of tobacco mosaic virus promotes translation through enhanced recruitment of eIF4F. Nucleic acids research, 30(15), 3401-3411.

Gambhira, R., Jagu, S., Karanam, B., Gravitt, P. E., Culp, T. D., Christensen, N. D., et al. (2007). Protection of Rabbits against Challenge with Rabbit Papillomaviruses by Immunization with the N Terminus of Human Papillomavirus Type 16 Minor Capsid Antigen L2. J. Virol. 81, 11585-11592. doi:10.1128/JVI.01577-07.

Gambhira, R., Karanam, B., Jagu, S., Roberts, J. N., Buck, C. B., Bossis, I., et al. (2007). A protective and broadly cross-neutralizing epitope of human papillomavirus L2. J. Virol. 81, 13927-31. doi:10.1128/JVI.00936-07.

Gaukroger, J. M., Chandrachud, L. M., O'Neil, B. W., Grindlay, G. J., Knowles, G., and Campo, M. S. (1996). Vaccination of cattle with bovine papillomavirus type 4 L2 elicits the production of virus-neutralizing antibodies. J. Gen. Virol. 77, 1577-1583. doi:10.1099/0022-1317-77-7-1577.

Gerhard, W., Mozdzanowska, K., Furchner, M., Washko, G., and Maiese, K. (1997). Role of the B-cell response in recovery of mice from primary influenza virus infection. Immunol. Rev. 159, 95-103. doi:10.1111/j.1600-065X.1997.tb01009.x.

Haiyan Zhao, A., Fernandez, E., Dowd, K. A., Pierson, T. C., Diamond, M. S., Fremont, D. H., Zhao, H., Speer, S. D., Platt, D. J., Gorman, M. J., et al. (2016). Structural Basis of Zika Virus-Specific Antibody Protection Accession Numbers 5KVD 5KVE 5KVF 5KVG Article Structural Basis of Zika Virus-Specific Antibody Protection. Cell 166.

Halweg, C., Thompson, W. F., & Spiker, S. (2005). The Rb7 matrix attachment region increases the likelihood and magnitude of transgene expression in tobacco cells: a flow cytometric study. The Plant Cell, 17(2), 418-429.

Hause, B. M., Collin, E. A., Liu, R., Huang, B., Sheng, Z., Lu, W., . . . & Li, F. (2014). Characterization of a novel influenza virus in cattle and swine: proposal for a new genus in the Orthomyxoviridae family. MBio, 5(2), e00031-14.

Hay, A. J., Gregory, V., Douglas, A. R., & Lin, Y. P. (2001). The evolution of human influenza viruses. Philosophical Transactions of the Royal Society of London. Series B, 356(1416), 1861.

Hefferon, K. L. (2014). DNA virus vectors for vaccine production in plants: spotlight on geminiviruses. Vaccines, 2(3), 642-653.

Heinz, F. X., Holzmann, H., Essl, A., and Kundi, M. (2007). Field effectiveness of vaccination against tick-borne encephalitis. Vaccine 25, 7559-7567.

Hiatt, A., Zeitlin, L., and Whaley, K. J. (2014). Plant-Derived Monoclonal Antibodies for Prevention and Treatment of Infectious Disease. Microbiol. Spectr. 2. doi: 10.1128/microbiolspec.AID-0004-2012.

Hioe, C. E., Visciano, M. L., Kumar, R., Liu, J., Mack, E. A., Simon, R. E., et al. (2009). The use of immune complex vaccines to enhance antibody responses against neutralizing epitopes on HIV-1 envelope gp120. Vaccine 28, 352-360. doi:10.1016/j.vaccine.2009.10.040.

Huang, Z., & Mason, H. S. (2004). Conformational analysis of hepatitis B surface antigen fusions in an *Agrobacterium*-mediated transient expression system. Plant Biotechnology Journal, 2(3), 241-249.

Huang, Z., Chen, Q., Hjelm, B., Arntzen, C., and Mason, H. (2009). A DNA replicon system for rapid high-level production of virus-like particles in plants. Biotechnol. Bioeng. 103, 706-714. doi:10.1002/bit.22299.

Huang, Z., Phoolcharoen, W., Lai, H., Piensook, K., Cardineau, G., Zeitlin, L., et al. (2010). High-level rapid production of full-size monoclonal antibodies in plants by a single-vector DNA replicon system. Biotechnol. Bioeng. 106, 9-17. doi:10.1002/bit.22652.

Huber, V. C., McKeon, R. M., Brackin, M. N., Miller, L. A., Keating, R., Brown, S. A., . . . & McCullers, J. A. (2006). Distinct contributions of vaccine-induced immunoglobulin G1 (IgG1) and IgG2a antibodies to protective immunity against influenza. Clin. Vaccine Immunol., 13(9), 981-990.

Ingle, N. B., Virkar, R. G., & Arankalle, V. A. (2017). Inter-Clade Protection Offered by Mw-Adjuvanted Recombinant HA, NP Proteins, and M2e Peptide Combination Vaccine in Mice Correlates with Cellular Immune Response. Frontiers in immunology, 7, 674.

Inglis, S. C., Carroll, A. R., Lamb, R. A., & Mahy, B. W. (1976). Polypeptides specified by the influenza virus genome: I. Evidence for eight distinct gene products specified by fowl plague virus. Virology, 74(2), 489-503.

Iuliano, A. D., Roguski, K. M., Chang, H. H., Muscatello, D. J., Palekar, R., Tempia, S., . . . & Wu, P. (2018). Estimates of global seasonal influenza-associated respiratory mortality: a modelling study. The Lancet, 391(10127), 1285-1300.

Jackson, L., Jackson, M. L., Phillips, C. H., Benoit, J., Belongia, E. A., Cole, D., . . . & Strey, S. K. (2013). Interim adjusted estimates of seasonal influenza vaccine effectiveness-United States, February 2013.

Jackson, M. L., Chung, J. R., Jackson, L. A., Phillips, C. H., Benoit, J., Monto, A. S., . . . & Murthy, K. (2017). Influenza vaccine effectiveness in the United States during the 2015-2016 season. New England Journal of Medicine, 377(6), 534-543.

Jackson, M. L., Phillips, C. H., Benoit, J., Jackson, L. A., Gaglani, M., Murthy, K., . . . & Flannery, B. (2018). Burden of medically attended influenza infection and cases averted by vaccination-United States, 2013/14 through 2015/16 influenza seasons. Vaccine, 36(4), 467-472.

Jefferis, R. (2009). Glycosylation as a strategy to improve antibody-based therapeutics. Nat. Rev. Drug Discov. 8, 226-234. doi:10.1038/nrd2804.

Kanda, Y., Yamada, T., Mori, K., Okazaki, A., Inoue, M., Kitajima-Miyama, K., et al. (2007). Comparison of biological activity among nonfucosylated therapeutic IgG1 antibodies with three different N-linked Fc oligosaccharides: The high-mannose, hybrid, and complex types. Glycobiology 17, 104-118. doi:10.1093/glycob/cw1057.

Kawana, K., Yoshikawa, H., Taketani, Y., Yoshiike, K., and Kanda, T. (1999). Common neutralization epitope in minor capsid protein L2 of human papillomavirus types 16 and 6. J. Virol. 73, 6188-90.

Kim, K. H., Kwon, Y. M., Lee, Y. T., Kim, M. C., Hwang, H., Ko, E. J., . . . & Kang, S. M. (2018). Virus-Like Particles Are a Superior Platform for Presenting M2e Epitopes to Prime Humoral and Cellular Immunity against Influenza Virus. Vaccines, 6(4), 66.

Kim, M. Y., Reljic, R., Kilbourne, J., Ceballos-Olvera, I., Yang, M. S., Reyes-del Valle, J., & Mason, H. S. (2015). Novel vaccination approach for dengue infection based on recombinant immune complex universal platform. Vaccine, 33(15), 1830-1838.

Kines, R. C., Thompson, C. D., Lowy, D. R., Schiller, J. T., and Day, P. M. (2009). The initial steps leading to papillomavirus infection occur on the basement membrane prior to cell surface binding. Proc. Natl. Acad. Sci. 106, 20458-20463. doi:10.1073/pnas.0908502106.

Kirnbauer, R., Booyt, F., Chengt, N., Lowy, D. R., and Schiller, J. T. (1992). Papillomavirus Li major capsid protein self-assembles into virus-like particles that are highly immunogenic. Med. Sci. 89, 12180-12184. doi: 10.1073/pnas.89.24.12180.

Kolpe, A., Schepens, B., Ye, L., Staeheli, P., & Saelens, X. (2018). Passively transferred M2e-specific monoclonal antibody reduces influenza A virus transmission in mice. Antiviral research, 158, 244-254.

Kondo, K., Ishii, Y., Ochi, H., Matsumoto, T., Yoshikawa, H., and Kanda, T. (2007). Neutralization of HPV16, 18, 31, and 58 pseudovirions with antisera induced by immunizing rabbits with synthetic peptides representing segments of the HPV16 minor capsid protein L2 surface region. Virology 358, 266-272. doi:10.1016/j.virol.2006.08.037.

Kondo, K., Ochi, H., Matsumoto, T., Yoshikawa, H., and Kanda, T. (2008). Modification of human papillomavirus-like particle vaccine by insertion of the cross-reactive L2-epitopes. J. Med. Virol. 80, 841-846. doi:10.1002/jmv.21124.

Kosik, I., Angeletti, D., Gibbs, J. S., Angel, M., Takeda, K., Kosikova, M., . . . & Yewdell, J. W. (2019). Neuraminidase inhibition contributes to influenza A virus neutralization by anti-hemagglutinin stem antibodies. Journal of Experimental Medicine, 216(2), 304-316.

Krammer, F., & Palese, P. (2019). Universal influenza virus vaccines that target the conserved hemagglutinin stalk and conserved sites in the head domain. The Journal of infectious diseases.

Krieger, G., Kneba, M., Bolz, I., Volling, P., Wessels, J., and Nagel, G. A. (1985). Binding characteristics of three complement dependent assays for the detection of immune complexes in human serum. J. Clin. Lab. Immunol. 18, 129-134.

Krishnavajhala, H. R., Williams, J., & Heidner, H. (2018). An influenza A virus vaccine based on an M2e-modified alphavirus. Archives of virology, 163(2), 483-488.

Lamb, R. A. (1983). The influenza virus RNA segments and their encoded proteins. In Genetics of influenza viruses (pp. 21-69). Springer, Vienna.

Lamb, R. A., Zebedee, S. L., & Richardson, C. D. (1985). Influenza virus M2 protein is an integral membrane protein expressed on the infected-cell surface. Cell, 40(3), 627-633.

Lazarowitz, S. G., & Shepherd, R. J. (1992). Geminiviruses: genome structure and gene function. Critical Reviews in Plant Sciences, 11(4), 327-349.

Lee, S. Y., Kang, J. O., & Chang, J. (2019). Nucleoprotein vaccine induces cross-protective cytotoxic T lymphocytes against both lineages of influenza B virus. Clinical and Experimental Vaccine Research, 8(1), 54-63.

Liu, W., Zou, P., Ding, J., Lu, Y., & Chen, Y. H. (2005). Sequence comparison between the extracellular domain of M2 protein human and avian influenza A virus provides new information for bivalent influenza vaccine design. Microbes and infection, 7(2), 171-177.

Mardanova, E. S., & Ravin, N. V. (2018). Plant-produced Recombinant Influenza A Vaccines Based on the M2e Peptide. Current pharmaceutical design, 24(12), 1317-1324.

Mardanova, E. S., Kotlyarov, R. Y., Kuprianov, V. V., Stepanova, L. A., Tsybalova, L. M., Lomonossoff, G. P., & Ravin, N. V. (2015). High immunogenicity of plant-produced influenza based on the M2e peptide fused to flagellin. Biotechnology, 15(42), 25.

Mariani, L., and Venuti, A. (2010). HPV vaccine: an overview of immune response, clinical protection, and new approaches for the future. J. Transl. Med. 8, 105. doi: 10.1186/1479-5876-8-105.

Markine-Goriaynoff, D., and Coutelier, J.-P. (2002). Increased Efficacy of the Immunoglobulin G2a Subclass in Antibody-Mediated Protection against Lactate Dehydrogenase-Elevating Virus-Induced Polioencephalomyelitis Revealed with Switch Mutants. J. Virol. 76, 432-435. doi:10.1128/JVI.76.1.432-435.2002.

Marusic, C., Pioli, C., Stelter, S., Novelli, F., Lonoce, C., Morrocchi, E., et al. (2017). N-glycan engineering of a plant-produced anti-CD20-hIL-2 immunocytokine significantly enhances its effector functions. Biotechnol. Bioeng. 115, 565-576. doi:10.1002/bit.26503.

Mason, H. S. (2016). Recombinant immune complexes as versatile and potent vaccines. Hum. Vaccines Immunother. 12, 988-989. doi:10.1080/21645515.2015.1116655.

Matsuzaki, Y., Katsushima, N., Nagai, Y., Shoji, M., Itagaki, T., Sakamoto, M., . . . & Nishimura, H. (2006). Clinical features of influenza C virus infection in children. The Journal of infectious diseases, 193(9), 1229-1235.

Maverakis, E., Kim, K., Shimoda, M., Gershwin, M. E., Wilken, R., Raychaudhuri, S., . . . & Lebrilla, C. B. (2015). Glycans in the immune system and The Altered Glycan Theory of Autoimmunity: a critical review. Journal of autoimmunity, 57, 1-13.

McGeoch, D., Fellner, P., & Newton, C. (1976). Influenza virus genome consists of eight distinct RNA species. Proceedings of the National Academy of Sciences, 73(9), 3045-3049.

Mechtcheriakova, I. A., Eldarov, M. A., Nicholson, L., Shanks, M., Skryabin, K. G., & Lomonossoff, G. P. (2006). The use of viral vectors to produce hepatitis B virus core particles in plants. Journal of virological methods, 131(1), 10-15.

Milich, D. R., & McLachlan, A. (1986). The nucleocapsid of hepatitis B virus is both a T-cell-independent and a T-cell-dependent antigen. Science, 234(4782), 1398-1401.

Milich, D. R., Peterson, D. L., Schodel, F., Jones, J. E., & Hughes, J. L. (1995). Preferential recognition of hepatitis B nucleocapsid antigens by Th1 or Th2 cells is epitope and major histocompatibility complex dependent. Journal of virology, 69(5), 2776-2785.

Mitnaul, L. J., Matrosovich, M. N., Castrucci, M. R., Tuzikov, A. B., Bovin, N. V., Kobasa, D., & Kawaoka, Y. (2000). Balanced hemagglutinin and neuraminidase activities are critical for efficient replication of influenza A virus. Journal of virology, 74(13), 6015-6020.

Mosmann, T. R., & Coffman, R. L. (1989). TH1 and TH2 cells: different patterns of lymphokine secretion lead to different functional properties. Annual review of immunology, 7(1), 145-173.

Mosnier, A., Daviaud, I., Casalegno, J. S., Ruetsch, M., Burugorri, C., Nauleau, E., . . . & Cohen, J. M. (2017). Influenza B burden during seasonal influenza epidemics in France. Medecine et maladies infectieuses, 47(1), 11-17.

Most, J., & Weiss, G. (2016). Consecutive infections with influenza A and B virus in children during the 2014-2015 seasonal influenza epidemic. The Journal of infectious diseases, 214(8), 1139-1141.

Nair, H., Brooks, W. A., Katz, M., Roca, A., Berkley, J. A., Madhi, S. A., . . . & Krishnan, A. (2011). Global burden of respiratory infections due to seasonal influenza in young children: a systematic review and meta-analysis. The Lancet, 378(9807), 1917-1930.

Nandi, S., Kwong, A. T., Holtz, B. R., Erwin, R. L., Marcel, S., and McDonald, K. A. (2016). Techno-economic analysis of a transient plant-based platform for monoclonal antibody production. MAbs 8, 1456-1466. doi:10.1080/19420862.2016.1227901.

Neirynck, S., Deroo, T., Saelens, X., Vanlandschoot, P., Jou, W. M., & Fiers, W. (1999). A universal influenza A vaccine based on the extracellular domain of the M2 protein. Nature medicine, 5(10), 1157-1163.

Nemchinov, L. G., & Natilla, A. (2007). Transient expression of the ectodomain of matrix protein 2 (M2e) of avian influenza A virus in plants. Protein expression and purification, 56(2), 153-159.

Neuberger, M. S., and Rajewsky, K. (1981). Activation of mouse complement by monoclonal mouse antibodies. Eur. J. Immunol. 11, 1012-1016. doi:10.1002/eji.1830111212.

Niwa, R., Natsume, A., Uehara, A., Wakitani, M., Iida, S., Uchida, K., . . . & Shitara, K. (2005). IgG subclass-independent improvement of antibody-dependent cellular cytotoxicity by fucose removal from Asn297-linked oligosaccharides. Journal of immunological methods, 306 (1-2), 151-160.

Nobusawa, E., & Sato, K. (2006). Comparison of the mutation rates of human influenza A and B viruses. Journal of virology, 80(7), 3675-3678.

Oliveira, E. R. A., Mohana-Borges, R., de Alencastro, R. B., and Horta, B. A. C. (2017). The flavivirus capsid protein: Structure, function and perspectives towards drug design. Virus Res. 227, 115-123.

Paprotka, T., Deuschle, K., Pilartz, M., & Jeske, H. (2015). Form follows function in geminiviral minichromosome architecture. Virus research, 196, 44-55.

Pastrana, D. V., Gambhira, R., Buck, C. B., Pang, Y. Y. S., Thompson, C. D., Culp, T. D., et al. (2005). Cross-neutralization of cutaneous and mucosal Papillomavirus types with anti-sera to the amino terminus of L2. Virology 337, 365-372. doi:10.1016/j.virol.2005.04.011.

Paules, C. I., Sullivan, S. G., Subbarao, K., & Fauci, A. S. (2018). Chasing seasonal influenza—The need for a universal influenza vaccine. New England Journal of Medicine, 378(1), 7-9.

Pepponi, I., Diogo, G. R., Stylianou, E., van Dolleweerd, C. J., Drake, P. M. W., Paul, M. J., et al. (2014). Plant-derived recombinant immune complexes as self-adjuvanting TB immunogens for mucosal boosting of BCG. Plant Biotechnol. J. 12, 840-850. doi:10.1111/pbi.12185.

Peyret, H. (2015). A protocol for the gentle purification of virus-like particles produced in plants. Journal of virological methods, 225, 59-63.

Peyret, H., Gehin, A., Thuenemann, E. C., Blond, D., El Turabi, A., Beales, L., et al. (2015). Tandem fusion of hepatitis B core antigen allows assembly of virus-like particles in bacteria and plants with enhanced capacity to accommodate foreign proteins. PLoS One 10. doi: 10.1371/journal.pone.0120751.

Phoolcharoen, W., Bhoo, S. H., Lai, H., Ma, J., Arntzen, C. J., Chen, Q., & Mason, H. S. (2011). Expression of an immunogenic Ebola immune complex in Nicotiana benthamiana. Plant biotechnology journal, 9(7), 807-816.

Phoolcharoen, W., Dye, J. M., Kilbourne, J., Piensook, K., Pratt, W. D., Arntzen, C. J., et al. (2011). A nonreplicating subunit vaccine protects mice against lethal Ebola virus challenge. Proc. Natl. Acad. Sci. U.S.A 108, 20695-700. doi:10.1073/pnas.1117715108.

Pumpens, P., & Grens, E. (2001). HBV core particles as a carrier for B cell/T cell epitopes. Intervirology, 44(2-3), 98-114.

Pushko, P., Tretyakova, I., Hidajat, R., Zsak, A., Chrzastek, K., Tumpey, T. M., & Kapczynski, D. R. (2017). Virus-like particles displaying H5, H7, H9 hemagglutinins and N1 neuraminidase elicit protective immunity to heterologous avian influenza viruses in chickens. Virology, 501, 176-182.

Putri, W. C., Muscatello, D. J., Stockwell, M. S., & Newall, A. T. (2018). Economic burden of seasonal influenza in the United States. Vaccine, 36(27), 3960-3966.

Rabaan, A. A., Bazzi, A. M., Al-Ahmed, S. H., Al-Ghaith, M. H., and Al-Tawfiq, J. A. (2017). Overview of Zika infection, epidemiology, transmission and control measures. J. Infect. Public Health 10, 141-149.

Radaev, S. (2002). Recognition of immunoglobulins by Fcγ receptors. Mol. Immunol. 38, 1073-1083. doi:10.1016/S0161-5890(02)00036-6.

Ramirez, A., Morris, S., Maucourant, S., D'Ascanio, I., Crescente, V., Lu, I. N., . . . & Rosenberg, W. (2018). A virus-like particle vaccine candidate for influenza A virus based on multiple conserved antigens presented on hepatitis B tandem core particles. Vaccine, 36(6), 873-880.

Rohovie, M. J., Nagasawa, M., & Swartz, J. R. (2017). Virus-like particles: Next-generation nanoparticles for targeted therapeutic delivery. Bioengineering & translational medicine, 2(1), 43-57.

Rolfes, M. A., Foppa, I. M., Garg, S., Flannery, B., Brammer, L., Singleton, J. A., . . . & Reed, C. (2018). Annual estimates of the burden of seasonal influenza in the United States: a tool for strengthening influenza surveillance and preparedness. Influenza and other respiratory viruses, 12(1), 132-137.

Rosenthal, S. H., Diamos, A. G., and Mason, H. S. (2018) An intronless form of the tobacco extensin gene terminator strongly enhances transient gene expression in plant leaves. Plant Mol Biol. 2018 Feb. 10. doi: 10.1007/s11103-018-0708-y. [Epub ahead of print].

Rybicki, E. P. (2010). Plant-made vaccines for humans and animals. Plant biotechnology journal, 8(5), 620-637.

Santi, L., Batchelor, L., Huang, Z., Hjelm, B., Kilbourne, J., Arntzen, C. J., Chen, Q., and Mason, H. S. (2008). An efficient plant viral expression system generating orally immunogenic Norwalk virus-like particles. Vaccine 26, 1846-1854.

Schellenbacher, C., Roden, R. B. S., and Kirnbauer, R. (2017). Developments in L2-based human papillomavirus (HPV) vaccines. Virus Res. 231, 166-175. doi:10.1016/j.virusres.2016.11.020.

Schödel, F., Moriarty, A. M., Peterson, D. L., Zheng, J. A., Hughes, J. L., Will, H., . . . & Milich, D. R. (1992). The position of heterologous epitopes inserted in hepatitis B virus core particles determines their immunogenicity. Journal of virology, 66(1), 106-114.

Scorza, F. B., Tsvetnitsky, V., & Donnelly, J. J. (2016). Universal influenza vaccines: Shifting to better vaccines. Vaccine, 34(26), 2926-2933.

Sharma, D. P., Ramsay, A. J., Maguire, D. J., Rolph, M. S., & Ramshaw, I. A. (1996). Interleukin-4 mediates down regulation of antiviral cytokine expression and cytotoxic T-lymphocyte responses and exacerbates vaccinia virus infection in vivo. Journal of Virology, 70(10), 7103-7107.

Shields, R. L., Lai, J., Keck, R., O'Connell, L. Y., Hong, K., Meng, Y. G., . . . & Presta, L. G. (2002). Lack of fucose on human IgG1 N-linked oligosaccharide improves binding to human FcγRIII and antibody-dependent cellular toxicity. Journal of Biological Chemistry, 277(30), 26733-26740.

Simón, D., Fajardo, A., Sóñora, M., Delfraro, A., and Musto, H. (2017). Host influence in the genomic composition of flaviviruses: A multivariate approach. Biochem. Biophys. Res. Commun. 492, 572-578.

Skehel, J. J., & Wiley, D. C. (2000). Receptor binding and membrane fusion in virus entry: the influenza hemagglutinin. Annual review of biochemistry, 69(1), 531-569.

Skowronski, D. M., Chambers, C., De Serres, G., Dickinson, J. A., Winter, A. L., Hickman, R., . . . & Gubbay, J. B. (2018). Early season co-circulation of influenza A (H3N2) and B (Yamagata): interim estimates of 2017/18 vaccine effectiveness, Canada, January 2018. Eurosurveillance, 23(5).

Smith, D. B., Gaunt, E. R., Digard, P., Templeton, K., & Simmonds, P. (2016). Detection of influenza C virus but not influenza D virus in Scottish respiratory samples. Journal of Clinical Virology, 74, 50-53.

Stanley, J. (1993). Geminiviruses: plant viral vectors. Current opinion in genetics & development, 3(1), 91-96.

Stemmer, W. P., Crameri, A., Ha, K. D., Brennan, T. M., & Heyneker, H. L. (1995). Single-step assembly of a gene and entire plasmid from large numbers of oligodeoxyribonucleotides. Gene, 164, 49-53.

Stepanova, L. A., Mardanova, E. S., Shuklina, M. A., Blokhina, E. A., Kotlyarov, R. Y., Potapchuk, M. V., . . . & Ravin, N. V. (2018). Flagellin-fused protein targeting M2e and HA2 induces potent humoral and T-cell responses and protects mice against various influenza viruses a subtypes. Journal of biomedical science, 25(1), 33.

Stettler, K., Beltramello, M., Espinosa, D. A., Graham, V., Cassotta, A., Bianchi, S., Vanzetta, F., Minola, A., Jaconi, S., Mele, F., et al. (2016). Specificity, cross-reactivity, and function of antibodies elicited by Zika virus infection. Science (80-). 353, 823-826.

Strasser, R., Stadlmann, J., Schahs, M., Stiegler, G., Quendler, H., Mach, L., et al. (2008). Generation of glyco-engineered Nicotiana benthamiana for the production of monoclonal antibodies with a homogeneous human-like N-glycan structure. Plant Biotechnol. J. 6, 392-402. doi: 10.1111/j.1467-7652.2008.00330.x.

Streatfield, S. J., Jilka, J. M., Hood, E. E., Turner, D. D., Bailey, M. R., Mayor, J. M., . . . & Tizard, I. R. (2001). Plant-based vaccines: unique advantages. Vaccine, 19(17), 2742-2748.

Su, S., Fu, X., Li, G., Kerlin, F., & Veit, M. (2017). Novel Influenza D virus: Epidemiology, pathology, evolution and biological characteristics. Virulence, 8(8), 1580-1591.

Suarez, D. L. (2016). Influenza A virus. Animal Influenza, 1-30.

Sullivan, S. G., Chilver, M. B., Carville, K. S., Deng, Y. M., Grant, K. A., Higgins, G., . . . & Tran, T. (2017). Low interim influenza vaccine effectiveness, Australia, 1 May to 24 Sep. 2017. Eurosurveillance, 22(43).

Takai, T., Li, M., Sylvestre, D., Clynes, R., and Ravetch, J. V. (1994). FcR γ chain deletion results in pleiotrophic effector cell defects. Cell 76, 519-529. doi:10.1016/0092-8674(94)90115-5.

Taylor, A., Foo, S.-S., Bruzzone, R., Vu Dinh, L., King, N. J. C., and Mahalingam, S. (2015). Fc receptors in antibody-dependent enhancement of viral infections. Immunol. Rev. 268, 340-364.

Thompson, W. W., Shay, D. K., Weintraub, E., Brammer, L., Bridges, C. B., Cox, N. J., & Fukuda, K. (2004). Influenza-associated hospitalizations in the United States. Jama, 292(11), 1333-1340.

Tiwari, S., Verma, P. C., Singh, P. K., & Tuli, R. (2009). Plants as bioreactors for the production of vaccine antigens. Biotechnology advances, 27(4), 449-467.

Turley, C. B., Rupp, R. E., Johnson, C., Taylor, D. N., Wolfson, J., Tussey, L., . . . & Shaw, A. (2011). Safety and immunogenicity of a recombinant M2e-flagellin influenza vaccine (STF2.4×M2e) in healthy adults. Vaccine, 29(32), 5145-515

Tusé, D., Tu, T., and McDonald, K. A. (2014). Manufacturing Economics of Plant-Made Biologics: Case Studies in Therapeutic and Industrial Enzymes. Biomed Res. Int. 2014, 1-16. doi:10.1155/2014/256135.

Tusé, D., Tu, T., and McDonald, K. A. (2014). Manufacturing Economics of Plant-Made Biologics: Case Studies in Therapeutic and Industrial Enzymes. Biomed Res. Int. 2014, 1-16.

Van den Hoecke, S., Ehrhardt, K., Kolpe, A., El Bakkouri, K., Deng, L., Grootaert, H., . . . & Schotsaert, M. (2017). Hierarchical and redundant roles of activating FcγRs in protection against influenza disease by M2e-specific IgG1 and IgG2a antibodies. Journal of virology, 91(7), e02500-16.

Vesikari, T., Brodszki, N., Van Damme, P., Diez-Domingo, J., Icardi, G., Petersen, L. K., et al. (2015). A Randomized, Double-Blind, Phase III Study of the Immunogenicity and Safety of a 9-Valent Human Papillomavirus L Virus-Like Particle Vaccine (V503) Versus Gardasil® in 9-15-Year-Old Girls. Pediatr. Infect. Dis. J. 34, 992-998. doi: 10.1097/INF.0000000000000773.

Webster, R. G., Laver, W. G., Air, G. M., & Schild, G. C. (1982). Molecular mechanisms of variation in influenza viruses. Nature, 296(5853), 115-121.

Wen Y-M, Mu L, Shi Y. Immunoregulatory functions of immune complexes in vaccine and therapy. EMBO Mol Med 2016; 8:1120-33. doi:10.15252/emmm.201606593.

Wheeler, C. M., Kjaer, S. K., Sigurdsson, K., Iversen, O., Hernandez-Avila, M., Perez, G., et al. (2009). The Impact of Quadrivalent Human Papillomavirus (HPV; Types 6, 11, 16, and 18) L1 Virus-Like Particle Vaccine on Infection and Disease Due to Oncogenic Nonvaccine HPV Types in Sexually Active Women Aged 16-26 Years. J. Infect. Dis. 199, 936-944. doi:10.1086/597309.

Whitacre, D. C., Lee, B. O., & Milich, D. R. (2009). Use of hepadnavirus core proteins as vaccine platforms. Expert Review of Vaccines, 8(11), 1565-1573.

Whitacre, D. C., Lee, B. O., and Milich, D. R. (2009). Use of hepadnavirus core proteins as vaccine platforms. Expert Rev. Vaccines 8, 1565-1573. doi:10.1586/erv.09.121.

Wilder-Smith, A., Vannice, K., Durbin, A., Hombach, J., Thomas, S. J., Thevarjan, I., and Simmons, C. P. (2018). Zika vaccines and therapeutics: landscape analysis and challenges ahead. BMC Med. 16.

Wilson, J. A., Hevey, M., Bakken, R., Guest, S., Bray, M., Schmaljohn, A. L. and Hart, M. K. (2000) Epitopes involved in antibody-mediated protection from Ebola virus. Science, 287, 1664-1666.

World Health Organization. (2018). Influenza (Seasonal) Fact Sheet. Retrieved Feb. 12, 2019.

Yang, M., Dent, M., Lai, H., Sun, H., and Chen, Q. (2017). Immunization of Zika virus envelope protein domain III induces specific and neutralizing immune responses against Zika virus. Vaccine 35, 4287-4294.

Yang, M., Lai, H., Sun, H., & Chen, Q. (2017). Virus-like particles that display Zika virus envelope protein domain III induce potent neutralizing immune responses in mice. Scientific reports, 7(1), 7679.

Yang, M., Sun, H., Lai, H., Hurtado, J., and Chen, Q. (2018). Plant-produced Zika virus envelope protein elicits neutralizing immune responses that correlate with protective immunity against Zika virus in mice. Plant Biotechnol. J. 16, 572-580.

Zebedee, S. L., & Lamb, R. A. (1988). Influenza A virus M2 protein: monoclonal antibody restriction of virus growth and detection of M2 in virions. Journal of virology, 62(8), 2762-2772.

Zeitlin, L., Pettitt, J., Scully, C., Bohorova, N., Kim, D., Pauly, M., et al. (2011). Enhanced potency of a fucose-free monoclonal antibody being developed as an Ebola virus immunoprotectant. Proc. Natl. Acad. Sci. 108, 20690-20694. doi:10.1073/pnas.1108360108.

Zhang, J., Fan, H. Y., Zhang, Z., Zhang, J., Zhang, J., Huang, J. N., . . . & Liao, M. (2016). Recombinant baculovirus vaccine containing multiple M2e and adjuvant LTB induces T cell dependent, cross-clade protection against H5N1 influenza virus in mice. Vaccine, 34(5), 622-629.

Zhang, X., Jia, R., Shen, H., Wang, M., Yin, Z., and Cheng, A. (2017). Structures and functions of the envelope glycoprotein in flavivirus infections. Viruses 9.

Zhou, C., Zhou, L., & Chen, Y. H. (2012). Immunization with high epitope density of M2e derived from 2009 pandemic H1N1 elicits protective immunity in mice. Vaccine, 30(23), 3463-3469.

We claim:

1. A recombinant immune complex comprising: an immunoglobulin heavy chain; an immunoglobulin light chain; an epitope tag, wherein the immunoglobulin heavy chain binds the epitope tag; and a fragment of a virus protein, wherein the fragment of the virus protein is linked to the N-terminus of the immunoglobulin heavy chain, the epitope tag is linked to the C-terminus of the immunoglobulin heavy chain, and the epitope tag is from a different protein than the virus protein.

2. The recombinant immune complex of claim 1, wherein the epitope tag is an Ebola antigen.

3. The recombinant immune complex of claim 1, wherein the immunoglobulin heavy chain is the immunoglobulin heavy chain of humanized 6D8 monoclonal antibody and the epitope tag is the 6D8 epitope tag.

4. The recombinant immune complex of claim 1, further comprising an immunoglobulin light chain.

5. The recombinant immune complex of claim 1, wherein the virus protein is HPV minor capsid protein L2 (GenBank Accession No. AGH32604.1).

6. The recombinant immune complex of claim 5, wherein the fragment of the virus protein comprises at least 8 continuous amino acids from the first 200 amino acid residues from the N-terminus of HPV minor capsid protein L2.

7. The recombinant immune complex of claim 5, wherein the fragment of the virus protein comprises at least one peptide sequence from the HPV minor capsid protein L2 selected from the group consisting of: amino acid residues 17-36, amino acid residues 56-75, amino acid residues 65-85, and amino acid residues 96-115.

8. The recombinant immune complex of claim 1, wherein the virus protein is M2e.

9. The recombinant immune complex of claim 8, wherein the fragment of the virus protein comprises the amino acid sequence set forth in SEQ ID NO. 9.

10. The recombinant immune complex of claim 8, wherein the fragment of the virus protein comprises the amino acid sequence set forth in SEQ ID NO. 10.

11. The recombinant immune complex of claim 1, wherein the virus protein is selected from the group consisting of: zika virus E protein domain 3 protein (ZE3), zika virus fusion loop antigen (ZE), and zika virus soluble envelope protein (Zse).

12. The recombinant immune complex of claim 11, wherein the fragment of the virus protein comprises amino acid residues 591-696 or amino acid residues 352-412 of GenBank Accession No. AMC13911.1.

13. The recombinant immune complex of claim 11, wherein the recombinant immune complex is encoded by the plasmid of SEQ ID NO. 36 or SEQ ID NO. 37.

14. A method of generating an immune response against a virus in a mammalian subject, the method comprising administering to the mammalian subject a recombinant immune complex (RIC), the RIC comprising:
    an immunoglobulin heavy chain;
    an epitope tag, wherein the immunoglobulin heavy chain binds the epitope tag; and
    a fragment of the virus protein,
    wherein the fragment of the virus protein is linked to the C-terminus of the immunoglobulin heavy chain, the epitope tag is linked to the C-terminus of the fragment of the virus protein, and the epitope tag is from a different protein than the virus protein.

15. The method of claim 14, wherein the epitope tag is an Ebola antigen.

16. The method of claim 14, wherein the immunoglobulin heavy chain is the immunoglobulin heavy chain of humanized 6D8 monoclonal antibody and the epitope tag is the 6D8 epitope tag.

17. The method of claim 14, wherein the RIC further comprises an immunoglobulin light chain.

* * * * *